US009828350B2

(12) United States Patent
Trabanco-Suárez et al.

(10) Patent No.: US 9,828,350 B2
(45) Date of Patent: Nov. 28, 2017

(54) 5,6-DIHYDRO-2H-[1,4]OXAZIN-3-YL-AMINE DERIVATIVES USEFUL AS INHIBITORS OF BETA-SECRETASE (BACE)

(71) Applicant: Janssen Pharmaceutica NV, Beerse (BE)

(72) Inventors: Andrés Avelino Trabanco-Suárez, Toledo (ES); Frederik Jan Rita Rombouts, Beerse (BE); Gary John Tresadern, Toledo (ES); Michiel Luc Maria Van Gool, Toledo (ES); Gregor James Macdonald, Beerse (BE); Carolina Martinez Lamenca, Beerse (BE); Henricus Jacobus Maria Gijsen, Beerse (BE)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 15/016,543

(22) Filed: Feb. 5, 2016

(65) Prior Publication Data

US 2016/0152581 A1    Jun. 2, 2016

Related U.S. Application Data

(62) Division of application No. 13/703,199, filed as application No. PCT/EP2011/059441 on Jun. 8, 2011, now abandoned.

(30) Foreign Application Priority Data

| Jun. 9, 2010 | (EP) | .................................... | 10165335 |
| Jan. 27, 2011 | (EP) | .................................... | 11152314 |
| Mar. 10, 2011 | (EP) | .................................... | 11157765 |
| May 5, 2011 | (EP) | .................................... | 11164999 |

(51) Int. Cl.
*C07D 265/30* (2006.01)
*C07D 413/10* (2006.01)
*C07D 413/04* (2006.01)

(52) U.S. Cl.
CPC ......... *C07D 265/30* (2013.01); *C07D 413/04* (2013.01); *C07D 413/10* (2013.01)

(58) Field of Classification Search
CPC ... C07D 265/30; C07D 413/10; C07D 413/04
See application file for complete search history.

(56) References Cited

U.S. PATENT DOCUMENTS

| 4,188,389 A | 2/1980 | Jirkovsky |
| 5,292,732 A | 3/1994 | Rover |
| 8,207,164 B2 * | 6/2012 | Holzer ............... C07D 265/30 514/233.2 |
| 8,846,658 B2 * | 9/2014 | Veenstra ............ C07D 265/30 514/211.15 |
| 2005/0282825 A1 | 12/2005 | Malamas |
| 2007/0005404 A1 | 1/2007 | Raz |
| 2007/0225372 A1 | 9/2007 | Bueno Melendo |
| 2008/0051420 A1 | 2/2008 | Berg |
| 2009/0082560 A1 | 3/2009 | Kobayashi |
| 2011/0009395 A1 | 1/2011 | Audui et al. |
| 2012/0238557 A1 | 9/2012 | Masui et al. |
| 2012/0277244 A1 | 11/2012 | Tintelnot-Blomley |
| 2014/0128385 A1 * | 5/2014 | Ruegger ............. C07D 417/12 514/233.2 |
| 2014/0256715 A1 | 9/2014 | Hurth et al. |
| 2016/0152581 A1 | 6/2016 | Trabanco-Suarez et al. |

FOREIGN PATENT DOCUMENTS

| CA | 2825620 | 9/2012 |
| EP | 2147914 | 1/2010 |
| EP | 2518 059 | 10/2012 |
| JP | 2013-513563 | 4/2013 |
| JP | 2012-147763 | 7/2014 |
| JP | 2014-505688 | 3/2015 |
| WO | WO 98/57641 | 12/1998 |
| WO | WO 03/089434 | 10/2003 |
| WO | WO 2004/026877 | 4/2004 |
| WO | WO 2004/058176 | 7/2004 |
| WO | WO 2005/037832 | 4/2005 |
| WO | WO 2006/034093 | 3/2006 |
| WO | WO 2006/076284 | 7/2006 |
| WO | WO 2006/138265 | 12/2006 |
| WO | WO 2007/005404 | 1/2007 |
| WO | WO 2007/058583 | 5/2007 |
| WO | WO 2007/114771 | 10/2007 |

(Continued)

OTHER PUBLICATIONS

International Search Report and Written Opinion—PCT/EP2011/059441.
International Search Report and Written Opinion—PCT/EP2011/059330.
International Search Report and Written Opinion—PCTEP2011/060712.
International Search Report and Written Opinion—PCT/EP2011/066343.
International Search Report and Written Opinion—PCT/EP2011/073522.

(Continued)

*Primary Examiner* — Sun Jae Yoo
(74) *Attorney, Agent, or Firm* — Yuriy P. Stercho

(57) ABSTRACT

The present invention relates to novel 5,6-dihydro-2H-[1,4]oxazin-3-ylamine derivatives as inhibitors of beta-secretase, also known as beta-site amyloid cleaving enzyme, BACE, BACE1, Asp2, or memapsin2. The invention is also directed to pharmaceutical compositions comprising such compounds, to processes for preparing such compounds and compositions, and to the use of such compounds and compositions for the prevention and treatment of disorders in which beta-secretase is involved, such as Alzheimer's disease (AD), mild cognitive impairment, senility, dementia, dementia with Lewy bodies, Down's syndrome, dementia associated with stroke, dementia associated with Parkinson's disease and dementia associated with beta-amyloid.

4 Claims, No Drawings

(56) References Cited

FOREIGN PATENT DOCUMENTS

| WO | WO 2009/022961 | 2/2009 |
|----|----------------|--------|
| WO | WO 2009/058300 | 5/2009 |
| WO | WO 2009/097278 | 8/2009 |
| WO | WO 2009/102468 | 8/2009 |
| WO | WO 2009/134617 | 11/2009 |
| WO | WO 2011/002409 | 1/2011 |
| WO | WO 2011/009943 | 1/2011 |
| WO | WO 2011/020806 | 2/2011 |
| WO | WO 2011/069934 | 6/2011 |
| WO | WO 2011/071135 | 6/2011 |
| WO | WO 2011/080176 | 7/2011 |
| WO | WO 2011/154374 | 12/2011 |
| WO | WO 2011/154431 | 12/2011 |
| WO | WO 2012/000933 | 1/2012 |
| WO | WO 2012/038438 | 3/2012 |
| WO | WO 2012/057247 | 5/2012 |
| WO | WO 2012/085038 | 6/2012 |
| WO | WO 2012/095463 | 7/2012 |
| WO | WO 2012/098064 | 7/2012 |
| WO | WO 2012/117027 | 9/2012 |
| WO | WO 2012/120023 | 9/2012 |
| WO | WO 2012/147763 | 11/2012 |
| WO | WO 2013/083556 | 6/2013 |
| WO | WO 2013/083557 | 6/2013 |
| WO | WO 2014/099794 | 6/2014 |
| WO | WO 2014/198851 | 12/2014 |
| WO | WO 2014/198853 | 12/2014 |
| WO | WO 2014/198854 | 12/2014 |
| WO | WO 2016/096979 | 6/2016 |

OTHER PUBLICATIONS

International Search Report and Written Opinion—PCT/EP2012/053455.
International Search Report and Written Opinion—PCT/EP2012/053863.
International Search Report and Written Opinion—PCT/EP2012/074349.
International Search Report and Written Opinion—PCT/EP2012/074351.
International Search Report and Written Opinion—PCT/EP2014/062285.
International Search Report and Written Opinion—PCT/EP2014/062286.
International Search Report and Written Opinion—PCT/EP2014/062283.
Cheret et al. 2013 EMBO Journal, "Bace1 and Neuregulin-1 cooperate to control formation and maintenance of muscle spindles", (2013), 32(14), 2015-2028.
Esterhazy et al_Cell Metabolism, "Bace2 is a β Cell-Enriched Protease that Regulates Pancreatic β Cell Function and Mass",_ 2011_14_365-377.
Fleck et al. 2012, Curr. Alzheimer Res., "Bace1Dependent Neuregulin Processing: review" 9, 178-183.
Ginman, et al., "Core refinement toward Permeable β-Secretase (BACE-1) Inhibitors with Low HERG Activity", Journal of Medicinal Chemistry, vol. 56, pp. 4181-4205, 2013.
Hackam, et al. JAMA, "Translation of Research Evidence From animals to Humans", 296(14), 2006, 1731-1732.
Haniu et al., 2000, J. Biol. Chem., "Protein Structure and folding: Characterization of Alzheimer's β-secretase protein BACE: a Pepsin Family member with Unusual Properties", 275, 21099-21106.
Hemming et al. 2009, PLoS ONE, "Identification of β-Secretase (BACE1) Substrates using Quantitative Proteomics", 4, e8477.
Hilpert, et al., "β-Secretase (BACE1) Inhibitors with High in vivo efficacy Suitable for Clinical Evaluation in Alzheimer's Disease", Journal of Medicinal Chemistry, vol. 56, No. 10, pp. 3980-3995, 2013.
Hong et al, 2000, Science, "Structure of the Protease domain of memapsin 2(β-Secretase) Complexed with Inhibitor" 290, 150-153.
J. G. Cannon, Chapter Nineteen in Burger's Medicinal Chemistry and Drug Discovery, Fifth edition, vol. I: Principles and Practice, Wiley-Interscience 1995, pp. 783-802, 784.
Jonsson et al. 2012, Nature, "A mutation in APP protects against Alzheimer's disease and age-related cognitive decline", 488, 96-99.
Jordan, V. C. Nature Reviews: Drug Discovery,"Tamoxifen: A Most Unlikely Pioneering Medicine", 2, 2003, 205.
Kim et al. 2011, J. Biol. Chem. "Molecular Bases of Disease: Reduced Sodium Channel Nav1.1 Levels in BACE1-null Mice", 286, 8106-8116.
Koike H et al.,J Biochem., "Thimet Oligopeptidase Cleaves the Full-Length Alzheimer Amyloid Precursor Protein at a β-Secretase Cleavage Site in COS Cells" 1999, 126, 235-42.
Kondoh et al. Breast Cancer Res.Treat., "A novel aspartic protease gene, ALP56, is up-regulated in human breast cancer independently from the cathepsin D gene", 2003, vol. 78, pp. 37-44.
Kuhn et al. 2012, EMBO J. "Secretome protein enrichment identifies physiological BACE1protease substrates in neurons" 31, 3157-3168.
Kuhn et al. J. Biol. Chem."Protein Synthesis, Post-translation Modification, and Degradation: Regulated Intramembrane Proteolysis of the Interleukin-1 receptor II by α-,β-, and γ-Secretase", 2007, vol. 282, No. 16, pp. 11982-11995.
Luo et al., 2001, Nat. Neurosci, "Mice deficient in BACE!, the Alzheimer's β-secretase, have normal phenotype and abolished β-amyloid generation", 4, 231-232.
Martic-Kehl et al., Eur J. Nucl Med Mol Imaging (2012) 39:1492-1496.
Mateu et al., Chem. Eur. J. 2015, 21, 11719-11726.
Naus et al. 2004, J. Biol. Chem.,"Enzyme Catalysis and Regulation: Extodomain Shedding of the Neural Recognition Molecule CHL1 by the Metalloprotease-disintegrin ADAM8 Promotes Neurite Outgrowth and Suppresses Neuronal Cell Death", 279, 16083-16090.
Oehlrich et al, The evolution of amidine-based brain penetrant BACE1 inhibitors_Bioorganic & Medicinal Chemistry Letters, 2014, vol. 24, pp. 2033-2045.
Ostermann et al, 2006, Journal of molecular biology, "Crystal Structure of Human BACE2 in Complex with a Hydroxyethylamine transition-state Inhibitor", 355, (2), 249-61.
Park, et al., Effects of Flourine Substitution on Drug Metabolism: Pharmacological and Toxicological Implicatins, Drug metabolism reviews, vol. 26(3), 1994, pp. 605-643.
Park, et al., "Metabolism of Fluorine-Containing Drugs", Annual Ref. Pharmacol. Toxicol. 2001, vol. 41, pp. 443-470.
Patani et al, Chem.Rev., "Bioisosterism: A Rational Approach in Drug Design", 1996, 96, 3147-3176.
Purser, et al., "Flourine in Medicinal Chemistry", Chemical Society Reviews, 2008, vol. 37, pp. 320-330.
Roberds et al., 2001, Hum. Mol. Genet, "BACE knockout mice are healthy despite lacking the primary β-secretase activity in the brain: implications for Alzheimer's disease therapeutics",10, 1317-1324.
Rochin et al. PNAS, "BACE2 processes PMEL to form the melanosome amyloid matrix in pigment cells", Jun. 25, 2013, vol. 110, No. 26, pp. 10658-10663.
Sheridan, et al., "The Most Common Chemical Replacements in Drug-Like Compounds", J. Chem. Inf. Comput. Sci., 2002 vol. 42, pp. 103-108.
Silvestri_Medicinal Research Reviews, "Boom in the development of Non-Peptidic β-secretase (BACE1) Inhibitors for the Treatment of Alzheimer's Disease", 295-238_2009.
Stutzer et al. 2013, J. Biol. Chem., "Systematic Proteomic Analysis Identifies β-Site Amyloid Precursor Protein Cleaving Enzyme 2 and 1 (BACE2 and BACE1) Substrates in Pancreatic β-Cells" 288, 10536-10547.
Vassar et al., J. Neurochem., "Function, therapeutic potential and cell biology of BACE proteases: current status and future prospects", (2014) 10.1111/jnc.12715.
Vippagunta, et al. Advanced Drug Delivery Reviews, "Crystalline Solids", 48, 2001, 18.
Wang et al. Trends in Pharmacological Sciences, Apr, "β-Secretase: its biology as a therapeutic target in diseases", 2013, vol. 34, No. 4, pp. 215-225.

(56) References Cited

OTHER PUBLICATIONS

Wang, et al., Fluroine in Pharmaceutical Industry: Flourine-Containing Drugs Introduced to the Market in the Last Decade (2001-2011), Chemical Review, pp. 2432-2506, 2014.
Willem et al. 2009, Semin. Cell Dev. Biol., Function, regulation and therapeutic properties of β-secretase (BACE1) 20, 175-182.
Woltering, et al., "BACE Inhibitors: A head group scan on a series of amides:", Biorganic & Medicinal Chemistry Letters, vol. 23, pp. 4239-4243, 2013.
Yan and Vassar Lancet Neurol. "Targeting the β secretase BACE1 for Alzheimer's disease therapy", 2014, vol. 13, pp. 319-329.
Yan et al. J Alzheimers Dis. "Can BACE! Inhibition Mitigate Early Axonal Pathology in Neurological Diseases?", 2014, 30 vol. 38, No. 4, pp. 705-718.
Zhang, et al, "Application of Amybidbeta Protein in the Diagnosis of Alzheimer's Disease", vol. 29, No. 1, 2008 (see English translation as provided).
Zhou et al. 2012, J. Biol. Chem. "The Neural Cell Adhesion Molecules L1and CHL1 are Cleaved by BACE1 Protease in Vivo", 287, 25927-25940.
Decision from the European Patent Office dated Mar. 3, 2017 revoking the European Patent No. 2456763.

\* cited by examiner

5,6-DIHYDRO-2H-[1,4]OXAZIN-3-YL-AMINE DERIVATIVES USEFUL AS INHIBITORS OF BETA-SECRETASE (BACE)

CROSS REFERENCE TO RELATED APPLICATIONS

This application is a divisional of U.S. application Ser. No. 13/703,199, filed on Dec. 10, 2012, which is the 371 national stage of International Application No PCT/EP2011/059441, filed on Jun. 8, 2011, which claims priority from European Patent Application No. 10165335.0, filed on Jun. 9, 2010, European Patent Application No. 11152314.8, filed on Jan. 27, 2011, European Patent Application No. 11157765.6, filed on Mar. 10, 2011, and European Patent Application No. 11164999.2, filed on May 5, 2011, the entire disclosures of which are hereby incorporated in their entirety.

FIELD OF THE INVENTION

The present invention relates to novel 5,6-dihydro-2H-[1,4]oxazin-3-ylamine derivatives as inhibitors of beta-secretase, also known as beta-site amyloid cleaving enzyme, BACE, BACE1, Asp2, or memapsin2. The invention is also directed to pharmaceutical compositions comprising such compounds, to processes for preparing such compounds and compositions, and to the use of such compounds and compositions for the prevention and treatment of disorders in which beta-secretase is involved, such as Alzheimer's disease (AD), mild cognitive impairment, senility, dementia, dementia with Lewy bodies, Down's syndrome, dementia associated with stroke, dementia associated with Parkinson's disease and dementia associated with beta-amyloid.

BACKGROUND OF THE INVENTION

Alzheimer's Disease (AD) is a neurodegenerative disease associated with aging AD patients suffer from cognition deficits and memory loss as well as behavioral problems such as anxiety. Over 90% of those afflicted with AD have a sporadic form of the disorder while less than 10% of the cases are familial or hereditary. In the United States, about 1 in 10 people at age 65 have AD while at age 85, 1 out of every two individuals are affected with AD. The average life expectancy from the initial diagnosis is 7-10 years, and AD patients require extensive care either in an assisted living facility which is very costly or by family members. With the increasing number of elderly in the population, AD is a growing medical concern. Currently available therapies for AD merely treat the symptoms of the disease and include acetylcholinesterase inhibitors to improve cognitive properties as well as anxiolytics and antipsychotics to control the behavioral problems associated with this ailment.

The hallmark pathological features in the brain of AD patients are neurofibrillary tangles which are generated by hyperphosphorylation of tau protein and amyloid plaques which form by aggregation of beta-amyloid 1-42 (Abeta 1-42) peptide. Abeta 1-42 forms oligomers and then fibrils, and ultimately amyloid plaques. The oligomers and fibrils are believed to be especially neurotoxic and may cause most of the neurological damage associated with AD. Agents that prevent the formation of Abeta 1-42 have the potential to be disease-modifying agents for the treatment of AD. Abeta 1-42 is generated from the amyloid precursor protein (APP), comprised of 770 amino acids. The N-terminus of Abeta 1-42 is cleaved by beta-secretase (BACE), and then gamma-secretase cleaves the C-terminal end. In addition to Abeta 1-42, gamma-secretase also liberates Abeta 1-40 which is the predominant cleavage product as well as Abeta 1-38 and Abeta 1-43. These Abeta forms can also aggregate to form oligomers and fibrils. Thus, inhibitors of BACE would be expected to prevent the formation of Abeta 1-42 as well as Abeta 1-40, Abeta 1-38 and Abeta 1-43 and would be potential therapeutic agents in the treatment of AD.

WO-2011/009943 (Novartis) discloses unsubstituted and 2-substituted oxazine derivatives and their use as BACE inhibitors for the treatment of neurological disorders. WO-2011/020806 (Hoffmann-LaRoche) discloses 2,6-unsubstituted 3-amino-5-phenyl-5,6-dihydro-2H-[1,4]oxazine derivatives having BACE1 and/or BACE2 inhibitory properties.

SUMMARY OF THE INVENTION

The present invention is directed to 5,6-dihydro-2H-[1,4]oxazin-3-ylamine derivatives of Formula

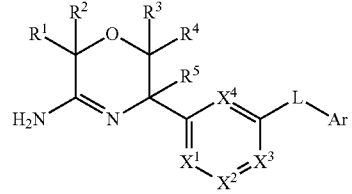

and the tautomers and the stereoisomeric forms thereof, wherein
$R^1$, $R^2$, $R^3$, $R^4$ are independently selected from the group consisting of hydrogen, fluoro, cyano, $C_{1-3}$alkyl, mono- and polyhalo-$C_{1-3}$alkyl, and $C_{3-6}$cycloalkyl; or
$R^1$ and $R^2$, or $R^3$ and $R^4$ taken together with the carbon atom to which they are attached may form a $C_{3-6}$cycloalkanediyl ring;
$R^5$ is selected from the group consisting of hydrogen, $C_{1-3}$alkyl, cyclopropyl, mono- and polyhalo-$C_{1-3}$alkyl, homoaryl and heteroaryl;
$X^1$, $X^2$, $X^3$, $X^4$ are independently $C(R^6)$ or N, provided that no more than two thereof represent N; each $R^6$ is selected from the group consisting of hydrogen, halo, $C_{1-3}$alkyl, mono- and polyhalo-$C_{1-3}$alkyl, cyano, $C_{1-3}$alkyloxy, mono- and polyhalo-$C_{1-3}$alkyloxy;
L is a bond or —N($R^7$)CO—, wherein $R^7$ is hydrogen or $C_{1-3}$alkyl;
Ar is homoaryl or heteroaryl;
wherein homoaryl is phenyl or phenyl substituted with one, two or three substituents selected from the group consisting of halo, cyano, $C_{1-3}$alkyl, $C_{1-3}$alkyloxy, mono- and polyhalo-$C_{1-3}$alkyl, mono- and polyhalo-$C_{1-3}$alkyloxy;
heteroaryl is selected from the group consisting of pyridyl, pyrimidyl, pyrazyl, pyridazyl, furanyl, thienyl, pyrrolyl, pyrazolyl, imidazolyl, triazolyl, tetrazolyl, thiazolyl, isothiazolyl, thiadiazolyl, oxazolyl, isoxazolyl, and oxadiazolyl, each optionally substituted with one, two or three substituents selected from the group consisting of halo, cyano, $C_{1-3}$alkyl, $C_{2-3}$alkynyl, $C_{1-3}$alkyloxy, mono- and polyhalo-$C_{1-3}$alkyl, mono- and polyhalo-$C_{1-3}$alkyloxy, and $C_{1-3}$alkyloxy$C_{1-3}$alkyloxy; and the addition salts and the solvates thereof.

Illustrative of the invention is a pharmaceutical composition comprising a pharmaceutically acceptable carrier and any of the compounds described above. An illustration of the invention is a pharmaceutical composition made by mixing any of the compounds described above and a pharmaceutically acceptable carrier. Illustrating the invention is a process for making a pharmaceutical composition comprising mixing any of the compounds described above and a pharmaceutically acceptable carrier.

Exemplifying the invention are methods of treating a disorder mediated by the beta-secretase enzyme, comprising administering to a subject in need thereof a therapeutically effective amount of any of the compounds or pharmaceutical compositions described above.

Further exemplifying the invention are methods of inhibiting the beta-secretase enzyme, comprising administering to a subject in need thereof a therapeutically effective amount of any of the compounds or pharmaceutical compositions described above.

An example of the invention is a method of treating a disorder selected from the group consisting of Alzheimer's disease, mild cognitive impairment, senility, dementia, dementia with Lewy bodies, Down's syndrome, dementia associated with stroke, dementia associated with Parkinson's disease and dementia associated with beta-amyloid, preferably Alzheimer's disease, comprising administering to a subject in need thereof, a therapeutically effective amount of any of the compounds or pharmaceutical compositions described above.

Another example of the invention is any of the compounds described above for use in treating: (a) Alzheimer's Disease, (b) mild cognitive impairment, (c) senility, (d) dementia, (e) dementia with Lewy bodies, (f) Down's syndrome, (g) dementia associated with stroke, (h) dementia associated with Parkinson's disease and (i) dementia associated with beta-amyloid, in a subject in need thereof.

DETAILED DESCRIPTION OF THE INVENTION

The present invention is directed to compounds of formula (I) as defined hereinbefore, and pharmaceutically acceptable salts thereof. The compounds of formula (I) are inhibitors of the beta-secretase enzyme (also known as beta-site cleaving enzyme, BACE, BACE1, Asp2 or memapsin 2), and are useful in the treatment of Alzheimer's disease, mild cognitive impairment, senility, dementia, dementia associated with stroke, dementia with Lewy bodies, Down's syndrome, dementia associated with Parkinson's disease and dementia associated with beta-amyloid, preferably Alzheimer's disease, mild cognitive impairment or dementia, more preferably Alzheimer's disease.

In particular the present invention is directed to 6-substituted 5,6-dihydro-2H-[1,4]oxazin-3-ylamine derivatives of Formula (I)

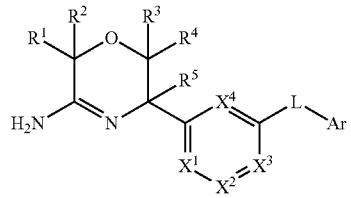

and the tautomers and the stereoisomeric forms thereof, wherein
$R^1$, $R^2$ and $R^3$ are independently selected from the group consisting of hydrogen, fluoro, cyano, $C_{1-3}$alkyl, mono- and polyhalo-$C_{1-3}$alkyl, and $C_{3-6}$cycloalkyl;

$R^4$ is fluoro or trifluoromethyl; or
$R^1$ and $R^2$, or $R^3$ and $R^4$ taken together with the carbon atom to which they are attached may form a $C_{3-6}$cycloalkanediyl ring;
$R^5$ is selected from the group consisting of hydrogen, $C_{1-3}$alkyl, cyclopropyl, mono- and polyhalo-$C_{1-3}$alkyl, homoaryl and heteroaryl;
$X^1$, $X^2$, $X^3$, $X^4$ are independently $C(R^6)$ or N, provided that no more than two thereof represent N; each $R^6$ is selected from the group consisting of hydrogen, halo, $C_{1-3}$alkyl, mono- and polyhalo-$C_{1-3}$alkyl, cyano, $C_{1-3}$alkyloxy, mono- and polyhalo-$C_{1-3}$alkyloxy;
L is a bond or —N($R^7$)CO—, wherein $R^7$ is hydrogen or $C_{1-3}$alkyl;
Ar is homoaryl or heteroaryl;
wherein homoaryl is phenyl or phenyl substituted with one, two or three substituents selected from the group consisting of halo, cyano, $C_{1-3}$alkyl, $C_{1-3}$alkyloxy, mono- and polyhalo-$C_{1-3}$alkyl, mono- and polyhalo-$C_{1-3}$alkyloxy;
heteroaryl is selected from the group consisting of pyridyl, pyrimidyl, pyrazyl, pyridazyl, furanyl, thienyl, pyrrolyl, pyrazolyl, imidazolyl, triazolyl, tetrazolyl, thiazolyl, isothiazolyl, thiadiazolyl, oxazolyl, isoxazolyl, and oxadiazolyl, each optionally substituted with one, two or three substituents selected from the group consisting of halo, cyano, $C_{1-3}$alkyl, $C_{2-3}$alkynyl, $C_{1-3}$alkyloxy, mono- and polyhalo-$C_{1-3}$alkyl, mono- and polyhalo-$C_{1-3}$alkyloxy, and $C_{1-3}$alkyloxy$C_{1-3}$alkyloxy; and the addition salts and the solvates thereof.

Compounds according to the invention wherein $R^4$ is an electronegative group such as fluoro or trifluoromethyl are more easily retained in the brain than prior art compounds lacking such electronegative groups in the 6 position of the oxazine because they are poorer substrates for permeability glycoprotein (PGP) which pumps xenobiotics out of the brain.

In an embodiment L is a direct bond.
In an embodiment L is a direct bond, and Ar is phenyl; phenyl substituted with one or two substituents selected from the group of halo, cyano, trifluoromethyl, trifluoromethoxy and $C_{1-3}$alkyloxy; pyridinyl; pyridinyl substituted with methyl, halo, methoxy, ethoxy or cyano; or pyrimidinyl.
In an embodiment L is a direct bond, $X^1$ is N, CH or CF, and $X^2$, $X^3$ and $X^4$ are CH.
In an embodiment L is a direct bond, $X^3$ is N, $X^1$ is CH or CF, $X^2$ and $X^4$ are CH.
In an embodiment L is a direct bond, $R^5$ is methyl.
In an embodiment L is a direct bond, $R^5$ is cyclopropyl.
In an embodiment L is a direct bond, $R^5$ is ethyl.
In an embodiment according to the invention, $R^1$, $R^2$ and $R^3$ are hydrogen, $R^4$ is fluoro and L is —N($R^7$)CO— wherein $R^7$ is hydrogen.
In an embodiment according to the invention, $R^1$, $R^2$ and $R^3$ are hydrogen, $R^4$ is fluoro, L is —N($R^7$)CO— wherein $R^7$ is hydrogen, and $R^5$ is methyl, ethyl or cyclopropyl.
In an embodiment according to the invention, $R^1$, $R^2$ and $R^3$ are hydrogen, $R^4$ is fluoro, L is —N($R^7$)CO— wherein $R^7$ is hydrogen, $R^5$ is methyl, ethyl or cyclopropyl, $X^2$, $X^3$ and $X^4$ are CH, and $X^1$ is CH, CF or N.
In an embodiment according to the invention, $R^1$, $R^2$ and $R^3$ are hydrogen, $R^4$ is fluoro, L is —N($R^7$)CO— wherein $R^7$ is hydrogen, $R^5$ is methyl, ethyl or cyclopropyl, and Ar is pyridyl, or pyrazyl, each optionally substituted with one or two substituents selected from halo, cyano, methoxy, trifluoroethoxy and difluoromethyl.

In an embodiment according to the invention, $R^1$, $R^2$ and $R^3$ are hydrogen, $R^4$ is fluoro, L is —N($R^7$)CO— wherein $R^7$ is hydrogen, $R^5$ is methyl, ethyl or cyclopropyl, and Ar is pyridyl, or pyrazyl, each optionally substituted with one or two substituents selected from halo, cyano, methoxy, trifluoroethoxy and difluoromethyl, and the 5 and 6 position of the dihydro-2H-[1,4]oxazin ring have both the R configuration.

In an embodiment according to the invention, $R^1$, $R^2$ and $R^3$ are hydrogen, $R^4$ is fluoro, L is —N($R^7$)CO— wherein $R^7$ is hydrogen, $R^5$ is methyl or cyclopropyl, and Ar is selected from the group consisting of 5-methoxypyrazyl, 5-ethoxy-pyrazyl, 5-(2,2,2-trifluoroethoxy)-pyrazyl, 5-cyano-pyridin-2-yl, 5-chloro-pyridin-2-yl, 3,5-dichloro-pyridin-2-yl, 3-fluoro-5-chloro-pyridin-2-yl, 3-chloro-5-cyano-pyridin-2-yl, and 5-cyanopyridin-3-yl.

In an embodiment according to the invention, $R^1$, $R^2$ and $R^3$ are hydrogen, $R^4$ is trifluoromethyl and L is —N($R^7$)CO— wherein $R^7$ is hydrogen.

In an embodiment according to the invention, $R^1$, $R^2$ and $R^3$ are hydrogen, $R^4$ is trifluoromethyl, L is —N($R^7$)CO— wherein $R^7$ is hydrogen, and $R^5$ is methyl, ethyl or cyclopropyl.

In an embodiment according to the invention, $R^1$, $R^2$ and $R^3$ are hydrogen, $R^4$ is trifluoromethyl, L is —N($R^7$)CO— wherein $R^7$ is hydrogen, $R^5$ is methyl, ethyl or cyclopropyl, $X^2$, $X^3$ and $X^4$ are CH, and $X^1$ is CH, CF or N.

In an embodiment according to the invention, $R^1$, $R^2$ and $R^3$ are hydrogen, $R^4$ is trifluoromethyl, L is —N($R^7$)CO— wherein $R^7$ is hydrogen, $R^5$ is methyl, ethyl or cyclopropyl, and Ar is pyridyl or pyrazyl, each optionally substituted with one or two substituents selected from halo, cyano, methoxy, trifluoroethoxy and difluoromethyl, and the 5 and 6 position of the dihydro-2H-[1,4]oxazin ring have both the R configuration.

In an embodiment according to the invention, $R^1$, $R^2$ and $R^3$ are hydrogen, $R^4$ is trifluoromethyl, L is —N($R^7$)CO— wherein $R^7$ is hydrogen, $R^5$ is methyl or cyclopropyl, and Ar is selected from the group consisting of 4-pyrimidyl, 5-methoxy-pyrazyl, 5-ethoxypyrazyl, 5-(2,2,2-trifluoroethoxy)pyrazyl, 5-cyanopyridin-2-yl, 5-chloro-pyridin-2-yl, 3,5-dichloro-pyridin-2-yl, 3-fluoro-5-chloro-pyridin-2-yl, 3-chloro-5-cyano-pyridin-2-yl, 5-methoxypyridin-3-yl and 5-cyanopyridin-3-yl.

In an embodiment according to the invention, $R^1$ and $R^2$ are hydrogen, $R^3$ is fluoro, $R^4$ is trifluoromethyl, and L is —N($R^7$)CO— wherein $R^7$ is hydrogen.

In an embodiment according to the invention, $R^1$ and $R^2$ are hydrogen, $R^3$ is fluoro, $R^4$ is trifluoromethyl, L is —N($R^7$)CO— wherein $R^7$ is hydrogen, and $R^5$ is methyl, ethyl or cyclopropyl.

In an embodiment according to the invention, $R^1$ and $R^2$ are hydrogen, $R^3$ is fluoro, $R^4$ is trifluoromethyl, L is —N($R^7$)CO— wherein $R^7$ is hydrogen, $R^5$ is methyl, ethyl or cyclopropyl, $X^2$, $X^3$ and $X^4$ are CH, and $X^1$ is CH, CF or N.

In an embodiment according to the invention, $R^1$ and $R^2$ are hydrogen, $R^3$ is fluoro, $R^4$ is trifluoromethyl, L is —N($R^7$)CO— wherein $R^7$ is hydrogen, $R^5$ is methyl, ethyl or cyclopropyl, and Ar is pyridyl or pyrazyl, each optionally substituted with one or two substituents selected from halo, cyano, methoxy, trifluoroethoxy and difluoromethyl, and the 5 and 6 position of the dihydro-2H-[1,4]oxazin ring have both the R configuration.

In an embodiment according to the invention, $R^1$ and $R^2$ are hydrogen, $R^3$ is fluoro, $R^4$ is trifluoromethyl, L is —N($R^7$)CO— wherein $R^7$ is hydrogen, $R^5$ is methyl or cyclopropyl, and Ar is selected from the group consisting of 4-pyrimidyl, 5-methoxy-pyrazyl, 5-ethoxypyrazyl, 5-(2,2,2-trifluoroethoxy)pyrazyl, 5-cyanopyridin-2-yl, 5-chloro-pyridin-2-yl, 3,5-dichloro-pyridin-2-yl, 3-fluoro-5-chloro-pyridin-2-yl, 3-chloro-5-cyano-pyridin-2-yl, 5-methoxypyridin-3-yl and 5-cyanopyridin-3-yl.

In an embodiment of the present invention, $R^1$, $R^2$, $R^3$, $R^4$ are independently selected from the group consisting of hydrogen, fluoro, cyano, $C_{1-3}$alkyl, mono- and polyhalo-$C_{1-3}$alkyl, and $C_{3-6}$cycloalkyl; or $R^1$ and $R^2$, or $R^3$ and $R^4$ taken together with the carbon atom to which they are attached may form a $C_{3-6}$cycloalkanediyl ring;

$R^5$ is selected from the group consisting of hydrogen, $C_{1-3}$alkyl, cyclopropyl, mono- and polyhalo-$C_{1-3}$alkyl, homoaryl and heteroaryl;

$X^1$, $X^2$, $X^3$, $X^4$ are independently $C(R^6)$ or N, provided that no more than two thereof represent N; each $R^6$ is selected from the group consisting of hydrogen, halo, $C_{1-3}$alkyl, mono- and polyhalo-$C_{1-3}$alkyl, cyano, $C_{1-3}$alkyloxy, mono- and polyhalo-$C_{1-3}$alkyloxy;

L is a bond or —N($R^7$)CO—, wherein $R^7$ is hydrogen or $C_{1-3}$alkyl;

Ar is homoaryl or heteroaryl;

homoaryl is phenyl or phenyl substituted with one, two or three substituents selected from the group consisting of halo, cyano, $C_{1-3}$alkyl, $C_{1-3}$alkyloxy, mono- and polyhalo-$C_{1-3}$alkyl, mono- and polyhalo-$C_{1-3}$alkyloxy;

heteroaryl is selected from the group consisting of pyridyl, pyrimidyl, pyrazyl, pyridazyl, furanyl, thienyl, pyrrolyl, pyrazolyl, imidazolyl, triazolyl, tetrazolyl, thiazolyl, isothiazolyl, thiadiazolyl, oxazolyl, isoxazolyl, and oxadiazolyl, each optionally substituted with one, two or three substituents selected from the group consisting of halo, cyano, $C_{1-3}$alkyl, $C_{1-3}$alkyloxy, mono- and polyhalo-$C_{1-3}$alkyl;

and the addition salts and the solvates thereof.

In an embodiment of the invention, $R^1$, $R^2$, $R^3$, $R^4$ are independently selected from the group consisting of hydrogen, fluoro, cyano, and polyhalo-$C_{1-3}$alkyl; or $R^1$ and $R^2$, taken together with the carbon atom to which they are attached may form a $C_{3-6}$cycloalkanediyl ring;

$R^5$ is $C_{1-3}$alkyl, cyclopropyl or trifluoromethyl;

$X^1$, $X^2$, $X^3$, $X^4$ are independently $C(R^6)$ wherein each $R^6$ is selected from hydrogen and halo; $X^1$ may also be N;

L is a bond or —N($R^7$)CO—, wherein $R^7$ is hydrogen;

Ar is homoaryl or heteroaryl;

homoaryl is phenyl or phenyl substituted with one or two substituents selected from the group consisting of halo, cyano, $C_{1-3}$alkyl, and $C_{1-3}$alkyloxy;

heteroaryl is selected from the group consisting of pyridyl, pyrimidyl, and pyrazyl, each optionally substituted with one or two substituents selected from the group consisting of halo, cyano, $C_{1-3}$alkyl, $C_{1-3}$alkyloxy, polyhalo$C_{1-3}$alkyl and polyhalo$C_{1-3}$alkyloxy or an addition salt or a solvate thereof.

In an embodiment of the present invention, $R^1$, $R^2$, $R^3$, $R^4$ are independently selected from the group consisting of hydrogen, fluoro, cyano, and polyhalo-$C_{1-3}$alkyl; or $R^1$ and $R^2$, taken together with the carbon atom to which they are attached may form a $C_{3-6}$cycloalkanediyl ring;

$R^5$ is $C_{1-3}$alkyl;

$X^1$, $X^2$, $X^3$, $X^4$ are independently $C(R^6)$ wherein each $R^6$ is selected from hydrogen and halo;

L is a bond or —N($R^7$)CO—, wherein $R^7$ is hydrogen;

Ar is homoaryl or heteroaryl;

homoaryl is phenyl or phenyl substituted with one or two substituents selected from the group consisting of halo, cyano, $C_{1-3}$alkyl, and $C_{1-3}$alkyloxy;

heteroaryl is selected from the group consisting of pyridyl, pyrimidyl, and pyrazyl, each optionally substituted with one or two substituents selected from the group consisting of halo, cyano, $C_{1-3}$alkyl, and $C_{1-3}$alkyloxy; or
an addition salt or a solvate thereof.

In another embodiment of the present invention, $R^1$ and $R^2$ are independently selected from the group consisting of hydrogen, fluoro, cyano, and trifluoromethyl; or
$R^1$ and $R^2$ taken together with the carbon atom to which they are attached may form a cyclopropyl ring;
$R^3$ and $R^4$ are both hydrogen;
$R^5$ is methyl;
$X^1$ and $X^3$ are CH or CF;
$X^2$ and $X^4$ are CH;
L is a bond or —$N(R^7)CO$—, wherein $R^7$ is hydrogen;
Ar is homoaryl or heteroaryl;
homoaryl is phenyl or phenyl substituted with one or two substituents selected from chloro and cyano;
heteroaryl is selected from the group consisting of pyridyl, pyrimidyl, and pyrazyl, each optionally substituted with one or two substituents selected from the group consisting of chloro, fluoro, cyano, methyl, and methoxy; or
an addition salt or a solvate thereof.

In another embodiment of the present invention, $R^1$ and $R^2$ are independently selected from the group consisting of hydrogen, fluoro, cyano, and trifluoromethyl; or
$R^1$ and $R^2$ taken together with the carbon atom to which they are attached may form a cyclopropyl ring;
$R^3$ and $R^4$ are both hydrogen;
$R^5$ is methyl;
$X^1$, $X^2$, $X^3$, $X^4$ are CH;
L is a bond or —$N(R^7)CO$—, wherein $R^7$ is hydrogen;
Ar is homoaryl or heteroaryl;
homoaryl is phenyl or phenyl substituted with one or two substituents selected from chloro and cyano;
heteroaryl is selected from the group consisting of pyridyl, pyrimidyl, and pyrazyl, each optionally substituted with one or two substituents selected from the group consisting of chloro, fluoro, cyano, methyl, and methoxy; or
an addition salt or a solvate thereof.

In another embodiment of the present invention, $R^1$ and $R^2$ are both hydrogen; $R^3$ and $R^4$ are independently selected from the group consisting of hydrogen, fluoro, and trifluoromethyl;
$R^5$ is methyl;
$X^1$ and $X^3$ are CH or CF;
$X^2$ and $X^4$ are CH;
L is a bond or —$N(R^7)CO$—, wherein $R^7$ is hydrogen;
Ar is homoaryl or heteroaryl;
homoaryl is phenyl or phenyl substituted with one or two substituents selected from chloro and cyano;
heteroaryl is selected from the group consisting of pyridyl, pyrimidyl, and pyrazyl, each optionally substituted with one or two substituents selected from the group consisting of chloro, fluoro, cyano, methyl, and methoxy; or
an addition salt or a solvate thereof.

DEFINITIONS

"Halo" shall denote fluoro, chloro and bromo; "$C_{1-3}$alkyl" shall denote a straight or branched saturated alkyl group having 1, 2 or 3 carbon atoms, e.g. methyl, ethyl, 1-propyl and 2-propyl; "$C_{1-3}$alkyloxy" shall denote an ether radical wherein $C_{1-3}$alkyl is as defined before; "mono- and polyhalo$C_{1-3}$alkyl" shall denote $C_{1-3}$alkyl as defined before, substituted with 1, 2, 3 or where possible with more halo atoms as defined before; "mono- and polyhalo$C_{1-3}$alkyloxy" shall denote an ether radical wherein mono- and polyhalo$C_{1-3}$ alkyl is as defined before; "$C_{3-6}$cycloalkyl" shall denote cyclopropyl, cyclobutyl, cyclopentyl and cyclohexyl; "$C_{3-6}$cycloalkanediyl" shall denote a bivalent radical such as cyclopropanediyl, cyclobutanediyl, cyclopentanediyl and cyclohexanediyl.

The term "subject" as used herein, refers to an animal, preferably a mammal, most preferably a human, who is or has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

Hereinbefore and hereinafter, the term "compound of formula (I)" is meant to include the addition salts, the solvates and the stereoisomers thereof.

The terms "stereoisomers" or "stereochemically isomeric forms" hereinbefore or hereinafter are used interchangeably.

The invention includes all stereoisomers of the compound of Formula (I) either as a pure stereoisomer or as a mixture of two or more stereoisomers.

Enantiomers are stereoisomers that are non-superimposable mirror images of each other. A 1:1 mixture of a pair of enantiomers is a racemate or racemic mixture.

Diastereomers (or diastereoisomers) are stereoisomers that are not enantiomers, i.e. they are not related as mirror images. If a compound contains a double bond, the substituents may be in the E or the Z configuration. If a compound contains a disubstituted cycloalkyl group, the substituents may be in the cis or trans configuration. Therefore, the invention includes enantiomers, diastereomers, racemates, E isomers, Z isomers, cis isomers, trans isomers and mixtures thereof.

The absolute configuration is specified according to the Cahn-Ingold-Prelog system. The configuration at an asymmetric atom is specified by either R or S. Resolved compounds whose absolute configuration is not known can be designated by (+) or (−) depending on the direction in which they rotate plane polarized light.

When a specific stereoisomer is identified, this means that said stereoisomer is substantially free, i.e. associated with less than 50%, preferably less than 20%, more preferably less than 10%, even more preferably less than 5%, in particular less than 2% and most preferably less than 1%, of the other isomers. Thus, when a compound of formula (I) is for instance specified as (R), this means that the compound is substantially free of the (S) isomer; when a compound of formula (I) is for instance specified as E, this means that the compound is substantially free of the Z isomer; when a compound of formula (I) is for instance specified as cis, this means that the compound is substantially free of the trans isomer.

For use in medicine, the salts of the compounds of this invention refer to non-toxic "pharmaceutically acceptable salts". Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts.

Representative acids which may be used in the preparation of pharmaceutically acceptable salts include, but are not limited to, the following: acetic acid, 2,2-dichloroactic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, capric acid, caproic acid, caprylic acid, cinnamic acid, citric acid, cyclamic acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, beta-oxo-glutaric acid, glycolic acid, hippuric acid, hydrobromic acid, hydrochloric acid, (+)-L-lactic acid, (+)-DL-lactic acid, lactobionic acid, maleic acid, (−)-L-malic acid, malonic acid, (+)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, trifluoromethylsulfonic acid, and undecylenic acid. Representative bases which may be used in the preparation of pharmaceutically acceptable salts include, but are not limited to, the following: ammonia, L-arginine, benethamine, benzathine, calcium hydroxide, choline, dimethylethanolamine, diethanolamine, diethylamine, 2-(diethylamino)-ethanol, ethanolamine, ethylene-diamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

The chemical names of the compounds of the present invention were generated according to the nomenclature rules agreed upon by the Chemical Abstracts Service.

Some of the compounds according to formula (I) may also exist in their tautomeric form. Such forms although not explicitly indicated in the above formula are intended to be included within the scope of the present invention.

Preparation of the Compounds

Experimental Procedure 1

The final compounds according to Formula (I), can be prepared by reacting an intermediate compound of Formula (II) with an appropriate source of ammonia such as, for example, ammonium chloride or aqueous ammonia, according to reaction scheme (1), a reaction that is performed in a suitable reaction-inert solvent, such as, for example, water or methanol, under thermal conditions such as, for example, heating the reaction mixture at 60° C., for example for 6 hours. In reaction scheme (1), all variables are defined as in Formula (I).

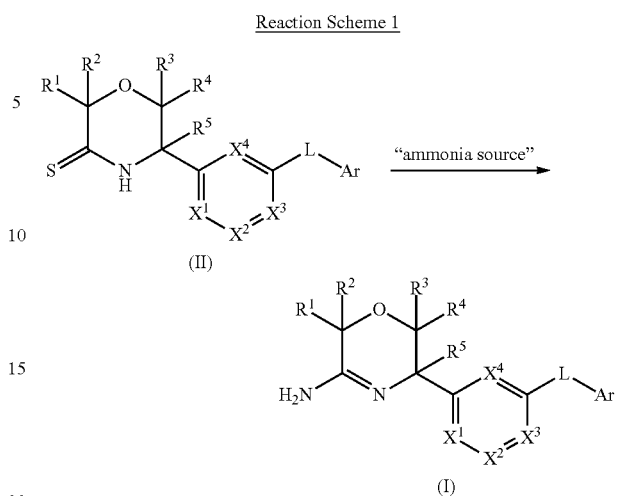

Experimental Procedure 2

The final compounds according to Formula (I-a) where in L is —N($R^7$)CO—, can be prepared by reacting an intermediate compound of Formula (III-a) with a compound of Formula (IV) according to reaction scheme (2), a reaction that is performed in a suitable reaction-inert solvent, such as, for example, N,N-dimethylformamide, in the presence of a suitable base, such as, for example, $K_3PO_4$, a copper catalyst such as, for example, CuI and a diamine such as for example (1R,2R)-(−)-1,2-diaminocyclohexane, under thermal conditions such as, for example, heating the reaction mixture at 180° C., for example for 135 minutes under microwave irradiation. In reaction scheme (2), all variables are defined as in Formula (I) and W is halo.

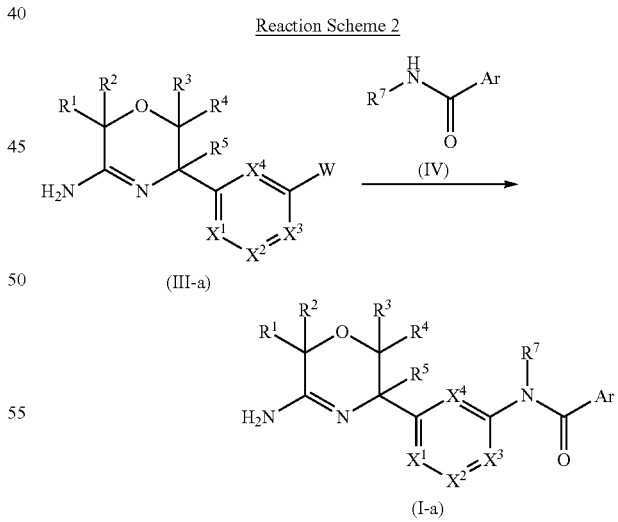

Experimental Procedure 3

Additionally, the final compounds according to Formula (I-a), can be prepared by reacting an intermediate compound of Formula (III-b) with a compound of Formula (V) according to reaction scheme (3), a reaction that is performed in a suitable reaction-inert solvent, such as, for example, dichloromethane, in the presence of a suitable base, such as, for example, triethylamine, in the presence of a condensation agent such as for example O-(7azabenzotriazol-1-yl)-N,N,N',N'-tetramethyluronium hexafluorophosphate [HATU, CAS 148893-10-1], under thermal conditions such as, for example, heating the reaction mixture at 25° C., for example for 2 hours. In reaction scheme (3), all variables are defined as in Formula (I).

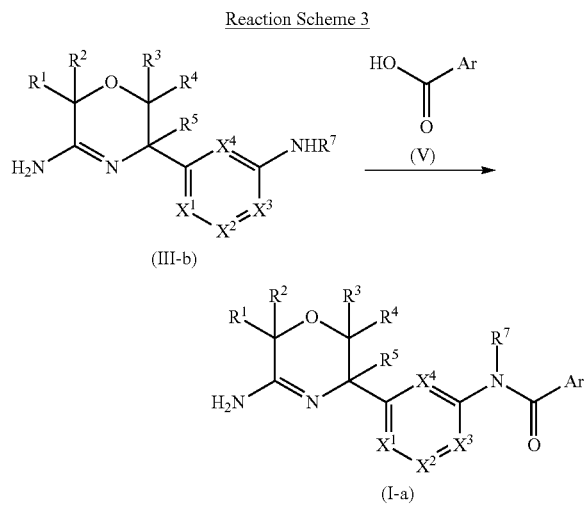

Experimental Procedure 4

Additionally, the final compounds according to Formula (I-a), can be prepared by reacting an intermediate compound of Formula (III-b) with a compound of Formula (VI) according to reaction scheme (4), a reaction that is performed in a suitable reaction-inert solvent, such as, for example, dichloromethane, in the presence of a suitable base, such as, for example, pyridine, at room temperature for 2 hours. In reaction scheme (4), all variables are defined as in Formula (I) and Y is halo.

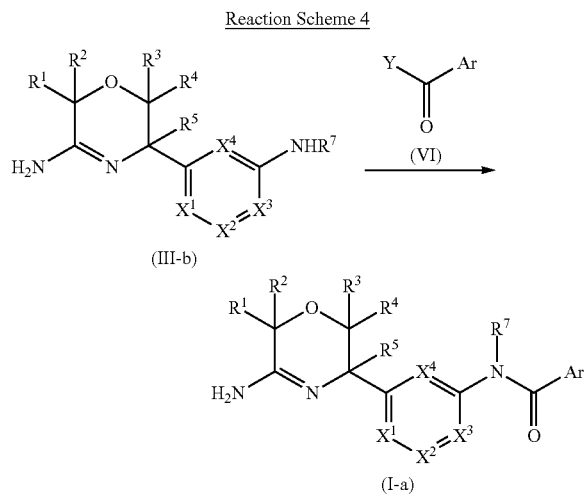

Experimental Procedure 5

The final compounds according to Formula (I-b) wherein L is a bond, can be prepared by reacting an intermediate compound of Formula (III-a) with a compound of Formula (VII) according to reaction scheme (5), a reaction that is performed in a suitable reaction-inert solvent, such as, for example, ethanol or mixtures of inert solvents such as, for example, 1,2-dimethoxyethane/water/ethanol, in the presence of a suitable base, such as, for example, aqueous $K_3PO_4$ or $Cs_2CO_3$, a Pd-complex catalyst such as, for example, [1,1'-bis(diphenylphosphino)ferrocene]dichloropalladium(II) [CAS 72287-26-4] or trans-bisdicyclohexylamine)palladium diacetate [DAPCy, CAS 628339-96-8] under thermal conditions such as, for example, heating the reaction mixture at 80° C., for example for 20 hours or for example, heating the reaction mixture at 130° C., for example for 10 minutes under microwave irradiation. In reaction scheme (5), all variables are defined as in Formula (I) and W is halo. $R^8$ and $R^9$ may be hydrogen or alkyl, or may be taken together to form for example a bivalent radical of formula —$CH_2CH_2$—, —$CH_2CH_2CH_2$—, or —$C(CH_3)_2C(CH_3)_2$—.

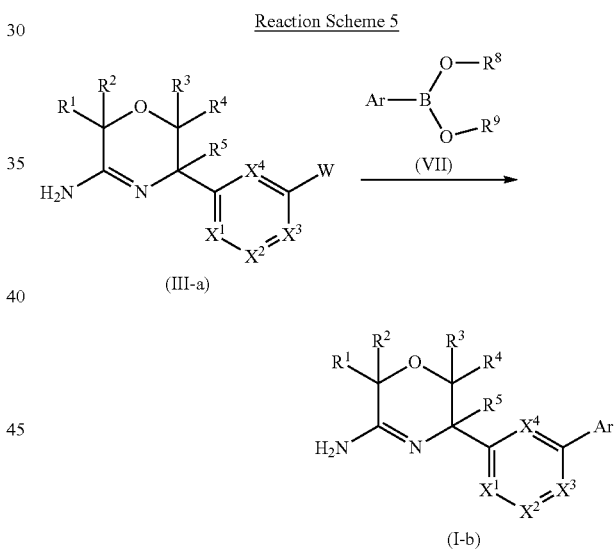

Experimental Procedure 6

The intermediates according to Formula (I-c) wherein $R^3$ is fluoro and $R^4$ trifluoromethyl, Formula (I-d) wherein $R^3$ is fluoro and $R^4$ hydrogen and Formula (I-e) wherein $R^3$ is hydrogen and $R^4$ trifluoromethyl can be prepared from the corresponding intermediate compounds of Formula (XXIII-a) and (XXIII-b) according to reaction scheme (6), a reaction that is performed in a suitable reaction-inert solvent, for example dichloromethane, in the presence of a suitable acid, for example trifluoroacetic acid at room temperature, for example for 2 hours. In reaction scheme (6), all variables are defined as in Formula (I).

Reaction Scheme 6

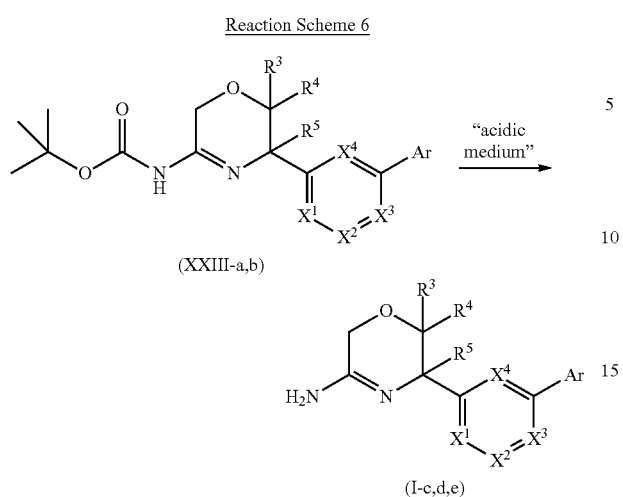

Experimental Procedure 7

The final compounds according to Formula (I-d) wherein $R^3$ is fluoro and $R^4$ hydrogen and Formula (I-e) wherein $R^3$ is hydrogen and $R^4$ trifluoromethyl, can be prepared from the corresponding intermediate compounds of Formula (XXXII) and (XXVIII) with an appropriate source of ammonia such as, for example, ammonium chloride or aqueous ammonia, according to reaction scheme (7), a reaction that is performed in a suitable reaction-inert solvent, such as, for example, water or methanol, under thermal conditions such as, for example, heating the reaction mixture at 60° C., for example for 6 hours. In reaction scheme (7), all variables are defined as in Formula (I).

Reaction Scheme 7

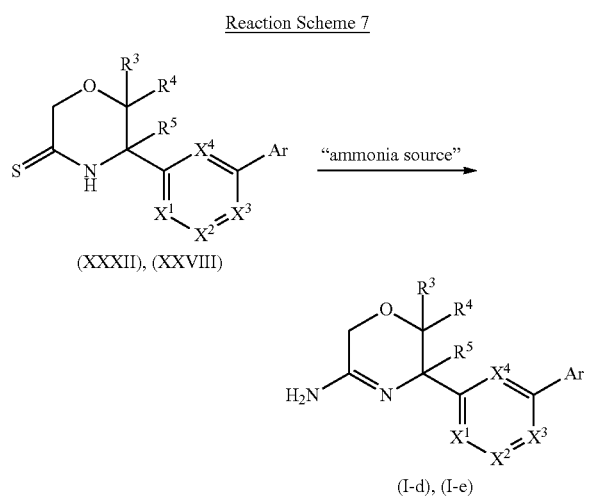

Experimental Procedure 8

The final compounds according to Formula (I-f) wherein L is a bond, can be prepared by reacting an intermediate compound of Formula (XXV-b) with a compound of Formula (VII) according to reaction scheme (8), a reaction that is performed in a suitable reaction-inert solvent, such as, for example, ethanol or mixtures of inert solvents such as, for example, 1,2-dimethoxyethane/water/ethanol, in the presence of a suitable base, such as, for example, aqueous $K_3PO_4$ or $Cs_2CO_3$, a Pd-complex catalyst such as, for example, [1,1'-bis(diphenylphosphino)ferrocene]dichloropalladium(II) [CAS 72287-26-4] or trans-bisdicyclohexylamine)palladium diacetate [DAPCy, CAS 628339-96-8] under thermal conditions such as, for example, heating the reaction mixture at 80° C., for example for 20 hours or for example, heating the reaction mixture at 130° C., for example for 10 minutes under microwave irradiation. In reaction scheme (8), all variables are defined as in Formula (I) and W is halo. $R^8$ and $R^9$ may be hydrogen or alkyl, or may be taken together to form for example a bivalent radical of formula —$CH_2CH_2$—, —$CH_2CH_2CH_2$—, or —$C(CH_3)_2 C(CH_3)_2$—.

Reaction Scheme 8

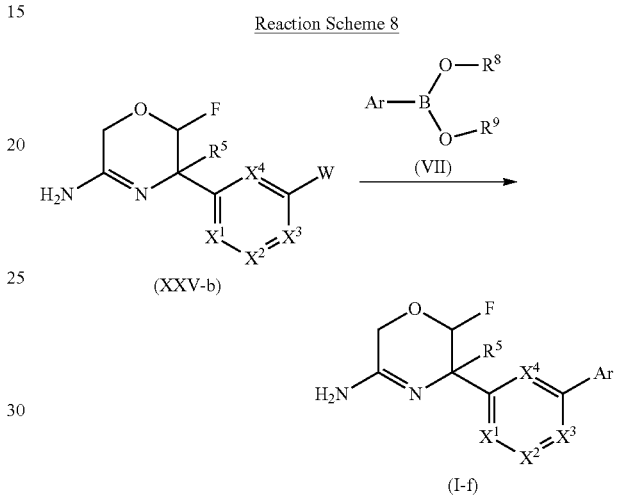

A number of intermediates and starting materials in the foregoing preparations are known compounds which may be prepared according to art-known methodologies of preparing said or similar compounds and some intermediates are new. A number of such preparation methods will be described hereinafter in more detail.

Experimental Procedure 9

The intermediates according to Formula (II), can be prepared by reacting an intermediate compound of Formula (VIII) with a suitable sulphur donating reagent for the synthesis of thioamides such as, for example, phosphorous pentasulfide or 2,4-bis-(4-methoxyphenyl)-1,3-dithia-2,4-diphosphetane 2,4-disulfide [Lawesson's reagent, CAS 19172-47-5], in a reaction inert solvent, such as for example tetrahydrofuran or 1,4-dioxane, under thermal conditions such as, for example, heating the reaction mixture at 50° C., for example for 50 minutes. In reaction scheme (9), all variables are defined as in Formula (I).

Reaction Scheme 9

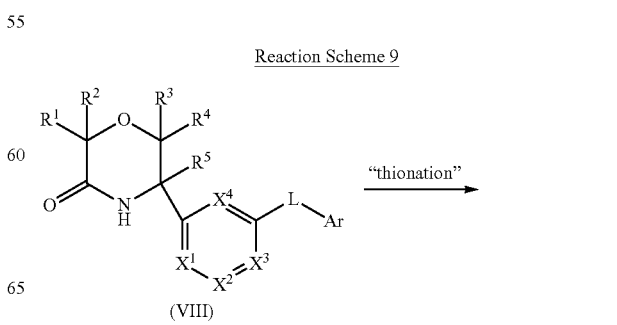

-continued

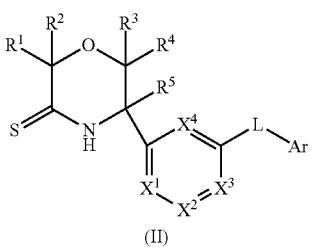

(II)

Experimental Procedure 10

The intermediates according to Formula (VIII), can be prepared by reacting an intermediate compound of Formula (IX) with an intermediate compound of Formula (X) in the presence of a base, such as potassium tert-butoxide, or a mixture of bases such as potassium tert-butoxide/N,N-diisopropylethylamine a reaction inert solvent, such as for example tetrahydrofuran, at −80° C. to 100° C., preferably −15° C. to 25° C. for 30 minutes to 100 hours, preferably 1 hour to 24 hours. In reaction scheme (10), all variables are defined as in Formula (I) and halo is chloro or bromo.

Reaction Scheme 10

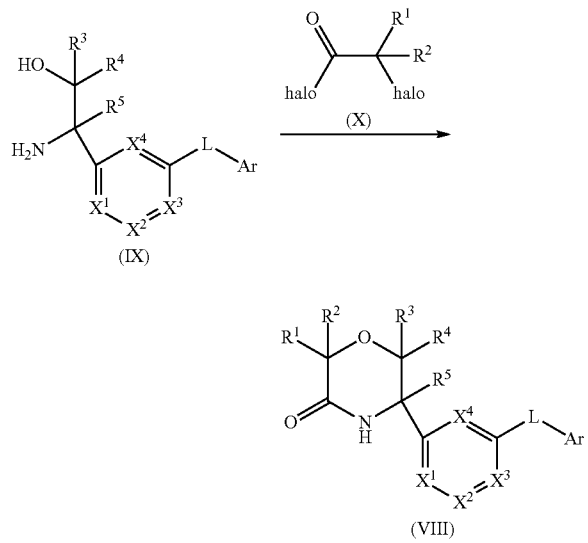

(VIII)

Experimental Procedure 11

The intermediates according to Formula (VIII-a) wherein $R^2$ is fluoro, can be prepared by reacting an intermediate compound of Formula (VIII-b), wherein $R^2$ is hydroxy, with a fluorinating agent, such as for example (diethylamino)sulfur trifluoride [DAST, CAS 38078-09-0] a reaction inert solvent, such as for example dichloromethane, at −80° C. to 100° C., preferably −15° C. to 25° C. for 30 minutes to 100 hours, preferably 1 hour to 24 hours. In reaction scheme (11), all variables are defined as in Formula (I).

Reaction Scheme 11

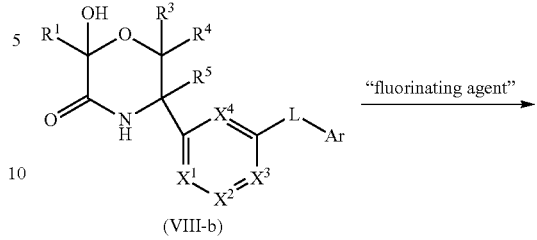

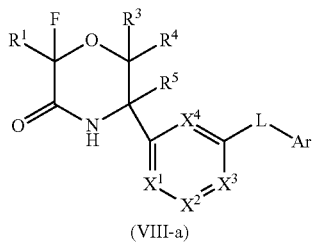

(VIII-a)

Experimental Procedure 12

The intermediates according to Formula (VIII-b) wherein $R^2$ is hydroxy, can be prepared by reacting an intermediate compound of Formula (IX), with an intermediate compound of Formula (XI) under thermal conditions such as, for example, heating the reaction mixture at 70° C., for example for 2 hours. In reaction scheme (12), all variables are defined as in Formula (I) and Alk is $C_{1-3}$alkyl.

Reaction Scheme 12

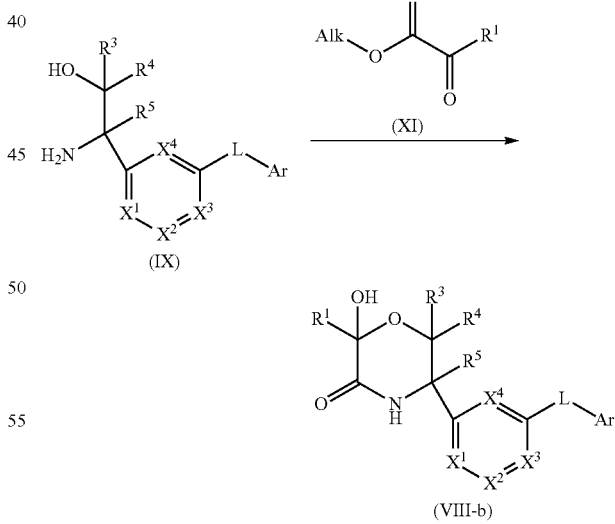

(VIII-b)

Experimental Procedure 13

The intermediate compounds of Formula (III-a) and (III-b) can generally be prepared following the reaction steps shown in the reaction scheme (13) below Reaction Scheme 13

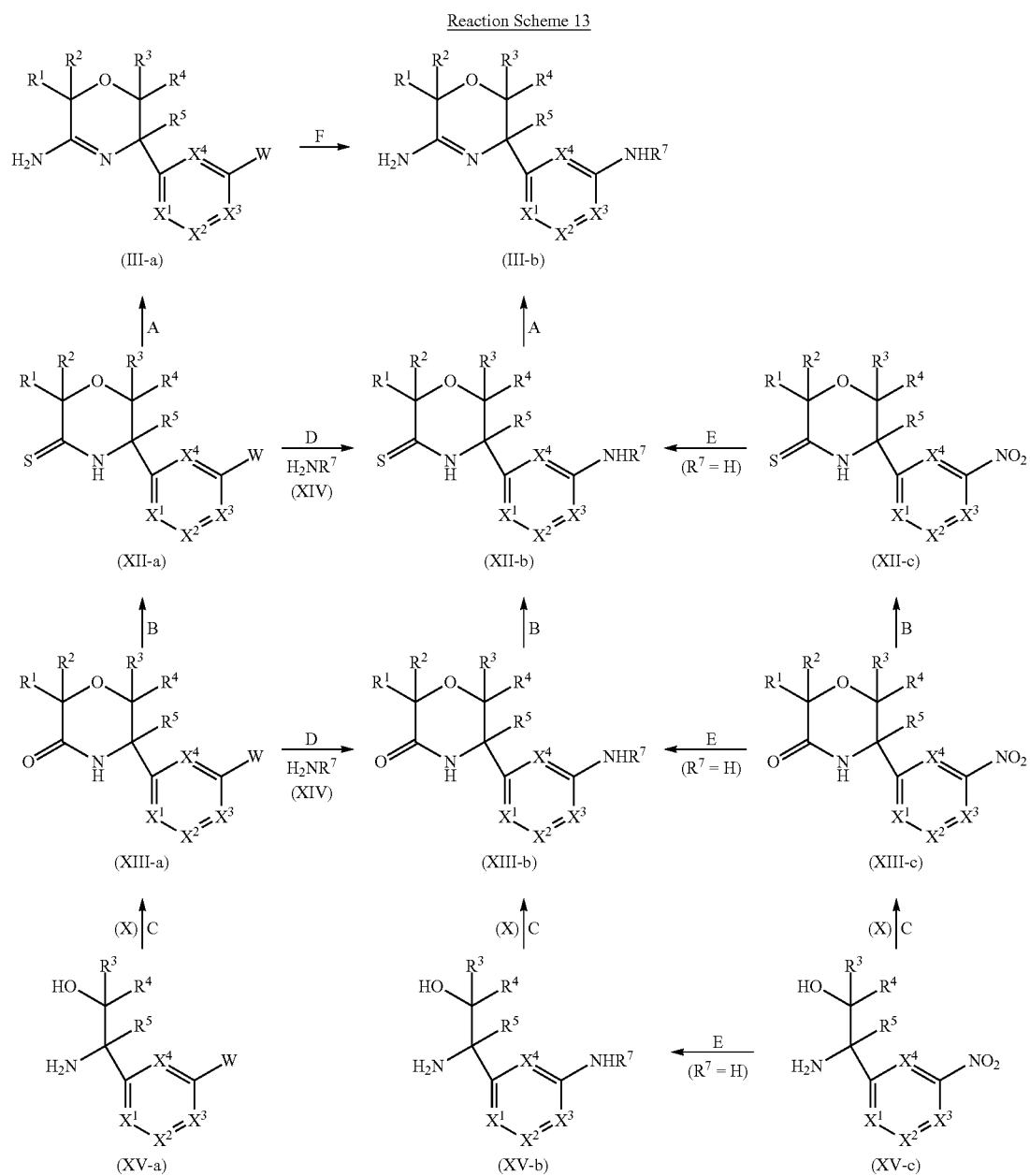

A: thioamide-to-amidine conversion
B: amide-to-thioamide conversion (thionation)
C: cyclization
D: Buchwald-Hartwig type coupling (when W is Halo)
E: nitro-to-amino reduction (when $R^7$ is H)
F: Bromo-to-amine conversion (when $R^7$ is H)

The amidine derivatives in the above reaction scheme may be conveniently prepared from the corresponding thioamide derivatives following art-known thioamide-to-amidine conversion procedures (reaction step A). Said conversion may conveniently be conducted by treatment of the said thioamides with an ammonia source such as, for example, ammonium chloride or aqueous ammonia, in a suitable reaction-inert solvent such as, for example, water or methanol and the like, under thermal conditions such as, for example, heating the reaction mixture at 60° C., for example for 6 hours.

Alternatively, intermediate compounds of Formula (III-b) wherein $R^7$ is hydrogen in the above reaction scheme (13) can be prepared from the corresponding intermediate compounds of Formula (III-a) via copper catalyzed type coupling procedure (reaction step F). Said coupling may be conducted by treatment of said intermediate compounds of Formula (III-a) with sodium azide in a suitable reaction-inert solvent, such as, for example, DMSO, in the presence of a mixture of suitable bases, such as, for example, dimethylethylenediamine and $Na_2CO_3$, and a copper catalyst such as, CuI, under thermal conditions such as, for example, heating the reaction mixture at 110° C., until completion of the reaction, for example 1 hour.

The thioamide derivatives in the above reaction scheme (13) can be prepared from amide derivatives following art-known thionation procedures (reaction step B). Said conversion may conveniently be conducted by treatment of the said amides with a thionation agent such as, for example, phosphorous pentasulfide or 2,4-bis-(4-methoxyphenyl)-1,3-dithia-2,4-diphosphetane 2,4-disulfide [Lawesson's reagent, CAS 19172-47-5], in a reaction inert solvent such as, for example, tetrahydrofuran or 1,4-dioxane and the like, under thermal conditions such as, for example, heating the reaction mixture at 50° C., for example for 50 minutes.

The amide derivatives in the above reaction scheme (13) can be prepared from the beta-aminoalcohol derivatives of Formula (XV) and intermediate compound of Formula (X) following art-known cyclization procedures (reaction step C). Said cyclization may conveniently be conducted by treatment of the said beta-aminoalcohols with an intermediate compound of Formula (X) in the presence of a base, such as potassium tert-butoxide, or a mixture of bases such as potassium tert-butoxide/N,N-diisopropylethylamine a reaction inert solvent, such as for example tetrahydrofuran and the like, at −80° C. to 100° C., preferably −15° C. to 25° C. for 30 minutes to 100 hours, preferably 1 hour to 24 hours.

Additionally intermediate compounds of Formula (XII-b) and (XIII-b) in the above reaction scheme (13) can be prepared from the corresponding intermediate compounds of Formula (XII-a) and (XIII-a) following art-known Buchwald-Hartwig type coupling procedures (reaction step D). Said coupling may be conducted by treatment of intermediate compounds of Formula (XII-a) and (XIII-a) with an intermediate compound of Formula (XIV) in a suitable reaction-inert solvent, such as, for example, ethanol or mixtures of inert solvents such as, for example, 1,2-dimethoxyethane/water/ethanol, in the presence of a suitable base, such as, for example, aqueous $K_3PO_4$ or $Cs_2CO_3$, a Pd-complex catalyst such as, for example, [1,1'-bis(diphenylphosphino)ferrocene]dichloropalladium(II) [CAS 72287-26-4] or trans-bis(dicyclohexylamine)palladium diacetate [DAPCy, CAS 628339-96-8] under thermal conditions such as, for example, heating the reaction mixture at 80° C., for example for 20 hours or for example, heating the reaction mixture at 130° C., for example for 10 minutes under microwave irradiation.

Additionally intermediate compounds of Formula (XII-b) and (XIII-b) in the above reaction scheme (13), wherein $R^7$=H, can be prepared from the corresponding intermediate compounds of Formula (XII-c) and (XIII-c) following art-known nitro-to-amino reduction procedures (reaction step E). Said reduction may conveniently be conducted following art-known catalytic hydrogenation procedures. For example, said reduction may be carried out by stirring the reactants under a hydrogen atmosphere and in the presence of an appropriate catalyst such as, for example, palladium-on-charcoal, platinum-on-charcoal, Raney-nickel and the like catalysts. Suitable solvents are, for example, water, alkanols, e.g. methanol, ethanol and the like, esters, e.g. ethyl acetate and the like. In order to enhance the rate of said reduction reaction it may be advantageous to elevate the temperature and/or the pressure of the reaction mixture. Undesired further hydrogenation of certain functional groups in the reactants and the reaction products may be prevented by the addition of a catalyst poison such as, for example, thiophene and the like, to the reaction mixture.

The intermediates compounds of Formula (IX), (XV-a), (XV-b) and (XV-c) can generally be prepared following art-known Strecker type procedures described in literature, followed by standard chemical transformations of the cyano group.

Experimental Procedure 14

The intermediate compounds of Formula (III-c) and (III-d), wherein $R^1$ and $R^2$ are taken together with the carbon atom to which they are attached to form a $C_{3-6}$cycloalkanediyl ring can generally be prepared following the reaction steps shown in the reaction schemes (14) and (15) below. The subscript n therein can be 1, 2, 3 or 4.

Reaction Scheme 14

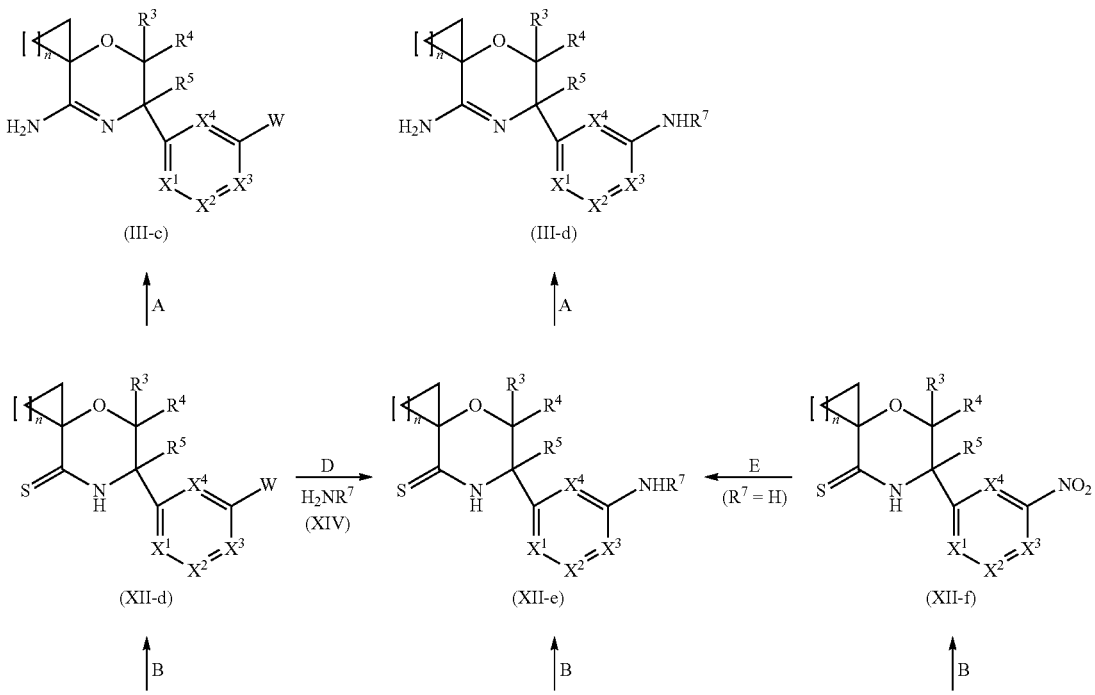

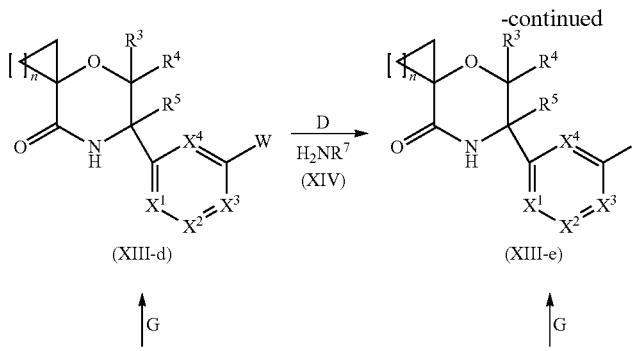
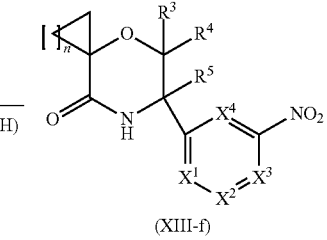

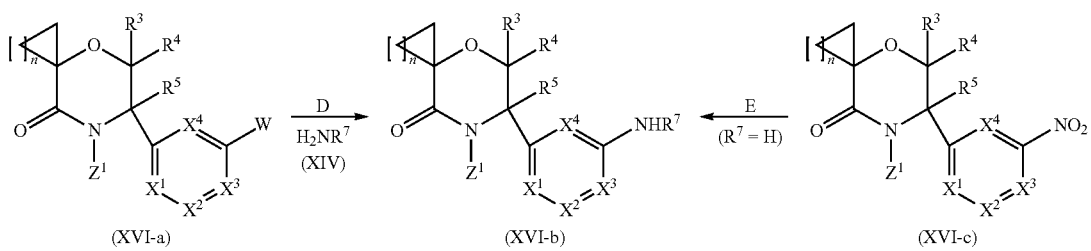

A: thioamide-to-amidine conversion
B: amide-to-thioamide conversion (thionation)
D: Buchwald-Hartwig type coupling (when W is Halo)
E: nitro-to-amino reduction (if $R^7$ = H)
F: amide-deprotection The amidine derivatives in the above reaction scheme may be conveniently prepared from the corresponding thioamide derivatives following art-known thioamide-to-amidine conversion procedures (reaction step A). Said conversion may conveniently be conducted by treatment of the said thioamides with an ammonia source such as, for example, ammonium chloride or aqueous ammonia, in a suitable reaction-inert solvent such as, for example, water or methanol and the like, under thermal conditions such as, for example, heating the reaction mixture at 60° C., for example for 6 hours.

The thioamide derivatives in the above reaction scheme (14) can be prepared from amide derivatives following art-known thionation procedures (reaction step B). Said conversion may conveniently be conducted by treatment of the said amides with a thionation agent such as, for example, phosphorous pentasulfide or 2,4-bis-(4-methoxyphenyl)-1,3-dithia-2,4-diphosphetane 2,4-disulfide [Lawesson's reagent, CAS 19172-47-5], in a reaction inert solvent such as, for example, tetrahydrofuran or 1,4-dioxane and the like, under thermal conditions such as, for example, heating the reaction mixture at 50° C., for example for 50 minutes.

The amide derivatives in the above reaction scheme (14) can be prepared from the N-protected amide derivatives, wherein the amide protecting group can be, for example, the p-methoxybenzyl group, following art-known N-deprotection procedures of amides (reaction step G). Said conversion may conveniently be conducted by treatment of the said N-protected amides with a suitable deprotecting agent of the amide function such as, for example, ammonium cerium (IV) nitrate, in a mixture of inert solvents such as, for example, acetonitrile/water, at a moderately high temperature such as, for example, 25° C., for example for 4 hours.

Additionally intermediate compounds of Formula (XII-e), (XIII-e) and (XVI-b) in the above reaction scheme (14) can be prepared from the corresponding intermediate compounds of Formula (XII-d), (XIII-d) and (XVI-a) following art-known Buchwald-Hartwig type coupling procedures such as the ones described in reaction scheme (13) (reaction step D).

Additionally intermediate compounds of Formula (XII-e), (XIII-e) and (XVI-b) in the above reaction scheme (14), wherein $R^7$=H, can be prepared from the corresponding intermediate compounds of Formula (XII-f), (XIII-f) and (XVI-c) following art-known nitro-to-amino reduction procedures such as the ones described in reaction scheme (13) (reaction step E).

Experimental Procedure 15
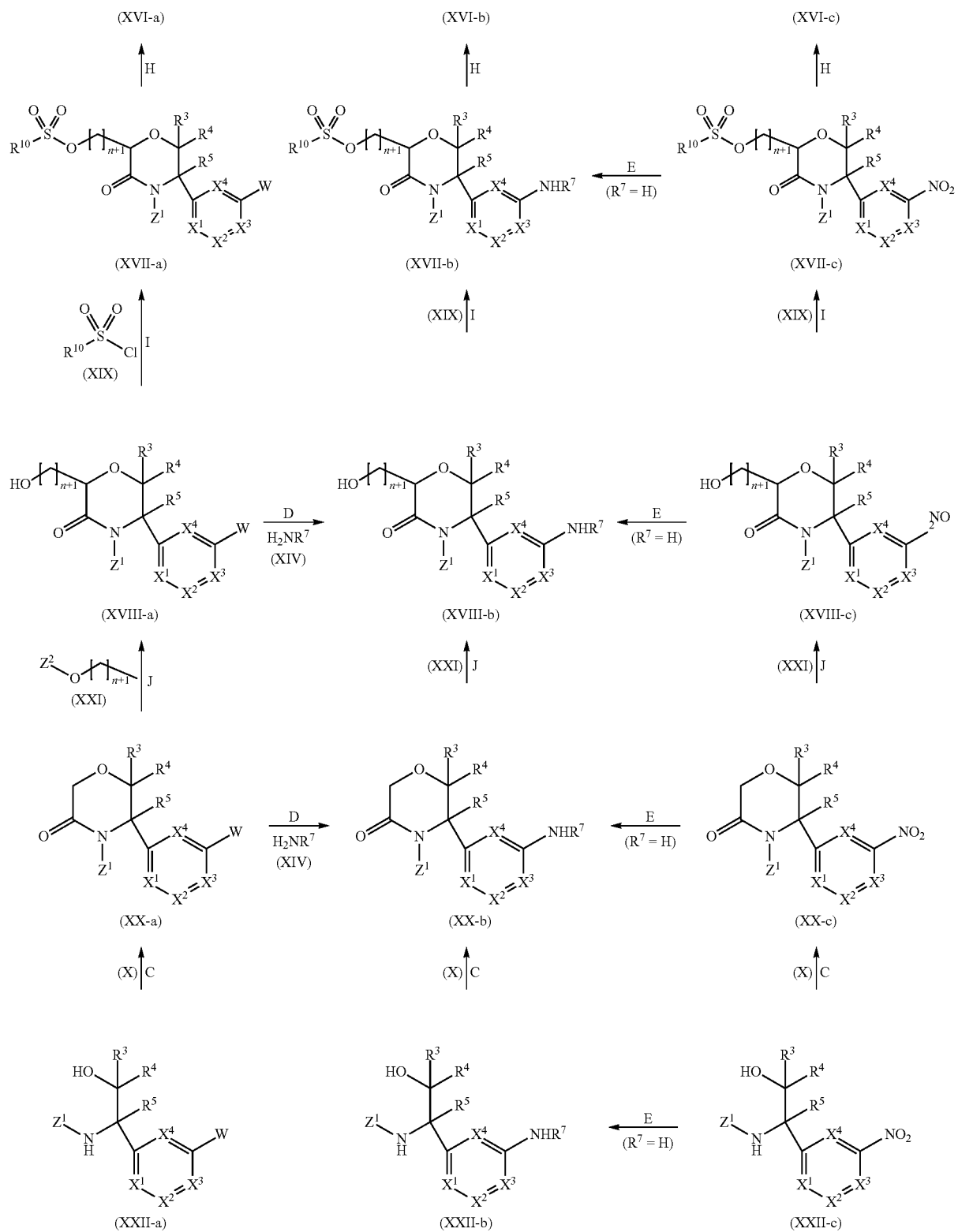
C: cyclization
H: intramolecular cyclization
I: alcohol sulfonylation
J: C-alkylation Intermediate compounds of Formula (XVI-a), (XVI-b) and (XVI-c) in the above reaction scheme (15) can be prepared from the corresponding intermediate compounds of Formula (XVII-a), (XVII-b) and (XVII-c) following art-known intramolecular cyclization procedures (reaction step H). Said intramolecular cyclization may conveniently be conducted by treatment of the said intermediate compounds of Formula (XVII-a), (XVII-b) and (XVII-c) in the presence of a suitable base such as, for example, lithium diisopropylamide, in a inert solvent such as, for example, tetrahydrofuran, at low temperature such as, for example, 0° C., for example for 30 minutes.

Intermediate compounds of Formula (XVII-a), (XVII-b) and (XVII-c) in the above reaction scheme (15) can be prepared from the corresponding intermediate compounds of Formula (XVIII-a), (XVIII-b) and (XVIII-c) following art-known alcohol sulfonylation procedures (reaction step I). Said conversion may conveniently be conducted by treatment of the said intermediate compounds of Formula (XVIII-a), (XVIII-b) and (XVIII-c) with an intermediate compound of Formula (XIX) such as for, example, methanesulfonyl chloride or p-toluenesulfonyl chloride, in the presence of a suitable base such as, for example, N,N-diisopropylethylamine, in a inert solvent such as, for example, dichloromethane, at low temperature such as, for example, 0° C., for example for 15 minutes.

Intermediate compounds of Formula (XVIII-a), (XVIII-b) and (XVIII-c) in the above reaction scheme (15) can be prepared from the corresponding intermediate compounds of Formula (XX-a), (XX-b) and (XX-c) following art-known C-alkylation procedures (reaction step J). Said conversion may conveniently be conducted by treatment of the said intermediate compounds of Formula (XX-a), (XX-b) and (XX-c) with an intermediate compound of Formula (XXI), wherein $Z^2$ is a suitable alcohol protecting group such as, for example, the tetrahydropyranyl group, and Y is halo, in the presence of a suitable base such as, for example, lithium diisopropylamide, in a inert solvent such as, for example, tetrahydrofuran, at low temperature such as, for example, 0° C., for example for 2 hours.

Intermediate compounds of Formula (XX-a), (XX-b) and (XX-c) in the above reaction scheme (15) can be prepared from the corresponding intermediate compounds of Formula (XXII-a), (XXII-b) and (XXII-c) following art-known known cyclization procedures (reaction step C). Said cyclization may conveniently be conducted by treatment of the said intermediate compounds of Formula (XXII-a), (XXII-b) and (XXII-c) with an intermediate compound of Formula (X), in the presence of a base, such as potassium tert-butoxide, or a mixture of bases such as potassium tert-butoxide/N,N-diisopropylethylamine a reaction inert solvent, such as for example tetrahydrofuran and the like, at −80° C. to 100° C., preferably −78° C. to 25° C. for 30 minutes to 100 hours, preferably 1 hour to 24 hours.

Additionally intermediate compounds of Formula (XVIII-b) and (XX-b) in reaction scheme (15) can be prepared from the corresponding intermediate compounds of Formula (XVIII-a) and (XX-a), wherein W=Halo, following art-known Buchwald-Hartwig type coupling procedures such as the ones described in reaction scheme (13) (reaction step D).

Additionally intermediate compounds of Formula (XVII-b), (XVIII-b) and (XX-b) in the above reaction scheme (15), wherein $R^7$=H, can be prepared from the corresponding intermediate compounds of Formula (XVII-c), (XVIII-c) and (XX-c) following art-known nitro-to-amino reduction procedures such as the ones described in reaction scheme (13) (reaction step E).

The intermediates compounds of Formula (XXII-a), (XXII-b) and (XXII-c), wherein $Z^1$ is a suitable N-protecting group such as, for example the p-methoxybenzyl group, can generally be prepared following art-known Strecker type procedures described in literature.

Experimental Procedure 16

The intermediate compounds of Formula (XXIII-a), (XXIII-b) and (XXXII) can generally be prepared following the reaction steps shown in the reaction scheme (16) below.

Reaction Scheme 16

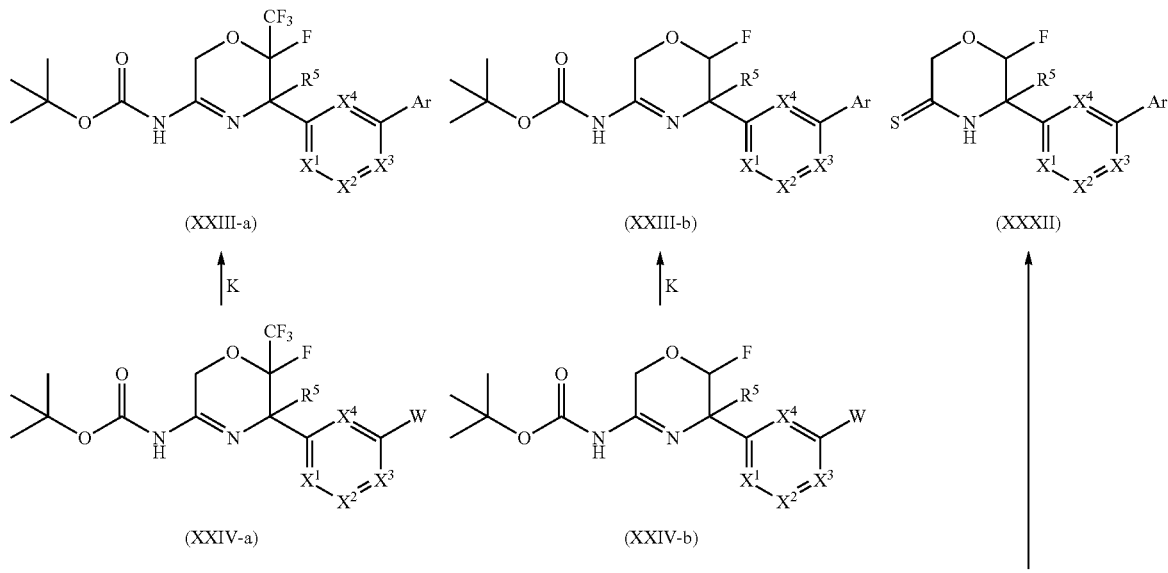

(XXIII-a)  (XXIII-b)  (XXXII)

(XXIV-a)  (XXIV-b)

-continued

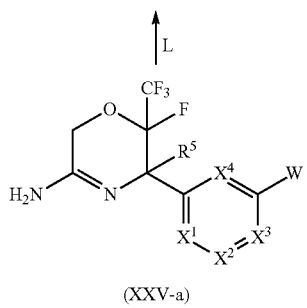

(XXV-a)

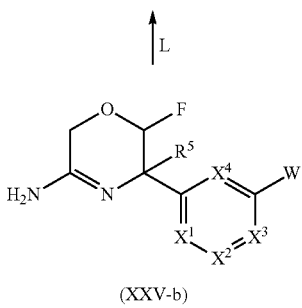

(XXV-b)

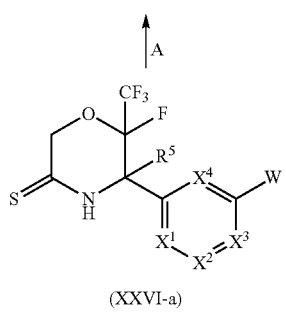

(XXVI-a)

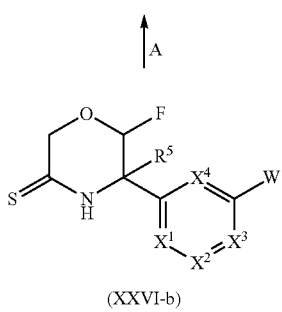

(XXVI-b)

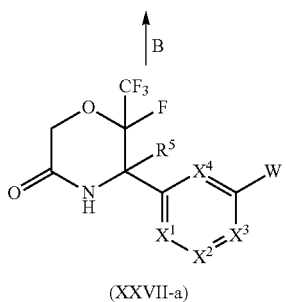

(XXVII-a)

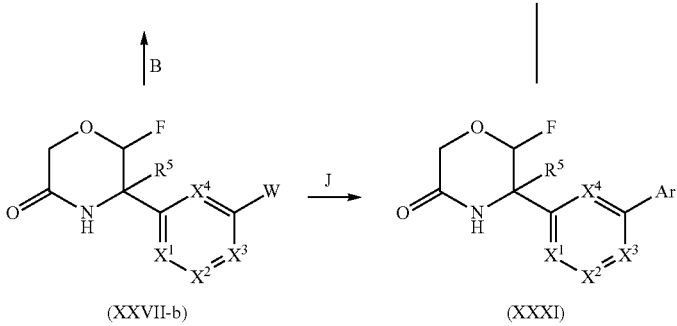

(XXVII-b)                    (XXXI)

A: thioamide-to-amidine conversion
B: amide-to-thioamide conversion (thionation)
K: Suzuki type coupling
L: N-Boc protection Intermediate compounds of Formula (XXIII-a) in the above reaction scheme (16), can be prepared by the reaction of an intermediate compound of Formula (XXIV-a) with an appropriate aryl-boronate or arylboronic acid in a Suzuki type reaction (reaction step K). Thus intermediate compounds of Formula (XXIV-a) can react in a suitable reaction-inert solvent, such as, for example, 1,4-dioxane, ethanol or mixtures of inert solvents such as, for example, 1,2-dimethoxyethane/water/ethanol, in the presence of a suitable base, such as, for example, aqueous $K_3PO_4$, $Na_2CO_3$ or $Cs_2CO_3$, a Pd-complex catalyst such as, for example, [1,1'-bis(diphenylphosphino)ferrocene]dichloropalladium(II) [CAS 72287-26-4] or trans-bisdicyclohexylamine)palladium diacetate [DAPCy, CAS 628339-96-8] or Tetrakistriphenylphosphine)palladium [CAS14221-01-3] under thermal conditions such as, for example, heating the reaction mixture at 80° C., for example for a period of time between 2-20 hours or for example, heating the reaction mixture at 130° C., for example for 10 minutes under microwave irradiation.

The amidine derivatives in the above reaction scheme (16) can be protected with N-Boc protecting group, following art-known N-protection procedures (reaction step L). Said conversion may conveniently be conducted by treatment of the said intermediate compounds of Formula (XXV-a) with di-tert-butyldicarbonate, in the presence of a base such as, for example, diisopropylethyl amine, in a mixture of inert solvents such as, for example, 1,4-dioxane/water, stirring the reaction mixture at suitable temperature such as, for example, 25° C., for the required time to consume the starting material.

The thioamide derivatives in the above reaction scheme (16) can be prepared from amide derivatives following art-known thionation procedures (reaction step B). Said conversion may conveniently be conducted by treatment of the said amides with a thionation agent such as, for example, phosphorous pentasulfide or 2,4-bis-(4-methoxyphenyl)-1,3-dithia-2,4-diphosphetane 2,4-disulfide [Lawesson's reagent, CAS 19172-47-5], in a reaction inert solvent such as, for example, tetrahydrofuran or 1,4-dioxane and the like, under thermal conditions such as, for example, heating the reaction mixture between 50-70° C., for example for 50-240 minutes.

The amidine derivatives in the above reaction scheme may be conveniently prepared from the corresponding thioamide derivatives following art-known thioamide-to-amidine conversion procedures (reaction step A). Said conversion may conveniently be conducted by treatment of the said thioamides with an ammonia source such as, for example, ammonium chloride or aqueous ammonia, in a suitable reaction-inert solvent such as, for example, water or methanol and the like, under thermal conditions such as, for example, heating the reaction mixture between 60-80° C., for example for 6-24 hours.

Experimental Procedure 17

The intermediate compounds of Formula (XXVIII) can generally be prepared following the reaction steps shown in the reaction scheme (17) below

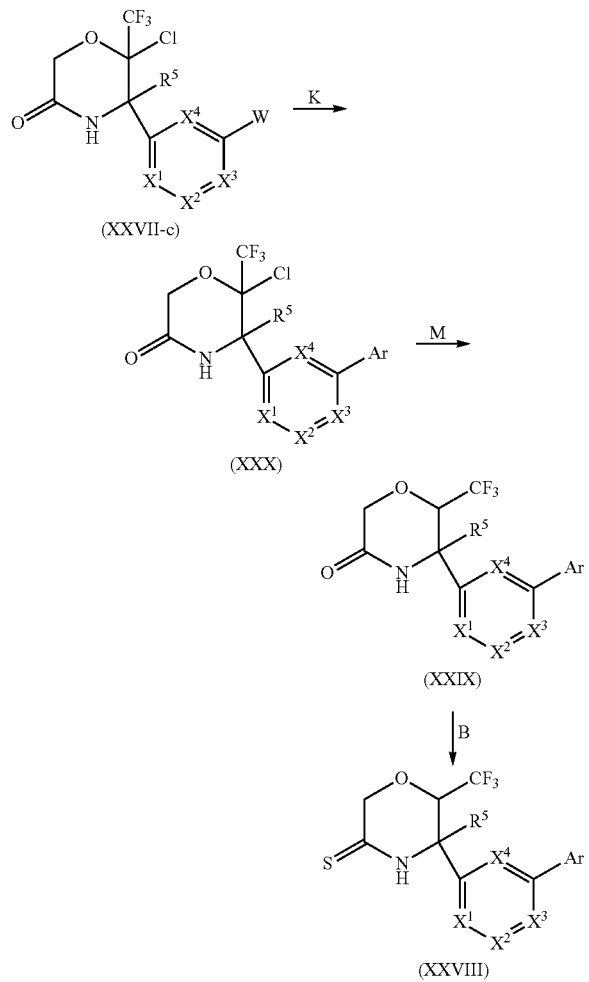

B: amide-to-thioamide conversion (thionation)
K: Suzuki type coupling
M: hydrogenation The thioamide derivatives in the above reaction scheme (17) can be prepared from amide derivatives following art-known thionation procedures (reaction step B). Said conversion may conveniently be conducted by treatment of the said amides with a thionation agent such as, for example, phosphorous pentasulfide or 2,4-bis-(4-methoxyphenyl)-1,3-dithia-2,4-diphosphetane 2,4-disulfide [Lawesson's reagent, CAS 19172-47-5], in a reaction inert solvent such as, for example, tetrahydrofuran or 1,4-dioxane and the like, under thermal conditions such as, for example, heating the reaction mixture between 50-70° C., for example for 50-240 minutes.

Intermediate compounds of Formula (XXIX) can be prepared from intermediate compounds of Formula (XXVII-c) following art-known hydrogenation procedures (reaction step M). Said conversion may be conducted by treatment of the intermediate compound of Formula (XXX) with hydrogen in the presence of potassium acetate, a catalyst such as, for example, Pd—C(10%), in a reaction-inert solvent, such as, for example, methanol. The mixture is stirred under hydrogen atmosphere, at suitable temperature, typically room temperature, for the required time to achieve completion of the reaction, typically 1 hour.

Intermediate compounds of Formula (XXX) in the above reaction scheme (17), can be prepared by the reaction of intermediate compounds of Formula (XXX) with an appropriate aryl-boronate or aryl boronic acid in a Suzuki type reaction (reaction step K). Thus intermediate compounds of Formula (XXVII-c) can react with an aryl-boronate or aryl boronic acid in a suitable reaction-inert solvent, such as, for example, 1,4-dioxane, ethanol or mixtures of inert solvents such as, for example, 1,2-dimethoxyethane/water/ethanol, in the presence of a suitable base, such as, for example, aqueous $K_3PO_4$, $Na_2CO_3$ or $Cs_2CO_3$, a Pd-complex catalyst such as, for example, [1,1'-bis(diphenylphosphino)ferrocene]dichloropalladium(II) [CAS 72287-26-4] or trans-bis-dicyclohexylamine)palladium diacetate [DAPCy, CAS 628339-96-8] or tetrakis(triphenylphosphine)palladium (0) [CAS14221-01-3] under thermal conditions such as, for example, heating the reaction mixture at 80° C., for example for a period of time between 2-20 hours or for example, heating the reaction mixture at 130° C., for example for 10 minutes under microwave irradiation.

Experimental Procedure 18

The intermediate compounds of Formula (XXVII-a), (XXVII-b) and (XXVII-c) can generally be prepared following the reaction steps shown in the reaction scheme (18) below.

Reaction Scheme 18

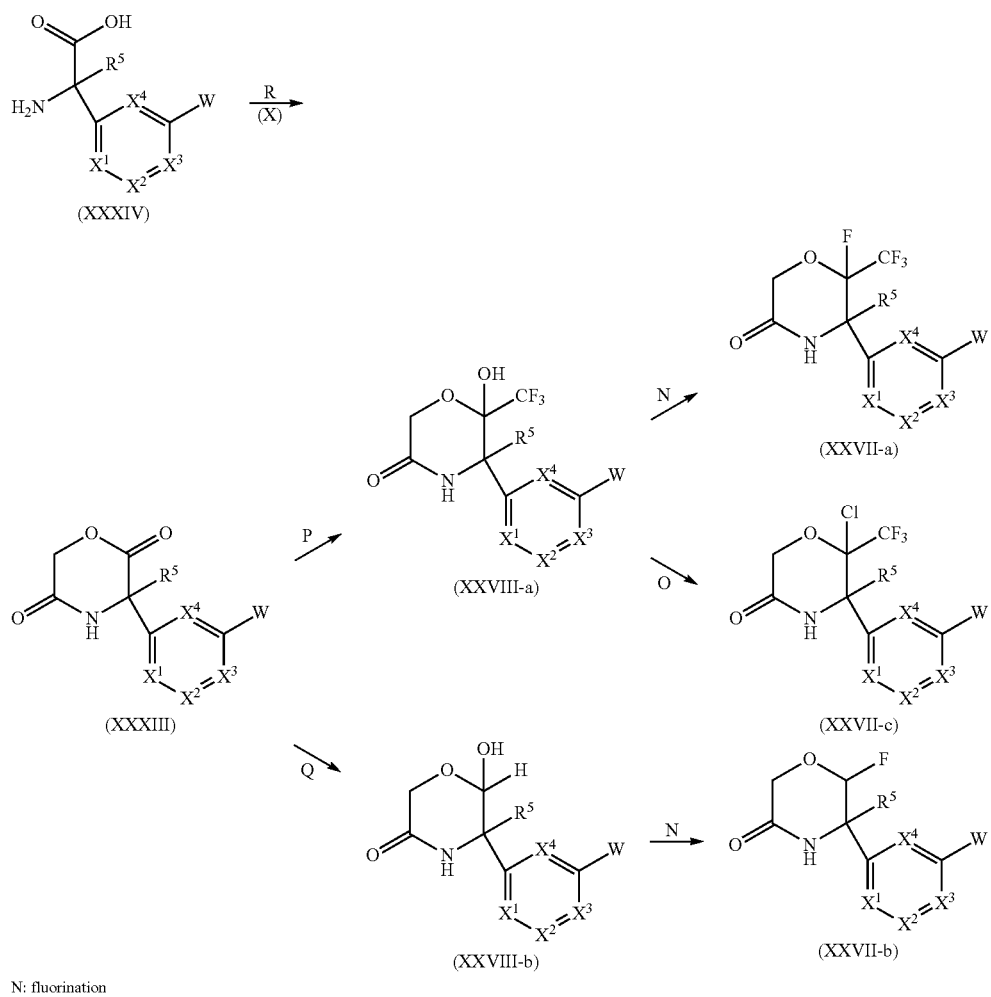

N: fluorination
O: chlorination
P: trifluoromethylation
Q: reduction
R: cyclization Intermediate compounds of Formula (XXVII-a) and (XXVII-b) in the above reaction scheme (18) can be prepared from an intermediate compound of Formula (XXVIII-a) and (XXVIII-b) following art-known fluorination procedures (reaction step N). Said conversion may be conducted by treatment of the intermediate compounds of Formula (XXVIII-a) and (XXVIII-b) in the presence of a fluorinating agent such as for example diethylaminosulphur trifluoride (DAST) in a suitable reaction inert solvent, such as for example dichloromethane. The reaction mixture is stirred at suitable temperature, for example 0° C. for the required time to achieve completion of the reaction, for example 20-40 minutes.

Intermediate compound of Formula (XXVII-c) in the above reaction scheme (18) can be prepared from intermediate compounds of Formula (XXVIII-a) following art-known chlorination procedures (reaction step O). Said conversion may be conducted by treatment of the intermediate compound of Formula (XXVII-a) with a suitable chlorinating agent such as, for example, thionyl chloride, in the presence of a base such as, for example, pyridine in a reaction-inert solvent, such as, for example, dichloromethane. The reaction mixture is stirred at suitable temperature, for example 0° C. for the required time to achieve completion of the reaction, for example 30-60 minutes.

Intermediate compounds of Formula (XXVIII-a) of the above reaction scheme (18) can be prepared from intermediate compounds of Formula (XXXIII) following art-known trifluoromethylation procedures (reaction step P). Said conversion may be conducted by treatment of the intermediate compound of Formula (XXIII) in the presence of tetrabutyl ammonium fluoride (TBAF), with a trifluoromethylating agent such as, for example, (trifluomethyl)trimethyl silane, in a suitable reaction-inert solvent, such as, for example, tetrahydrofuran. The reaction mixture is stirred at suitable temperature, for example room temperature for the required time to achieve completion of the reaction, for example two hours.

Intermediate compounds of Formula (XXVIII-b) in the above reaction scheme (18) can be prepared from intermediate compounds of Formula (XXXIII) following art-known reduction procedures (reaction step Q). Said conversion may be conducted by treatment of the intermediate compound of Formula (XXXIII) with a reducing agent such as, for example, diisobutylaluminium hydride, in a suitable reaction-inert solvent, such as for example tetrahydrofuran. The reaction mixture is stirred at suitable temperature, typically from −78° C. to room temperature for the required time to achieve completion of the reaction, for example two hours.

Intermediate compounds of Formula (XXXIII) in the above reaction scheme (18) can be prepared from intermediate compounds of Formula (XXXIV) following art-known two-step cyclization procedures (reaction step R). Said conversion may be conducted by first, treatment of the intermediate compounds of Formula (XXXIV) with an intermediate compound of Formula (X), such as, for example, chloroacetylchloride in the presence of a base such as, for example, NaOH, in a suitable mixture of inert solvents such as, for example, water and 1,4-dioxane or water and THF. The pH of the reaction mixture is adjusted to a suitable pH value, for example, 10-11, by addition of a suitable base such as, for example, NaOH. The reaction mixture is stirred at a suitable temperature, for example, 0° C. to 25° C. for the required time to achieve completion of the reaction, for example 1-4 hours. The obtained crude residue can subsequently be cyclised to provide the intermediate (XXXIII) by the addition of a suitable base such as, for example, $K_2CO_3$, $Cs_2CO_3$, N,N-diisopropylethylamine or $NaHCO_3$, in a suitable reaction-inert solvent, such as for example, acetonitrile or DMF. The reaction mixture is stirred under thermal conditions such as, for example, heating the reaction mixture at 25° C. to 80° C. for 2-24 hours or for example, heating the reaction mixture at 140° C. for 15-30 minutes under microwave irradiation. This conversion can also be performed in the absence of a base in a suitable reaction-inert solvent, such as for example, acetonitrile or DMF, at a suitable temperature, typically 40° C. to 110° C., for a period of, for example, 24-48 hours.

Experimental Procedure 19

Intermediate compound of Formula (XV-d) in the above reaction scheme (19), wherein $R^3$ and $R^4$ are H and $R^5$ is $C_{1-3}$alkyl or cyclopropyl, can be prepared from intermediate compounds of Formula (XXXV), wherein R is $C_{1-4}$alkyl, by Grignard addition followed by reduction of carboxylic group to the corresponding alcohol function (reaction step S). Said conversion may be conducted by treatment of an intermediate compound of Formula (XXXV) with an appropriate Grignard reagent, such as, for example, methylmagnesium bromide, in a reaction-inert solvent, such as, for example, THF. The reaction mixture is stirred at suitable temperature, for example −10° C. for the required time to achieve consumption of the starting material, for example one hour. Then a reducing agent, such as for example lithium aluminum hydride is added and the reaction mixture is slowly warmed to 0° C. and stirred for the required time to achieve completion of the reduction reaction, typically 1 hour Intermediate compounds of Formula (XXXV) in the above reaction scheme (19), can be prepared by the reaction between an intermediate compound of Formula (XXXVI) and tert-butylsulfinamide (reaction step T), in a suitable reaction-inert solvent, such as, for example, heptane in the presence of titanium tetraethoxide under thermal conditions such as, for example, heating the reaction mixture at 80° C., for example for a period of 2 hours.

In reaction scheme (19), R is defined as $C_{1-4}$alkyl and all other variables are defined as in Formula (I), $R^3$ and $R^4$ are H, $R^5$ is $C_{1-3}$alkyl or cyclopropyl and W is halo.

Intermediate compounds of Formula (XXXVI) are commercially available or can be synthesized by art-known reaction procedures.

Experimental Procedure 20

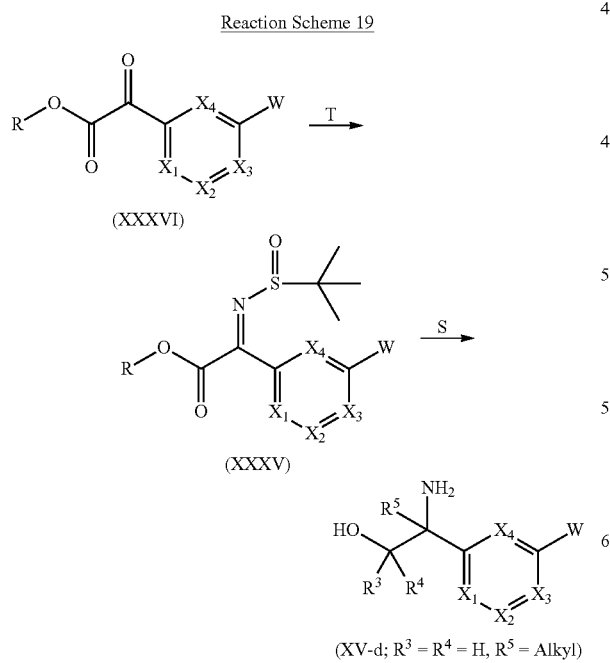

Reaction Scheme 19

(XXXVI)

(XXXV)

(XV-d; $R^3 = R^4 = H$, $R^5$ = Alkyl)

T: sulfonylimino formation
S: Grignard addition followed by reduction

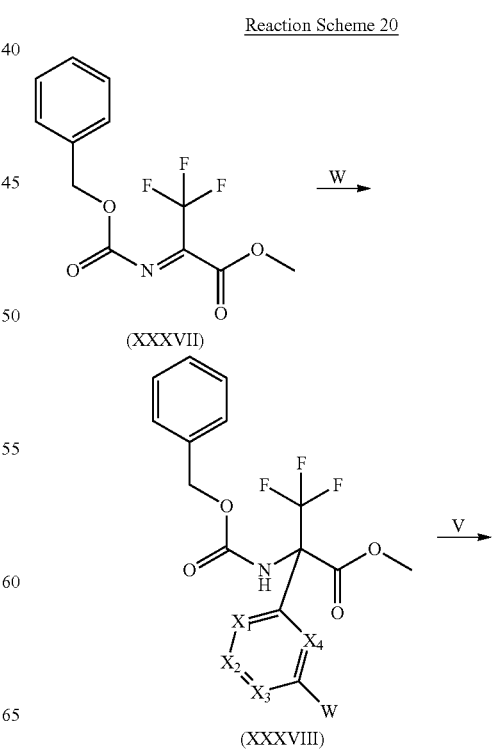

Reaction Scheme 20

(XXXVII)

(XXXVIII)

-continued

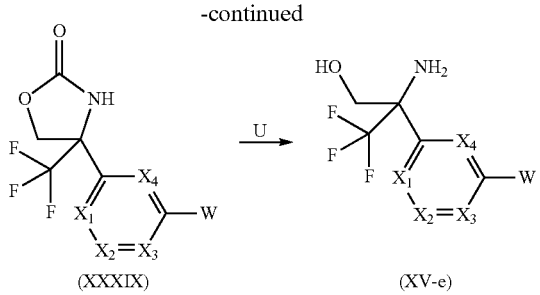

(XXXIX) → (XV-e)

U: hydrolysis
V: oxazolidinone formation
W: Grignard addition

Intermediate compounds of Formula (XV-e) in the above reaction scheme (20) wherein $R^3$ and $R^4$ are hydrogen and $R^5$ is $CF_3$ can be prepared from intermediate compounds of Formula (XXXIX) following art-known hydrolysis reactions of the carbamate function (reaction step U). Said conversion can be conducted by treatment of the intermediate compound of Formula (XXXIX) with an aqueous base such as for example sodium hydroxide (50% in water) in a reaction-inert solvent, such as for example ethanol, at suitable temperature, typically under reflux for the required time to achieve completion of the reaction, for example 24 hours.

Intermediate compounds of Formula (XXXIX) in the above reaction scheme (20) wherein $R^5$ is $CF_3$ can be prepared from intermediate compound of Formula (XXXVIII) by carboxylic ester reduction followed by cyclization under basic conditions (reaction step V). Said conversion may be conducted by treatment of the intermediate compound of Formula (XXXVIII) with a reducing agent, such as for example lithium aluminium hydride, in a reaction-inert solvent, such as for example, THF. The reaction mixture is stirred at a suitable temperature, for example 0° C. for the required time to achieve consumption of the starting material, for example 24 hours. Then, after the work up of the reaction, the crude material is re-dissolved in a reaction-inert solvent, such as for example ethanol and hydrolyzed with an aqueous inorganic base, such as sodium hydroxide at a suitable temperature, typically under reflux for the required time to achieve completion of the reaction, typically 1 hour.

Intermediate compounds of Formula (XXXVIII) in the above reaction scheme (20) can be prepared from intermediate compounds of Formula (XXXVII) following art-known Grignard addition reactions (reaction step W). Said conversion may be conducted by treatment of the intermediate compound of Formula (XXXVII) with a suitable aryl Grignard reagent, such as, for example, 3-chlorophenylmagnesium bromide, in a reaction-inert solvent, such as for example tetrahydrofuran. The reaction mixture is stirred at a suitable temperature, typically from −78° C. to room temperature for the required time to achieve completion of the reaction, for example two hours.

In reaction scheme (20), all variables are defined as in Formula (I), $R^3$ and $R^4$ are H, $R^5$ is $CF_3$ and W is halo.

Intermediate compounds of Formula (XXXVII) are either commercially available (for example CAS 128970-26-3) or can be synthesized following art-known literature procedures.

Experimental Procedure 21

Reaction Scheme 21

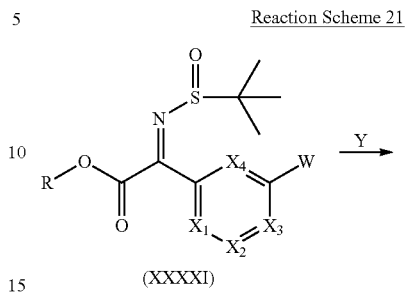

(XXXXI)

(XXXX)

(XXXIV; $R^5$ = Alkyl, cyclopropyl)

X: Ester hydrolysis and sulfinyl group removal
Y: Grignard addition

Intermediate compound of Formula (XXXIV) in the above reaction scheme (21), wherein $R^5$ is $C_{1-3}$alkyl or cyclopropyl, can be prepared from intermediate compounds of Formula (XXXX), wherein R is defined as $C_{1-4}$alkyl, by art-known hydrolysis reactions of the carboxylic ester function, followed by removal of the sulfinyl group (reaction step X). Said conversion can be conducted by treatment of the intermediate of Formula (XXXX) with an aqueous base, such as, for example, sodium hydroxide (1M in water) in a reaction-inert solvent, such as, for example, methanol, at a suitable temperature, typically under reflux for the required time to achieve completion of the reaction, for example 4 hours. Then, removal of sulfinyl group is performed by addition of a suitable inert solvent, such as, for example, 1,4-dioxane, in the presence of a suitable acid, such as, for example, hydrochloric acid at room temperature, for the required time to achieve completion of the reaction for example 30 minutes.

Intermediate compound of Formula (XXXX) in the above reaction scheme (21), wherein $R^5$ is $C_{1-3}$alkyl or cyclopropyl, can be prepared from intermediate compounds of Formula (XXXXI) by Grignard addition (reaction step Y). Said conversion may be conducted by treatment of an intermediate compound of Formula (XXXXI) with an appropriate Grignard reagent, such as, for example, cyclopropylmagnesium bromide, in a reaction-inert solvent, such as for example, dichloromethane. The reaction mixture is stirred at suitable temperature, for example −40° C. for the required time to achieve consumption of the starting material, for example one hour.

In reaction scheme (21), R is defined as $C_{1-4}$alkyl and all other variables are defined as in Formula (I), $R^5$ is $C_{1-3}$alkyl or cyclopropyl and W is halo.

Intermediate compounds of Formula (XXXXI) can be synthesized following art-known procedures such as the ones described in reaction scheme (19) (reaction step T).

Experimental Procedure 22

Compounds of Formula (I-b) can generally be prepared following the reaction steps shown in the reaction scheme (22) below tion procedures of amides such as the ones described in reaction scheme (14) (reaction step G).

Intermediate compounds of Formula (XXXXV) in the above reaction scheme (22) can be prepared from an intermediate compound of Formula (XXXXVI) with an appropriate aryl halide following art-known Suzuki type coupling procedures such as the ones described in reaction scheme (16) (reaction step K). Intermediate compounds of Formula (XXXXVI) in the above reaction scheme (22), can be

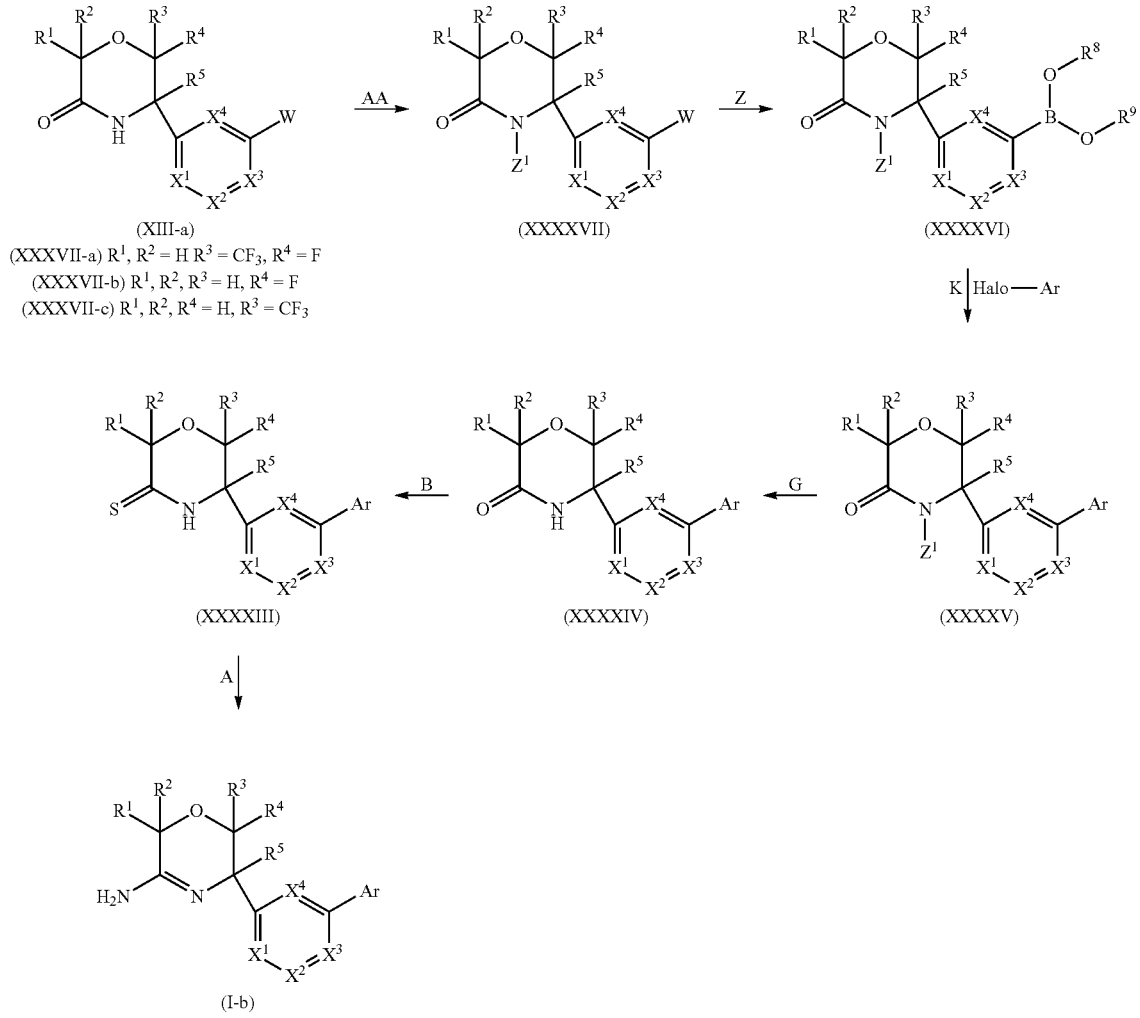

A: thioamide-to-amidine conversion
B: amide-to-thioamide conversion (thionation)
G: amide-deprotection
K: Suzuki type coupling
Z: halide-to-boronate ester conversion
AA: amide protection Compounds of Formula (I-b) can be prepared from an intermediate of Formula (XXXXIV) via the two step (steps A and B) procedure as described in experimental procedures 9 (step B) and 1 (step A).

Intermediate compounds of Formula (XXXXIV) in the above reaction scheme (22) can be prepared from an intermediate compound of Formula (XXXXV) wherein $Z^1$ is a suitable amide protecting group such as, for example, the p-methoxybenzyl group, following art-known N-deprotecprepared from an intermediate compound of Formula (XXXXVII) following art-known halide-to-boronate ester conversion procedures (reaction step Z). Said conversion may be conducted by treatment of an intermediate compound of Formula (XXXXVII) with, for example, a tetra (alkoxo)diboron, such as, for example, bis(pinacolato)diboron [CAS 73183-34-3] in a suitable reaction-inert solvent, such as, for example, 1,4-dioxane or mixtures of inert solvents such as, for example, DMF and 1,4-dioxane, in the presence of a suitable base, such as, for example, KOAc, a Pd-complex catalyst such as, for example, [1,1'-bis(diphenylphosphino)ferrocene]dichloropalladium(II) [CAS 72287-26-4] under thermal conditions such as, for example, heating the reaction mixture at 150° C., for example for 20 minutes under microwave irradiation.

Intermediate compounds of Formula (XXXXVII), in the above reaction scheme (22), wherein $Z^1$ is a suitable amide protecting group such as, for example, the p-methoxybenzyl group, can be prepared from an intermediate compound of Formula (XIII-a), (XXXVII-a), (XXXVII-b), or (XXVII-c) following art-known amide protection procedures of amides (reaction step AA). Said conversion may be conducted by treatment of an intermediate compound of Formula (XIII-a) with a N-PMB protecting group, such as, for example, 4-methoxybenzyl chloride, in a suitable reaction-inert solvent, such as, for example, DMF, in the presence of a suitable base, such as, for example, sodium hydride at room temperature, for the required time to achieve completion of the reaction, for example 3 hours.

In reaction scheme (22), all variables are defined as in Formula (I), $R^5$ is $C_{1-3}$alkyl or cyclopropyl and W is halo.

Experimental Procedure 23

An intermediate of Formula (XXXIII), wherein $X^2$ and $X^4$ are CH, and wherein either $X^1$ or $X^3$ is N and the other is CH, hereby named intermediate of Formula (XXXXVII), can generally be prepared following the reaction steps shown in the reaction scheme (23) below.

Reaction Scheme 23

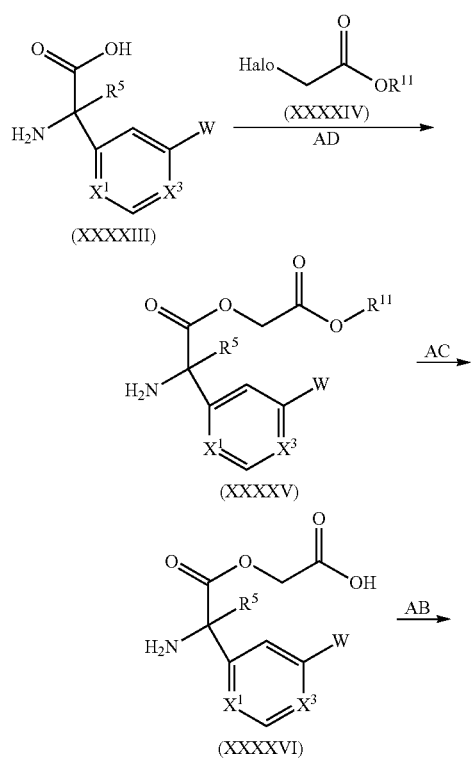

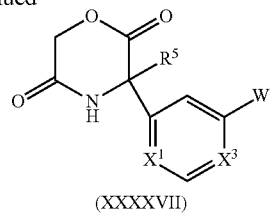

(XXXXVII)

AB: cyclization
AC: hydrolysis
AD: alkylation

An intermediate of Formula (XXXXVII) in the above reaction scheme (23) can be prepared from an intermediate of Formula (XXXXVI) following art-known cyclization procedures (reaction step AB). Said conversion may be conducted by treatment of the intermediate of Formula (XXXXVI) with an appropriate condensation agent such as for example O-(7azabenzotriazol-1-yl)-N,N,N',N'-tetramethyluronium hexafluorophosphate [HATU, CAS 148893-10-1] or 4-(4,6-dimethoxy-1,3,5-triazin-2-yl)-4-methylmorpholinium chloride [DMTMM, CAS 3945-69-5], in a suitable reaction-inert solvent, such as, for example, dimethylformamide, in the presence of a suitable base, such as, for example, diisopropylethyl amine, at suitable temperature, typically room temperature, for the required time to achieve completion of the reaction, for example 15-60 minutes.

An intermediate of Formula (XXXXVI) in the above reaction scheme (23) wherein either $X^1$ or $X^3$ is N and the other is CH, can be prepared from an intermediate of Formula (XXXXV), wherein $R^{11}$ is defined as an alkyl or benzyl group, such as, for example, a tert-butyl group, following art-known hydrolysis procedures of the ester function (reaction step AC). Said conversion can be conducted by treatment of the intermediate of Formula (XXXXV) with an appropriate acid, such as, for example, trifluoroacetic acid in a reaction-inert solvent, such as, for example, dichloromethane, at a suitable temperature, typically at room temperature, for the required time to achieve completion of the reaction, for example 15-60 minutes.

An intermediate of Formula (XXXXV) in the above reaction scheme (23) wherein either $X^1$ or $X^3$ is N and the other is CH, can be prepared from the corresponding intermediate of Formula (XXXXIII) following art-known alkylation procedures of the acid function (reaction step AD). Said conversion may conveniently be conducted by treatment of the intermediate of Formula (XXXXIII) with an intermediate of Formula (XXXXIV), such as, for example, tert-butyl chloroacetate in the presence of a base such as for example, $K_2CO_3$ or $Cs_2CO_3$ and a suitable reaction-inert solvent, such as for example, acetonitrile or DMF. The reaction mixture is stirred at a suitable temperature, typically at room temperature for the required time to achieve completion of the reaction, for example 2-6 hours.

In reaction scheme (23), all variables are defined as in Formula (I) and either $X^1$ or $X^3$ is N and the other is CH. $R^{11}$ may be $C_{1-6}$-alkyl or benzyl.

Experimental Procedure 24

Compounds of Formula (LVI), wherein either $X^1$ or $X^3$ is N and the other is CH, can generally be prepared following the reaction steps shown in the reaction scheme (24) below.

Reaction Scheme 24

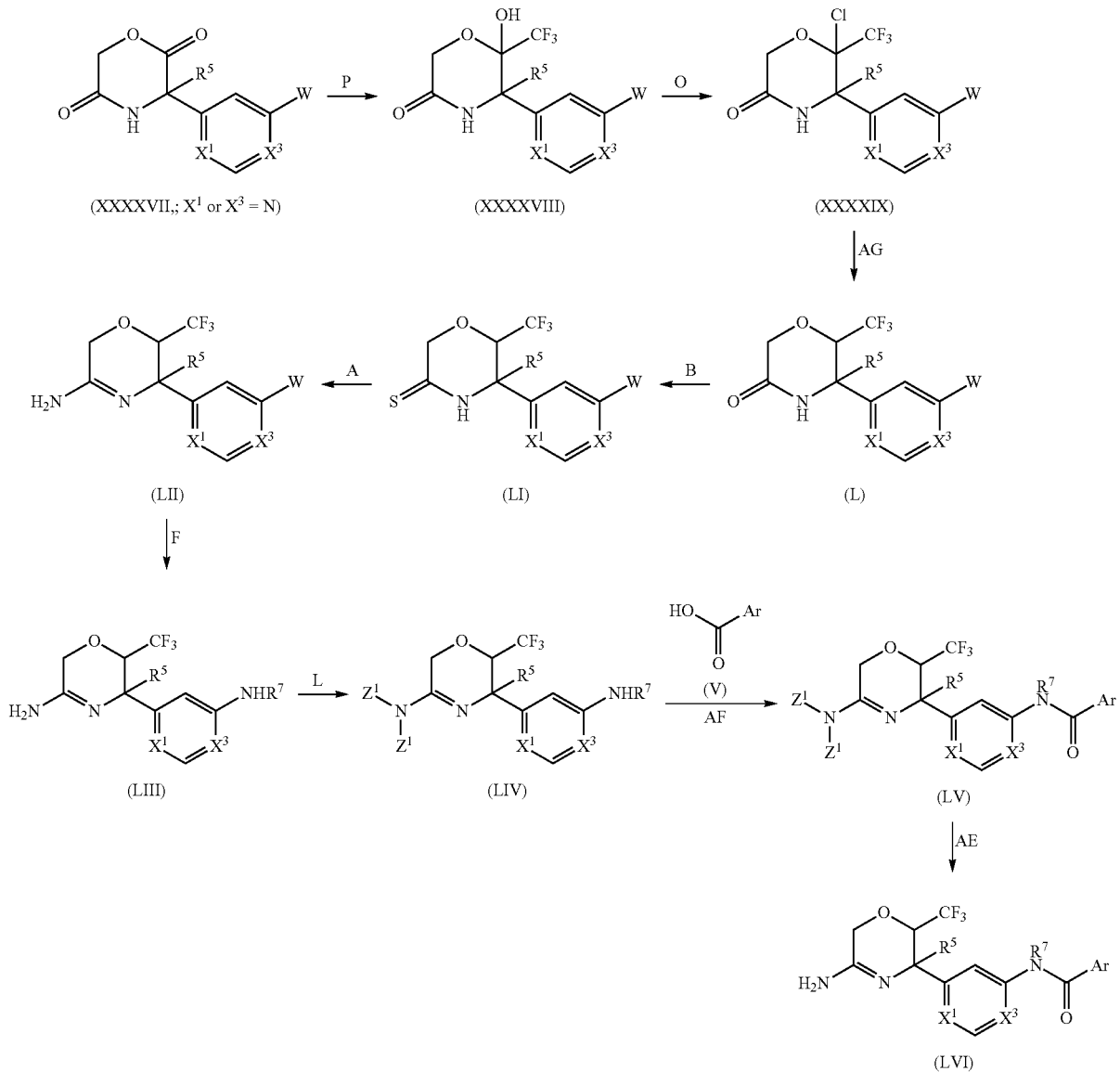

A: thioamide-to-amidine-conversion
AE: N-Boc deprotection
AF: amide coupling
AG: reductive dehalogenation
F: halo-to-amine conversion (when $R^7$ is H, W = halo)
B: amide-to-thioamide conversion (thionation)
L: N-Boc protection
P: trifluoromethylation
O: chlorination Compounds of Formula (LVI) in the above reaction scheme (24) can be prepared from an intermediate of Formula (LV) wherein $Z^1$ is a suitable amidine protecting group such as, for example, the N-Boc group, following art-known N-deprotection procedures (reaction step AE). Said conversion may conveniently be conducted by treatment of the intermediate of Formula (LV) in the presence of a suitable acid such as, for example, trifluoroacetic acid, in a suitable reaction-inert solvent, for example dichloromethane, at room temperature, for example for 15 minutes to 2 hours.

An intermediate of Formula (LV) in the above reaction scheme (24) can be prepared from an intermediate of Formula (LIV), following art-known coupling procedures (reaction step AF). Said conversion may conveniently be conducted by reacting an intermediate of Formula (LIV) with an intermediate of Formula (V), in a suitable reaction-inert solvent, such as, for example, methanol, in the presence of a condensation agent such as, for example, 4-(4,6-dimethoxy-1,3,5-triazin-2-yl)-4-methylmorpholinium chloride [DMTMM, CAS 3945-69-5], at a suitable temperature such as, for example, 25° C., for the required time to consume the starting material, for example 2-6 hours.

An intermediate of Formula (LIV) in the above reaction scheme (24) wherein $Z^1$ is a suitable amidine protecting group such as, for example, the N-Boc group, can be prepared from intermediate compounds of Formula (LIII), following art-known N-protection procedures (reaction step L). Said conversion may conveniently be conducted by treatment of the said intermediate compounds of Formula (LIII) with a suitable N-protecting group such as, for example, di-tert-butyldicarbonate, in the presence of a base such as, for example, diisopropylethyl amine or triethylamine, in a suitable inert solvent such as THF, stirring the reaction mixture at suitable temperature such as, for example, 25° C., for the required time to consume the starting material.

An intermediate of Formula (LIII) in the above reaction scheme (24) can be prepared from an intermediate of Formula (L) wherein W is halo via the three step (steps F, A and B) procedure as described in experimental procedures 13 (step F), 9 (step B) and 1 (step A).

An intermediate of Formula (L) in the above reaction scheme (24) can be prepared from an intermediate of Formula (XXXXIX), following art-known reductive dehalogenation procedures (reaction step AG). Said conversion may be conducted by treatment of the intermediate of Formula (XXXXIX) with a suitable reducing agent such as, for example, zinc dust and acetic acid, at a suitable temperature, for example 80° C., for the required time to achieve completion of the reaction time, for example 1-12 hours.

An intermediate of Formula (XXXXIX) in the above reaction scheme (24) can be prepared from an intermediate of Formula (XXXXVII) via the two step (steps P and O) procedure as described in experimental procedure 17 (steps P and O).

In reaction scheme (24), all variables are defined as in Formula (I) and either $X^1$ or $X^3$ is N, and the other is CH.

Experimental Procedure 25

Compounds of Formula (LXIV), wherein either $X^1$ or $X^3$ is N and the other is CH, can generally be prepared following the reaction steps shown in the reaction scheme (25) below.

Reaction Scheme 25

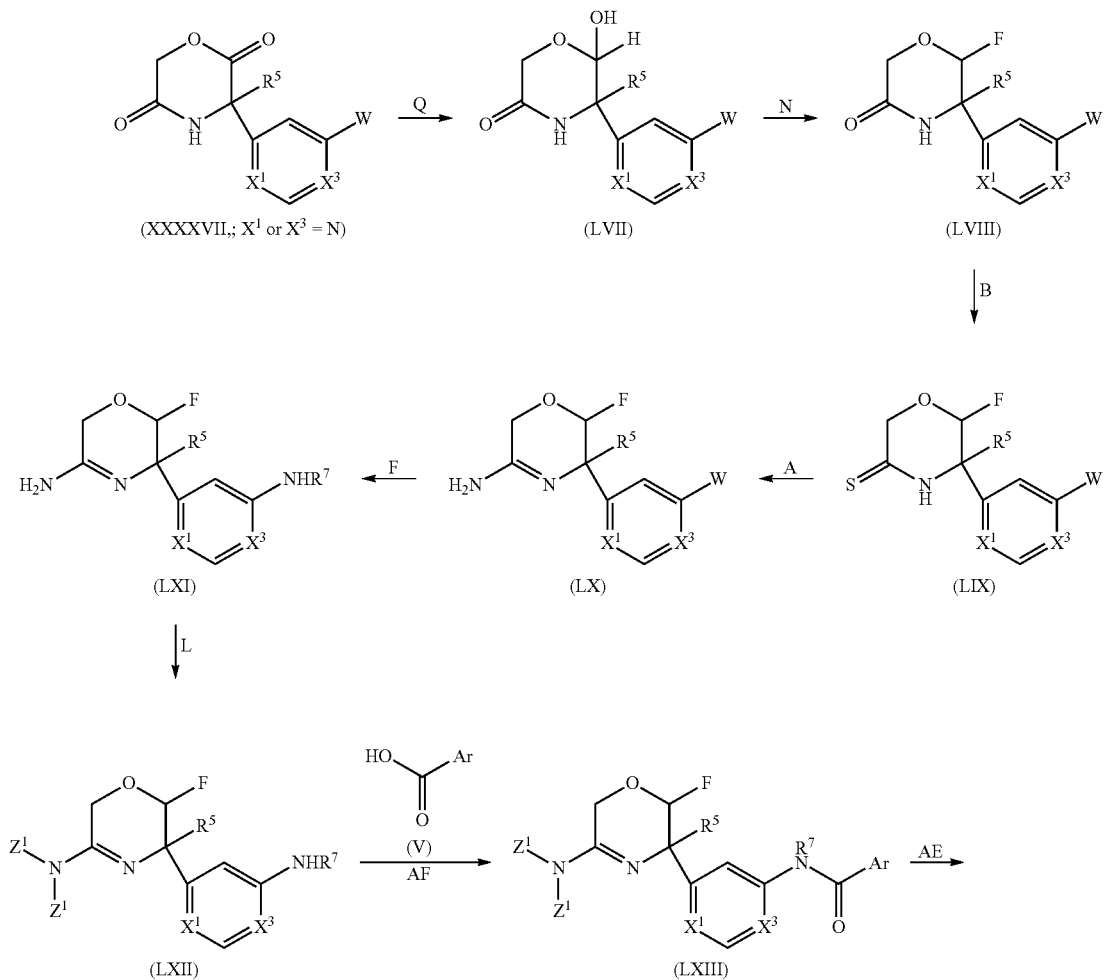

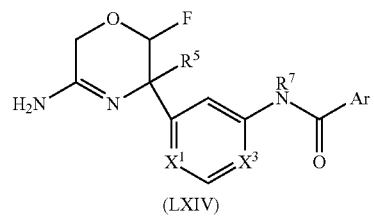

(LXIV)

A: thioamide-to-amidine conversion
AE: N-Boc deprotection
AF: amide coupling
F: halo-to-amine conversion (when $R^7$ is H, W = halo)
B: amide-to-thioamide conversion (thionation)
L: N-Boc protection
N: fluorination
Q: reduction Compounds of Formula (LXIV) in the above reaction scheme (25) can be prepared from an intermediate of Formula (LXI) via the three step (steps AD, AE and L) procedure as described in experimental procedure 24 (steps AE, AF and L).

An intermediate of Formula (LXI) in the above reaction scheme (25) can be prepared from an intermediate of Formula (LVIII) wherein W is halo via the three step (steps F, A and B) procedure as described in experimental procedures 13 (step F), 9 (step B) and 1 (step A).

An intermediate of Formula (LVIII) in the above reaction scheme (25) can be prepared from an intermediate of Formula (XXXXVIII) via the two step (steps N and Q) procedure as described in experimental procedure 18 (steps N and Q).

In reaction scheme (25), all variables are defined as in Formula (I) and either $X^1$ or $X^3$ is N, and the other is CH.

Pharmacology

The compounds of the present invention and the pharmaceutically acceptable compositions thereof inhibit BACE and therefore may be useful in the treatment or prevention of Alzheimer's Disease (AD), mild cognitive impairment (MCI), senility, dementia, dementia with Lewy bodies, cerebral amyloid angiopathy, multi-infarct dementia, Down's syndrome, dementia associated with Parkinson's disease and dementia associated with beta-amyloid.

The invention relates to a compound according to the general Formula (I), a stereoisomeric form thereof or a pharmaceutically acceptable acid or base addition salt or a solvate thereof, for use as a medicament.

The invention also relates to a compound according to the general Formula (I), a stereoisomeric form thereof or a the pharmaceutically acceptable acid or base addition salt or a solvate thereof, for use in the treatment or prevention of diseases or conditions selected from the group consisting of AD, MCI, senility, dementia, dementia with Lewy bodies, cerebral amyloid angiopathy, multi-infarct dementia, Down's syndrome, dementia associated with Parkinson's disease and dementia associated with beta-amyloid.

The invention also relates to the use of a compound according to the general Formula (I), a stereoisomeric form thereof or a pharmaceutically acceptable acid or base addition salt or a solvate thereof, for the manufacture of a medicament for the treatment or prevention of any one of the disease conditions mentioned hereinbefore.

In view of the utility of the compound of Formula (I), there is provided a method of treating warm-blooded animals, including humans, suffering from or a method of preventing warm-blooded animals, including humans, to suffer from any one of the diseases mentioned hereinbefore.

Said methods comprise the administration, i.e. the systemic or topical administration, preferably oral administration, of an effective amount of a compound of Formula (I), a stereoisomeric form thereof, a pharmaceutically acceptable addition salt or solvate thereof, to a warm-blooded animal, including a human.

A method of treatment may also include administering the active ingredient on a regimen of between one and four intakes per day. In these methods of treatment the compounds according to the invention are preferably formulated prior to administration. As described herein below, suitable pharmaceutical formulations are prepared by known procedures using well known and readily available ingredients.

The compounds of the present invention, that can be suitable to treat or prevent Alzheimer's disease or the symptoms thereof, may be administered alone or in combination with one or more additional therapeutic agents. Combination therapy includes administration of a single pharmaceutical dosage formulation which contains a compound of Formula (I) and one or more additional therapeutic agents, as well as administration of the compound of Formula (I) and each additional therapeutic agents in its own separate pharmaceutical dosage formulation. For example, a compound of Formula (I) and a therapeutic agent may be administered to the patient together in a single oral dosage composition such as a tablet or capsule, or each agent may be administered in separate oral dosage formulations.

Pharmaceutical Compositions

The present invention also provides compositions for preventing or treating diseases in which inhibition of beta-secretase is beneficial, such as Alzheimer's disease (AD), mild cognitive impairment, senility, dementia, dementia with Lewy bodies, Down's syndrome, dementia associated with stroke, dementia associated with Parkinson's disease and dementia associated with beta-amyloid. Said compositions comprising a therapeutically effective amount of a compound according to formula (I) and a pharmaceutically acceptable carrier or diluent.

While it is possible for the active ingredient to be administered alone, it is preferable to present it as a pharmaceutical composition. Accordingly, the present invention further provides a pharmaceutical composition comprising a compound according to the present invention, together with a pharmaceutically acceptable carrier or diluent. The carrier or diluent must be "acceptable" in the sense of being compatible with the other ingredients of the composition and not deleterious to the recipients thereof.

The pharmaceutical compositions of this invention may be prepared by any methods well known in the art of pharmacy. A therapeutically effective amount of the particular compound, in base form or addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for systemic administration such as oral, percutaneous or parenteral administration; or topical administration such as via inhalation, a nose spray, eye drops or via a cream, gel, shampoo or the like. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included.

Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The exact dosage and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

Depending on the mode of administration, the pharmaceutical composition will comprise from 0.05 to 99% by weight, preferably from 0.1 to 70% by weight, more preferably from 0.1 to 50% by weight of the active ingredient, and, from 1 to 99.95% by weight, preferably from 30 to 99.9% by weight, more preferably from 50 to 99.9% by weight of a pharmaceutically acceptable carrier, all percentages being based on the total weight of the composition.

The present compounds can be used for systemic administration such as oral, percutaneous or parenteral administration; or topical administration such as via inhalation, a nose spray, eye drops or via a cream, gel, shampoo or the like. The compounds are preferably orally administered. The exact dosage and frequency of administration depends on the particular compound according to formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

The amount of a compound of Formula (I) that can be combined with a carrier material to produce a single dosage form will vary depending upon the disease treated, the mammalian species, and the particular mode of administration. However, as a general guide, suitable unit doses for the compounds of the present invention can, for example, preferably contain between 0.1 mg to about 1000 mg of the active compound. A preferred unit dose is between 1 mg to about 500 mg. A more preferred unit dose is between 1 mg to about 300 mg. Even more preferred unit dose is between 1 mg to about 100 mg. Such unit doses can be administered more than once a day, for example, 2, 3, 4, 5 or 6 times a day, but preferably 1 or 2 times per day, so that the total dosage for a 70 kg adult is in the range of 0.001 to about 15 mg per kg weight of subject per administration. A preferred dosage is 0.01 to about 1.5 mg per kg weight of subject per administration, and such therapy can extend for a number of weeks or months, and in some cases, years. It will be understood, however, that the specific dose level for any particular patient will depend on a variety of factors including the activity of the specific compound employed; the age, body weight, general health, sex and diet of the individual being treated; the time and route of administration; the rate of excretion; other drugs that have previously been administered; and the severity of the particular disease undergoing therapy, as is well understood by those of skill in the area.

A typical dosage can be one 1 mg to about 100 mg tablet or 1 mg to about 300 mg taken once a day, or, multiple times per day, or one time-release capsule or tablet taken once a day and containing a proportionally higher content of active ingredient. The time-release effect can be obtained by capsule materials that dissolve at different pH values, by capsules that release slowly by osmotic pressure, or by any other known means of controlled release.

It can be necessary to use dosages outside these ranges in some cases as will be apparent to those skilled in the art. Further, it is noted that the clinician or treating physician will know how and when to start, interrupt, adjust, or terminate therapy in conjunction with individual patient response.

For the compositions, methods and kits provided above, one of skill in the art will understand that preferred compounds for use in each are those compounds that are noted as preferred above. Still further preferred compounds for the compositions, methods and kits are those compounds provided in the non-limiting Examples below.

EXPERIMENTAL PART

Hereinafter, the term "m.p." means melting point, "aq." means aqueous, "r.m." means reaction mixture, "r.t." means room temperature, 'DIPEA' means N,N-diisopropylethylamine, "DIPE" means diisopropylether, 'THF' means tetrahydrofuran, 'DMF' means dimethylformamide, 'DCM' means dichloromethane, "EtOH" means ethanol 'EtOAc' means ethylacetate, "AcOH" means acetic acid, "iPrOH" means isopropanol, "iPrNH$_2$" means isopropylamine, "MeCN" means acetonitrile, "MeOH" means methanol, "Pd(OAc)$_2$" means palladium(II)diacetate, "rac" means racemic, 'sat.' means saturated, 'SFC' means supercritical fluid chromatography, 'SFC-MS' means supercritical fluid chromatography/mass spectrometry, "LC-MS" means liquid chromatography/mass spectrometry, "GCMS" means gas chromatography/mass spectrometry, "HPLC" means high-performance liquid chromatography, "RP" means reversed phase, "UPLC" means ultra-performance liquid chromatography, "R$_t$" means retention time (in minutes), "[M+H]$^+$" means the protonated mass of the free base of the compound, "DAST" means diethylaminosulfur trifluoride, "DMTMM" means 4-(4,6-dimethoxy-1,3,5-triazin-2-yl)-4-methylmorpholinium chloride, "HATU" means O-(7-azabenzotriazol-1-yl)-N,N,N',N'-tetramethyluronium hexafluorophosphate, "Xantphos" means. (9,9-dimethyl-9H-xanthene-4,5-diyl)bis[diphenylphosphine], "TBAT" means tetrabutyl ammonium triphenyldifluorosilicate, "TFA" means trifuoroacetic acid, "Et2O" means diethylether, "DMSO" means dimethylsulfoxide.

For key intermediates, as well as some final compounds, the absolute configuration of chiral centers (indicated as R and/or S) were established via comparison with samples of known configuration, or the use of analytical techniques suitable for the determination of absolute configuration, such as VCD (vibrational cicular dichroism) or X-ray crystallography.

A. Preparation of the Intermediates

Example A1

Preparation of Intermediate 1: rac-2-amino-2-(3-bromo-phenyl)-propionitrile

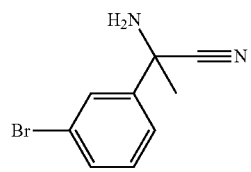

Trimethylsilylcyanide (20 g, 200 mmol) was added to a stirred solution of 3-bromoacetophenone (20 g, 100 mmol) and NH$_4$Cl (11 g, 200 mmol) in NH$_3$/MeOH (400 mL). The mixture was stirred at room temperature for 4 days. Then the solvent was evaporated in vacuo and the residue was taken up in EtOAc (100 mL). The solid was filtered and the filtrate was evaporated in vacuo to yield intermediate 1 (20 g, 86% yield) which was used in the next step without further purification.

Example A2

Preparation of Intermediate 2:
rac-2-amino-2-(3-bromo-phenyl)-propionic acid methyl ester

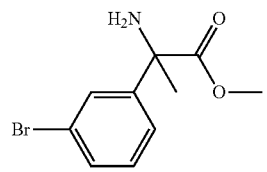

Intermediate 1 (20 g, 88.9 mmol) was dissolved in HCl/MeOH (500 mL) and the mixture was refluxed for 4 days. After cooling to room temperature, EtOAc (100 mL) and water (100 mL) were added and the mixture was extracted with EtOAc (2×100 mL). The combined aqueous layers were basified with aqueous ammonia solution to pH 8 and extracted with EtOAc (5×100 mL). The combined organic layers were dried (Na$_2$SO$_4$), filtered and the solvents evaporated in vacuo to yield rac-intermediate 2 (10.6 g, 46% yield) as an oil.

Example A3

Preparation of Intermediate 3: rac-2-amino-2-(3-bromo-phenyl)-propan-1-ol

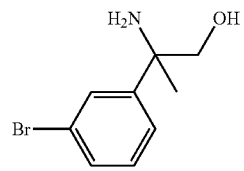

Lithium aluminium hydride (1 M in THF; 22 mL, 22 mmol) was added dropwise to a stirred solution of intermediate 2 (7.5 g, 29.1 mmol) in THF (200 mL) at −15° C. The mixture was left warming up slowly to 0° C. during 1 hour. Then more THF (150 mL) was added and sat. Na$_2$SO$_4$ was added dropwise until no more hydrogen was formed. Then anhydrous Na$_2$SO$_4$ was added and left stirring overnight at room temperature. The mixture was filtered over diatomaceous earth, rinsed with THF and the solvent evaporated in vacuo. The crude product was purified by flash column chromatography (silica; 7 M solution of ammonia in methanol/DCM 0/100 to 3/97). The desired fractions were collected and concentrated in vacuo to yield intermediate 3 (5.70 g, 85% yield) as an oil.

Example A4

Preparation of Intermediate 4: (R)-2-amino-2-(3-bromo-phenyl)-propan-1-ol

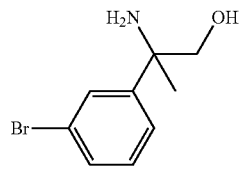

A sample of intermediate 3 (15.4 g) was separated into the corresponding enantiomers by preparative SFC on (Chiralpak® Daicel AD×250 mm). Mobile phase ($CO_2$, MeOH with 0.2% $iPrNH_2$) to yield intermediate 4 (7.21 g, 40% yield). $α_D$: −14.9° (589 nm, c 0.2946 w/v %, MeOH, 20° C.).

Example A5

Preparation of Intermediate 5: rac-5-(3-bromo-phenyl)-5-methyl-morpholin-3-one

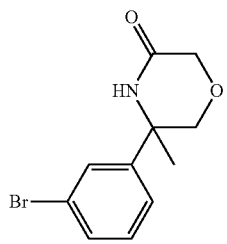

Chloro-acetyl chloride (0.55 mL, 6.95 mmol) was added dropwise to a stirred solution of intermediate 3 (1.6 g, 6.95 mmol) in THF (60 mL) and diisopropylethyl amine (1.44 mL, 8.34 mmol) at −78° C. The mixture was stirred for 30 minutes at −78° C. Then potassium tert-butoxide (1.95 g, 17.38 mmol) was added and the mixture was stirred at −15° C. and left warming up to 0° C. during 90 minutes. The mixture was diluted with saturated $NH_4Cl$ and extracted with DCM. The organic layer was separated, dried ($Na_2SO_4$), filtered and the solvents evaporated in vacuo. The crude product was triturated with $Et_2O$, filtered and dried to yield intermediate 5 (1.65 g, 88% yield) as a white solid.

Example A6

Preparation of Intermediate 6: rac-5-[3-(5-methoxy-pyridin-3-yl)-phenyl]-5-methyl-morpholin-3-one

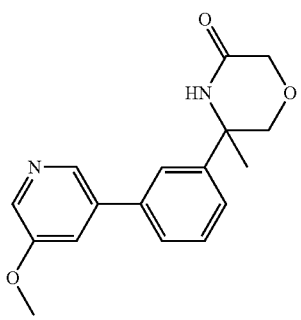 [SMILES: COc1cncc(-c2cccc(C3(C)COCC(=O)N3)c2)c1]

1,4-Dioxane (15 mL) and sat. aq. $Na_2CO_3$ (5 mL) were added to a mixture of intermediate 5 (0.5 g, 1.85 mmol), 3-methoxy-5-(4,4,5,5-tetramethyl-[1,3,2]dioxaborolan-2-yl)-pyridine (0.87 g, 3.70 mmol) and tetrakis(triphenylphosphine)palladium (0.214 g, 0.185 mmol). The mixture was stirred and $N_2$ flushed for a few minutes and then heated at 80° C. for 2 h. After cooling the mixture was diluted with water and extracted with DCM. The organic layer was separated, dried ($Na_2SO_4$), filtered and the solvents evaporated in vacuo. The crude product was purified by flash column chromatography (silica; 7 M solution of ammonia in methanol/DCM 0/100 to 4/96). The desired fractions were collected and concentrated in vacuo to yield intermediate 6 (0.51 g, 92% yield) as an off white solid.

Example A7

Preparation of Intermediate 7: rac-5-[3-(5-methoxy-pyridin-3-yl)-phenyl]-5-methyl-morpholine-3-thione

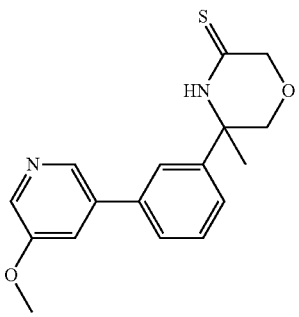 [SMILES: COc1cncc(-c2cccc(C3(C)COCC(=S)N3)c2)c1]

THF (15 mL) was added to a mixture of intermediate 6 (0.5 g, 1.56 mmol) and phosphorus pentasulfide (0.3 g, 1.35 mmol) at room temperature. The mixture was stirred at 50° C. for 60 minutes. The mixture was cooled to room temperature and pyridine (10 mL) was added. The mixture was stirred at 80° C. for 5 hours. The mixture was cooled to room temperature and filtered over cotton, the solid residue was triturated with a mixture of DCM and MeOH and filtered over cotton. The combined organic layers were evaporated in vacuo. The crude product was purified by flash column chromatography (silica; MeOH/DCM 0/100 to 3/97). The desired fractions were collected and evaporated in vacuo to yield intermediate 7 (0.4 g, 82% yield) as a solid.

Example A8

Preparation of Intermediate 8: rac-5-(3-bromo-phenyl)-5-methyl-morpholine-3-thione

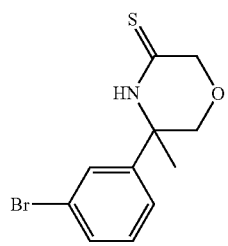

THF (40 mL) was added to a mixture of intermediate 5 (1.14 g, 3.92 mmol) and phosphorus pentasulfide (0.704 g, 3.17 mmol) at room temperature. The mixture was stirred at 50° C. for 50 minutes. Then the mixture was cooled to room temperature and filtered over cotton and evaporated in vacuo. The crude product was purified by flash column chromatography (silica; DCM). The desired fractions were collected and evaporated in vacuo to yield intermediate 8 (1.05 g, 93% yield) as a yellow solid.

Example A9

Preparation of Intermediate 9: rac-5-(3-bromo-phenyl)-5-methyl-5,6-dihydro-2H-[1,4]oxazin-3-ylamine trifluoroacetate salt

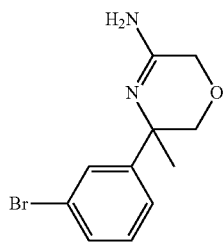

Intermediate 8 (0.205 g, 0.716 mmol) and 32% aqueous ammonia solution (12 mL) was stirred in a sealed tube at 60° C. for 4 hours. After cooling, the mixture was diluted with water and extracted with DCM. The organic layer was separated, dried (Na$_2$SO$_4$), filtered and the solvent evaporated in vacuo. DCM (15 mL) and TFA (0.25 mL) were added, mixed and evaporated. To this residue, Et$_2$O and heptane were added and evaporated. DIPE was added, sonicated and then stirred overnight at room temperature. The white precipitate was filtered and washed with DIPE and dried to yield intermediate 9 (0.19 g, 69% yield) as a white solid.

Example A10

Preparation of Intermediate 10: rac-5-(3-aminophenyl)-5-methyl-5,6-dihydro-2H-[1,4]oxazin-3-ylamine

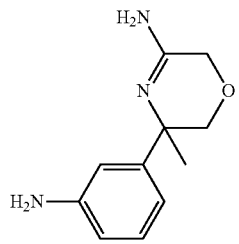

Toluene (1.5 mL) was added to a mixture of intermediate 9 (0.05 g, 0.13 mmol), tris(dibenzylideneacetone)dipalladium(0) (0.012 g, 0.013 mmol), rac-2,2'-bis(diphenylphosphino)-1,1'-binaphthyl (0.024 g, 0.04 mmol) and sodium tert-butoxide (0.031 g, 0.326 mmol) in a sealed tube and under nitrogen at room temperature. The mixture was flushed with nitrogen for a few minutes and then benzophenone imine (0.028 mL, 0.17 mmol) was added and the mixture was stirred at 80° C. for 7 hours. After cooling, a mixture of 1N HCl/THF (1/1.4 mL) was added and the mixture was stirred at room temperature overnight. The mixture was diluted with water and washed with EtOAc. The aqueous layer was basified with sat Na$_2$CO$_3$ and extracted with DCM/EtOH 9/1 (10 times). The combined organic layers were dried (Na$_2$SO$_4$), filtered and the solvents evaporated in vacuo. The crude product was purified by flash column chromatography (silica; 7 M solution of ammonia in methanol/DCM 0/100 to 8/92). The desired fractions were collected and concentrated in vacuo to yield intermediate 10 (0.012 g, 45% yield) as an oil.

Example A11

Preparation of Intermediate 11: rac-5-(3-bromophenyl)-2-hydroxy-5-methyl-2-trifluoromethyl-morpholin-3-one

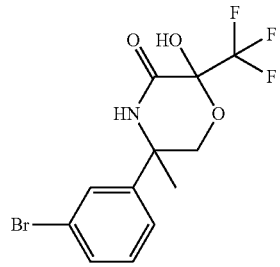 [SMILES: CC1(c2cccc(Br)c2)COC(O)(C(F)(F)F)C(=O)N1]

Ethyl trifluoropyruvate (0.59 mL, 4.48 mmol) was added to a stirred solution of intermediate 4 (1.33 g, 5.77 mmol) in DIPE (5 mL) at 0° C. The mixture was stirred for 2 hours at 70° C. to give a semi-crystalline product. DIPE (15 mL) was added and the mixture was stirred overnight at room temperature. The solid precipitated was filtered and dried in vacuo to yield intermediate 11 (1.083 g, 68% yield) as white crystals.

Example A12

Preparation of Intermediate 12: rac-5-(3-bromophenyl)-2-fluoro-5-methyl-2-trifluoromethyl-morpholin-3-one

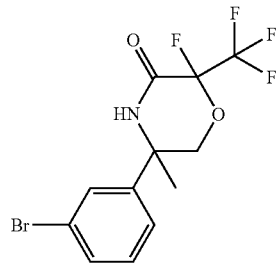

Diethylaminosulfurtrifluoride (0.45 mL, 3.66 mmol) was added to a stirred suspension of intermediate 11 (1.08 g, 3.05 mmol) in DCM (8 mL) at 0° C. The mixture was stirred for 30 minutes and then poured into a mixture of ice and sat. NaHCO$_3$. The organic layer was separated and the aqueous layer was extracted with DCM (3×25 mL). The combined organic layers were washed with brine. The organic layer was separated, dried (MgSO$_4$), filtered and the solvents evaporated in vacuo. The crude product was purified by flash column chromatography (silica; DCM). The desired fractions were collected and concentrated in vacuo to yield intermediate 12 (0.91 g, 85% yield) as beige crystals.

Example A13

Preparation of Intermediate 13: rac-5-(3-bromo-phenyl)-2-fluoro-5-methyl-2-trifluoromethyl-morpholin-3-thione

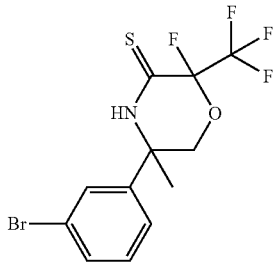 [SMILES: CC1(c2cccc(Br)c2)COC(F)(C(F)(F)F)C(=S)N1]

Lawesson's reagent (1.23 g, 3.03 mmol) was added to a stirred suspension of intermediate 12 (0.9 g, 2.53 mmol) in toluene (10 mL) at −78° C. Then, the mixture was allowed to warm to room temperature and stirred for 30 minutes. The mixture was evaporated in vacuo and the residue was diluted in DCM and washed with sat NaHCO$_3$.

The organic layer was separated and the aqueous layer was extracted with DCM (2×5 mL). The combined organic layers were dried (MgSO$_4$), filtered and the solvents evaporated in vacuo to yield intermediate 13 (1.35 g, 99% yield) as a yellow glass.

Example A14

Preparation of Intermediate 14: rac-5-(3-bromo-phenyl)-2-fluoro-5-methyl-2-trifluoromethyl-5,6-dihydro-2[1,4]oxazin-3-ylamine

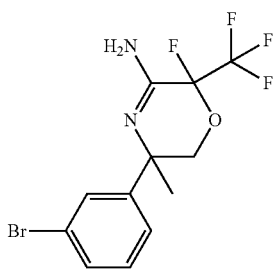 [SMILES: CC1(c2cccc(Br)c2)COC(F)(C(F)(F)F)C(N)=N1]

A solution of intermediate 13 (1.35 g, 2.50 mmol) in EtOH (25 mL) and ammonium hydroxide (40 mL) was stirred for 48 hours at 40° C. Then, DCM (100 mL) was added. The organic layer was separated and the aqueous layer was extracted with DCM (3×20 mL). The combined organic layers were washed with brine. The organic layer was separated, dried (Na$_2$SO$_4$), filtered and the solvents evaporated in vacuo. The crude product was purified by flash column chromatography (silica; 7 M solution of ammonia in methanol in DCM 0.5/99.5). The desired fractions were collected and concentrated in vacuo and the residue was again purified by flash column chromatography (silica; 7 M solution of ammonia in methanol/DCM 0.5/99.5). The desired fractions were collected and concentrated in vacuo to yield intermediate 14 (0.72 g, 81% yield) as yellow crystals.

Example A15

Preparation of Intermediate 15: rac-2-(3-bromo-phenyl)-2-(4-methoxy-benzylamino)-propan-1-ol

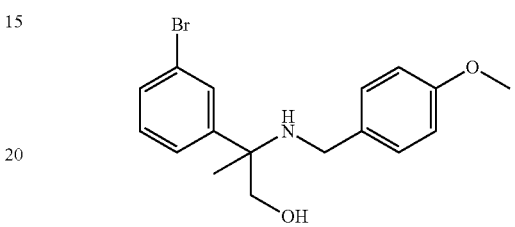

A mixture of intermediate 3 (9.66 g, 41.97 mmol) and p-anisaldehyde (5.11 mL, 41.97 mmol) in dry MeOH (84 mL) was stirred at room temperature overnight. The mixture was cooled down to 0° C. and sodium borohydride (1.59 g, 41.97 mmol) was carefully added portionwise. The mixture was stirred at room temperature for 30 minutes, quenched with 1N HCl, basified with 50% NaOH and extracted with DCM. The organic layer was separated, dried (MgSO$_4$), filtered and the solvents evaporated in vacuo. The crude product was purified by flash column chromatography (silica gel; MeOH in DCM 0/100 to 5/95). The desired fractions were collected and concentrated in vacuo. The residue was taken up in a mixture of toluene and 32% HCl. The aqueous layer was separated and the organic layer was extracted with 32% HCl (5×150 mL). The combined aqueous layers were cooled down on dry ice/acetone and 50% NaOH was slowly added until pH 10. The aqueous layer was saturated with NaCl and extracted with DCM (3×250 mL). The combined organic layers were dried (MgSO$_4$), filtered and the solvents evaporated in vacuo to yield intermediate 15 (9.10 g, 62% yield) as a colorless oil.

Example A16

Preparation of Intermediate 16: rac-5-(3-bromo-phenyl)-4-(4-methoxy-benzyl)-5-methyl-morpholin-3-one

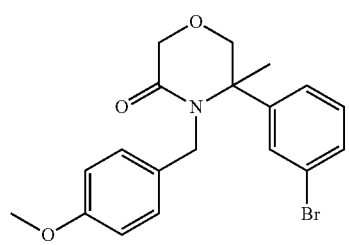 [SMILES: COc1ccc(CN2C(=O)COCC2(C)c2cccc(Br)c2)cc1]

Chloroacetyl chloride (0.96 mL, 12 mmol) was added dropwise to a stirred solution of intermediate 15 (4.20 g, 12 mmol) and DIPEA (2.48 mL, 14.4 mmol) in dry THF (137 mL) at −78° C. The mixture was stirred at −78° C. for 30 minutes. Then potassium tert-butoxide (3.37 g, 30 mmol) was added and the mixture was allowed to warm to room temperature. The mixture was diluted with 1N HCl and extracted with DCM. The organic layer was separated and washed with sat. NaHCO₃. The organic layer was separated, dried (MgSO₄), filtered and the solvents evaporated in vacuo. The crude product was purified by flash column chromatography (silica gel; DCM). The desired fractions were collected and concentrated in vacuo to yield intermediate 16 (3.96 g, 85% yield) as a colorless oil that crystallized upon standing.

Example A17

Preparation of Intermediate 17: rac-5-(3-bromo-phenyl)-2-(2-hydroxy-ethyl)-4-(4-methoxy-benzyl)-5-methyl-morpholin-3-one

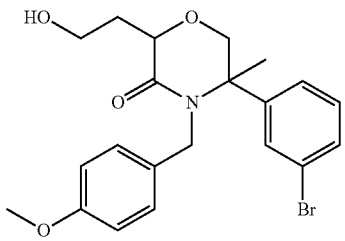 [SMILES: COc1ccc(CN2C(=O)C(CCO)OCC2(C)c2cccc(Br)c2)cc1]

Lithium diisopropylamide (2M in THF/heptanes/ethylbenzene) (11.53 mL, 23.06 mmol) was added to a solution of intermediate 16 (3 g, 7.69 mmol) in dry THF (100 mL) at 0° C. After stirring for 30 minutes 2-(2-bromoethoxy) tetrahydro-2H-pyran (1.63 mL, 11.53 mmol) was added. The mixture was stirred at 0° C. for 2 hours, quenched with 1N HCl (100 mL) and stirred at room temperature for 1 hour. The mixture was extracted with DCM (3×100 mL). The combined organic layers were washed with brine. The organic layer was separated, dried (MgSO₄), filtered and the solvents evaporated in vacuo. The crude product was purified by flash column chromatography (silica gel; MeOH/DCM 0/100 to 5/95). The desired fractions were collected and concentrated in vacuo to yield intermediate 17 (2.10 g, 63% yield) as a yellow oil.

Example A18

Preparation of Intermediate 18: rac-methanesulfonic acid 2-[5-(3-bromo-phenyl)-4-(4-methoxy-benzyl)-5-methyl-3-oxo-morpholin-2-yl]-ethyl ester

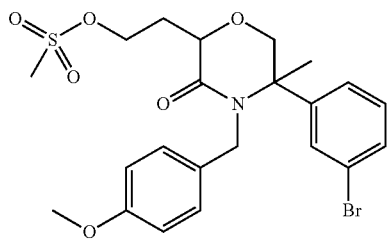 [SMILES: COc1ccc(CN2C(=O)C(CCOS(C)(=O)=O)OCC2(C)c2cccc(Br)c2)cc1]

Methanesulfonyl chloride (0.27 mL, 3.49 mmol) was added to a mixture of intermediate 17 (2.02 g, 2.32 mmol) and DIPEA (1.20 mL, 6.98 mmol) in DCM (50 mL) at 0° C. The mixture was stirred for 15 minutes, quenched with 1N HCl (100 mL) and extracted with DCM (3×100 mL). The combined organic layers were washed with brine. The organic layer was separated, dried (MgSO₄), filtered and the solvents evaporated in vacuo. The crude product was purified by flash column chromatography (silica gel; DCM). The desired fractions were collected and concentrated in vacuo to yield intermediate 18 (1.01 g, 42% yield) as a colorless oil.

Example A19

Preparation of Intermediate 19: rac-6-(3-bromo-phenyl)-7-(4-methoxy-benzyl)-6-methyl-4-oxa-7-aza-spiro[2.5]octan-8-one

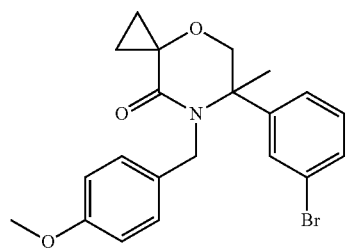 [SMILES: COc1ccc(CN2C(=O)C3(CC3)OCC2(C)c2cccc(Br)c2)cc1]

Lithium diisopropylamide (2M in cyclohexane/ethylbenzene/THF) (1.48 mL, 2.95 mmol) was slowly added to a solution of intermediate 18 (1.01 g, 0.985 mmol) in THF (19 mL) at 0° C. The mixture was stirred for 30 minutes, quenched with 1N HCl and extracted with DCM (3×50 mL). The combined organic layers were washed with brine. The organic layer was separated, dried (MgSO₄), filtered and the solvents evaporated in vacuo. The crude product was purified by flash column chromatography (silica; DCM). The desired fractions were collected and concentrated in vacuo to give colorless oil that was crystallized from DIPE. The mother liquor was decanted off and the solid was washed with heptane to yield intermediate 19 (0.51 g, 62% yield) as white crystals.

Example A20

Preparation of Intermediate 20: rac-6-(3-bromo-phenyl)-6-methyl-4-oxa-7-aza-spiro[2.5]octan-8-one

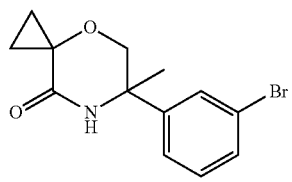 [SMILES: CC1(c2cccc(Br)c2)COC2(CC2)C(=O)N1]

Ammonium cerium(IV) nitrate (0.99 g, 1.80 mmol) was added to a mixture of intermediate 19 (0.25 g, 0.60 mmol) in a mixture of acetonitrile/water 1/1 (5 mL). The mixture was stirred at room temperature for 4 hours. The crude was treated with sat. Na₂CO₃ (the solution became milky) and extracted with DCM (3×50 mL). The combined organic layers were washed with brine. The organic layer was separated, dried (MgSO$_4$), filtered and the solvents evaporated in vacuo. The crude product was purified by flash column chromatography (silica gel; MeOH/DCM 0/100 to 10/90). The desired fractions were collected and concentrated in vacuo to yield intermediate 20 (0.17 g, 94% yield) as a colorless oil.

Example A21

Preparation of Intermediate 21: rac-6-[3-(5-methoxy-pyridin-3-yl)-phenyl]-6-methyl-4-oxa-7-aza-spiro[2.5]octan-8-one

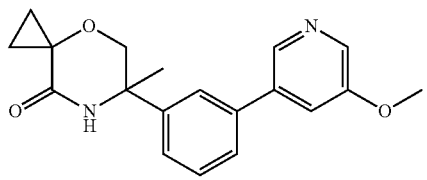 [SMILES: COc1cncc(-c2cccc(C3(C)COC4(CC4)C(=O)N3)c2)c1]

A solution of intermediate 20 (0.17 g, 0.56 mmol), (3-methoxypyridin-5-yl) boronic acid pinacol ester (0.265 g, 1.13 mmol) and tetrakis(triphenylphosphine)palladium(0) (0.065 g, 0.056 mmol) in sat. Na$_2$CO$_3$ (2 mL) and 1,4-dioxane (14 mL) was nitrogen flushed for a few minutes and then stirred at 80° C. for 4 hours. Then water (50 mL) and DCM (50 mL) were added. The organic layer was separated and the aqueous layer was extracted with DCM (3×50 mL). The combined organic layers were separated, dried (Na$_2$SO$_4$), filtered and the solvents evaporated in vacuo. The crude product was purified by flash column chromatography (silica gel; 7 M solution of ammonia in methanol/DCM 0/100 to 5/95). The desired fractions were collected and concentrated in vacuo. The residue was crystallised with Et$_2$O to yield intermediate 21 (0.175 g, 96% yield) as yellow crystals.

Example A22

Preparation of Intermediate 22: rac-6-[3-(5-methoxy-pyridin-3-yl)-phenyl]-6-methyl-4-oxa-7-aza-spiro[2.5]octane-8-thione

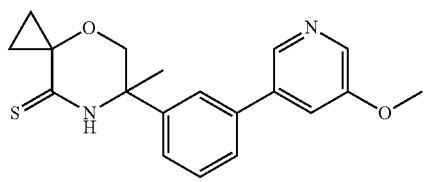 [SMILES: COc1cncc(-c2cccc(C3(C)COC4(CC4)C(=S)N3)c2)c1]

Lawesson's reagent (0.25 g, 0.63 mmol) was added to a solution of intermediate 21 (0.17 g, 0.52 mmol) in a mixture of toluene (5 mL) and THF (5 mL). The mixture was stirred at 85° C. for 5 hours. The solvent was evaporated in vacuo and the residue was purified by flash column chromatography (silica gel; DCM). The desired fractions were collected and concentrated in vacuo and the crude product was purified again by flash column chromatography (silica gel; DCM). The desired fractions were collected and concentrated in vacuo to yield intermediate 22 (0.18 g, 88% yield) as a yellow oil.

Example A23

Preparation of Intermediate 23: (R)-5-(3-bromo-phenyl)-5-methyl-morpholin-3-one

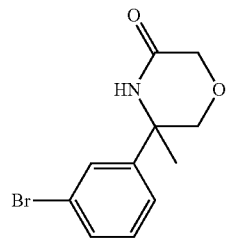

Chloro-acetyl chloride (0.66 mL, 8.26 mmol) was added dropwise to a stirred solution of intermediate 4 (1.9 g, 8.26 mmol) in THF (70 mL) and diisopropylethyl amine (1.71 mL, 9.91 mmol) at −78° C. The mixture was stirred for 20 minutes at −78° C. Then potassium tert-butoxide (2.32 g, 20.64 mmol) was added and the mixture was stirred at −15° C. and left warming up to 0° C. during 60 minutes. The mixture was diluted with saturated NH$_4$Cl and extracted with DCM. The organic layer was separated, dried (Na$_2$SO$_4$), filtered and the solvents evaporated in vacuo. The crude product was purified by flash column chromatography (silica gel; MeOH/DCM 0/100 to 3/97). The desired fractions were collected and concentrated in vacuo. Then Et$_2$O was added to the residue and the solvents evaporated in vacuo to yield intermediate 23 (1.93 g, 86% yield) as a white solid.

$\alpha_D$: −71.6° (589 nm, c 0.62 w/v %, DMF, 20° C.)

Example A24

Preparation of Intermediate 24: (R)-5-(3-bromo-phenyl)-5-methyl-morpholine-3-thione

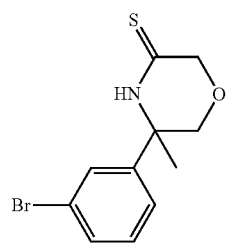

THF (70 mL) was added to a mixture of intermediate 23 (1.9 g, 7.03 mmol) and phosphorus pentasulfide (1.25 g, 5.62 mmol) at room temperature. The mixture was stirred at 50° C. for 60 minutes. Then the mixture was cooled to room temperature and filtered over cotton and evaporated in vacuo. The crude product was purified by flash column chromatography (silica; DCM). The desired fractions were collected and evaporated in vacuo. Heptane and DCM were added to the residue and the solvents evaporated in vacuo to yield intermediate 24 (1.89 g, 94% yield) as a white sticky foam.

$\alpha_D$: −190° (589 nm, c 0.6 w/v %, DMF, 20° C.)

Example A25

Preparation of Intermediate 25: (R)-5-(3-bromo-phenyl)-5-methyl-5,6-dihydro-2H-[1,4]oxazin-3-ylamine

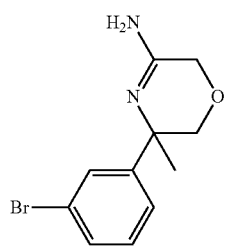

32% aqueous ammonia solution (30 mL) was added to intermediate 24 (1.86 g, 6.50 mmol) and the mixture was stirred in a sealed tube at 60° C. for 1 hour. After cooling to 0° C., 7N ammonia in MeOH (10 mL) was added and the mixture was stirred at 60° C. for 3 hours. After cooling to room temperature the mixture was diluted with water and extracted with DCM. The organic layer was separated, dried ($Na_2SO_4$), filtered and the solvent evaporated in vacuo. The crude product was purified by flash column chromatography (silica gel; MeOH/DCM 0/100 to 5/95 and then 7 M solution of ammonia in methanol/DCM 5/95). The desired fractions were collected and concentrated in vacuo to yield intermediate 25 (1.45 g, 83% yield) as a sticky oil. $\alpha_D$: −112.6° (589 nm, c 0.662 w/v %, DMF, 20° C.)

Example A26

Preparation of Intermediate 26: (R)-5-(3-amino-phenyl)-5-methyl-5,6-dihydro-2H-[1,4]oxazin-3-ylamine

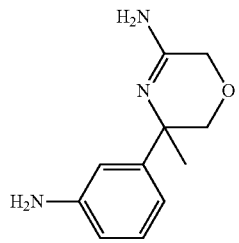

Toluene (30 mL) was added to a mixture of intermediate 25 (1 g, 3.72 mmol), tris(dibenzylideneacetone)dipalladium (0) (0.34 g, 0.37 mmol), rac-2,2'-bis(diphenylphosphino)-1,1'-binaphthyl (0.69 g, 1.12 mmol) and sodium tert-butoxide (0.54 g, 5.57 mmol) in a sealed tube and under nitrogen at room temperature. The mixture was flushed with nitrogen for a few minutes and then benzophenone imine (0.81 mL, 4.83 mmol) was added and the mixture was stirred at 70° C. for 18 hours. After cooling, a mixture of 1N HCl (20 mL) was added and the mixture was stirred at room temperature for 1 hour. The mixture was diluted with water and washed with EtOAc. The aqueous layer was basified with saturated aqueous $Na_2CO_3$ and extracted with DCM/EtOH 9/1 (10 times). The combined organic layers were dried ($Na_2SO_4$), filtered and the solvents evaporated in vacuo. The crude product was purified by flash column chromatography (silica gel; 7 M solution of ammonia in methanol/DCM 0/100 to 10/90). The desired fractions were collected and concentrated in vacuo to yield intermediate 26 as a sticky white solid.

Example A27

Preparation of Intermediate 27: trans-rac-5-(3-bromo-phenyl)-2,5-dimethyl-morpholin-3-one

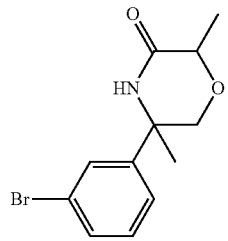 [SMILES: CC1OCC(C)(c2cccc(Br)c2)NC1=O]

2-Chloropropionyl chloride (0.84 mL, 8.69 mmol) was added dropwise to a stirred solution of intermediate 3 (2.0 g, 8.69 mmol) in THF (70 mL) and diisopropylethyl amine (1.80 mL, 10.43 mmol) at −78° C. The mixture was stirred for 90 minutes at −78° C. Then potassium tert-butoxide (2.44 g, 21.73 mmol) was added and the mixture was stirred at 0° C. for 2 hours. The mixture was diluted with saturated aqueous $NH_4Cl$ and extracted with DCM. The organic layer was separated, dried ($Na_2SO_4$), filtered and the solvents evaporated in vacuo. The crude product (approx. 1:1 mixture of cis/trans diastereoisomers) was purified by flash column chromatography (silica gel; MeOH/DCM 0/100 to 2/98). The desired fractions were collected and concentrated in vacuo to yield intermediate 27 (2.05 g, 83% yield, trans) as a white solid.

Example A28

Preparation of Intermediate 28: cis/trans rac-5-(3-bromo-phenyl)-2,5-dimethyl-morpholin-3-thione

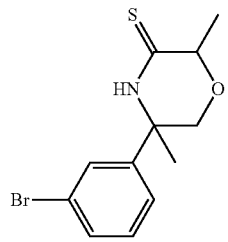

THF (70 mL) was added to a mixture of intermediate 27 (2.0 g, 7.04 mmol) and phosphorus pentasulfide (1.25 g, 5.63 mmol) at room temperature. The mixture was stirred at 50° C. for 3 hours. Then the mixture was cooled to room temperature and filtered over cotton and evaporated in vacuo. The crude product was purified by flash column chromatography (silica gel; DCM). The desired fractions were collected and evaporated in vacuo to yield as a 1:1 mixture of diastereoisomers intermediate 28 (1.81 g, 86% yield, approx. 1:1 mixture of cis/trans diastereoisomers) as a transparent sticky product.

Example A29

Preparation of Intermediate 29: trans-rac-5-(3-bromo-phenyl)-2,5-dimethyl-5,6-dihydro-2H-[1,4]oxazin-3-ylamine, intermediate 30: cis-rac-5-(3-bromo-phenyl)-2,5-dimethyl-5,6-dihydro-2H-[1,4]oxazin-3-ylamine and intermediate 31: mixture trans/cis rac-5-(3-bromo-phenyl)-2,5-dimethyl-5,6-dihydro-2H-[1,4]oxazin-3-ylamine

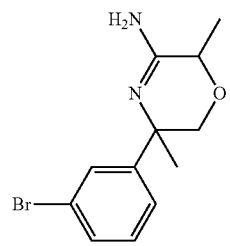 [SMILES: CC1OCC(C)(c2cccc(Br)c2)N=C1N]

7N ammonia in MeOH (10 mL) was added to a mixture of intermediate 28 (1.8 g, 6.00 mmol) and 32% aqueous ammonia solution (30 mL) in a sealed tube. The mixture was stirred at 60° C. for 6 hours. After cooling to room temperature the mixture was diluted with water and extracted with DCM. The organic layer was separated, dried ($Na_2SO_4$), filtered and the solvent evaporated in vacuo. The crude product was purified by flash column chromatography (silica gel; 7 M solution of ammonia in methanol/DCM 0/100 to 3/97). The desired fractions were collected and concentrated in vacuo to yield intermediate 29 (0.23 g, 14% yield, trans), intermediate 30 (0.41 g, 24% yield, cis) and intermediate 31 (0.60 g, 35% yield, approx. 1:1 mixture of cis/trans diastereoisomers) as sticky white products.

Example A30

Preparation of Intermediate 32: cis/trans-rac-5-(3-amino-phenyl)-2,5-dimethyl-5,6-dihydro-2H-[1,4]oxazin-3-ylamine

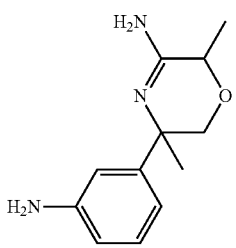

Toluene (15 mL) was added to intermediate 31 (0.59 g, 2.08 mmol), tris(dibenzylideneacetone)dipalladium(0) (0.19 g, 0.21 mmol), rac-2,2'-bis(diphenylphosphino)-1,1'-binaphthyl (0.39 g, 0.63 mmol) and sodium tert-butoxide (0.36 g, 3.75 mmol) in a sealed tube and under nitrogen at room temperature. The mixture was flushed with nitrogen for a few minutes and then benzophenone imine (0.7 mL, 4.17 mmol) was added and the mixture was stirred at 80° C. for 2 hours. After cooling, a mixture of 1N HCl/THF (20/20 mL) was added and the mixture was stirred at room temperature for 1 hour. The mixture was diluted with water and washed with EtOAc. The aqueous layer was basified with saturated aqueous $Na_2CO_3$ and extracted with DCM/EtOH 9/1 (10 times). The combined organic layers were dried ($Na_2SO_4$), filtered and the solvents evaporated in vacuo. The crude product was purified by flash column chromatography (silica gel; 7 M solution of ammonia in methanol/DCM 0/100 to 10/90). The desired fractions were collected and concentrated in vacuo. The residue was triturated with heptane to yield intermediate 32 (0.21 g, 45% yield, approx. 1:1 mixture of cis/trans diastereoisomers) as an off white solid.

Example A31

Preparation of Intermediate 33: rac-2-(5-bromo-2,4-difluoro-phenyl)-2-(2-chloro-acetylamino) propionic acid

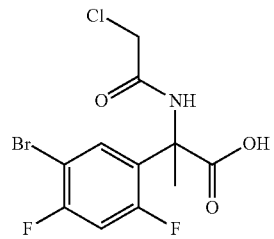 [SMILES: CC(NC(=O)CCl)(C(=O)O)c1cc(Br)c(F)cc1F]

To a cooled solution of rac-2-amino-2-(5-bromo-2,4-difluoro-phenyl)-propionic acid (2 g, 7.14 mmol) in NaOH (1M in $H_2O$, 8.57 mL), a solution of chloroacetyl chloride (0.625 mL, 7.85 mmol) in 1,4-dioxane (4 mL) was added dropwise. Simultaneously, NaOH (5M in $H_2O$, 1.43 mL) was added to adjust the pH at 10-11. Extra 1,4-dioxane (20 mL) was then added and the resulting mixture was vigorously stirred at room temperature for 1 hour. The organic layer was separated, and the aqueous layer extracted with $Et_2O$. Then the aqueous layer was acidified with HCl (6 M, in $H_2O$) until pH 2. The resulting white solid was collected by filtration, washed with $H_2O$ and dried to yield intermediate 33 (1.7 g, 66.7%).

Example A32

Preparation of Intermediate 34: rac-3-(5-bromo-2,4-difluoro-phenyl)-3-methyl-morpholine-2,5-dione

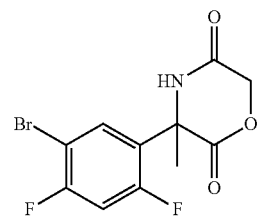 [SMILES: CC1(c2cc(Br)c(F)cc2F)NC(=O)COC1=O]

intermediate 33 (1 g, 2.8 mmol) was dissolved in DMF (37 mL), and the reaction mixture was stirred at 110° C. for 48 hours. The mixture cooled down and was then diluted with water and extracted with EtOAc, the organic layers were separated, dried ($Na_2SO_4$), filtered and the solvents evaporated in vacuo. The solid material obtained was then washed with DIPE to yield intermediate 34 which was used as such in the next reaction step (1 g, 65.5%)

Example A33

Preparation of Intermediate 35: cis/trans-rac-5-(5-bromo-2,4-difluoro-phenyl)-6-hydroxy-5-methyl-morpholin-3-one

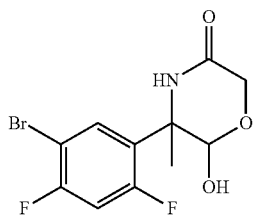 [SMILES: CC1(c2cc(Br)c(F)cc2F)NC(=O)COC1O]

A solution of intermediate 34 (1.5 g, 4.7 mmol) in THF (23 mL) was cooled to −78° C. under $N_2$ atmosphere. Then, diisobutylaluminium hydride (9.5 mL, 9.5 mmol) was slowly added. The reaction mixture was stirred for 2 hours allowing it slowly to warm up to room temperature The reaction mixture was cooled down to 0° C. and it was quenched by slow addition of water (1 mL). The mixture was then extracted with EtOAc, the organic layers were separated, dried ($Na_2SO_4$), filtered and the solvents evaporated in vacuo to yield intermediate 35 (1 g, 65.4% yield) which was used as such in the next reaction step.

Example A34

Preparation of Intermediate 36: cis/trans-rac-5-(5-bromo-2,4-difluoro-phenyl)-6-fluoro-5-methyl-morpholin-3-one

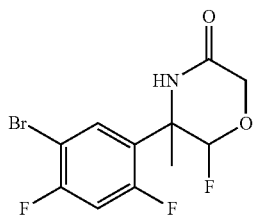 [SMILES: CC1(c2cc(Br)c(F)cc2F)NC(=O)COC1F]

Intermediate 35 (1 g, 3.1 mmol) was suspended in DCM (7.7 mL) and the reaction was cooled down to 0° C. Then DAST (0.45 mL, 3.7 mmol) was added dropwise. After 20 min at 0° C. the reaction mixture was quenched with aqueous $NaHCO_3$ (sat. sol.), then extracted with DCM. The organic layers were separated, dried ($Na_2SO_4$), filtered and the solvents evaporated in vacuo to yield intermediate 36 (1 g, quant. yield) which was used as such in the next reaction step.

Example A35

Preparation of Intermediate 37: cis/trans-rac-5-(5-bromo-2,4-difluoro-phenyl)-6-fluoro-5-methyl-morpholine-3-thione

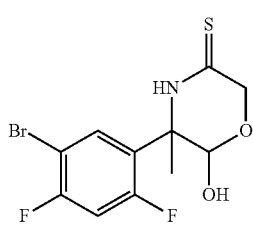 [SMILES: CC1(c2cc(Br)c(F)cc2F)NC(=S)COC1O]

Intermediate 36 (1 g, 3.1 mmol) was dissolved in THF (30 mL) and then $P_2S_5$ (0.686 g, 3.1 mmol) was added at room temperature The mixture was stirred at 70° C. for 1 hour. Then it was cooled to room temperature, the solid residue was filtered off and the organic solvent evaporated to dryness to give intermediate 37 which was used as such in the next reaction step (quant. yield).

Example A36

Preparation of Intermediate 38: cis-rac-5-(5-bromo-2,4-difluoro-phenyl)-6-fluoro-5-methyl-5,6-dihydro-2H-[1,4]oxazin-3-ylamine and intermediate 39: trans-rac-5-(5-bromo-2,4-difluoro-phenyl)-6-fluoro-5-methyl-5,6-dihydro-2H-[1.4]oxazin-3-ylamine

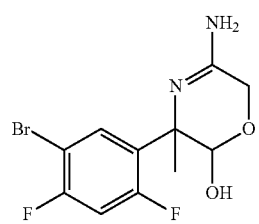 [SMILES: CC1(c2cc(Br)c(F)cc2F)N=C(N)COC1O]

Intermediate 35 (1.3 g, 3.83 mmol), was dissolved in 7N ammonia in MeOH (13 mL) and the reaction mixture was stirred at 60° C. for 20 hours. Additional 7N ammonia in MeOH was added (8 mL) and the mixture was stirred at 60° C. for an additional 8 hours. Then the solvent was evaporated and the crude product purified by column chromatography (silica gel; eluents: 7 M solution of ammonia in methanol/DCM 0/100 to 10/90). The desired fractions were collected and concentrated in vacuo to yield intermediate 39 (0.423 g, 34% yield) and intermediate 38 (0.405 g, 33% yield).

Example A37

Preparation of Intermediate 40: rac-2-(3-bromo-phenyl)-2-(2-chloro-acetylamino)-propionic acid

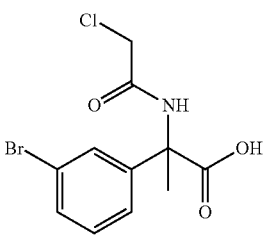 [SMILES: CC(NC(=O)CCl)(C(=O)O)c1cccc(Br)c1]

Intermediate 40 was synthesized following the same approach described in the Example A31. Starting from rac-2-amino-2-(3-bromo-phenyl)-propionic acid (12 g, 50 mmol) intermediate 40 was obtained (12 g, 75% yield).

Example A38

Preparation of Intermediate 41: rac-3-(3-bromo-phenyl)-3-methyl-morpholine-2,5-dione

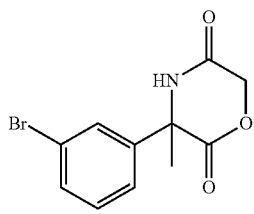 [SMILES: CC1(c2cccc(Br)c2)NC(=O)COC1=O]

Intermediate 40 (2.4 g, 7.54 mmol) was dissolved in DMF (58 mL), and then K₂CO₃ (1.04 g, 7.54 mmol) was added. The reaction mixture was stirred for 3 days at room temperature. The mixture was then cooled down in an ice bath and diluted with water and extracted with EtOAc, the organic layers were separated, dried (Na₂SO₄), filtered and the solvents evaporated in vacuo to yield intermediate 41 as a white solid (1.77 g, 83% yield).

Example A39

Preparation of Intermediate 42: cis/trans-rac-5-(3-bromo-phenyl)-6-hydroxy-5-methyl-morpholin-3-one

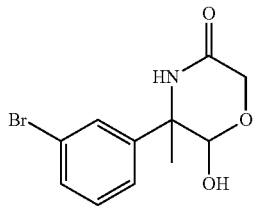 [SMILES: CC1(c2cccc(Br)c2)NC(=O)COC1O]

Intermediate 42 was synthesized following the same approach described in the Example A33. Starting from intermediate 41 (2.95 g, 10.38 mmol) intermediate 42 was obtained (2.9 g, quant. yield; mixture of diastereoisomers 69/31).

Example A40

Preparation of Intermediate 43: cis/trans-rac-5-(3-bromo-phenyl)-6-fluoro-5-methyl-morpholin-3-one

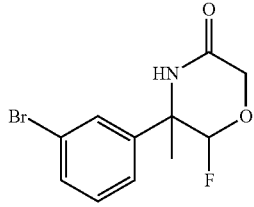 [SMILES: CC1(c2cccc(Br)c2)NC(=O)COC1F]

Intermediate 43 was synthesized following the same approach described in the Example A34. Starting from intermediate 42 (3.2 g, 11.18 mmol) intermediate 43 was obtained as solid material (3.2 g, quant. yield).

Example A41

Preparation of Intermediate 44: cis/trans-rac-5-(3-bromo-phenyl)-6-fluoro-5-methyl-morpholine-3-thione

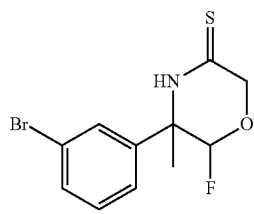 [SMILES: CC1(c2cccc(Br)c2)NC(=S)COC1F]

Intermediate 44 was synthesized following the same approach described in the Example A35. Starting from intermediate 43 (6.84 g, 23.7 mmol) intermediate 44 was obtained as a white solid (6 g, 83% yield)

Example A42

Preparation of Intermediate 45: cis-rac-5-(3-bromo-phenyl)-6-fluoro-5-methyl-5,6-dihydro-2H-[1,4]oxazin-3-ylamine and intermediate 46: trans-rac-5-(3-bromo-phenyl)-6-fluoro-5-methyl-5,6-dihydro-2H-[1,4]oxazin-3-ylamine

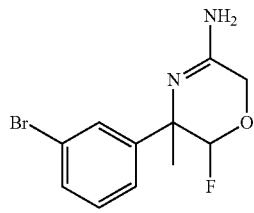 [SMILES: CC1(c2cccc(Br)c2)N=C(N)COC1F]

Intermediate 45 and intermediate 46 were synthesized following the same approach described in the Example A36. Starting from intermediate 44 (6 g, 19.72 mmol) intermediate 45 (0.33 g, 6% yield) and intermediate 46 (1.9 g, 35% yield) were obtained.

Example A43

Preparation of Intermediate 47: trans-rac-5-(3-amino-phenyl)-6-fluoro-5-methyl-5,6-dihydro-2H-[1,4]oxazin-3-ylamine

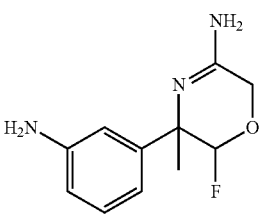

Intermediate 46 (0.32 g, 1.12 mmol) was combined with NaN₃ (0.182, 2.8 mmol), CuI (0.266 g, 1.4 mmol) and Na₂CO₃ (0.237 g, 2.43 mmol) in DMSO (16 mL) and the reaction was degassed. After that, N,N'-dimethylethylenediamine (0.211 mL, 1.96 mmol) was added and the mixture was heated at 110° C. until completion of the reaction, about 1 hour. The reaction mixture was filtered off and the filter cake was washed with water. EtOAc and water were added and the mixture was acidified by addition of HCl (1M in H₂O). The organic layer was then separated and the aqueous layer washed with EtOAc. Then the water layer was basified with NaOH (1M in H₂O) and extracted again with EtOAc. The combined organic layers were dried, (Na₂SO₄) filtered and concentrated in vacuo to yield intermediate 47 which was used as such in 15 the next reaction step (0.5 g, impure with DMSO solvent).

Example A44

Preparation of Intermediate 48: rac-2-(5-bromo-2-fluoro-phenyl)-2-(2-chloro-acetylamino)-propionic acid

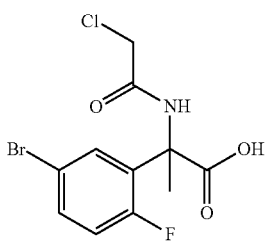

Intermediate 48 was synthesized following the same approach described in the Example A31. Starting from rac-2-amino-2-(5-bromo-2-fluoro-phenyl)-propionic acid (6 g, 22.9 mmol) intermediate 48 was obtained (6.6 g, 85% yield Example A45

Preparation of Intermediate 49: rac-3-(5-bromo-2-fluoro-phenyl)-3-methyl-morpholine-2,5-dione

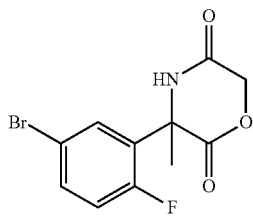 [SMILES: CC1(c2cc(Br)ccc2F)NC(=O)COC1=O]

Intermediate 49 was synthesized following the same approach described in the Example A38. Starting from intermediate 48 (6.6 g, 19.5 mmol) intermediate 49 was obtained (5.6 g, 95% yield).

Example A46

Preparation of Intermediate 50: cis/trans-rac-5-(5-bromo-2-fluoro-phenyl)-6-hydroxy-5-methyl-6-trifluoromethylmorpholin-3-one

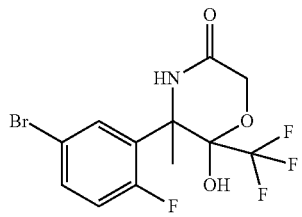 [SMILES: CC1(c2cc(Br)ccc2F)NC(=O)COC1(O)C(F)(F)F]

To a solution of intermediate 49 (0.5 g, 1.65 mmol) in THF (10 mL) was added (trifluoromethyl)trimethyl silane (1.95 mL, 13.2 mmol) and then slowly TBAF (1M solution in THF, 0.083 mL, 0.083 mmol). The initially yellow reaction turned dark orange. Then, the reaction mixture was stirred at room temperature during 2 hours. The mixture was quenched with aqueous NaCl, extracted with EtOAc, the organic phase was separated, dried (MgSO₄) and concentrated in vacuo. The resulting oil was purified by column chromatography (silica gel; 7 M solution of NH₃ in methanol/DCM 0/100 to 5/95) to afford intermediate 50 as a solid (0.52 g, 84% yield).

Example A47

Preparation of Intermediate 51: cis/trans-rac-5-(5-bromo-2-fluoro-phenyl)-6-chloro-5-methyl-6-trifluoromethyl-morpholin-3-one

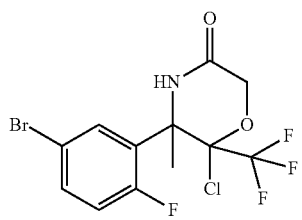 [SMILES: CC1(c2cc(Br)ccc2F)NC(=O)COC1(Cl)C(F)(F)F]

Intermediate 50 (1 g, 2.68 mmol) was dissolved in DCM (13.5 mL) and cooled to 0° C. and then thionyl chloride (0.294 mL, 4.03 mmol) was added dropwise. The reaction mixture was stirred for 30 min at 0° C. and then pyridine (0.324 mL, 4.03 mmol) was added. After 30 min. the reaction was hydrolyzed with HCl (1M in H₂O) and then extracted with DCM. The organic layers were separated, dried (MgSO₄), filtered and evaporated in vacuo. The crude product was purified by flash column chromatography (silica gel; 7 M solution of ammonia in methanol/DCM 0/100 to 2/98) to yield intermediate 51 (0.54 g, 51.5% yield).

Example A48

Preparation of Intermediate 52: cis/trans-rac-5-(5-bromo-2-fluoro-phenyl)-5-methyl-6-trifluoromethyl-morpholin-3-one

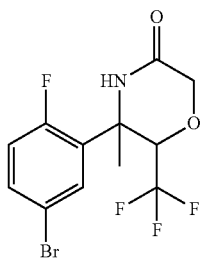 [SMILES: CC1(c2cc(Br)ccc2F)NC(=O)COC1C(F)(F)F]

To a solution of intermediate 51 (0.9 g, 2.3 mmol) in acetic acid (41 mL), zinc (0.376 g, 5.76 mmol) was added. The reaction mixture was then stirred at 80° C. for 12 hours, after that the reaction was then filtered off and concentrated in vacuo. The residue was dissolved in DCM and washed with an aqueous saturated solution of NaHCO$_3$, the organic phase was separated, dried (MgSO$_4$) and the solvent concentrated in vacuo. The crude compound was purified by flash column chromatography (silica gel; 7 M solution of ammonia in methanol/DCM 0/100 to 3/97) to yield intermediate 52 (0.75 g, 91% yield).

Example A49

Preparation of Intermediate 53: cis/trans-rac-5-(5-bromo-2-fluoro-phenyl)-5-methyl-6-trifluoromethyl-morpholine-3-thione

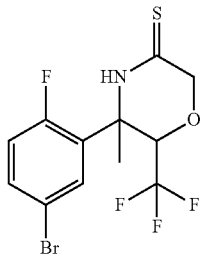 [SMILES: CC1(c2cc(Br)ccc2F)NC(=S)COC1C(F)(F)F]

Lawesson's reagent (0.96 g, 2.38 mmol) was added to a solution of intermediate 52 (0.85 g, 2.38 mmol) dissolved in THF (10 mL) at room temperature. The mixture was stirred at 60° C. for 4 hours. Then the mixture was cooled to room temperature, filtered off and the organic solvent evaporated in vacuo. The crude product was purified by flash column chromatography (silica gel; heptanes/DCM 100/0 to 50/50). The desired fractions were collected and evaporated in vacuo to yield intermediate 53 (0.63 g, 71% yield) as an oil.

Example A50

Preparation of Intermediate 54: cis/trans-rac-5-(5-bromo-2-fluoro-phenyl)-5-methyl-6-trifluoromethyl-5,6-dihydro-2H-[1,4]oxazin-3-ylamine

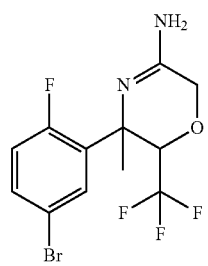 [SMILES: CC1(c2cc(Br)ccc2F)N=C(N)COC1C(F)(F)F]

Intermediate 54 was synthesized following the same approach described in the Example A36. Starting from intermediate 53 (0.63 g, 1.69 mmol intermediate 54 was obtained (0.5 g, 83% yield).

Example A51

Preparation of Intermediate 55: cis/trans-rac-5-(5-amino-2-fluoro-phenyl)-5-methyl-6-trifluoromethyl-5,6-dihydro-2H-[1,4]oxazin-3-ylamine

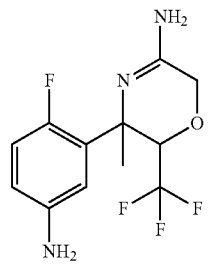 [SMILES: CC1(c2cc(N)ccc2F)N=C(N)COC1C(F)(F)F]

Intermediate 55 was synthesized following the same approach described in the Example A43. Starting from intermediate 54 (0.2 g, 0.56 mmol) intermediate 55 was obtained (0.15 g, 91% yield).

Example A52

Preparation of Intermediate 56: cis/trans-rac-5-(5-bromo-2-fluoro-phenyl)-6-fluoro-5-methyl-6-trifluoromethyl-morpholin-3-one

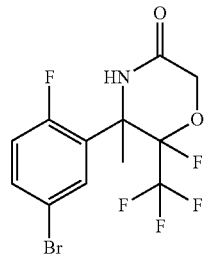 [SMILES: CC1(c2cc(Br)ccc2F)NC(=O)COC1(F)C(F)(F)F]

Intermediate 50 (3.72 g, 10 mmol) was suspended in DCM (25 mL) and after cooling the reaction mixture at 0° C., DAST (1.47 mL, 12 mmol) was added dropwise. The reaction mixture was stirred at 0° C. for 1 hour and then quenched with saturated aqueous NaHCO$_3$. The organic layer was separated and the aqueous layer was extracted with DCM. The combined organic layers were dried (MgSO$_4$), filtered, and the solvent evaporated in vacuo to yield intermediate 56 (3.7 g, 99% yield) as a solid compound.

Example A53

Preparation of Intermediate 57: cis/trans-rac-5-(5-bromo-2-fluoro-phenyl)-6-fluoro-5-methyl-6-trifluoromethyl-morpholine-3-thione

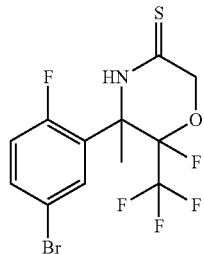 [SMILES: CC1(c2cc(Br)ccc2F)NC(=S)COC1(F)C(F)(F)F]

Intermediate 57 was synthesized following the same approach described in the Example A49. Starting from intermediate 56 (4.27 g, 11.41 mmol) intermediate 57 was obtained as a white solid (3.17 g, 71% yield)

Example A54

Preparation of Intermediate 58: cis-rac-5-(5-bromo-2-fluoro-phenyl)-6-fluoro-5-methyl-6-trifluoromethyl-5,6-dihydro-2H-[1,4]oxazin-3-ylamine and intermediate 59: trans-rac-5-(5-bromo-2-fluoro-phenyl)-6-fluoro-5-methyl-6-trifluoromethyl-5,6-dihydro-2H-[1,4]oxazin-3-ylamine

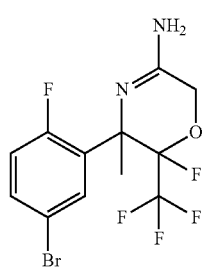 [SMILES: CC1(c2cc(Br)ccc2F)N=C(N)COC1(F)C(F)(F)F]

Intermediate 58 and intermediate 59 were synthesized following the same approach described in the Example A36.

Starting from intermediate 57 (0.5 g, 1.28 mmol) intermediate 58 (0.035 g, 7% yield) and intermediate 59 (0.145 g, 30% yield) were obtained.

Example A55

Preparation of Intermediate 60: trans-rac-5-(5-amino-2-fluoro-phenyl)-6-fluoro-5-methyl-6-trifluoromethyl-5,6-dihydro-2H-[1,4]oxazin-3-ylamine

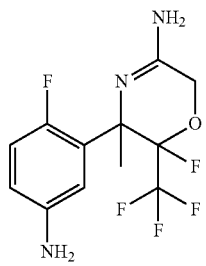 [SMILES: CC1(c2cc(N)ccc2F)N=C(N)COC1(F)C(F)(F)F]

Intermediate 60 synthesized following the same approach described in the Example A43. Starting from intermediate 59 (0.56 g, 1.5 mmol) intermediate 60 was obtained (0.487 g, quant. yield)

Example A56

Preparation of Intermediate 61: rac-2-benzyloxycarbonylamino-2-(3-chloro-phen)-3,3,3-trifluoro-propionic acid methyl ester

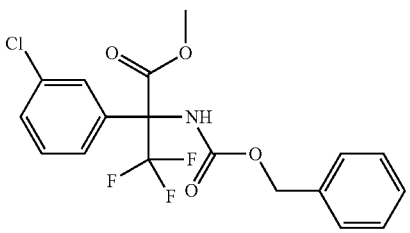 [SMILES: COC(=O)C(NC(=O)OCc1ccccc1)(c1cccc(Cl)c1)C(F)(F)F]

To a mixture of 2-benzoxycarbonylimino-3,3,3-trifluoropropionate [(CAS 128970-26-3), 8 g, 27.66 mmol], in THF (50 mL), 3-chlorophenylmagnesium bromide (0.5 M in THF, 66.4 mL, 33.2 mmol) was added dropwise at −78° C. The reaction mixture was stirred at this temperature for 2 hours and then 2 additional hours at room temperature. The reaction mixture cooled to −20° C. and was quenched by addition of HCl (1M in H$_2$O). The reaction mixture was partitioned between EtOAc and water. The organic layers were separated, dried (Na$_2$SO$_4$), and the solvent concentrated in vacuo. The crude compound was purified by chromatography (silica gel; DCM/heptane 0/100 to 10/90), the desired fractions were collected and the solvent concentrated in vacuo to yield intermediate 61 as a colourless oil (6.7 g, 60% yield)

Example A57

Preparation of Intermediate 62: rac-4-(3-chloro-phenyl)-4-trifluoromethyl-oxazolidin-2-one

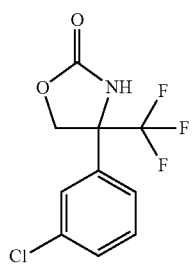 [SMILES: O=C1NC(c2cccc(Cl)c2)(C(F)(F)F)CO1]

To a mixture of intermediate 61 (6.7 g, 16.67 mmol) in THF (400 mL), lithium aluminiumhydride (1M in THF, 25 mL, 25 mmol) was added at 0° C. The reaction mixture was slowly allowed to warm to room temperature and it was further stirred at this temperature for 24 hours. The reaction mixture was cooled to 0° C. and treated (carefully) with an aq. saturated solution of tartaric acid (40 mL) and DCM (100 mL). The mixture was stirred for 1 hour at room temperature. The organic phase was separated and the solvent evaporated in vacuo to afford a sticky oil, which was dissolved in EtOH (10 mL) and treated with NaOH (50% in H$_2$O). This reaction mixture was heated at reflux for 1 hour. The solvent was evaporated in vacuo, water (40 mL) and DCM (40 mL) were added, and the aqueous phase separated and acidified with HCl (2 M in H$_2$O) to reach pH 3. This aqueous phase was extracted with DCM, and the organic phase was separated, dried (Na$_2$SO$_4$) and evaporated to dryness to afford a transparent oil which was triturated with Et$_2$O to afford intermediate 62 as white solid (2.7 g, 61% yield).

Example A58

Preparation of Intermediate 63: rac-2-amino-2-(3-chloro-phenyl)-3,3,3-trifluoro-propan-1-ol

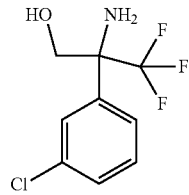

To a mixture of intermediate 62 (1.2 g, 4.51 mmol) in EtOH (7.2 mL), NaOH (50% in H$_2$O) was added at room temperature. The reaction mixture was stirred at reflux for 24 hours. Then the solvent was evaporated and the crude mixture was partitioned between EtOAc and water. The organic phase was separated, dried (Na$_2$SO$_4$) and the solvent evaporated in vacuo to afford intermediate 63 as colourless oil (0.8 g, 74% yield)

Example A59

Preparation of Intermediate 64: rac-5-(3-chloro-phenyl)-5-trifluoromethyl-morpholin-3-one

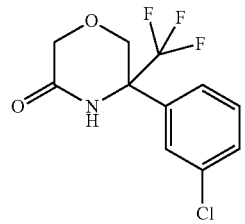 [SMILES: O=C1COCC(c2cccc(Cl)c2)(C(F)(F)F)N1]

Chloro acetylchloride (0.266 mL, 3.33 mmol) was added dropwise to a stirred solution of intermediate 63 (0.8 g, 3.33 mmol) in THF (32 mL) and DIPEA (0.69 mL, 4 mmol) at −78° C. The mixture was stirred at this temperature for 30 minutes, then KOtBu (0.937 g, 8.34 mmol) was added and the mixture was allowed to warm to room 15 temperature. over 20 minutes. After that, the temperature was elevated to 50° C. and the reaction mixture stirred for an additional 2 hours. The mixture was diluted with saturated aqueous NH$_4$Cl and extracted with DCM. The organic layer was separated, dried (Na$_2$SO$_4$), filtered and the solvents evaporated in vacuo. The resulting residue was washed with a mixture of EtOH/Et$_2$O to afford intermediate 64 as white solid (0.8 g, 86% yield)

Example A60

Preparation of Intermediate 65: rac-5-[3-(5-methoxy-pyridin-3-yl)-phenyl]-5-trifluoromethyl-morpholin-3-one

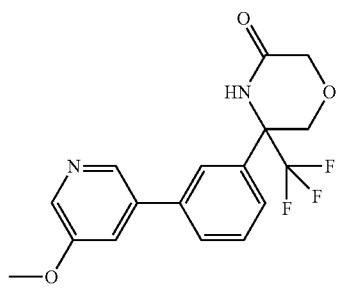 [SMILES: COc1cncc(-c2cccc(C3(C(F)(F)F)COCC(=O)N3)c2)c1]

Intermediate 64 was added to a solution of Pd$_2$(dba)$_3$ (0.006 g, 0.007 mmol), 3-methoxy-5-(4,4,5,5-tetramethyl-[1,3,2]dioxaborolan-2-yl)-pyridine (0.12 g, 0.78 mmol), tricyclohexylphosphine (0.004 g, 0.017 mmol) in 1,4-dioxane (4.5 mL). The mixture was stirred and flushed with N$_2$ for a few minutes and then a solution of K$_3$PO$_4$ (0.258 g, 1.2 mmol) in H$_2$O (2 mL) was added. The reaction mixture was heated at 100° C. for 18 hours. After cooling to room temperature, the mixture was diluted with water and extracted with DCM. The organic layer was separated, dried (Na$_2$SO$_4$), filtered and the solvents evaporated in vacuo. The crude product was purified by flash column chromatography (silica gel; EtOAc). The desired fractions were collected and concentrated in vacuo to yield intermediate 65 as a white solid (0.13 g, 51.5% yield).

Example A61

Preparation of Intermediate 66: rac-5-[3-(5-methoxy-pyridin-3-yl)-phenyl]-5-trifluoromethyl-morpholine-3-thione

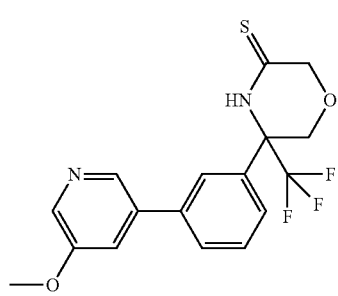 [SMILES: COc1cncc(-c2cccc(C3(C(F)(F)F)COCC(=S)N3)c2)c1]

Intermediate 66 was synthesized following a similar approach to that described in Example A7, with the difference that THF was replaced by pyridine as solvent. Thus starting from intermediate 65 (0.13 g, 0.343 mmol), the desired product intermediate 66 was obtained as an oil (0.08 g, 63% yield).

Example A62

Preparation of Intermediate 67: rac-(3-bromo-phenyl)-(2-methyl-propane-2-sulfinylimino)-acetic acid ethyl ester

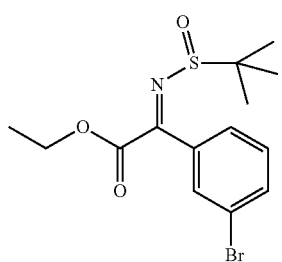 [SMILES: CCOC(=O)/C(=N/S(=O)C(C)(C)C)c1cccc(Br)c1]

Titanium(IV) ethoxyde (1.32 mL, 6.17 mmol) was added to a stirred mixture of (3-bromo-phenyl)-oxo-acetic acid ethylester [(CAS 81316-36-1), 1 g, 4.11 mmol] and 2-methyl-2-propanesulfinamide (0.598 g, 4.9 mmol) in heptanes (40 mL). The mixture was stirred at 80° C. for 2 hours. Then it was cooled to room temperature, diluted with heptane and solid $Na_2SO_4$ was added. The solids were filtered off and the solvents were evaporated in vacuo. The residue thus obtained was purified by short open column chromatography (silica; DCM/heptane 50/50 to 0/100; then EtOAc in DCM 0/100 to 5/95). The desired fractions were collected and the solvents evaporated in vacuo to yield intermediate 67 as yellow oil (1.3 g, 87% yield).

Example A63

Preparation of Intermediate 68: rac-2-amino-2-(3-bromo-phenyl)-2-cyclopropyl-ethanol

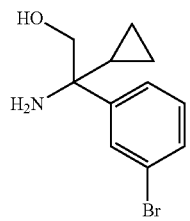 [SMILES: NC(CO)(c1cccc(Br)c1)C1CC1]

Cyclopropylmagnesium bromide (0.5 M, 5 mL, 2.5 mmol) was added dropwise to a stirred solution of intermediate 67 in THF (3 mL) at −10° C. The mixture was stirred at this temperature for 1 hour and then lithium aluminium-hydride (1M in THF, 10 mL, 122.8 mmol) was added to the mixture and stirred for an additional 1 hour while slowly warming to 0° C. Solid $Na_2SO_4$ decahydrate was added to the mixture until no more gas evolution was observed. The mixture was stirred for 1 additional hour at room temperature. The mixture was filtered over a diatomaceous earth pad and rinsed with THF. The collected organic layer was evaporated to dryness in vacuo and MeOH (10 mL) followed by conc. HCl (0.5 mL) were added. The mixture was then stirred for 1 hour at 40° C. The solvent was partially evaporated and the mixture basified with sat. $Na_2CO_3$. The inorganic phase was extracted with DCM. The organic layer was separated, dried ($Na_2SO_4$), filtered and concentrated in vacuo. The crude product was purified by flash column chromatography (silica gel; 7N $NH_3$ in MeOH/DCM 0/100 to 2/98). The desired fractions were collected and concentrated in vacuo to yield intermediate 68 as a transparent oil that partially solidified upon standing (0.11 g, 39.6% yield).

Example A64

Preparation of Intermediate 69: rac-5-(3-bromo-phenyl)-5-cyclopropyl-morpholin-3-one

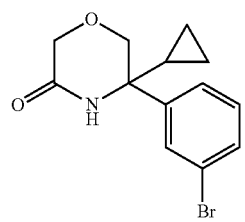 [SMILES: O=C1COCC(c2cccc(Br)c2)(C2CC2)N1]

Intermediate 69 was synthesized following the same approach described in Example A59. Thus starting form intermediate 68 (0.11 g, 0.43 mmol), the desired compound intermediate 69 was obtained as a sticky solid (0.115 g, 90% yield)

Example A65

Preparation of Intermediate 70: rac-5-(3-bromophenyl)-5-cyclopropyl-morpholine-3-thione

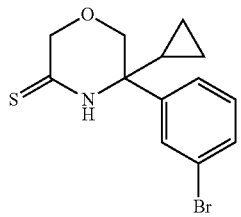 [SMILES: S=C1COCC(c2cccc(Br)c2)(C2CC2)N1]

Intermediate 70 was synthesized following a similar approach described in Example A7. Thus starting from intermediate 69 (0.115 g, 0.338 mmol), the desired product intermediate 70 was obtained as a white solid (0.09 g, 73% yield).

Example A66

Preparation of Intermediate 71: rac-5-(3-bromophenyl)-5-cyclopropyl-5,6-dihydro-2H-[1,4]oxazin-3-ylamine

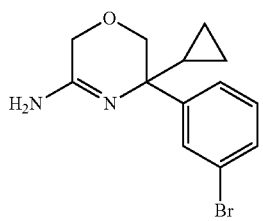 [SMILES: NC1=NC(c2cccc(Br)c2)(C2CC2)COC1]

Intermediate 71 was synthesized following a similar approach described in Example A29. Thus starting from intermediate 70 (0.09 g, 0.28 mmol), the desired product intermediate 71 was obtained as a white solid (0.05 g, 60% yield).

Example A67

Preparation of Intermediate 72: rac-5-(3-aminophenyl)-5-cyclopropyl-5,6-dihydro-2H-[1,4]oxazin-3-ylamine

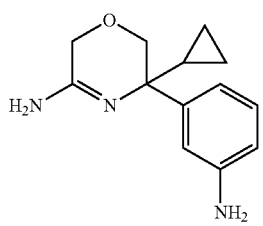 [SMILES: NC1=NC(c2cccc(N)c2)(C2CC2)COC1]

Intermediate 72 was synthesized following a similar approach described in Example A43. Thus starting from intermediate 71 (0.3 g, 1.01 mmol), the desired product intermediate 72 was obtained as a yellow solid (0.084 g, 36% yield).

Example A68

Preparation of Intermediate 73

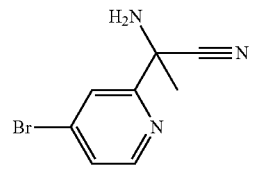

Trimethylsilylcyanide (26.8 g, 270 mmol) was added to a stirred solution of 1-(4-bromo-2-pyridinyl)-ethanone (18 g, 90 mmol) and $NH_4Cl$ (14.5 g, 270 mmol) in 4N $NH_3$/MeOH (1000 mL). The mixture was stirred at 12° C. for 4 days. Then the solvent was evaporated in vacuo and the residue was taken up in DCM (500 mL). The solid was filtered and the filtrate was evaporated in vacuo to yield crude intermediate 73, which was purified by column chromatography (silica; petroleum ether/EtOAc 50/). The desired fractions were collected and concentrated in vacuo to yield intermediate 73 (11 g, 54% yield).

Example A69

Preparation of Intermediate 74

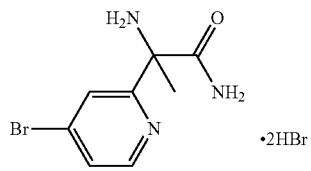

Intermediate 73 (23 g, 101.7 mmol) was dissolved in a solution of 48% HBr in acetic acid (200 mL) and the mixture was refluxed for 12 h. After cooling to room temperature, EtOAc (40 mL) was added and the precipitate was filtered off and washed with EtOAc (100 mL), then dried to give rac-intermediate 74 (25 g, 61% yield).

Example A70

Preparation of Intermediate 75

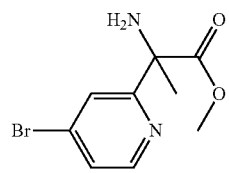

A mixture of intermediate 74 (25 g, 61.6 mmol) in a solution of 10% $H_2SO_4$ in methanol (50 mL) was refluxed for 24 h. The r.m. was concentrated in vacuo, and the residue was partitioned between EtOAc (1000 mL) and water (400 mL). The aqueous layer was washed with EtOAc (1000 mL), and the pH of the solution was adjusted to pH=7. The aqueous layer was then extracted with EtOAc (1000 mL). The organic layer was separated, dried (Na₂SO₄), filtered and concentrated in vacuo. The crude intermediate 75 was used as such in the next step (13 g, 82% yield).

Example A71

Preparation of Intermediate 76

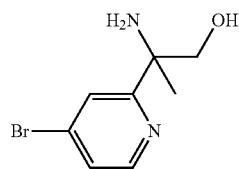

A mixture of NaBH₄ (3.8 g, 100 mmol) and intermediate 75 (13 g, 50 mmol) in ethanol (250 ml) was stirred at 14° C. for 24 h. The r.m. was concentrated in vacuo, and the residue was partitioned between EtOAc and water. The organic layer was separated, dried (Na₂SO₄), filtered and concentrated in vacuo. The crude rac-intermediate 76 was used as such in the next step (10.2 g, 88% yield).

Example A72

Preparation of Intermediate 77

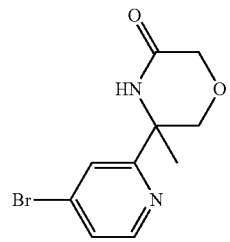

Chloro-acetyl chloride (0.69 mL, 8.66 mmol) was added dropwise to a stirred solution of intermediate 76 (2 g, 8.66 mmol) in THF (84 mL) and diisopropylethyl amine (1.79 mL, 10.4 mmol) at −78° C. The mixture was stirred for 30 minutes at −78° C. Then potassium tert-butoxide (2.23 g, 19.9 mmol) was added and the mixture was stirred at r.t. for 60 minutes. The mixture was diluted with saturated NH₄Cl and water and extracted with DCM. The organic layer was separated, dried (Na₂SO₄), filtered and the solvents evaporated in vacuo. The crude product was purified by flash column chromatography (silica gel; 7N NH₃ in MeOH/DCM 0/100 to 3/97). The desired fractions were collected and concentrated in vacuo to yield rac-intermediate 77 (1.8 g, 77% yield).

Example A73

Preparation of Intermediate 78

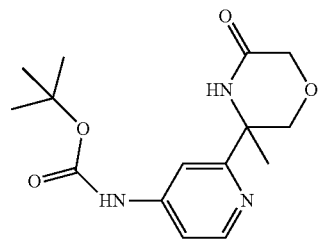 [SMILES: CC(C)(C)OC(=O)Nc1ccnc(C2(C)COCC(=O)N2)c1]

A mixture of intermediate 77 (0.55 g, 2.03 mmol), carbamic acid tert-butyl ester (0.309 g, 2.64 mmol), Pd(OAc)₂ (0.046 g, 0.2 mmol), Xantphos (0.176 g, 0.3 mmol) and Cs₂CO₃ (0.99 g, 3 mmol) in dioxane (10 mL) was heated under nitrogen at 90° C. for 1 h. After cooling, the solids were filtered off and washed with DCM. The filtrate was concentrated in vacuo, and the residue was purified by flash column chromatography (silica; 7 M solution of ammonia in methanol/DCM 0/100 to 3/97). The desired fractions were collected and concentrated in vacuo to yield rac-intermediate 78 (0.55 g, 88% yield).

Example A74

Preparation of Intermediate 79

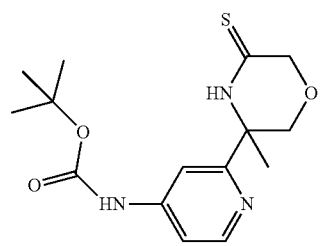 [SMILES: CC(C)(C)OC(=O)Nc1ccnc(C2(C)COCC(=S)N2)c1]

Pyridine (16 mL) was added to a mixture of intermediate 78 (0.53 g, 1.72 mmol) and phosphorus pentasulfide (0.7 g, 3.15 mmol) at room temperature. The mixture was stirred at 90° C. for 5 h. Then the mixture was cooled to room temperature and concentrated in vacuo. The residue was partitioned between water and DCM. The organic layer was separated, dried (Na₂SO₄), filtered and the solvents evaporated in vacuo. The crude product was purified by flash column chromatography (silica gel; 7N NH₃ in MeOH/DCM 0/100 to 1/99). The desired fractions were collected and concentrated in vacuo. The residue was dissolved in DCM and toluene, then again concentrated in vacuo to yield rac-intermediate 79 (0.46 g, 82% yield).

Example A75

Preparation of Intermediate 80

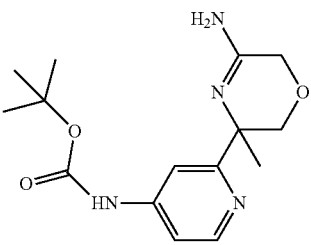 [SMILES: CC(C)(C)OC(=O)Nc1ccnc(C2(C)COCC(N)=N2)c1]

A 32% aqueous ammonia solution (10 mL) was added to a mixture of intermediate 79 (0.45 g, 1.39 mmol) in 7N NH₃/MeOH (8 mL), and the reaction mixture was stirred in a sealed tube at 70° C. for 2 hours. After cooling, the mixture was diluted with water and an aq. Na₂CO₃ solution, then extracted with DCM. The organic layer was separated, dried (Na₂SO₄), filtered and the solvent evaporated in vacuo. The residue was purified by flash column chromatography (silica; 7 M solution of ammonia in methanol/DCM 0/100 to 10/90). The desired fractions were collected and concentrated in vacuo to yield rac-intermediate 80 (0.4 g, 94% yield).

Example A76

Preparation of Intermediate 81

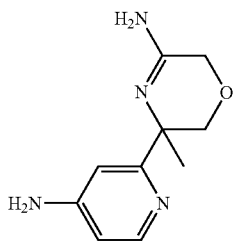

TFA (2 mL) was added to a mixture of intermediate 80 (0.395 g, 1.29 mmol) in DCM (8 mL), and the r.m. was stirred at r.t. for 3 hours. The mixture was concentrated in vacuo, and a 7N NH3/MeOH solution (3 mL) was added. The mixture was again concentrated in vacuo, and the residue dissolved in MeOH, then purified by ion exchange chromatography using an ISOLUTE® SCX2 cartridge, eluents MeOH. The desired fractions were collected and concentrated in vacuo to yield rac-intermediate 81 (0.25 g, 94% yield).

Example A77

Preparation of Intermediate 82: (R)-[1-(3-bromo-phenyl)-2-hydroxy-1-methyl-ethyl]-carbamic acid tert butyl ester

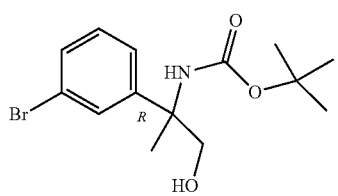

Di-tert-butyldicarbonate (19.8 g, 90.7 mmol) was added portionwise to a stirred solution of intermediate 4(R) (11.6 g, 50.4 mmol) in a mixture of saturated solution of NaHCO₃ (100 mL) and THF (100 mL) at 0° C. The mixture was stirred at 0° C. for 10 minutes and at room temperature for 15 hours. The mixture was cooled in an ice water bath and acidified with stirring till pH 1-2 with NaHSO₄. The organic layer was separated and the aqueous layer was further extracted with EtOAc. The combined organic layers were separated, dried (MgSO₄), filtered and the solvents evaporated in vacuo. The crude product was purified by short column chromatography (silica gel; EtOAc/DCM 0/100 to 20/80). The desired fractions were collected and concentrated in vacuo to yield intermediate 82 (16.47 g, 99% yield) as a colorless oil that solidified upon standing.

Example 78

Preparation of intermediate 83: (R)-[3-(tert-butyloxycarbonyl)-4-(3-bromo-phenyl)-4-methyl-[1,1,3] oxathiazolidine-2-oxide

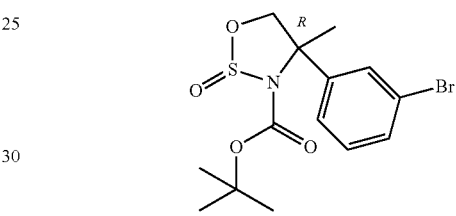

A solution of intermediate 82 (14.3 g, 43.3 mmol) in dry MeCN (80 mL) was added dropwise to a stirred solution of thionyl chloride (7.9 mL, 108.3 mmol) in dry MeCN (226 mL) cooled to −40° C. and under a nitrogen atmosphere. The reaction mixture was stirred for 30 minutes at −40° C. before pyridine (17.4 mL, 216.5 mmol) was added. The reaction was allowed to warm to room temperature and stirred for 64 hours. The solvents were evaporated in vacuo. The residue was treated with Et₂O. The solids were filtered and the filtrate concentrated in vacuo to yield intermediate 83 (15.5 g, 95% yield) as a red oil. The product was used in the next reaction without further purification.

Example 79

Preparation of intermediate 84: (R)-[3-(tert-butyloxycarbonyl)-4-(3-bromo-phenyl)-4-methyl-[1,1,3] oxathiazolidine-2,2-dioxide

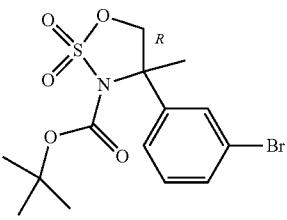

Ruthenium (III) chloride (0.085 g, 0.41 mmol) was added to solution of intermediate 83 (15.3 g, 40.8 mmol) in a mixture of MeCN and H₂O (1:1) (438 mL) at 0° C., followed by the addition of sodium periodate (13.1 g, 61.2 mmol). The reaction was allowed to warm to room temperature and stirred for 2 hours. The mixture was filtered through diatomaceous earth and washed with EtOAc (125 mL). H₂O (125 mL) and EtOAc (250 mL) were added to the filtrate. The organic layer was separated, dried (MgSO₄), filtered and the solvents evaporated in vacuo. The product was purified by flash column chromatography (silica gel; DCM). The desired fractions were collected and the solvents evaporated in vacuo to yield intermediate 84 (14.4 g, 90% yield) as a white solid. m.p. 133.1° C.

Example 80

Preparation of intermediate 85: rac-[3-(tert-butyloxycarbonyl)-4-(3-bromo-phenyl)-4-methyl-[1,1,3] oxathiazolidine-2,2-dioxide

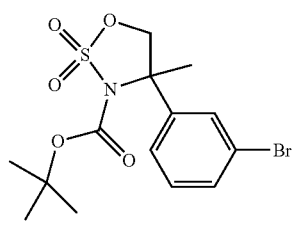 [SMILES: CC(C)(C)OC(=O)N1C(C)(c2cccc(Br)c2)COS1(=O)=O]

Racemic intermediate 85 was prepared starting from racemic intermediate 3, according to the procedures described in Examples 77-79 for intermediate 84.

Example 81

Preparation of intermediate 86

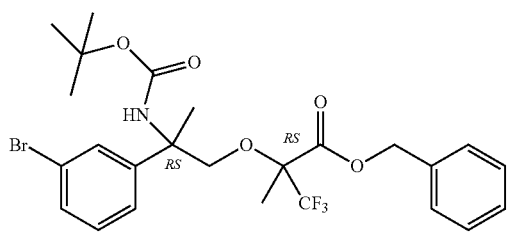

NaH (60% in mineral oil, 0.48 g, 12 mmol) was added to a mixture of (RS)-3,3,3-trifluoro-2-hydroxy-2-methyl-propanoic acid phenylmethyl ester in DMF (120 mL) at r.t., and the mixture was stirred at r.t. for 15 min. Subsequently, intermediate 85 (4.71 g, 12 mmol) was added, and the mixture was heated at 100° C. for 1 hour. The r.m. was concentrated in vacuo, and the residue was partitioned between water and DCM. The organic layers were separated, dried (MgSO₄), filtered and the solvents evaporated in vacuo. The product was purified by flash column chromatography (silica gel; eluents n-heptane/DCM 50/50 to 0/100). The desired fractions were collected and the solvents evaporated in vacuo to yield intermediate 86 (3.59 g, 53% yield).

Example A82

Preparation of Intermediate 87

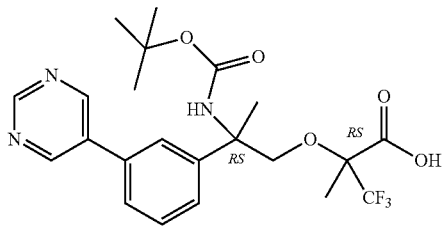

1,4-Dioxane (66 mL) and sat. aq. Na₂CO₃ (19 mL) were added to a mixture of intermediate 86 (3.59 g, 6.4 mmol), pyrimidine-5-boronic acid (1.59 g, 12.8 mmol) and tetrakis(triphenylphosphine)palladium (0.74 mg, 0.64 mmol). The mixture was stirred and N₂ flushed for a few minutes and then heated at 80° C. for 2 h. After cooling the mixture was diluted with water and washed with DCM. The aqueous layer was acidified with citric acid, and subsequently extracted with DCM. This organic layer was dried (MgSO₄), filtered and the solvents evaporated in vacuo to yield intermediate 87 (0.89 g, 30% yield).

Example A83

Preparation of Intermediate 88

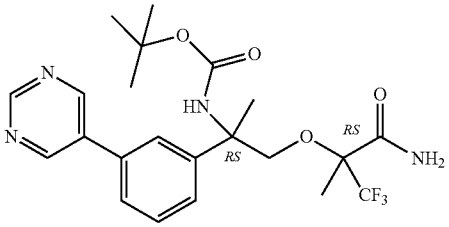

A mixture of intermediate 87 (0.85 g, 1.81 mmol), a solution of NH₃ in dioxane (0.5M, 10.8 mL, 5.4 mmol), DIPEA (0.624 mL, 3.62 mmol) in DCM (11.6 mL) was stirred at r.t, and HATU (1.03 g, 2.7 mmol) was added. The r.m. was stirred at r.t. overnight, and then the mixture was concentrated in vacuo. The residue was partitioned between DCM and a 1N aq. NaOH solution. This organic layer was dried (MgSO₄), filtered and the solvents evaporated in vacuo to yield intermediate 88 (0.94 g, quantitative yield), which was used as such in the next step.

Example A84

Preparation of Intermediate 89

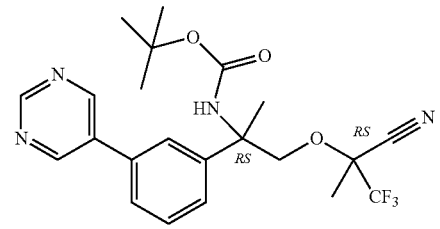

To a solution of intermediate 88 (0.1 g of 91% purity, 0.194 mmol) and pyridine (0.31 mL) in acetonitrile (2 mL) was added POCl3 (0.036 mL, 0.388 mmol) at r.t. The r.m. was stirred at r.t. overnight, and subsequently ice-water and an aq. 10% Na₂CO₃ solution (5 mL) were added. The mixture was extracted with DCM, and the combined organic layers were dried (MgSO₄), filtered and the solvents evaporated in vacuo. The residue was purified by flash column chromatography (silica gel; eluents DCM/methanol 100/0 to 90/10). The desired fractions were collected and the solvents evaporated in vacuo to yield intermediate 89 (0.058 g, 66% yield).

Example A85

Preparation of Intermediate 90: cis/trans-5R-5-(5-bromo-2-fluoro-phenyl)-5-methyl-6-trifluoromethyl-morpholine-3-thione

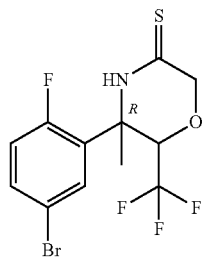

Starting from (2R)-2-amino-2-(5-bromo-2-fluorophenyl) propanoic acid (CAS 1213204-93-3), intermediate 90 was prepared according to the same reaction procedures as described for the racemic intermediate 53 in Examples A44-A49.

Example A86

Preparation of Intermediate 91 and Intermediate 92

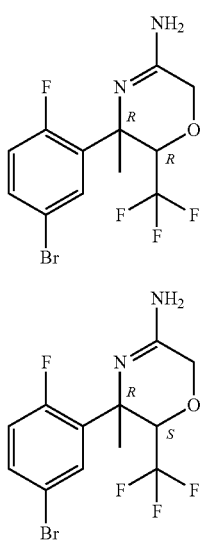

Intermediate 90 (6 g, 16.1 mmol) was dissolved in 7N ammonia in MeOH (97 mL) and the reaction mixture was stirred at 80° C. for 24 hours. Then the solvent was evaporated and the crude product purified by column chromatography (silica gel; eluents: 7 M solution of ammonia in methanol/DCM 0/100 to 2/98). The desired fractions were collected and concentrated in vacuo to yield intermediate 91 (3.4 g, 59% yield) and a fraction containing a mixture of intermediate 91 and 92 (0.75 g, 13% yield).

Example A87

Preparation of Intermediate 93

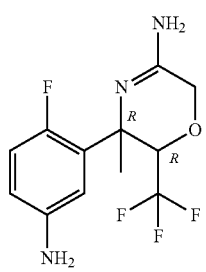

Intermediate 91 (3.4 g, 9.6 mmol) was combined with NaN₃ (1.56 g, 24 mmol), CuI (2.28 g, 12 mmol) and Na₂CO₃ (2.03 g, 19.1 mmol) in DMSO (137 mL) and the reaction was degassed. After that, N,N'-dimethylethylenediamine (1.8 mL, 16.8 mmol) was added and the mixture was heated at 110° C. until completion of the reaction, about 1 hour. The reaction mixture was filtered off and the filter cake was washed with EtOAc. Water and EtOAc were added to the filtrate and the mixture was acidified by addition of HCl (1M in H₂O). The organic layer was then separated and the aqueous layer washed with EtOAc. Then the water layer was basified with an aq. ammonia solution and extracted again with EtOAc. The combined organic layers were dried, (Na₂SO₄) filtered and concentrated in vacuo to yield intermediate 93 (2.5 g, 90% yield). Optical rotation: $[\alpha]_D^{20°}$ c.=−94.90 (0.393 g/100 ml, methanol)

Example A88

Preparation of Intermediate 94

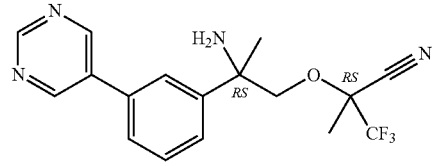 [SMILES: CC(N)(COC(C)(C#N)C(F)(F)F)c1cccc(-c2cncnc2)c1]

TFA (1.07 mL) was added to intermediate 89 (0.058 g) and the resulting mixture was stirred at r.t. for 15 min. The r.m. was concentrated in vacuo, and the residue was partitioned between DCM and an aq. sat. NaHCO₃ solution. The organic layer was separated, dried (MgSO₄), filtered and the solvents evaporated in vacuo. The residue was purified by flash column chromatography (silica gel; eluents DCM/7N ammonia in methanol 100/0 to 93/7). The desired fractions were collected and the solvents evaporated in vacuo to yield intermediate 94 (0.03 g).

Example A89

Preparation of Intermediate 95: (S)-(3-bromo-phenyl)-(2-methyl-propane-2-sulfinylimino)-acetic acid isopropyl ester

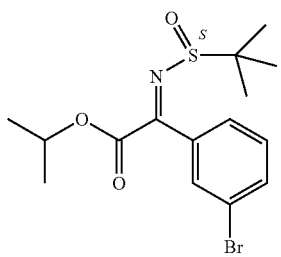

Titanium(IV) isopropoxide (69.8 mL, 233 mmol) was added to a stirred mixture of (3-bromo-phenyl)-oxo-acetic acid ethylester [(CAS 81316-36-1), 40 g, 155 mmol] and (S)-2-methyl-2-propanesulfinamide (22.6 g, 187 mmol) in n-heptane (1000 mL). The mixture was stirred at 80° C. for 24 hours. The mixture was partly concentrated in vacuo, then diluted with EtOAc. The mixture was cooled to room temperature, and water was added. The resulting mixture was filtered over a diatomaceous earth pad and rinsed with EtOAc and water. The organic layer was separated, dried (MgSO$_4$), filtered and concentrated in vacuo. The residue was purified by flash column chromatography (silica gel; eluents n-heptane/EtOAc 100/0 to 50/50). The desired fractions were collected and concentrated in vacuo to yield intermediate 95 (41.8 g 72% yield).

Example A90

Preparation of Intermediate 96

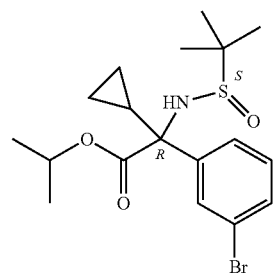

Cyclopropylmagnesium bromide (0.5 M, 214 mL, 107 mmol) was added dropwise to a stirred solution of intermediate 95 in DCM (333 mL) at −40° C. The mixture was stirred at this temperature for 40 min., and then the reaction was quenched by the addition of a sat. aq. NH4Cl solution, followed by water. The mixture was extracted with DCM. The organic layer was separated, dried (MgSO$_4$), filtered and the solvents evaporated in vacuo. The residue, containing mainly intermediate 96 (20 g), was used as such in the next step.

Example A91

Preparation of Intermediate 97

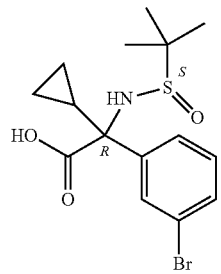

A 1M aq. NaOH solution (110 mL, 110 mmol) was added to a solution of crude intermediate 96 (20 g) in MeOH (95 mL). The resulting mixture was stirred at reflux for 4 hours. The mixture was cooled to r.t., and then partitioned between water and EtOAc. The aqueous layer was separated and neutralized by the addition of a 1M aq. HCl solution (110 mL), and then extracted with DCM. The organic layer was separated, dried (MgSO4), filtered and the solvents evaporated in vacuo. The residue was triturated with DIPE/MeCN, and the resulting solids were filtered off and dried in vacuo to yield intermediate 97 (9.8 g, 49% from intermediate 95). Optical rotation: [α$_D$ ]+36.4° (589 nm, c 0.695 w/v %, MeOH, 20° C.). The absolute configuration was determined by X-ray diffraction.

Example A92

Preparation of Intermediate 98

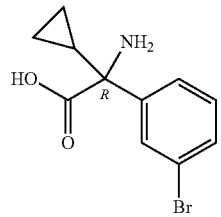

Hydrochloric acid salt

A solution of intermediate 97 (20.2 g, 54 mmol) in a 4M HCl solution in dioxane (100 mL) was stirred at r.t. for 30 min. To the resulting suspension, DIPE was added, and the precipitate was filtered off and dried in vacuo to yield intermediate 98 (20 g).

α$_D$: −68.89° (589 nm, c 0.646 w/v %, MeOH, 20° C.)

Example A93

Preparation of Intermediate 99

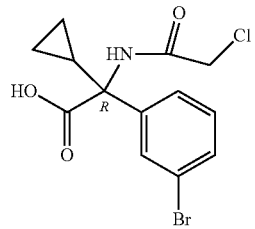

A 1M aq. NaOH solution (116.6 mL, 116.6 mmol) was added to a solution of intermediate 98 (20 g from the previous step), and the mixture was cooled on an ice-bath. To this mixture, a solution of chloroacetylchloride 11.6 mL, 148 mmol) in THF (179 mL) was added dropwise at 15° C., while simultaneously adding a solution of a 25% aq. NaOH solution to maintain the pH around 10-11. Then the reaction was acidified to pH 2 via the addition of a conc. aq. HCl solution. The mixture was partly concentrated in vacuo, and the resulting precipitate was filtered off, washed with DIPE, and dried in vacuo to give intermediate 99 (21 g).

$\alpha_D$: -6.49° (589 nm, c 0.5855 w/v %, MeOH, 20° C.)

Example A94

Preparation of Intermediate 100

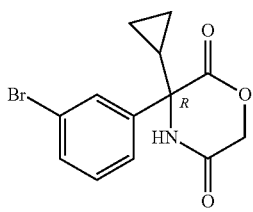

Intermediate 99 (0.7 g, 2.02 mmol) and NaHCO$_3$ (0.34 g, 4.04 mmol) were dissolved in DMF (17 mL), and the reaction mixture was stirred at 80° C. for 2 hours. The mixture was partially concentrated under reduced pressure, cooled to r.t. and then filtered over diatomaceous earth. The filtrate was concentrated in vacuo, and the residue was purified by flash column chromatography (silica gel; eluents n-heptane/EtOAc 100/0 to 50/50). The desired fractions were collected and concentrated in vacuo to yield intermediate 100 (0.54 g, 86% yield). Optical rotation: [α] -15.68° (589 nm, c 0.37 w/v %, MeOH, 20° C.)

Example A95

Preparation of Intermediate 101

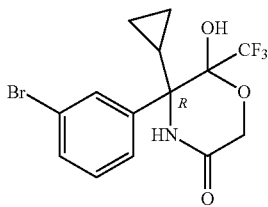

To a solution of intermediate 100 (4.2 g, 13.54 mmol) in THF (55 mL) was added TBAT (0.73 g, 1.35 mmol). Then, (trifluoromethyl)trimethyl silane (4.0 mL, 27 mmol) was added dropwise, and the r.m. was stirred at room temperature for 2 hours. The mixture was quenched with aqueous NaCl, extracted with EtOAc, the organic phase was separated, dried (MgSO$_4$) and concentrated in vacuo. The resulting oil was purified by column chromatography (silica gel; eluents DCM/EtOAc 100/0 to 0/100). The desired fractions were collected and concentrated in vacuo to yield intermediate 101 (3 g, 58% yield) as a mixture of cis and trans isomers, which was used as such in 15 the next step.

Example A96

Preparation of Intermediate 102

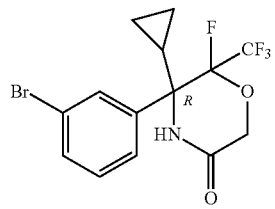

Intermediate 101 (3 g, 7.9 mmol) was dissolved in DCM (20 mL) and DAST (1.16 mL, 9.5 mmol) was added dropwise at r.t. The reaction mixture was stirred at r.t. for 1 hour and then the r.m. was concentrated under reduced pressure. The residue was partitioned between DCM and an aq. sat. NaHCO$_3$ solution. The organic layer was separated and the aqueous layer was extracted with DCM. The combined organic layers were dried (MgSO$_4$), filtered, and the solvent evaporated in vacuo. The residue was purified by flash column chromatography (silica gel; eluents n-heptane/EtOAc 100/0 to 0/100). The desired fractions were collected and concentrated in vacuo to yield intermediate 102 (2 g, 66% yield) as a mixture of cis and trans isomers, which was used as such in the next step.

Example A97

Preparation of Intermediate 103

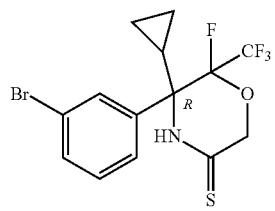

P$_2$S$_5$ (1.16 g, 5.23 mmol) was added to a solution of intermediate 102 (2 g, 5.23 mmol) in THF (43 mL) at room temperature. The mixture was stirred at 70° C. for 3 hours. Then the mixture was cooled to room temperature, filtered off and the organic solvent evaporated in vacuo. The crude product was purified by flash column chromatography (silica gel; n-heptane/DCM 80/100 to 0/100). The desired fractions were collected and evaporated in vacuo to yield intermediate 103 (1.6 g, 77% yield) as a mixture of cis and trans isomers, which was used as such in the next step.

Example A98

Preparation of Intermediate 104 and 105

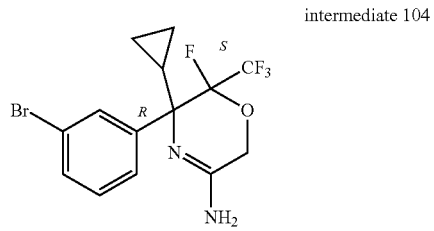

intermediate 104

-continued intermediate 105

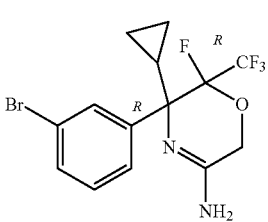

Intermediate 103 (4.2 g, 10.55 mmol), was added to a mixture of 7N ammonia in MeOH (16 mL) and an aq. NH₄OH solution (40 mL), and the reaction mixture was stirred at 140° C. for 1 hour under microwave irradiation. Then the solvent was evaporated and the residue was dissolved in DCM, dried (MgSO₄), filtered, and the solvent evaporated in vacuo. The residue was purified by flash column chromatography (silica gel; eluents n-heptane/EtOAc 100/0 to 50/50). The desired fractions were collected and concentrated in vacuo to yield intermediate 104 (2.44 g, 61% yield) and intermediate 105 (0.7 g, 17% yield).

Example A99

Preparation of Intermediate 106

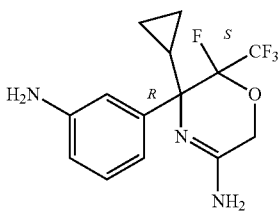

Intermediate 104 (2.44 g, 6.4 mmol) was combined with NaN₃ (1.04 g, 16 mmol), CuI (1.52 g, 8.0 mmol) and Na₂CO₃ (1.357 g, 12.8 mmol) in DMSO (92 mL) and the reaction was degassed. After that, N,N'-dimethylethylenediamine (1.2 mL, 11.2 mmol) was added and the mixture was heated at 110° C. until completion of the reaction, about 6 hours. The reaction mixture was poured in DCM. Ammonium hydroxide (28% in water) was added and the organic layer was separated and washed three times with ammonium hydroxide. Then the organic layer was dried (Mg₂SO₄), filtered and concentrated in vacuo to yield intermediate 106 (2 g, 98% yield).

Example A100

Preparation of Intermediate 107

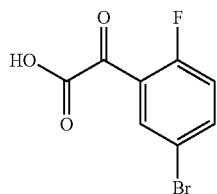 [SMILES: O=C(O)C(=O)c1cc(Br)ccc1F]

5-Bromo-2-fluorobenzaldehyde [(CAS 93777-26-5), 70 g, 322 mmol) and selenium oxide (71.6 g, 645 mmol) were dissolved in pyridine (520 mL). The reaction mixture was stirred at 100° C. for 2 hours. The solvent was evaporated and aqueous HCl 1N solution was added. The aqueous layer was extracted with EtOAc. The combined organic layers were dried (Mg₂SO₄), filtered and concentrated in vacuo to yield intermediate 107 (62 g, 78% yield), which was used as such in the next reaction.

Example A101

Preparation of Intermediate 108

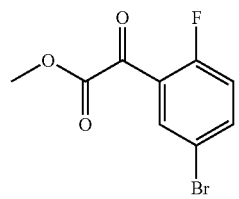

Thionyl chloride (37 mL, 510 mmol) was added dropwise to a stirred solution of intermediate 107 (42 g, 170 mmol) in MeOH (456 mL) at 0° C. The mixture was refluxed for 18 hours. The solvents were evaporated in vacuo and the residue was partitioned between saturated Na₂CO₃ and DCM. The organic layer was separated, dried (Mg₂SO₄), filtered and concentrated in vacuo to yield intermediate 108 (30 g, 68% yield) as a yellow oil.

Example A102

Preparation of Intermediate 109: (S)-(5-bromo-2-fluorophenyl)-(2-methyl-propane-2-sulfinylimino)-acetic acid isopropyl ester

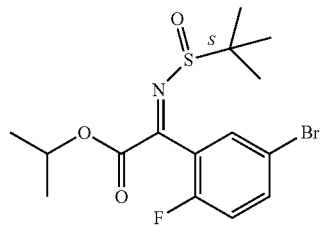

Intermediate 109 was synthesized following the same approach described in the Example A89. Starting from intermediate 108 (30 g, 115 mmol) intermediate 109 was obtained as a yellow oil (40 g, 89% yield) which was used as such in the next reaction step.

Example A103

Preparation of Intermediate 110

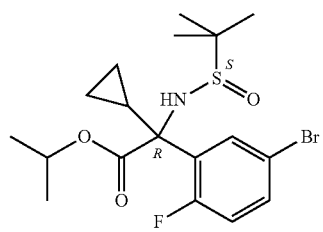

Intermediate 110 was synthesized following the same approach described in the Example A90. Starting from intermediate 109 (35 g, 89 mmol) intermediate 110 was obtained as an oil (22 g, 57% yield) which was used as such in the next reaction step.

Example A104

Preparation of Intermediate 111

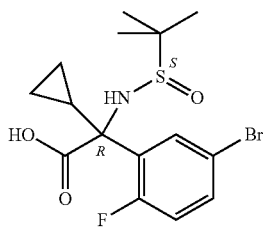

Intermediate 111 was synthesized following the same approach described in the Example A91. Starting from intermediate 110 (21 g, 48 mmol) intermediate 111 was obtained (15.5 g, 82% yield) and used as such in the next reaction step.

Example A105

Preparation of Intermediate 112

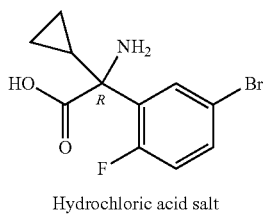

Hydrochloric acid salt

Intermediate 112 was synthesized following the same approach described in the Example A92. Starting from intermediate 111 (15.5 g, 39.5 mmol) intermediate 112 was obtained as a solid (10 g, 88% yield) which was used as such in the next reaction step.

$\alpha_D$: −65.45° (589 nm, c 0.631 w/v %, MeOH, 20° C.)

Example A106

Preparation of Intermediate 113

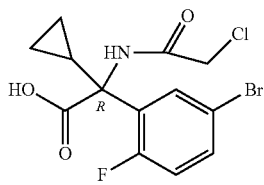

Intermediate 113 was synthesized following the same approach described in the Example A93. Starting from intermediate 112 (10 g, 27.7 mmol) intermediate 113 was obtained as a solid (10 g, 99% yield) which was used as such in the next reaction step.

$\alpha_D$: −76.4° (589 nm, c 0.5275 w/v %, MeOH, 20° C.)

Example A107

Preparation of Intermediate 114

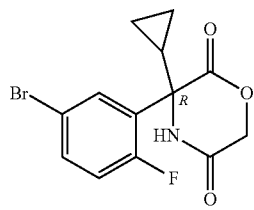

Intermediate 114 was synthesized following the same approach described in the Example A94. Starting from intermediate 113 (10 g, 27.4 mmol) intermediate 114 was obtained (7.4 g, 82% yield).

Example A108

Preparation of Intermediate 115

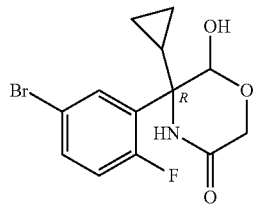

A solution of intermediate 114 (7.20 g, 21.94 mmol) in THF (107 mL) was cooled to −78° C. under N$_2$ atmosphere. Then, diisobutylaluminium hydride (25.6 mL, 30.7 mmol) was slowly added. The reaction mixture was stirred for 2 hours allowing it to slowly warm up to room temperature. The reaction mixture was cooled down to 0° C. and it was quenched by slow addition of water (8 mL). The mixture was then extracted with EtOAc, the organic layers were separated, dried (Na$_2$SO$_4$), filtered and the solvents evaporated in vacuo to yield intermediate 115 (6.5 g, 90% yield, mixture of diastereoisomers 60/40) which was used as such in the next reaction step.

Example A109

Preparation of Intermediate 116

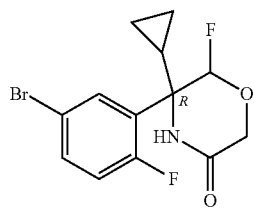

Intermediate 116 was synthesized following the same approach described in the Example A96. Starting from intermediate 115 (6.5 g, 19.69 mmol) intermediate 116 was obtained as solid material (6 g, 92% yield; mixture of diastereoisomers 63/37) which was used as such in the next reaction step.

Example A110

Preparation of Intermediate 117

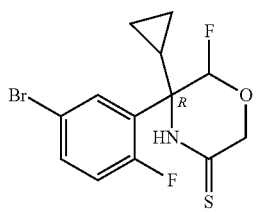

Intermediate 117 was synthesized following the same approach described in the Example A97. Starting from intermediate 116 (3 g, 9.0 mmol) intermediate 117 was obtained as a white solid (2.8 g, 89% yield).

Example A111

Preparation of Intermediate 118 and 119

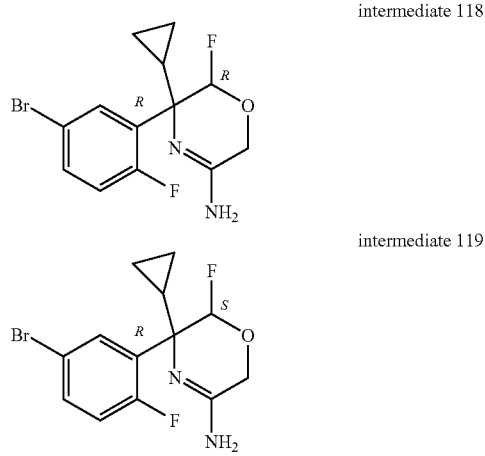

intermediate 118 intermediate 119

Intermediate 117 (6 g, 17.23 mmol) was dissolved in 7N ammonia in MeOH (277 mL) and the reaction mixture was stirred at 60° C. for 3 hours. The solvent was evaporated and additional 7N ammonia in MeOH was added (277 mL) and the mixture was stirred at 60° C. for an additional 18 hours. Then the solvent was evaporated and the crude product purified by column chromatography (silica gel; eluents: 7 M solution of ammonia in methanol/DCM 0/100 to 10/90). The desired fractions were collected and concentrated in vacuo to yield intermediate 118 (2.1 g, 37% yield) and intermediate 119 (2.5 g, 44% yield).

Example A112

Preparation of Intermediate 120

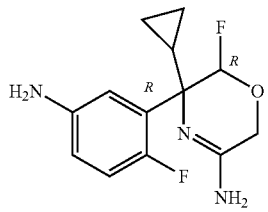

Intermediate 120 was synthesized following the same approach described in the Example A99. Starting from intermediate 118 (1.7 g, 5.133 mmol) intermediate 120 was obtained as an oil (0.81 g, 59% yield).

Example A113

Preparation of Intermediate 121

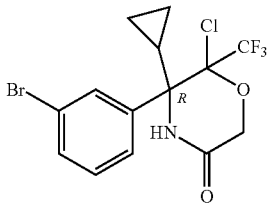

Intermediate 101 (5.5 g, 14.47 mmol) was dissolved in DCM (65 mL) and cooled to 0° C. and then thionyl chloride (1.58 mL, 21.7 mmol) was added dropwise. The reaction mixture was stirred for 30 min at 0° C. and then pyridine (1.75 mL, 21.7 mmol) was added. After 30 min. the reaction was hydrolyzed with an aqueous 1N HCl solution and then extracted with DCM. The organic layers were separated, dried (MgSO$_4$), filtered and evaporated in vacuo. The crude product was suspended in heptanes, filtered and dried at 50° C. in vacuo to yield intermediate 121 (4.5 g, 78% yield; mixture of diastereoisomers 3/1).

Example A114

Preparation of Intermediate 122

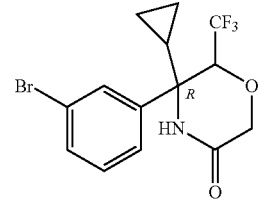

To a solution of intermediate 121 (4 g, 10.03 mmol) in acetic acid (178 mL), zinc (3.28 g, 50.17 mmol) was added. The reaction mixture was then stirred at 100° C. for 1 hour, filtered off and concentrated in vacuo. The residue was dissolved in DCM and washed with an aqueous saturated solution of NaHCO$_3$, the organic phase was separated, dried (MgSO$_4$) and the solvent concentrated in vacuo. The crude compound was purified by flash column chromatography (silica gel; 7 M solution of ammonia in methanol/DCM 0/100 to 1/99) to yield intermediate 122 as a solid (2.5 g, 68% yield).

Example A115

Preparation of Intermediate 123

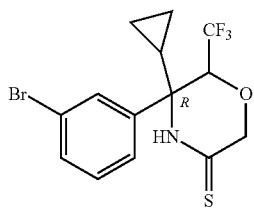

Intermediate 123 was synthesized following the same approach described in the Example A97. Starting from intermediate 122 (2.2 g, 6.04 mmol) intermediate 123 was obtained as a white solid (1.8 g) which was used as such in the next reaction step.

Example A116

Preparation of Intermediate 124 and 125

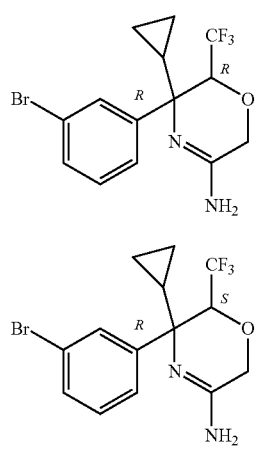

intermediate 124 intermediate 125

Intermediate 124 and intermediate 125 were synthesized following the same approach described in the Example A98. Starting from intermediate 123 (1.5 g, 3.95 mmol) intermediate 124 (0.4 g, 28% yield) and intermediate 125 (0.53 g, 37% yield) were obtained.

Example A117

Preparation of Intermediate 126

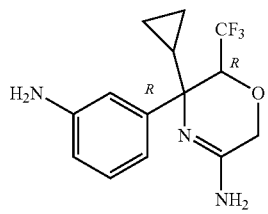

Intermediate 126 was synthesized following the same approach described in the Example A99. Starting from intermediate 124 (0.6 g, 1.652 mmol) intermediate 126 was obtained as an oil (0.35 g, 71% yield) which was used as such in the next reaction step.

Example A118

Preparation of Intermediate 127

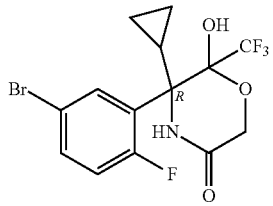

Intermediate 127 was synthesized following the same approach described in the Example A95. Starting from intermediate 114 (5 g, 15.2 mmol) intermediate 127 was obtained as an oil (4 g, 66% yield).

Example A119

Preparation of Intermediate 128

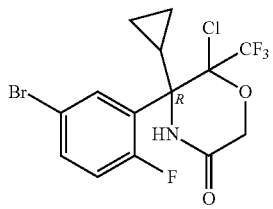

Intermediate 128 was synthesized following the same approach described in the Example A113. Starting from intermediate 127 (6.5 g, 16.3 mmol) intermediate 128 was obtained (6 g, 88% yield).

Example A120

Preparation of Intermediate 129

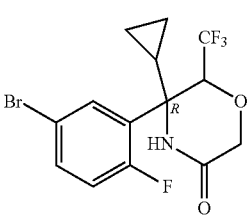

Intermediate 129 was synthesized following the same approach described in the Example A114. Starting from intermediate 128 (6.4 g, 15.3 mmol) intermediate 129 was obtained (4.1 g) and used as such in the next reaction.

Example A121

Preparation of Intermediate 130

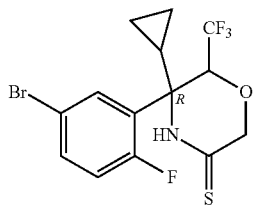

Intermediate 130 was synthesized following the same approach described in the Example A97. Starting from intermediate 129 (4.1 g, 10.7 mmol) intermediate 130 was obtained as a white solid (4 g, 93% yield).

Example A122

Preparation of Intermediate 131 and 132

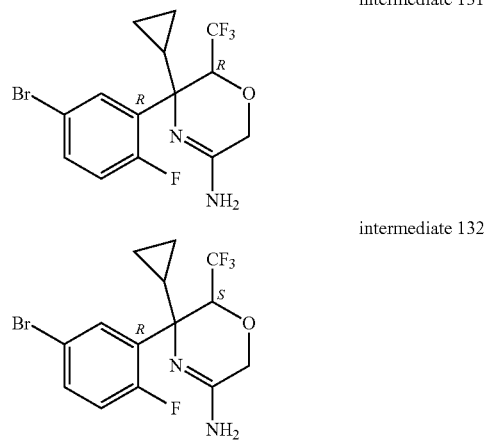

Intermediate 131 and intermediate 132 were synthesized following the same approach described in the Example A111. Starting from intermediate 130 (4 g, 10 mmol) intermediate 131 (2.5 g, 65% yield) and intermediate 132 (1 g, 26% yield) were obtained.

Example A123

Preparation of Intermediate 133

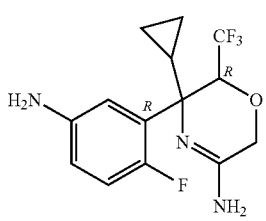

Intermediate 133 was synthesized following the same approach described in the Example A99. Starting from intermediate 131 (2.5 g, 6.6 mmol) intermediate 133 was obtained as an oil (2 g, 96% yield).

Example A124

Preparation of Intermediate 134

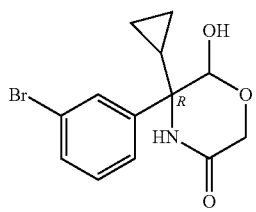

Intermediate 134 was synthesized following the same approach described in the Example A108. Starting from intermediate 100 (23.3 g, 75 mmol) intermediate 134 was obtained (19 g, 81% yield; mixture of diastereoisomers 55/45) which was used as such in the next reaction step.

Example A125

Preparation of Intermediate 135

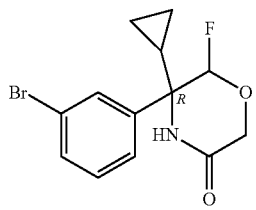

Intermediate 135 was synthesized following the same approach described in the Example A96. Starting from intermediate 134 (19 g, 60.9 mmol) intermediate 135 was obtained (15.6 g, 82% yield; mixture of diastereoisomers 72/28).

Example A126

Preparation of Intermediate 136

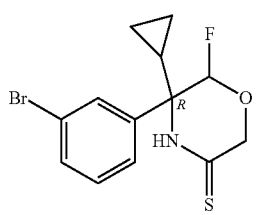

Intermediate 136 was synthesized following the same approach described in the Example A97. Starting from intermediate 135 (5.3 g, 16.87 mmol) intermediate 136 was obtained (4.5 g, 81% yield) as a mixture of diastereomers.

Example A127

Preparation of Intermediate 137

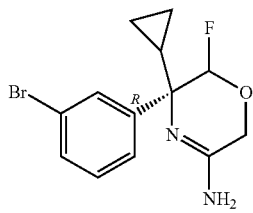

Intermediate 137 was synthesized following the same approach described in the Example A111. Starting from intermediate 136 (4 g, 12.1 mmol) intermediate 137 was obtained (3.44 g, 91% yield) as a mixture of diastereomers.

Example A128

Preparation of Intermediate 138 and intermediate 139 intermediate 138

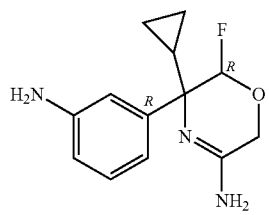

intermediate 139

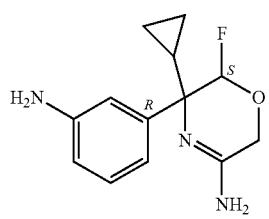

Intermediate 138 and intermediate 139 were synthesized following the same approach described in the Example A99. Starting from intermediate 137 (3 g, 9.56 mmol) intermediate 138 (0.16 g, 7% yield) and a fraction containing a mixture of intermediate 138 and 139 (1 g, 42% yield; mixture of diastereoisomers) were obtained.

Example A129

Preparation of Intermediate 140

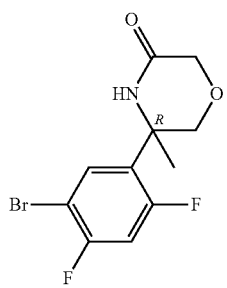

Intermediate 140 was synthesized following the same approach described in the Example A5. Starting from (2R)-2-amino-2-(5-bromo-2,4-difluoro-phenyl)propan-1-ol (7.6 g, 28.6 mmol) intermediate 140 was obtained (8 g, 96% yield) as a white solid.

Example A130

Preparation of Intermediate 141

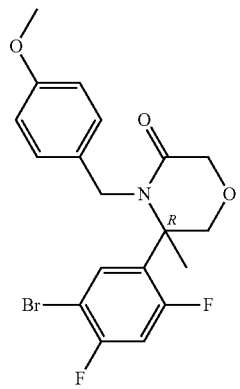

NaH (60% in mineral oil, 0.3 g, 7.84 mmol) was added to a solution of intermediate 140 (2 g, 6.5 mmol) in DMF (40 mL) at 0° C. The mixture was stirred at r.t. for 15 min. Subsequently, 4-methoxybenzyl chloride (1.23 g, 7.84 mmol) was added at 0° C. and the mixture was stirred at rt for 3 hours. The r.m. was poured into ice-water and extracted with EtOAc. The combined organic layers were dried ($MgSO_4$), filtered and the solvents evaporated in vacuo. The product was purified by flash column chromatography (silica gel; MeOH/DCM 0/100 to 3/97). The desired fractions were collected and concentrated in vacuo to yield intermediate 141 (2.6 g, 93% yield).

Example A131

Preparation of Intermediate 142

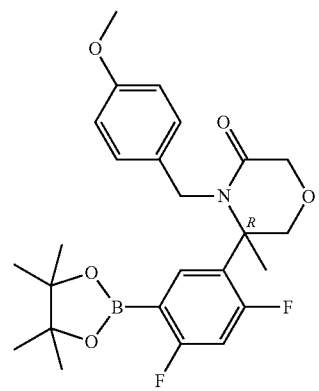

Bis(pinacolato)diboron (1.86 g, 7.32 mmol), bis(diphenylphosphino)ferrocene]dichloropalladium (II) (0.178 g, 0.244 mmol) and potassium acetate (1.8 g, 18.3 mmol) were added to a solution of intermediate 141 (2.6 g, 6.1 mmol) in 1,4-dioxane (3 mL) and DMF (0.8 mL). The reaction was then microwaved at 150° C. for 20 minutes. The reaction mixture was diluted with water and extracted with EtOAc.

The combined organic layers were dried (MgSO$_4$), filtered and the solvents evaporated in vacuo to yield intermediate 142 (2.2 g, 76% yield), which was used as such in the next reaction.

Example A132

Preparation of Intermediate 143

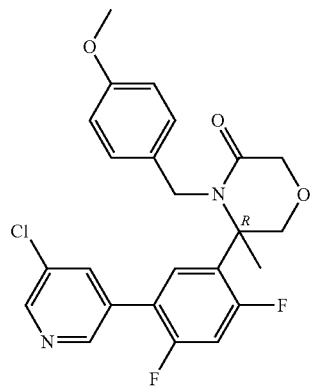

Intermediate 142 (1 g, 2.1 mmol), 3-bromo-5-chloropyridine (0.41 g, 2.1 mmol) and tetrakis(triphenylphosphine)palladium (0.24 mg, 0.21 mmol) were dissolved in 1,4-dioxane (10 mL) and sat. aq. NaHCO$_3$ (10 mL). The mixture was stirred and N$_2$ flushed for a few minutes and then heated at 80° C. for 2 h. After cooling, the mixture was diluted with water and DCM. The organic layer was separated and the aqueous layer was extracted with DCM. The combined organic layers were dried (MgSO$_4$), filtered and the solvents evaporated in vacuo. The product was purified by flash column chromatography (silica gel; 7N NH$_3$ in MeOH/DCM 0/100 to 10/90). The desired fractions were collected and concentrated in vacuo to yield intermediate 143 (0.8 g, 83% yield).

Example A133

Preparation of Intermediate 144

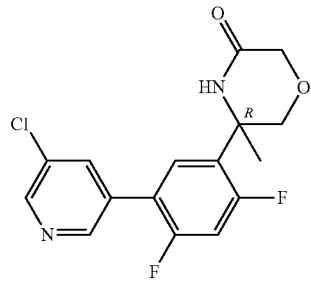

Intermediate 144 was synthesized following the same approach described in the Example A20. Starting from intermediate 143 (0.8 g, 1.7 mmol) intermediate 144 was obtained (0.35 g, 59% yield).

Example A134

Preparation of Intermediate 145

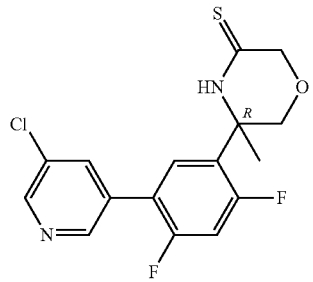

Intermediate 145 was synthesized following the same approach described in the Example A7. Starting from intermediate 144 (0.35 g, 1.03 mmol) intermediate 145 was obtained (0.37 g, 100% yield).

Example A135

Preparation of Intermediate 146

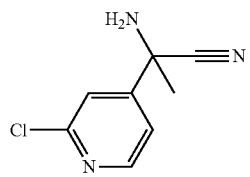

Intermediate 146 was synthesized following the same approach described in the Example A68. Starting from 4-acetyl-2-chloropyridine (10 g, 64.27 mmol) intermediate 146 was obtained (11.4 g, 98% yield) as a yellow solid.

Example A136

Preparation of Intermediate 147

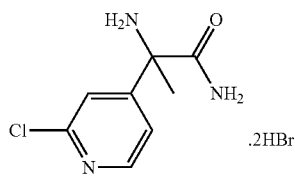

Intermediate 146 (6 g, 33.04 mmol) was dissolved in HCl (1M in AcOH, 165 mL) and HBr (33% in AcOH, 25 mL) and the mixture was stirred at 75° C. for 3 hours. After cooling to room temperature, EtOAc (250 mL) was added and the precipitate was filtered off, washed with EtOAc (100 mL) and dried in vacuo to give intermediate 147 (9.7 g, 81% yield).

Example A136

Preparation of Intermediate 148

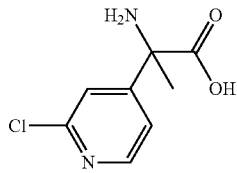

Intermediate 147 (9.7 g, 26.84 mmol) was dissolved in NaOH (1M in H₂O, 134 mL) and the mixture was stirred at room temperature for 60 hours. The reaction mixture was concentrated to half volume in vacuo and then cooled on an ice bath. The pH of the solution was adjusted to pH=7 by addition of HCl (1N in H₂O) and a white solid precipitated. The precipitate was filtered off, washed with Et₂O and dried in vacuo to give intermediate 148 (5.48 g, quant. yield) as a white solid.

Example A137

Preparation of Intermediate 149

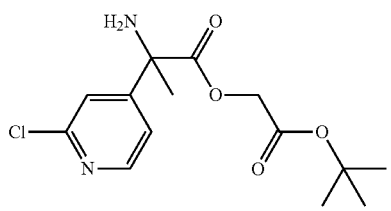 [SMILES: CC(C)(C)OC(=O)COC(=O)C(C)(N)c1ccnc(Cl)c1]

Tert-butyl chloroacetate (3.77 mL, 26.36 mmol) was added to a solution of intermediate 148 (5.29 g, 26.36 mmol) and cesium carbonate (12.89 g, 39.54 mmol) in DMF (200 mL). The mixture was stirred at room temperature for 3 hours. The mixture was diluted with water and DCM and the organic layer was separated. The aqueous layer was extracted with DCM. The combined organic layers were dried (MgSO₄), filtered and the solvents evaporated in vacuo to afford intermediate 149 (5.38 g, 65% yield) which was used as such in the next reaction step.

Example A138

Preparation of Intermediate 150

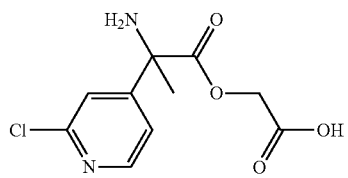

Intermediate 149 (5.38 g, 17.09 mmol) was dissolved in TFA (100 mL) and the mixture was stirred at room temperature for 15 minutes. The solvent was evaporated in vacuo providing an off-white solid which was triturated in Et₂O, filtered and dried in vacuo to give intermediate 150 (6.12 g, 96% yield) as a trifluoroacetate salt.

Example A139

Preparation of Intermediate 151

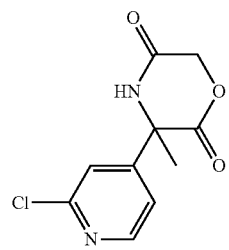 [SMILES: CC1(c2ccnc(Cl)c2)NC(=O)COC1=O]

HATU (9.7 g, 25.5 mmol) was added to a stirred solution of intermediate 150 (6 g, 23.2 mmol) and DIPEA (12 mL, 69.6 mmol) in DMF (250 mL) at room temperature. The mixture was stirred at room temperature for 15 minutes. Then the solvent was evaporated in vacuo and the residue was partitioned between DCM and sat. aq. NaHCO₃ solution. The organic layer was separated and the aqueous layer was extracted with DCM. The combined organic layers were dried (MgSO₄), filtered and the solvents evaporated in vacuo. The crude product was purified by flash column chromatography (silica gel; EtOAc/DCM). The desired fractions were collected and concentrated in vacuo to yield intermediate 151 (1.1 g, 19% yield) as white crystals.

Example A140

Preparation of Intermediate 152

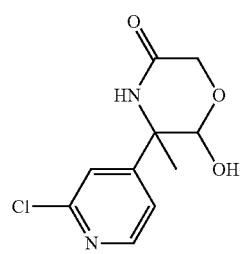 [SMILES: CC1(c2ccnc(Cl)c2)NC(=O)COC1O]

A solution of intermediate 151 (0.25 g, 1.04 mmol) in THF (5 mL) was cooled to −78° C. under N₂ atmosphere. Then, diisobutylaluminium hydride (1M in DCM, 3.12 mL, 3.12 mmol) was slowly added. The reaction mixture was stirred for 2 hours allowing it to slowly warm to room temperature. The reaction mixture was cooled to −78° C. again and extra diisobutylaluminium hydride (1M in DCM, 1.04 mL, 1.04 mmol) was added. The reaction mixture was slowly warmed to room temperature. The reaction mixture was cooled to 0° C. and it was quenched by slow addition of citric acid until acidic pH. After filtration, the aqueous layer was extracted with EtOAc. The combined organic layers were dried (Na₂SO₄), filtered and the solvents evaporated in vacuo to yield intermediate 152 (0.265 g, 68% yield) as a transparent oil, which was used as such in the next reaction step.

Example A141

Preparation of Intermediate 153

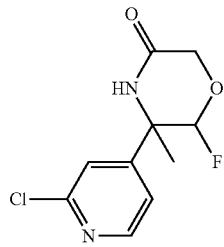 [SMILES: CC1(c2ccnc(Cl)c2)NC(=O)COC1F]

Intermediate 153 was synthesized following the same approach described in the Example A96. Starting from intermediate 152 (0.265 g, 0.71 mmol) intermediate 153 was obtained (0.164 g, 94% yield; mixture of diastereoisomers).

Example A142

Preparation of Intermediate 154

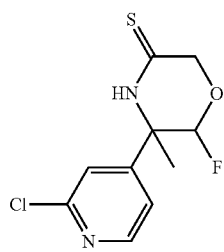 [SMILES: CC1(c2ccnc(Cl)c2)NC(=S)COC1F]

Intermediate 154 was synthesized following the same approach described in the Example A97. Starting from intermediate 153 (0.374 g, 1.53 mmol) intermediate 154 was obtained (0.389 g, 98% yield; mixture of diastereoisomers).

Example A143

Preparation of Intermediate 155

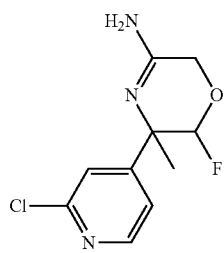

Intermediate 155 was synthesized following the same approach described in the Example A111. Starting from intermediate 154 (0.389 g, 1.49 mmol) intermediate 155 was obtained (0.25 g, 69% yield).

Example A144

Preparation of Intermediate 156

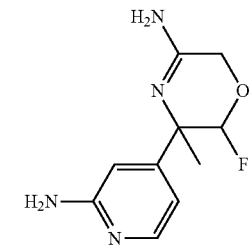

Intermediate 155 (0.1 g, 0.41 mmol) was combined with $NaN_3$ (0.067 g, 1.03 mmol), CuI (0.098 g, 0.51 mmol) and $Na_2CO_3$ (0.087 g, 0.82 mmol) in DMSO (6 mL) and the reaction was degassed. After that, N,N'-dimethylethylenediamine (0.077 mL, 0.72 mmol) was added and the mixture was heated at 110° C. until completion of the reaction, about 24 hours. The reaction mixture was filtered through cotton wool and concentrated under high vacuum to yield intermediate 156, which was used as such in the next reaction step.

Example A145

Preparation of Intermediate 157

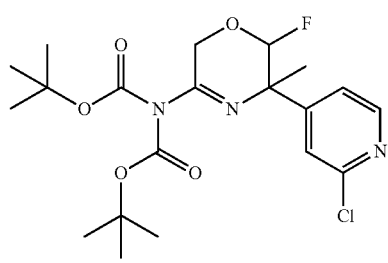 [SMILES: CC(C)(C)OC(=O)N(C(=O)OC(C)(C)C)C1=NC(C)(c2ccnc(Cl)c2)C(F)OC1]

Di-tert-butyldicarbonate (0.215 g, 0.985 mmol) was added portionwise to a stirred solution of intermediate 155 (0.12 g, 0.49 mmol), triethylamine (0.08 mL, 0.59 mmol) and 4-dimethylaminopyridine (0.006 g, 0.05 mmol) in THF (1 mL) at room temperature for three hours. The mixture was quenched with sat. aq. $NaHCO_3$ solution. The aqueous layer was extracted with EtOAc. The organic layer was dried ($MgSO_4$), filtered and the solvents evaporated in vacuo to yield intermediate 157 (0.185 g, 85% yield) which was used as such in the next reaction step.

Example A146

Preparation of Intermediate 158

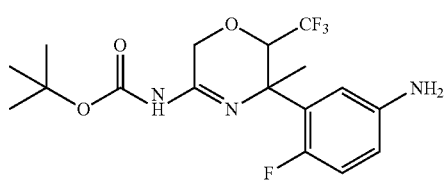 [SMILES: CC(C)(C)OC(=O)NC1=NC(C)(c2cc(N)ccc2F)C(C(F)(F)F)OC1]

Di-tert-butyldicarbonate (0.089 g, 0.412 mmol) was added portionwise to a stirred solution of intermediate 55 (0.1 g, 0.343 mmol) in DCM (2 mL) at room temperature and the r.m. was stirred at r.t. for 20 hours. The mixture was quenched with sat. aq. NaHCO₃ solution. The aqueous layer was extracted with EtOAc. The organic layer was dried (MgSO₄), filtered and the solvents evaporated in vacuo. The crude product was purified by flash column chromatography (silica gel; EtOAc/DCM 0/100 to 50/50). The desired fractions were collected and concentrated in vacuo to yield to yield intermediate 158 (0.025 g, 20% yield).

Preparation of the Final Compounds

Example B1

Preparation of compound 1: rac-5-biphenyl-3-yl-5-methyl-5,6-dihydro-2H-1,4-oxazin-3-amine trifluoroacetate salt

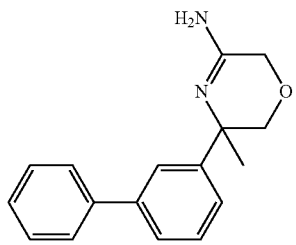 [SMILES: CC1(c2cccc(-c3ccccc3)c2)COCC(N)=N1]

MeOH (4 mL) was added to a suspension of intermediate 9 (0.2 g, 0.52 mmol), trans-(bisdicyclohexylamine)palladium diacetate [DAPCy, CAS 628339-96-8](0.006 g, 0.010 mmol), phenylboronic acid (0.076 g, 0.626 mmol) and potassium phosphate (0.44 g, 2.08 mmol). The mixture was stirred at 60° C. for 18 hours and then at 80° C. for 3 hours. After cooling the mixture was diluted with water and extracted with DCM. The organic layer was separated, dried (Na₂SO₄), filtered and the solvents evaporated in vacuo. The crude product was purified by flash column chromatography (silica gel; 7 M solution of ammonia in methanol/DCM 0/100 to 3/97). The desired fractions were collected and concentrated in vacuo. The residue was dissolved in DCM and converted into the trifluoroacetate salt. The solvents were evaporated in vacuo and the product was triturated with DIPE to yield compound 1 (0.12 g, 62% yield) as a white solid.

Example B2

Preparation of Compound 2: rac-5-(3',5'-dichlorobiphenyl-3-yl)-5-methyl-5,6-dihydro-2H-1,4-oxazin-3-amine

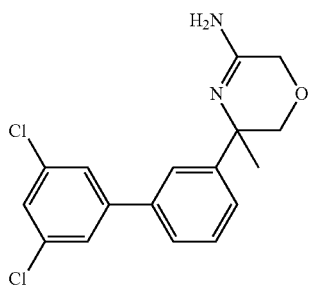 [SMILES: CC1(c2cccc(-c3cc(Cl)cc(Cl)c3)c2)COCC(N)=N1]

EtOH (5 mL) was added to a suspension of intermediate 9 (0.25 g, 0.65 mmol), trans-(bisdicyclohexylamine)palladium diacetate [DAPCy, CAS 628339-96-8](0.038 g, 0.065 mmol), potassium phosphate (0.69 g, 3.26 mmol) and 2,3-dichlorophenylboronic acid (0.19 g, 0.98 mmol). The mixture was stirred at 80° C. for 3 hours. After cooling the mixture was diluted with water and extracted with DCM. The organic layer was separated, dried (Na₂SO₄), filtered and the solvents evaporated in vacuo. The crude product was purified by flash column chromatography (silica gel; 7 M solution of ammonia in methanol/DCM 0/100 to 3/97). The desired fractions were collected and concentrated in vacuo and the residue was purified by preparative HPLC (C18 XBridge 19×100 5 um), mobile phase (gradient from 80% 0.1% NH₄CO₃H/NH₄OH pH 9 solution in Water, 20% CH₃CN to 0% 0.1% NH₄CO₃H/NH₄OH pH 9 solution in Water, 100% CH₃CN), and re-purified under other mobile phase conditions (gradient from 80% 0.1% NH₄CO₂CH₃ solution in Water, 20% CH₃CN to 0% 0.1% NH₄CO₂CH₃ solution in Water, 100% CH₃CN) to give compound 2 (0.031 g, 14% yield) as a solid.

Example B3

Preparation of Compound 3: rac-5-methyl-5-(3-pyrimidin-5-ylphenyl)-5,6-dihydro-2H-1,4-oxazin-3-amine trifluoroacetate salt

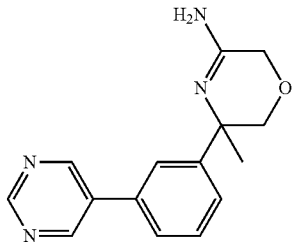 [SMILES: CC1(c2cccc(-c3cncnc3)c2)COCC(N)=N1]

1,2-Dimethoxyethane (3 mL), water (1.5 mL) and EtOH (0.5 mL) were added to a mixture of intermediate 9 (0.135 g, 0.352 mmol), pyrimidine-5-boronic acid (0.052 g, 0.423 mmol), [1,1'-bis(diphenylphosphino)ferrocene]dichloropalladium (II) (0.026 g, 0.035 mmol) and cesium carbonate (0.34 g, 1.06 mmol) in a sealed tube and under nitrogen. The mixture was stirred at 130° C. for 10 minutes under microwave irradiation. After cooling the mixture was diluted with water and saturated aqueous Na₂CO₃ and extracted with DCM. The organic layer was separated, dried (Na₂SO₄), filtered and the solvents evaporated in vacuo. The crude product was purified by flash column chromatography (silica gel; 7 M solution of ammonia in methanol/DCM 0/100 to 4/96). The desired fractions were collected and concentrated in vacuo. The residue was dissolved in DCM (5 mL) and TFA (0.2 mL) was added. The mixture was mixed well and the solvents were evaporated in vacuo. The residue was purified by flash column chromatography (silica gel; MeOH/1% solution of TFA in DCM 0/100 to 10/90). The desired fractions were collected and concentrated in vacuo and the product was triturated with Et₂O and washed with EtOAc to yield compound 3 (0.022 g, 16% yield) as a white solid.

Example B4

Preparation of Compound 4: rac-5-[3-(5-methoxy-pyridin-3-yl)phenyl]-5-methyl-5,6-dihydro-2H-1,4-oxazin-3-amine

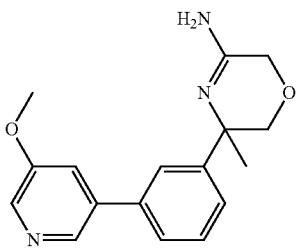 [SMILES: COc1cncc(-c2cccc(C3(C)COCC(N)=N3)c2)c1]

Method A

EtOH (5 mL) was added to a suspension of intermediate 9 (0.25 g, 0.65 mmol), trans-(bisdicyclohexylamine)palladium diacetate [DAPCy, CAS 628339-96-8] (0.038 g, 0.065 mmol), potassium phosphate (0.69 g, 3.26 mmol) and 3-methoxy-5-pyridineboronic acid pinacol ester (0.23 g, 0.98 mmol). The mixture was stirred at 80° C. for 22 hours. After cooling the mixture was diluted with water and saturated aqueous $Na_2CO_3$ and extracted with DCM. The organic layer was separated, dried ($Na_2SO_4$), filtered and the solvents evaporated in vacuo. The crude product was purified by flash column chromatography (silica gel; 7 M solution of ammonia in methanol/DCM 0/100 to 5/95). The desired fractions were collected and concentrated in vacuo. The residue was dissolved in DCM (4 mL) and TFA (0.2 mL) was added. The mixture was mixed well and the solvents were evaporated in vacuo. The residue was purified by flash column chromatography (silica gel; MeOH/1% solution of TFA in DCM 0/100 to 7/93). The desired fractions were collected and concentrated in vacuo. The product was dissolved in DCM and washed with saturated aqueous $Na_2CO_3$. The organic layer was separated, dried ($Na_2SO_4$), filtered and the solvents evaporated in vacuo and the product was triturated with heptane to yield compound 4 (0.056 g, 29% yield) as an off white solid.

Method B

A solution of 7 N $NH_3$ in MeOH (10 mL) was added to a stirred mixture of intermediate 7 (0.4 g, 1.27 mmol) and 32% aqueous ammonia (10 mL). The mixture was stirred at 60° C. for 6 hours. After cooling the mixture was diluted with water and saturated aqueous $Na_2CO_3$ and extracted with DCM. The organic layer was separated, dried ($Na_2SO_4$), filtered and the solvents evaporated in vacuo. The crude product was purified by flash column chromatography (silica gel; 7 M solution of ammonia in methanol/DCM 0/100 to 8/92). The desired fractions were collected and concentrated in vacuo and the residue was purified by circular chromatography (silica gel; MeOH/DCM 1/99 to 10/90 and then 7 M solution of ammonia in methanol/DCM 10/90). The desired fractions were collected and concentrated in vacuo to yield compound 4 (0.25 g, 66% yield) as a white solid.

Example B5

Preparation of Compound 8: (R)-5-[3-(5-methoxy-pyridin-3-yl)phenyl]-5-methyl-5,6-dihydro-2H-1,4-oxazin-3-amine

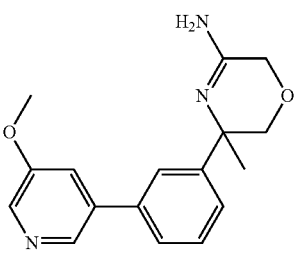 [SMILES: COc1cncc(-c2cccc(C3(C)COCC(N)=N3)c2)c1]

A sample of compound 4 (0.237 g) was separated into the corresponding enantiomers (R) and (S) by preparative SFC on (Chiralpak® Daicel AD×250 mm). Mobile phase ($CO_2$, MeOH with 0.2% $iPrNH_2$) to yield compound 8 (0.095 g) as a transparent glass that was crystallized by sonication in heptane (5 mL) with two drops of DIPE.

Example B6

Preparation of Compound 5: rac-N-[3-(5-amino-3-methyl-3,6-dihydro-2H-1,4-oxazin-3-yl)phenyl]-5-chloropyridine-2-carboxamide

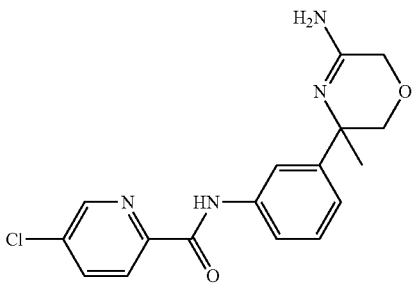 [SMILES: CC1(c2cccc(NC(=O)c3ccc(Cl)cn3)c2)COCC(N)=N1]

HATU (0.024 g, 0.064 mmol) was added to a stirred solution of intermediate 10 (0.012 g, 0.058 mmol) and 5-chloro-2-pyridinecarboxylic acid (0.010 g, 0.064 mmol) in DCM (1 mL) at room temperature. The mixture was stirred at room temperature for 2 hours. Then, $Et_3N$ (0.010 mL, 0.070 mmol) was added and the mixture was stirred for a further 15 minutes. The mixture was diluted with water and saturated aqueous $Na_2CO_3$ and extracted with DCM. The organic layer was separated, dried ($Na_2SO_4$), filtered and the solvents evaporated in vacuo. The crude product was purified by flash column chromatography (silica gel; 7 M solution of ammonia in methanol/DCM 0/100 to 5/95). The desired fractions were collected and concentrated in vacuo and the residue was purified by HPLC to yield compound 5 (0.0065 g, 31% yield).

Example B7

Preparation of Compound 6: rac-N-[3-(5-amino-3-methyl-3,6-dihydro-2H-1,4-oxazin-3-yl)phenyl]-3-fluoropyridine-2-carboxamide

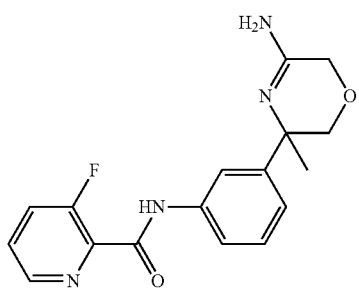 [SMILES: CC1(c2cccc(NC(=O)c3ncccc3F)c2)COCC(N)=N1]

3-Fluoropyridine-2-carboxylic acid (0.120 g, 0.853 mmol) was added to a stirred solution of intermediate 10 (0.125 g, 0.609 mmol) in DCM (5 mL) at room temperature. Then N,N-dimethylaniline (0.108 mL, 0.853 mmol) was added and after stirring at room temperature for 5 minutes HATU (0.301 g, 0.792 mmol) was added. The mixture was stirred at room temperature for 18 hours. The mixture was diluted with water and aqueous saturated $Na_2CO_3$ and extracted with DCM. The organic layer was separated, dried ($Na_2SO_4$), filtered and the solvents evaporated in vacuo. The crude product was purified by flash column chromatography (silica gel; 7 M solution of ammonia in methanol/DCM 0/100 to 5/95). The desired fractions were collected and concentrated in vacuo and the residue was triturated with DIPE to yield compound 6 (0.133 g, 66% yield) as a white solid.

Example B8

Preparation of Compound 9: rac-N-{3-[5-amino-6-fluoro-3-methyl-6-(trifluoromethyl)-3,6-dihydro-2H-1,4-oxazin-3-yl]phenyl}-5-chloropyridine-2-carboxamide

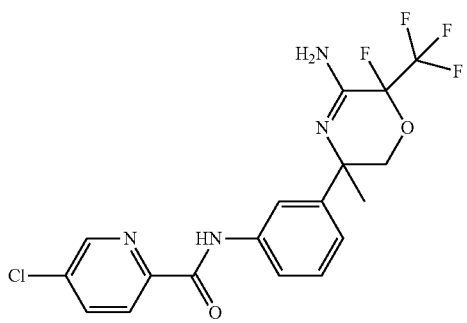 [SMILES: CC1(c2cccc(NC(=O)c3ccc(Cl)cn3)c2)COC(F)(C(F)(F)F)C(N)=N1]

Potassium phosphate tribasic (anhydrous) (0.12 g, 0.56 mmol), copper(I) iodide (0.003 g, 0.014 mmol) and (1R,2R)-(−)-1,2-diaminocyclohexane (0.003 g, 0.028 mmol) were added to a stirred solution of intermediate 14 (0.1 g, 0.28 mmol) and 5-chloro-2-pyridinecarboxamide (0.044 g, 0.28 mmol) in degassed DMF (1 mL) in a sealed tube and under nitrogen. The mixture was stirred at 180° C. for 135 minutes under microwave irradiation. The mixture was diluted with water (10 mL), aqueous saturated $NH_4OH$ (20 mL), DCM (50 mL) and stirred for 1 hour at room temperature. The organic layer was separated and the aqueous layer was extracted with DCM. The combined organic layers were dried ($MgSO_4$), filtered and the solvents evaporated in vacuo. The crude product was purified by flash column chromatography (silica gel; 7 M solution of ammonia in methanol/DCM 0.5/99.5). The desired fractions were collected and concentrated in vacuo. The residue was crystallized with $Et_2O$ (0.5 mL). Then, heptane (2 mL) was added and the resulting mixture was shaken in a sealed vial for 2 hours at 60° C. After cooling to room temperature the crystals were filtered and dried in vacuo to yield as a single diastereoisomer compound 9 (0.015 g, 13% yield) as white crystals.

Example B9

Preparation of Compound 16: rac-6-[3-(5-methoxy-pyridin-3-yl)phenyl]-6-methyl-4-oxa-7-azaspiro[2.5]oct-7-en-8-amine

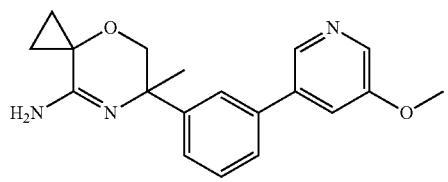 [SMILES: COc1cncc(-c2cccc(C3(C)COC4(CC4)C(N)=N3)c2)c1]

A mixture of intermediate 22 (0.023 g, 0.068 mmol) and 2 M $NH_3$ in MeOH (5 mL) was heated in a sealed tube at 120° C. for 7 days. Then the solvent was evaporated in vacuo and the residue was purified by flash column chromatography (silica gel; 7 M solution of ammonia in methanol/DCM 0/100 to 10/90). The desired fractions were collected and concentrated in vacuo to yield compound 16 (0.009 g, 40% yield) as a yellow glass.

Example B10

Preparation of Compound 12: (R)—N-[3-(5-amino-3-methyl-3,6-dihydro-2H-1,4-oxazin-3-yl)phenyl]-5-chloropyridine-2-carboxamide

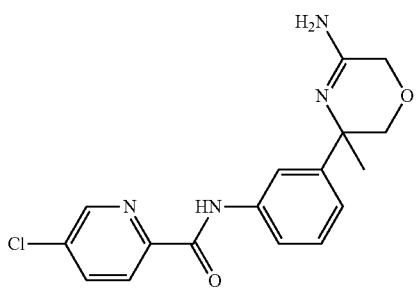 [SMILES: CC1(c2cccc(NC(=O)c3ccc(Cl)cn3)c2)COCC(N)=N1]

5-Chloro-2-pyridinecarboxylic acid (0.27 g, 1.717 mmol) was added to a stirred solution of intermediate 26 (0.235 g, 1.145 mmol) in DCM (10 mL) at room temperature. Then, N,N-dimethylaniline (0.218 mL, 1.717 mmol) was added and after stirring for 5 minutes at room temperature HATU (0.500 g, 1.317 mmol) was added. The mixture was stirred at room temperature for 5 hours. The mixture was diluted with water and saturated aqueous $Na_2CO_3$ and extracted with DCM. The organic layer was separated, dried ($Na_2SO_4$), filtered and the solvents evaporated in vacuo. The crude product was purified by flash column chromatography (silica gel; 7 M solution of ammonia in methanol/DCM 0/100 to 4/96). The desired fractions were collected and concentrated in vacuo. The resulting product was triturated with DIPE, filtered and dried. The product was purified again by flash column chromatography (silica gel; 7 M solution of ammonia in methanol/EtOAc 0/100 to 4/96). The desired fractions were collected and concentrated in vacuo to yield compound 12 (0.16 g, 41% yield).

Example B11

Preparation of Compound 15: (R*,R*)—N-{3-[5-amino-6-fluoro-3-methyl-6-(trifluoromethyl)-3,6-dihydro-2H-1,4-oxazin-3-yl]phenyl}-5-chloropyridine-2-carboxamide

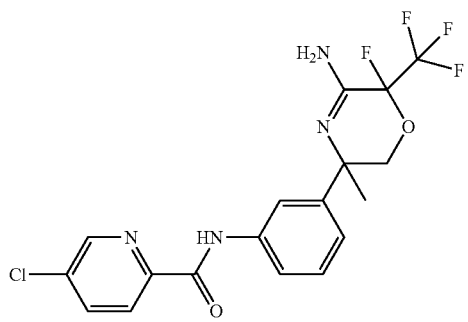 [SMILES: CC1(c2cccc(NC(=O)c3ccc(Cl)cn3)c2)COC(F)(C(F)(F)F)C(N)=N1]

A sample of compound 9 (0.01 g) was separated into the corresponding enantiomers (R,R) and (S,S) by preparative SFC (Chiralpak® Daicel OD 20×250 mm, mobile phase $CO_2$, iPrOH with 0.2% iPrNH$_2$) to yield compound 15 (0.0038 g) as white crystals.

Example B12

Preparation of Compound 18: trans-rac-5-[3-(5-methoxypyridin-3-yl)phenyl]-2,5-dimethyl-5,6-dihydro-2H-1,4-oxazin-3-amine and compound 19: cis-rac-5-[3-(5-methoxypyridin-3-yl)phenyl]-2,5-dimethyl-5,6-dihydro-2H-1,4-oxazin-3-amine

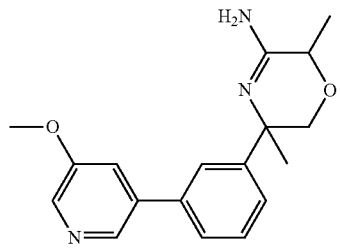

EtOH (3 mL) was added to a suspension of intermediate 30 (0.1 g, 0.25 mmol), trans-(bisdicyclohexylamine)palladium diacetate [DAPCy, CAS 628339-96-8](0.015 g, 0.025 mmol), potassium phosphate (0.27 g, 1.26 mmol) and 3-methoxy-5-pyridineboronic acid pinacol ester (0.077 g, 0.50 mmol). The mixture was stirred at 80° C. for 18 hours. After cooling the mixture was diluted with water and saturated aqueous $Na_2CO_3$ and extracted with DCM. The organic layer was separated, dried ($Na_2SO_4$), filtered and the solvents evaporated in vacuo. The crude product was purified by flash column chromatography (silica gel; 7 M solution of ammonia in methanol/DCM 0/100 to 4/96). The desired fractions were collected and concentrated in vacuo and the residue was purified by preparative HPLC (C18 XBridge 19×100 5 um), mobile phase (gradient from 80% 0.1% $NH_4CO_3H/NH_4OH$ pH 9 solution in Water, 20% $CH_3CN$ to 0% 0.1% $NH_4CO_3H/NH_4OH$ pH 9 solution in Water, 100% $CH_3CN$)
to yield compound 18 (0.0046 g, 6% yield; trans isomer) as a white solid. The remaining fractions were combined and re-purified by preparative HPLC (same previous conditions) to yield a residue which was further diluted with water and sat. $Na_2CO_3$ and extracted with DCM. The organic layer was separated, dried ($Na_2SO_4$), filtered and the solvent evaporated in vacuo to yield compound 19 (0.011 g, 14% yield; cis isomer) as a white solid.

Example B13

Preparation of Compound 20: trans-rac-N-[3-(5-Amino-3,6-dimethyl-3,6-dihydro-2H-1,4-oxazin-3-yl)phenyl]-5-chloropyridine-2-carboxamide and compound 151: cis-rac-N-[3-(5-Amino-3,6-dimethyl-3,6-dihydro-2H-1,4-oxazin-3-yl)phenyl]-5-chloropyridine-2-carboxamide

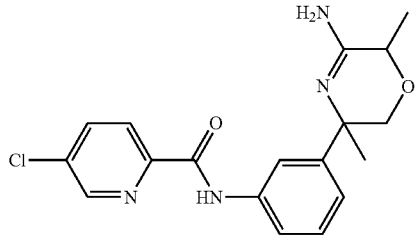 [SMILES: CC1OCC(C)(c2cccc(NC(=O)c3ccc(Cl)cn3)c2)N=C1N]

5-Chloro-2-pyridinecarboxylic acid (0.180 g, 1.14 mmol) was added to a stirred solution intermediate 32 (0.2 g, 0.91 mmol) in DCM (8 mL) at room temperature. Then N,N-dimethylaniline (0.15 mL, 1.19 mmol) was added and after stirring at room temperature for 5 minutes HATU (0.382 g, 1 mmol) was added. The mixture was stirred at room temperature for 5 hours. The mixture was diluted with water and saturated aqueous $Na_2CO_3$ and extracted with DCM. The organic layer was separated, dried ($Na_2SO_4$), filtered and the solvents evaporated in vacuo. The crude product was purified by flash column chromatography (silica gel; 7 M solution of ammonia in methanol/DCM 0/100 to 4/96). The desired fractions were collected and concentrated 10 in vacuo and the residue was triturated with heptane to yield compound 20 (0.129 g, 39% yield; trans isomer) as a white solid. The remaining fractions were combined and re-purified flash column chromatography (silica gel; 7 M solution of ammonia in methanol/DCM 0/100 to 3/97). The desired fractions were collected and concentrated in vacuo to yield compound 151 (0.049 g, 15% yield; cis isomer) as a white solid.

Example B14

Preparation of Compound 82: (S*,S*)-5-(2,4-difluoro-5-pyrimidin-5-ylphenyl)-6-fluoro-5-methyl-5,6-dihydro-2H-1,4-oxazin-3-amine and compound 148: (R*,R*)-5-(2,4-difluoro-5-pyrimidin-5-ylphenyl)-6-fluoro-5-methyl-5,6-dihydro-2H-1,4-oxazin-3-amine and compound 83: trans-rac-5-(2,4-difluoro-5-pyrimidin-5-ylphenyl)-6-fluoro-5-methyl-5,6-dihydro-2H-1,4-oxazin-3-amine

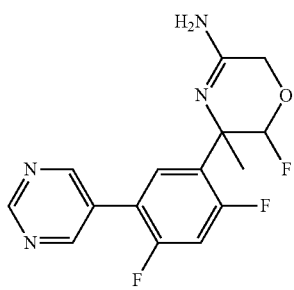 [SMILES: CC1(c2cc(-c3cncnc3)c(F)cc2F)N=C(N)COC1F]

Intermediate 39 (0.25 g, 0.774 mmol), 5-pyrimidinylboronic acid (0.143 g, 1.16 mmol) and tetrakis(triphenylphosphine)palladium(0) (0.089 g, 0.077 mmol) were dissolved in a mixture of 1,4-dioxane (11 mL) and aqueous $NaHCO_3$ (sat. sol., 7.5 mL). The resulting mixture was flushed with $N_2$ and then heated at 80° C. for 2 hours. The reaction mixture was then diluted with water and then extracted with DCM. The organic layer was separated, dried ($Na_2SO_4$), filtered and the solvents evaporated in vacuo. The crude product was purified by flash column chromatography (silica gel; 7 M solution of ammonia in methanol/DCM 0/100 to 10/90). The desired fractions were collected and concentrated in vacuo to yield compound 83 (0.18 g, 72%). This racemic compound was then purified by preparative SFC on Chiralpak Diacel AD (30×250 mm), mobile phase ($CO_2$, iPrOH with 0.2% $iPrNH_2$), yielding compound 82 and compound 148 (0.050 g, 20% yield) as pure enantiomers (both as solid compounds).

Example B15

Preparation of Compound 91: trans-rac-N-[3-(5-amino-2-fluoro-3-methyl-3,6-dihydro-2H-1,4-oxazin-3-yl)phenyl]-5-chloropyridine-2-carboxamide and compound 85: (S*,S*)—N-[3-(5-amino-2-fluoro-3-methyl-3,6-dihydro-2H-1,4-oxazin-3-yl)phenyl]-5-chloropyridine-2-carboxamide and compound 86: (R*,R*)—N-[3-(5-amino-2-fluoro-3-methyl-3,6-dihydro-2H-1,4-oxazin-3-yl)phenyl]-5-chloropyridine-2-carboxamide

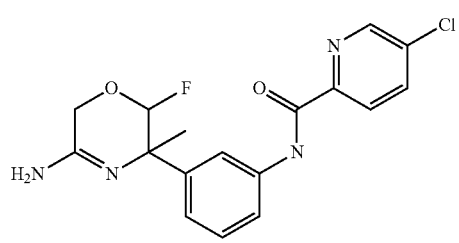 [SMILES: CC1(c2cccc(NC(=O)c3ccc(Cl)cn3)c2)N=C(N)COC1F]

5-Chloro-2-pyridinecarboxylic acid (0.176 g, 1.12 mmol) was dissolved in MeOH (5 mL) and DMTMM (0.37 g, 1.34 mmol) was added. After stirring the mixture for 5 minutes, a solution of intermediate 47 (0.25 g, 1.12 mmol) in MeOH (5 mL) was added at 0° C., and the mixture was stirred for an additional 16 h. After that, the reaction mixture was quenched with NaOH (1M in $H_2O$) at 0° C. and then extracted with EtOAc. The organic layer was washed with brine, then separated, dried ($MgSO_4$) and the solvent evaporated in vacuo. The crude material was purified by flash column chromatography (silica gel; 7 M solution of ammonia in methanol/DCM 0/100 to 5/95), the desired fractions were collected and the solvent evaporated in vacuo to afford compound 91 (0.215 g, 53%). Compound 91 was then purified by preparative SFC on Chiralpak Diacel AD (20×250 mm), mobile phase ($CO_2$, iPrOH with 0.2% $iPrNH_2$), the desired fractions were collected, evaporated, dissolved in MeOH and evaporated again yielding compound 85 (0.061 g, 15% yield) and compound 86 (0.064 g, 15.8% yield) as pure enantiomers (both as solid compounds).

Example B16

Preparation of Compound 107: trans-rac-N-{3-[5-amino-3-methyl-2-(trifluoromethyl)-3,6-dihydro-2H-1,4-oxazin-3-yl]-4-fluorophenyl}-5-chloropyridine-2-carboxamide

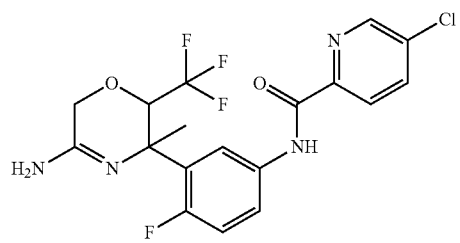 [SMILES: CC1(c2cc(NC(=O)c3ccc(Cl)cn3)ccc2F)N=C(N)COC1C(F)(F)F]

Compound of the Example B16, was synthesized following the same approach described in the Example B15. Starting from intermediate 55 (0.2 g, 0.24 mmol), compound 107 (0.085 g, 82% yield) was obtained as solid compound.

Example B17

Preparation of trans-rac-N-{3-[5-amino-2-fluoro-3-methyl-2-(trifluoromethyl)-3,6-dihydro-2H-1,4-oxazin-3-yl]-4-fluorophenyl}-5-chloropyridine-2-carboxamide and compound 110: (2S*,3R*)—N-{3-[5-amino-2-fluoro-3-methyl-2-(trifluoromethyl)-3,6-dihydro-2H-1,4-oxazin-3-yl]-4-fluorophenyl}-5-chloropyridine-2-carboxamide and compound 109: (2R*,3S*)—N-{3-[5-amino-2-fluoro-3-methyl-2-(trifluoromethyl)-3,6-dihydro-2H-1,4-oxazin-3-yl]-4-fluorophenyl}-5-chloropyridine-2-carboxamide

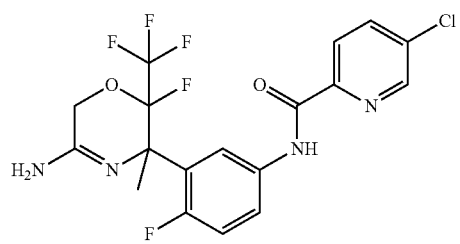 [SMILES: CC1(c2cc(NC(=O)c3ccc(Cl)cn3)ccc2F)N=C(N)COC1(F)C(F)(F)F]

Compound 110 and compound 109, were synthesized following the same approach described in the Example B15. Starting from intermediate 60 (0.465 g; 1.5 mmol), derivative trans-rac-5-chloro-pyridine-2-carboxylic acid[3-(5-amino-2-fluoro-3-methyl-2-trifluoromethyl-3,6-dihydro-2H-[1,4]oxazin-3-yl)-4-fluoro-phenyl]-amide (0.55 g, 79%) was obtained. This racemic compound was then further purified by preparative SFC on Chiralpak Diacel AD (20× 250 mm), mobile phase (CO$_2$, iPrOH with 0.2% iPrNH$_2$), to yield compound 110 (0.2 g, 29.5%) and compound 109. This last derivative was then dissolved in Et$_2$O and converted into the hydrochloric acid salt by adding HCl (1M in Et$_2$O, 1 mL). The solvent was evaporated to yield compound 109 as hydrochloric salt (0.19 g, 24% yield).

Example B18

Preparation of Compound 152: rac-5-[3-(5-methoxypyridin-3-yl)phenyl]-5-(trifluoromethyl)-5,6-dihydro-2H-1,4-oxazin-3-amine

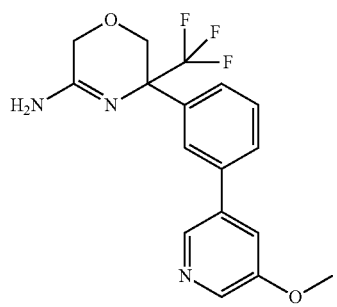 [SMILES: COc1cncc(-c2cccc(C3(C(F)(F)F)COCC(N)=N3)c2)c1]

Compound 152 was synthesized following the same approach described in Example B4 method B. Thus starting from intermediate 66 (0.08 g, 0.217 mmol), compound 152 was obtained as a white solid (0.06 g, 78.6% yield).

Example B19

Preparation of Compound 153: rac-N-[3-(5-Amino-3-cyclopropyl-3,6-dihydro-2H-1,4-oxazin-3-yl)phenyl]-5-chloropyridine-2-carboxamide, and the corresponding enantiomeric compounds 195 and 196

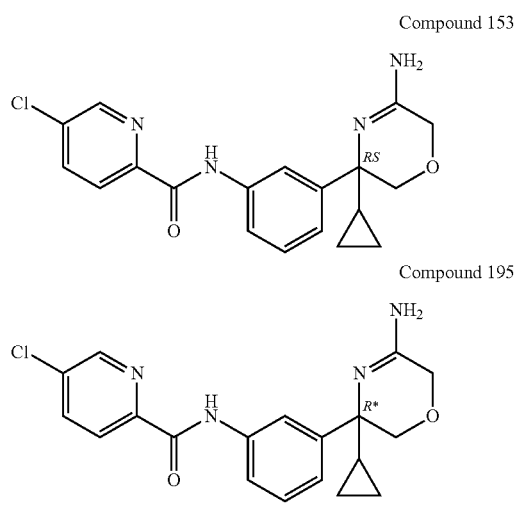

Compound 153

Compound 195

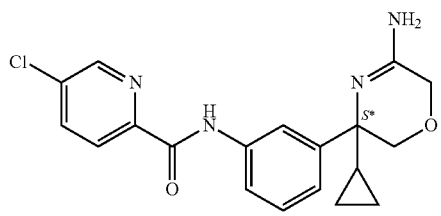

Compound 196

Compound 153 was synthesized following the same approach described in Example B15. Thus starting from intermediate 72 (0.09 g, 0.385 mmol), compound 153 was obtained as a white solid (0.067 g, 47.4% yield).

This racemic compound was then purified by preparative SFC on Chiralpak Daicel OD-H5 µM (20×250 mm), mobile phase (CO$_2$, EtOH with 0.3% iPrNH$_2$), yielding the two enantiopure fractions (0.027 g each). Both fractions were purified further via flash column chromatography (silica gel; 7 M solution of ammonia in methanol/DCM 0/100 to 3/97). The desired fractions for each enantiomer were collected and concentrated in vacuo to yield compound 195 (0.015 g), and compound 196 (0.013 g) after trituration from n-heptane.

Example B21

Preparation of Compound 166: (2R,3R)—N-{3-[5-amino-3-methyl-2-(trifluoromethyl)-3,6-dihydro-2H-1,4-oxazin-3-yl]-4-fluorophenyl}-5-methoxypyrazine-2-carboxamide

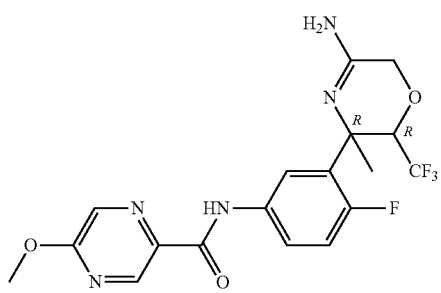

5-Methoxypyrazine-2-carboxylic acid (0.106 g, 0.69 mmol) was dissolved in MeOH (14 mL) and DMTMM (0.24 g, 0.82 mmol) was added. After stirring the mixture for 5 minutes, a solution of intermediate 93 (0.20 g, 0.687 mmol) in MeOH (14 mL) was added at 0° C., and the mixture was stirred for an additional 6 h. The solvent was evaporated in vacuo. The crude material was purified by flash column chromatography (silica gel; 7 M solution of ammonia in methanol/DCM 0/100 to 5/95), the desired fractions were collected and the solvent evaporated in vacuo. The residue was triturated with DIPE to give compound 166 (0.190 g, 65% yield).

Example B22

Preparation of Compound 161: trans-rac-2,5-dimethyl-5-(3-pyrimidin-5-ylphenyl)-2-(trifluoromethyl)-5,6-dihydro-2H-1,4-oxazin-3-amine and compound 162: cis-rac-2,5-dimethyl-5-(3-pyrimidin-5-ylphenyl)-2-(trifluoromethyl)-5,6-dihydro-2H-1,4-oxazin-3-amine

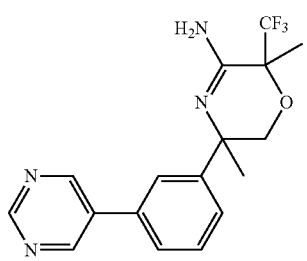

Compound 161: racemic cis
Compound 162: racemic trans

A 2M solution of trimethylaluminum in toluene (42 μL, 0.084 mmol) was added to a stirred solution of intermediate 94 (0.03 g, 0.084 mmol) in toluene (1.5 mL) at 0° C. The mixture was heated at 100° C. for 1 hour, then cooled to r.t. A sat. aq. Na₂CO₃ solution was added, the mixture was filtered, and the filtrate was extracted with EtOAc. The combined organic layers were separated, dried (Na₂SO₄), filtered and the solvents evaporated in vacuo. The crude product was purified by flash column chromatography (silica gel; 7 M solution of ammonia in methanol/DCM 0/100 to 10/90). The desired fractions were collected and concentrated in vacuo. The residue was purified further by preparative HPLC (RP Sunfire Prep C18 OBD-10 μM 30×150 mm), mobile phase (a gradient from 0.5% NH₄OAc solution in water+10% MeCN to MeCN). The two fractions containing compound 161 and 162, respectively, were each purified further via preparative HPLC (RP Sunfire Prep C18 OBD-10 μM 30×150 mm), mobile phase (a gradient from 0.25% NH₄HCO₃ solution in water to MeCN) to yield compound 161 (0.011 g, 38% yield) and compound 162 (0.013 g, 44% yield).

Example B23

Preparation of Compound 199: (2S,3R)—N-{3-[5-amino-3-cyclopropyl-2-fluoro-2-(trifluoromethyl)-3,6-dihydro-2H-1,4-oxazin-3-yl]phenyl}-5-cyanopyridine-2-carboxamide

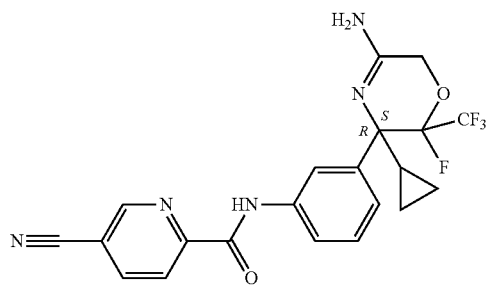

5-Cyanopyridine-2-carboxylic acid (0.182 g, 1.23 mmol) was dissolved in MeOH (24 mL) and DMTMM (0.435 g, 1.48 mmol) was added. After stirring the mixture for 5 minutes, a solution of intermediate 106 (0.39 g, 1.23 mmol) in MeOH (24 mL) was added at 0° C., and the mixture was stirred for an additional 4 h. The mixture was partitioned between DCM and a sat. aq. Na₂CO₃ solution. The combined organic layers were separated, dried (MgSO₄), filtered and the solvents evaporated in vacuo. The crude product was purified by flash column chromatography (silica gel; methanol/DCM 0/100 to 5/95). The desired fractions were collected and concentrated in vacuo. The residue was crystallized from DIPE to yield compound 199 (0.235 g, 43% yield).

Example B24

Preparation of Compound 214: (2R,3R)—N-[3-(5-amino-3-cyclopropyl-2-fluoro-3,6-dihydro-2H-1,4-oxazin-3-yl)-4-fluorophenyl]-5-cyanopyridine-2-carboxamide

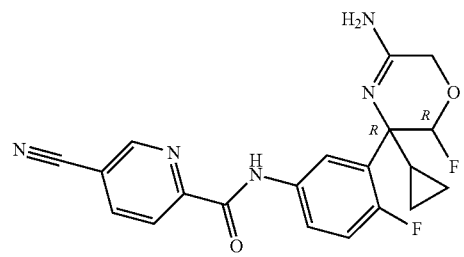

5-Cyanopyridine-2-carboxylic acid (0.088 g, 0.6 mmol) was dissolved in MeOH (25 mL) and DMTMM (0.211 g, 0.718 mmol) was added. After stirring the mixture for 5 minutes, a solution of intermediate 120 (0.160 g, 0.6 mmol) in MeOH (10 mL) was added at 0° C., and the mixture was stirred for an additional 6 h. The solvent was evaporated in vacuo. The crude material was purified by flash column chromatography (silica gel; 7 M solution of ammonia in methanol/DCM 0/100 to 5/95), the desired fractions were collected and the solvent evaporated in vacuo. The residue was triturated with DIPE to give compound 214 (0.05 g, 21% yield).

Example B25

Preparation of Compound 224: (5R,6S)-5-cyclopropyl-6-fluoro-5-(2-fluoro-5-pyrimidin-5-ylphenyl)-5,6-dihydro-2H-1,4-oxazin-3-amine

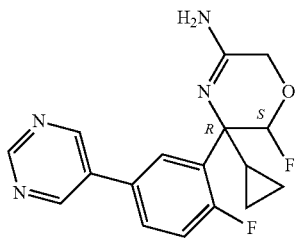

Intermediate 119 (0.3 g, 0.906 mmol), 5-pyrimidinylboronic acid (0.168 g, 1.36 mmol) and tetrakis(triphenylphos-

Example B26

Preparation of Compound 225: (2R,3R)—N-{3-[5-amino-3-cyclopropyl-2-(trifluoromethyl)-3,6-dihydro-2H-1,4-oxazin-3-yl]phenyl}-5-cyanopyridine-2-carboxamide

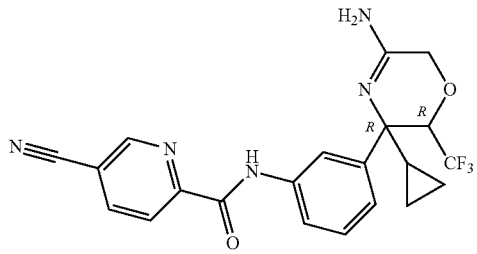

5-Cyano-2-pyridinecarboxylic acid (0.413 g, 1.169 mmol) was dissolved in MeOH (46 mL) and DMTMM (0.413 g, 1.4 mmol) was added. After stirring the mixture for 5 minutes, a solution of intermediate 126 (0.35 g, 1.169 mmol) in MeOH (15 mL) was added at 0° C., and the mixture was stirred for an additional 4 h. The solvent was evaporated in vacuo. The crude product was purified by flash column chromatography (silica gel; methanol/DCM 0/100 to 2/98). The desired fractions were collected and concentrated in vacuo. The residue was then dissolved in Et$_2$O and converted to the HCl salt by addition of HCl (1M in Et$_2$O). The solvent was evaporated and the resulting solid was crystallized from Et$_2$O to yield compound 225 (0.1 g, 18% yield) as hydrochloric salt.

Example B27

Preparation of Compound 229: (2R,3R)—N-{3-[5-amino-3-cyclopropyl-2-(trifluoromethyl)-3,6-dihydro-2H-1,4-oxazin-3-yl]-4-fluorophenyl}-5-cyanopyridine-2-carboxamide

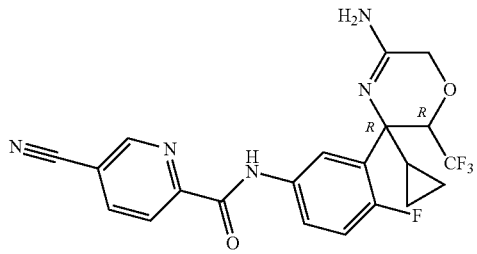

5-Cyano-2-pyridinecarboxylic acid (0.102 g, 0.693 mmol) was dissolved in MeOH (28 mL) and DMTMM (0.245 g, 0.832 mmol) was added. After stirring the mixture for 5 minutes, a solution of intermediate 133 (0.22 g, 0.693 mmol) in MeOH (10 mL) was added at 0° C., and the mixture was stirred for an additional 4 h. The solvent was evaporated in vacuo. The crude product was purified by flash column chromatography (silica gel; methanol/DCM 0/100 to 5/95). The desired fractions were collected and concentrated in vacuo. The residue was crystallized from DIPE to yield compound 229 (0.17 g, 54% yield).

Example B28

Preparation of Compound 249: (2S,3R)—N-[3-(5-amino-3-cyclopropyl-2-fluoro-3,6-dihydro-2H-1,4-oxazin-3-yl)phenyl]-5-chloro-3-fluoropyridine-2-carboxamide and compound 250: (2R,3R)—N-[3-(5-amino-3-cyclopropyl-2-fluoro-3,6-dihydro-2H-1,4-oxazin-3-yl)phenyl]-5-chloro-3-fluoropyridine-2-carboxamide

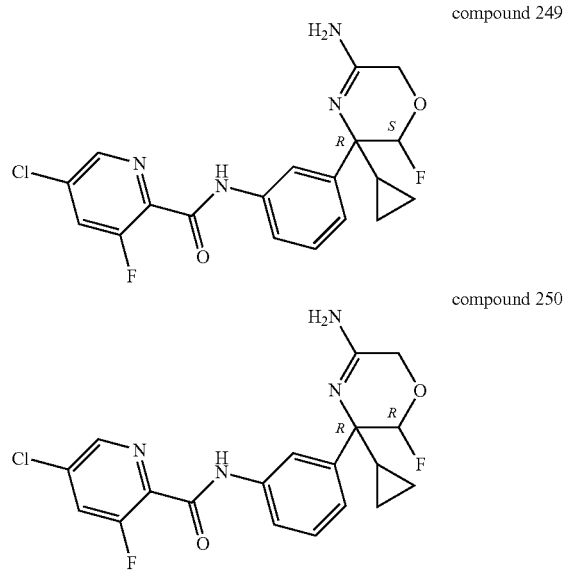

5-Chloro-3-fluoropyridine-2-carboxylic acid (0.253 g, 1.444 mmol) was dissolved in MeOH (49 mL) and DMTMM (0.461 g, 1.564 mmol) was added. After stirring the mixture for 5 minutes, a solution of a mixture of intermediates 138 and 139 (0.3 g, 0.1.2 mmol) in MeOH (20 mL) was added at 0° C., and the mixture was stirred for an additional 6 h. The solvent was evaporated in vacuo. The crude material was purified by flash column chromatography (silica gel; 7 M solution of ammonia in methanol/DCM 0/100 to 5/95). The desired fractions of each diastereomer were collected and the solvent evaporated in vacuo to yield compound 249 (0.03 g, 6% yield) and compound 250 (0.082 g, 18% yield) as solids after precipitation in DIPE.

Example B29

Preparation of Compound 253: (5R,6R)-5-{3-[5-amino-3-cyclopropyl-2-(trifluoromethyl)-3,6-dihydro-2H-1,4-oxazin-3-yl]phenyl}pyridine-3-carbonitrile

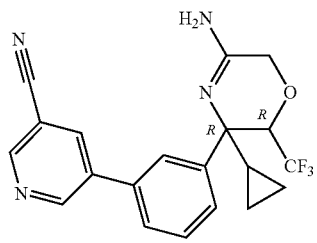

Intermediate 124 (0.1 g, 0.275 mmol), 5-cyano-3-pyridinylboronic acid (0.061 g, 0.41 mmol) and tetrakis(triphenylphosphine)palladium(0) (0.048 g, 0.041 mmol) were dissolved in a mixture of 1,4-dioxane (4 mL) and aqueous NaHCO₃ (sat. sol., 0.5 mL). The resulting mixture was flushed with N₂ and then heated at 80° C. for 2 hours. The reaction mixture was then diluted with water and then extracted with DCM. The organic layer was separated, dried (Na₂SO₄), filtered and the solvents evaporated in vacuo. The crude product was purified by flash column chromatography (silica gel; 7 M solution of ammonia in methanol/DCM 0/100 to 10/90). The desired fractions were collected and concentrated in vacuo to yield compound 253 (0.025 g, 24% yield).

Example B30

Preparation of Compound 277: (5R*,6R*)-5-[2-(3,5-dichlorophenyl)pyridin-4-yl]-6-fluoro-5-methyl-5,6-dihydro-2H-1,4-oxazin-3-amine, compound 278: (5S*,6S*)-5-[2-(3,5-dichlorophenyl)pyridin-4-yl]-6-fluoro-5-methyl-5,6-dihydro-2H-1,4-oxazin-3-amine and compound 279: cis-rac-5-[2-(3,5-dichlorophenyl)pyridin-4-yl]-6-fluoro-5-methyl-5,6-dihydro-2H-1,4-oxazin-3-amine

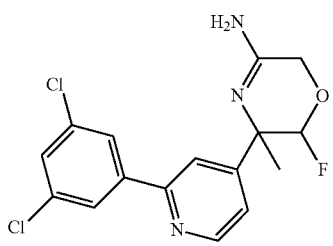 [SMILES: CC1(c2ccnc(-c3cc(Cl)cc(Cl)c3)c2)N=C(N)COC1F]

Intermediate 157 (0.073 g, 0.212 mmol), 3,5-dichlorophenylboronic acid (0.082 g, 0.425 mmol) and tetrakis(triphenylphosphine)palladium(0) (0.024 g, 0.021 mmol) were dissolved in a mixture of 1,4-dioxane (4 mL) and aqueous NaHCO₃ (sat. sol., 2 mL). The resulting mixture was flushed with N₂ and then heated at 80° C. for 2 hours.

The reaction mixture was then diluted with water and then extracted with DCM. The combined organic layer were washed with brine, dried (MgSO₄), filtered and the solvents evaporated in vacuo. The crude product was dissolved in DCM (5 mL) and TFA (0.8 mL) was added. The mixture was stirred at room temperature for 2 h. The solvents were evaporated in vacuo. The crude product was purified by flash column chromatography (silica gel; methanol/DCM 0/100 to 10/90). The desired fractions were collected and concentrated in vacuo to yield an oil, which was crystallized in DIPE as an off-white solid (0.025 g, 33% yield).

This racemic mixture of diastereomers was then purified by preparative SFC on Chiralpak Diacel OD-H5 µM (20× 250 mm), mobile phase (CO₂, iPrOH with 0.2% iPrNH₂), the desired fractions were collected and evaporated yielding compound 278 (0.0074 g, 10% yield), compound 277 (0.008 g, 11% yield) and compound 279 (0.0072 g, 9.6% yield).

Example B31

Preparation of Compound 166: (2R,3R)—N-{3-[5-amino-3-methyl-2-(trifluoromethyl)-3,6-dihydro-2H-1,4-oxazin-3-yl]-4-fluorophenyl}-5-methoxypyrazine-2-carboxamide

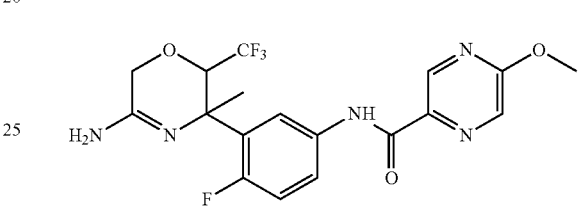

5-Methoxypyrazine-2-carboxylic acid (0.009 g, 0.05 mmol) was dissolved in MeOH (2 mL) and DMTMM (0.018 g, 0.06 mmol) was added. After stirring the mixture for 5 minutes, a solution of intermediate 158 (0.02 g, 0.05 mmol) in MeOH (1 mL) was added at 0° C., and the mixture was stirred for an additional 20 h. The mixture was concentrated in vacuo. The crude product was dissolved in DCM (1 mL) and TFA (0.1 mL) was added. The mixture was stirred at room temperature for 2 h. The solvents were evaporated in vacuo to yield compound 166 (0.02 g, 84% yield).

Compounds 1 to 280 in tables 1-13 list the compounds that were prepared by analogy to one of the above Examples. In case no salt form is indicated, the compound was obtained as a free base. 'Ex. No.' refers to the Example number according to which protocol the compound was synthesized. 'Co. No.' means compound number.

TABLE 1

| Co. No. | Ex. No. | X¹ | X³ | ----L—Ar | C₅-stereochemistry |
|---|---|---|---|---|---|
| 1 | B1 | CH | CH | phenyl | RS ·TFA salt |
| 2 | B2 | CH | CH | 3,5-dichlorophenyl | RS |

TABLE 1-continued

| Co. No. | Ex. No. | $X^1$ | $X^3$ | ---L—Ar | $C_5$-stereochemistry |
|---|---|---|---|---|---|
| 3 | B3 | CH | CH | pyrimidin-5-yl | RS •TFA salt |
| 4 | B4 | CH | CH | 5-methoxypyridin-3-yl | RS |
| 5 | B6 | CH | CH | 5-chloro-N-methylpyridine-2-carboxamide | RS |
| 6 | B7 | CH | CH | 3-fluoro-N-methylpyridine-2-carboxamide | RS |
| 7 | B7 | CH | CH | 5-methyl-N-methylpyrazine-2-carboxamide | RS |
| 8 | B5 | CH | CH | 5-methoxypyridin-3-yl | R* |
| 10 | B1 | CH | CH | 3-cyanophenyl | RS |
| 11 | B1 | CH | CH | 5-methylpyridin-3-yl | RS |
| 12 | B10 | CH | CH | 5-chloro-N-methylpyridine-2-carboxamide | R •HCl salt |
| 13 | B7 | CF | CF | 5-(trifluoromethyl)-N-methylpyridine-2-carboxamide | RS |

TABLE 1-continued
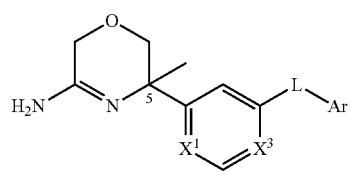
| Co. No. | Ex. No. | X¹ | X³ | ----L—Ar | C₅-stereochemistry |
|---|---|---|---|---|---|
| 14 | B7 | CH | CH | ![pyridine-2-carboxamide-5-CF3] | RS |
| 17 | B7 | CF | CH | ![pyridine-2-carboxamide-5-Cl] | RS |
| 21 | B7 | CF | CH | ![pyridine-2-carboxamide-3,5-diCl] | R |
| 22 | B15 | CF | CH | ![pyrazine-2-carboxamide-5-CF3] | R |
| 23 | B2 | CF | CF | ![5-chloropyridin-3-yl] | R |
| 24 | B15 | CF | CH | ![5-methylpyridine-2-carboxamide] | R |
| 25 | B15 | CF | CH | ![5-fluoropyridine-2-carboxamide] | R |
| 26 | B15 | CF | CH | ![pyridazine-3-carboxamide-6-CF3] | R |

TABLE 1-continued

| Co. No. | Ex. No. | $X^1$ | $X^3$ | ----L—Ar | $C_5$-stereochemistry |
|---|---|---|---|---|---|
| 27 | B15 | CF | CH | —NH—C(O)—(2-F,4-Cl-phenyl) | R •HCl salt |
| 28 | B15 | CF | CH | —NH—C(O)—(pyrimidin-4-yl) | R |
| 29 | B15 | CF | CH | —NH—C(O)—(5-Cl-thiophen-2-yl) | R |
| 30 | B3 | CF | CH | —NH—C(O)—(3-Me-pyridin-2-yl) | R |
| 31 | B3 | CF | CF | 3-CF$_3$-phenyl | R |
| 32 | B3 | CF | CF | 3-CN-phenyl | R |
| 33 | B3 | CF | CF | 4-OMe-phenyl | R |
| 34 | B3 | CF | CF | 4-Cl-phenyl | R |
| 35 | B15 | CF | CH | —NH—C(O)—(3-F,5-Cl-pyridin-2-yl) | R |
| 36 | B3 | CF | CF | 3-OCF$_3$-phenyl | R •HCl salt |

TABLE 1-continued
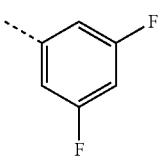
| Co. No. | Ex. No. | X¹ | X³ | ----L—Ar | C₅-stereochemistry |
|---|---|---|---|---|---|
| 37 | B3 | CF | CF | 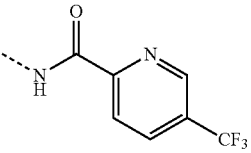 | R |
| 38 | B15 | CF | CH | 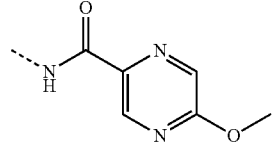 | R |
| 39 | B15 | CF | CH | 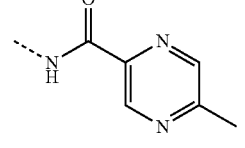 | R |
| 40 | B15 | CF | CH | 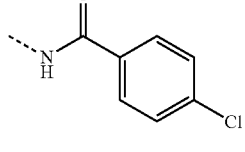 | R |
| 41 | B15 | CF | CH | 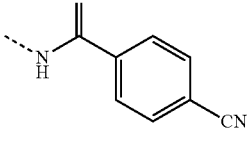 | R |
| 42 | B15 | CH | CH | 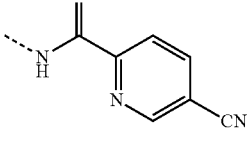 | RS •HCl salt |
| 43 | B15 | CF | CH | 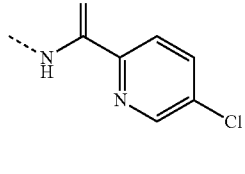 | R |
| 44 | B15 | CF | CH | | R |

TABLE 1-continued

| Co. No. | Ex. No. | X¹ | X³ | ----L—Ar | C₅-stereochemistry |
|---|---|---|---|---|---|
| 45 | B15 | CF | CH | N-H-C(=O)-(2-methoxy-4-chlorophenyl) | R |
| 46 | B3 | CF | CF | 3-chlorophenyl | R |
| 47 | B3 | CF | CF | 3-methoxyphenyl | R |
| 48 | B3 | CF | CF | 3,5-dichlorophenyl | R |
| 49 | B15 | CH | CH | N-H-C(=O)-(5-cyanopyridin-2-yl) | S* |
| 50 | B15 | CH | CH | N-H-C(=O)-(5-cyanopyridin-2-yl) | R* |
| 51 | B4 (method B) | CH | CH | 3-cyanophenyl | R |
| 52 | B4 (method B) | CH | CH | 3,5-dichlorophenyl | R |
| 53 | B3 | CF | CH | pyrimidin-5-yl | S* |
| 54 | B3 | CF | CH | pyrimidin-5-yl | R* |

TABLE 1-continued
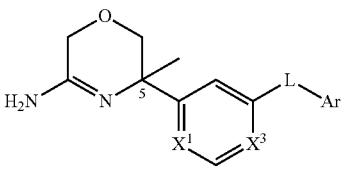
| Co. No. | Ex. No. | X¹ | X³ | ----L—Ar | C₅-stereochemistry |
|---|---|---|---|---|---|
| 55 | B3 | CF | CF | 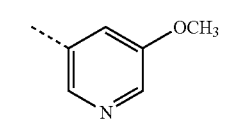 | R* |
| 56 | B3 | CF | CH | 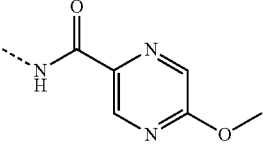 | R* |
| 57 | B7 | CF | CH | 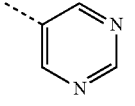 | RS |
| 58 | B3 | CF | CH | 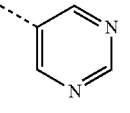 | RS |
| 59 | B3 | CF | CF | 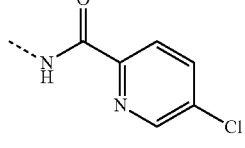 | RS |
| 60 | B3 | CF | CF | 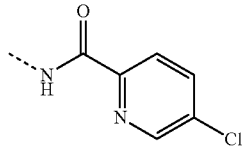 | RS |
| 61 | B7 | CF | CH | 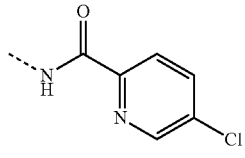 | S* |
| 62 | B7 | CF | CH | 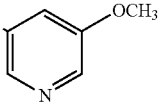 | R |
| 63 | B3 | CF | CH | 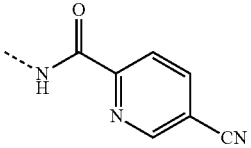 | RS |
| 64 | B7 | CH | CH |  | RS |

TABLE 1-continued

| Co. No. | Ex. No. | X¹ | X³ | ----L—Ar | C₅-stereochemistry |
|---|---|---|---|---|---|
| 65 | B7 | CF | CH | (N-H C(=O) pyridine 5-Cl) | RS |
| 66 | B4 (method B) | CF | CF | (pyridine with OCH₃) | RS |
| 67 | B3 | CH | CH | (pyridine with CN) | RS |
| 68 | B15 | CF | CH | (N-H C(=O) phenyl 2-F, 4-Cl) | R •HCl salt |
| 143 | B15 | CF | CH | (N-H C(=O) pyridine 3-Me, 5-Cl) | R |
| 144 | B15 | CF | CH | (N-H C(=O) pyrimidine 5-Cl) | R |
| 145 | B4 (method B) | CF | CF | (pyridine with OCH₃) | R •HCl salt |
| 146 | B15 | CH | CH | (N-H C(=O) pyrazine CF₃) | R |

TABLE 1-continued

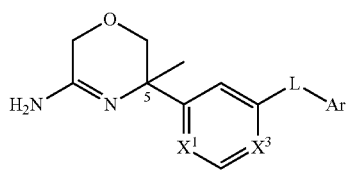

| Co. No. | Ex. No. | $X^1$ | $X^3$ | ----L—Ar | $C_5$-stereochemistry |
|---|---|---|---|---|---|
| 147 | B15 | CF | CH | ![structure] | R |
| 155 | B3 | CF | CF | ![structure] | S |
| 156 | B3 | CF | CH | ![structure] | R* |

TABLE 2

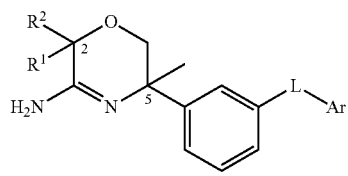

| Co. No. | Ex. No. | $R^1$ | $R^2$ | ----L—Ar | stereochemistry |
|---|---|---|---|---|---|
| 9 | B8 | F | CF$_3$ | ![structure] | $C_2$(RS); $C_5$(RS) Single diastereoisomer (trans) |
| 15 | B11 | F | CF$_3$ | ![structure] | $C_2$(R*); $C_5$(R*) Single diastereoisomer Pure enantiomer |
| 18 | B12 | CH$_3$ | H | ![structure] | $C_2$(RS); $C_5$(RS) Single diastereoisomer (trans) |
| 19 | B12 | H | CH$_3$ | ![structure] | $C_2$(RS); $C_5$(RS) Single diastereoisomer (cis) |

TABLE 2-continued
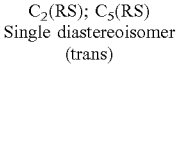
| Co. No. | Ex. No. | R¹ | R² | ----L—Ar | stereochemistry |
|---|---|---|---|---|---|
| 20 | B13 | CH₃ | H | 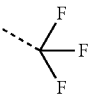 | C₂(RS); C₅(RS) Single diastereoisomer (trans) |
| 69 | B15 | F | 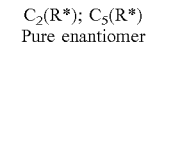 | 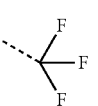 | C₂(R*); C₅(R*) Pure enantiomer |
| 70 | B15 | F | 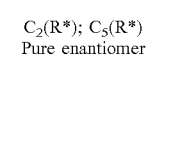 | 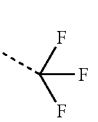 | C₂(R*); C₅(R*) Pure enantiomer |
| 71 | B15 | F | 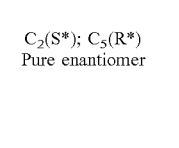 | 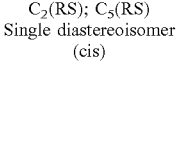 | C₂(S*); C₅(R*) Pure enantiomer |
| 151 | B13 | H | CH₃ | 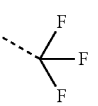 | C₂(RS); C₅(RS) Single diastereoisomer (cis) |
| 154 | B11 | F | 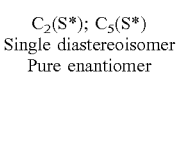 | 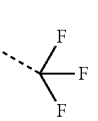 | C₂(S*); C₅(S*) Single diastereoisomer Pure enantiomer |
| 157 | B15 | F | 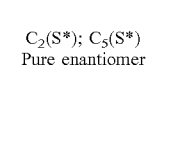 | 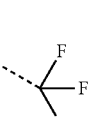 | C₂(S*); C₅(S*) Pure enantiomer |
| 158 | B15 | F | | 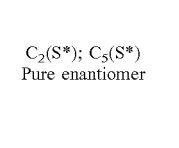 | C₂(S*); C₅(S*) Pure enantiomer |

TABLE 2-continued

[Structure: morpholine ring with R² and R¹ substituents at C2, methyl and aryl-L-Ar at C5, H₂N-C=N]

| Co. No. | Ex. No. | R¹ | R² | ----L—Ar | stereochemistry |
|---|---|---|---|---|---|
| 161 | B22 | CH₃ | CF₂-CF (CHF-CF₃ type, with three F) | 5-pyrimidinyl | C₂(RS); C₅(RS) Single diastereoisomer (cis) |
| 162 | B22 | CH₃ | CF₂-CF (three F) | 5-pyrimidinyl | C₂(RS); C₅(RS) Single diastereoisomer (trans) |

TABLE 3

[Structure: spiro cyclopropane-morpholine with H₂N-C=N, methyl at C5, and six-membered aromatic ring with X₁, X₂, X₃, X₄ positions bearing L—Ar]

| Co. No. | Ex. No. | X₁, X₂, X₃, X₄ | ----L—Ar | C₅-stereochemistry |
|---|---|---|---|---|
| 16 | B9 | X₁ = X₂ = X₃ = X₄ = CH | 5-methoxy-3-pyridinyl | RS |
| 72 | B14 | X₁ = X₃ = CF<br>X₂ = X₄ = CH | 5-pyrimidinyl | RS |
| 73 | B15 | X₁ = X₂ = X₃ = X₄ = CH | -NH-C(=O)-(5-chloro-2-pyridinyl) | R |
| 74 | B9 | X₁ = X₂ = X₃ = X₄ = CH | 5-pyrimidinyl | R<br>•Fumarate salt |
| 149 | B14 | X₁ = X₃ = CF<br>X₂ = X₄ = CH | 5-pyrimidinyl | S |
| 150 | B14 | X₁ = X₃ = CF<br>X₂ = X₄ = CH | 5-pyrimidinyl | R |

TABLE 4

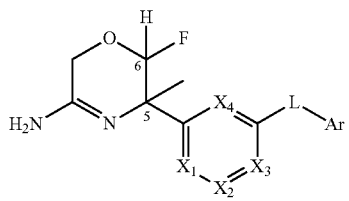

| Co. No. | Ex. No. | $X_1, X_2, X_3, X_4$ | ----L—Ar | stereochemistry |
|---|---|---|---|---|
| 75 | B14 | $X_1$ = CF<br>$X_2 = X_3 = X_4$ = CH | pyrimidin-5-yl | $C_5(R^*); C_6(S^*)$<br>Single diastereoisomer<br>Pure enantiomer |
| 76 | B15 | $X_1$ = CF<br>$X_2 = X_3 = X_4$ = CH | —NHC(O)-(5-CN-pyridin-2-yl) | $C_5(RS); C_6(RS)$<br>Single diastereoisomer<br>(Trans) |
| 77 | B15 | $X_1$ = CF<br>$X_2 = X_3 = X_4$ = CH | —NHC(O)-(3-F-5-Cl-pyridin-2-yl) | $C_5(RS); C_6(RS)$<br>Single diastereoisomer<br>(Trans) |
| 78 | B15 | $X_1$ = CF<br>$X_2 = X_3 = X_4$ = CH | —NHC(O)-(3,5-diCl-pyridin-2-yl) | $C_5(RS); C_6(RS)$<br>Single diastereoisomer<br>(Trans) |
| 79 | B15 | $X_1$ = CF<br>$X_2 = X_3 = X_4$ = CH | —NHC(O)-(5-OMe-pyrazin-2-yl) | $C_5(RS); C_6(RS)$<br>Single diastereoisomer<br>(trans) |
| 80 | B15 | $X_1 = X_2 = X_3 = X_4$ = CH | —NHC(O)-(5-OMe-pyrazin-2-yl) | $C_5(RS); C_6(RS)$<br>Single diastereoisomer<br>(Trans) |
| 81 | B14 | $X_1 = X_3$ = CF<br>$X_2 = X_4$ = CH | pyrimidin-5-yl | $C_5(R^*); C_6(S^*)$<br>Single diastereoisomer<br>Pure enantiomer |
| 82 | B14 | $X_1 = X_3$ = CF<br>$X_2 = X_4$ = CH | pyrimidin-5-yl | $C_5(R^*); C_6(R^*)$<br>Single diastereoisomer<br>Pure enantiomer |
| 83 | B14 | $X_1 = X_3$ = CF<br>$X_2 = X_4$ = CH | pyrimidin-5-yl | $C_5(RS); C_6(RS)$<br>Single diastereoisomer<br>(trans) |

TABLE 4-continued

| Co. No. | Ex. No. | $X_1, X_2, X_3, X_4$ | ----L—Ar | stereochemistry |
|---|---|---|---|---|
| 84 | B14 | $X_1 = X_3 = CF$<br>$X_2 = X_4 = CH$ | 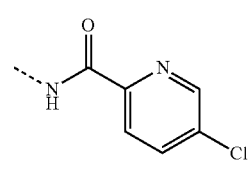 | $C_5(RS); C_6(RS)$<br>Single diastereoisomer<br>(Cis) |
| 85 | B15 | $X_1 = X_2 = X_3 = X_4 = CH$ | 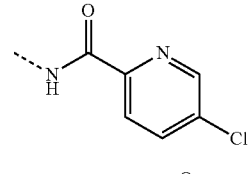 | $C_5(S^*); C_6(S^*)$<br>Single diastereoisomer<br>Pure enantiomer |
| 86 | B15 | $X_1 = X_2 = X_3 = X_4 = CH$ | 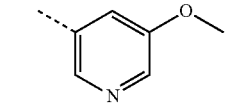 | $C_5(R^*); C_6(R^*)$<br>Single diastereoisomer<br>Pure enantiomer |
| 87 | B14 | $X_1 = X_2 = X_3 = X_4 = CH$ | 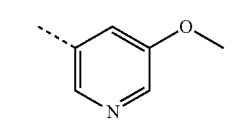 | $C_5(RS); C_6(RS)$ |
| 88 | B14 | $X_1 = X_2 = X_3 = X_4 = CH$ | 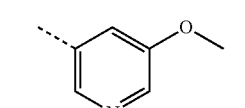 | $C_5(S^*); C_6(R^*)$<br>Single diastereoisomer<br>Pure enantiomer |
| 89 | B14 | $X_1 = X_2 = X_3 = X_4 = CH$ | 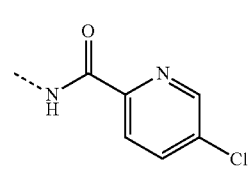 | $C_5(R^*); C_6(S^*)$<br>Single diastereoisomer<br>Pure enantiomer |
| 90 | B15 | $X_1 = X_2 = X_3 = X_4 = CH$ | 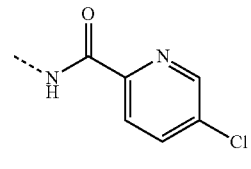 | $C_5(R^*); C_6(S^*)$<br>Single diastereoisomer<br>Pure enantiomer |
| 91 | B15 | $X_1 = X_2 = X_3 = X_4 = CH$ | 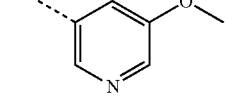 | $C_5(RS); C_6(RS)$<br>Single diastereoisomer<br>(trans) |
| 92 | B3 | $X_1 = X_2 = X_3 = X_4 = CH$ | 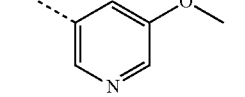 | $C_5(S^*); C_6(S^*)$<br>Single diastereoisomer<br>Pure enantiomer |
| 93 | B3 | $X_1 = X_2 = X_3 = X_4 = CH$ | 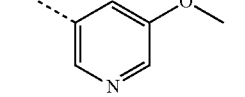 | $C_5(R^*); C_6(R^*)$<br>Single diastereoisomer<br>Pure enantiomer |

TABLE 4-continued

| Co. No. | Ex. No. | $X_1, X_2, X_3, X_4$ | ----L—Ar | stereochemistry |
|---|---|---|---|---|
| 94 | B3 | $X_1 = X_2 = X_3 = X_4 = CH$ | pyrimidin-5-yl | $C_5(S^*); C_6(S^*)$<br>Single diastereoisomer<br>Pure enantiomer |
| 95 | B3 | $X_1 = X_2 = X_3 = X_4 = CH$ | pyrimidin-5-yl | $C_5(R^*); C_6(R^*)$<br>Single diastereoisomer<br>Pure enantiomer |
| 96 | B3 | $X_1 = X_2 = X_3 = X_4 = CH$ | pyrimidin-5-yl | $C_5(S^*); C_6(R^*)$<br>Single diastereoisomer<br>Pure enantiomer |
| 97 | B3 | $X_1 = X_2 = X_3 = X_4 = CH$ | pyrimidin-5-yl | $C_5(R^*); C_6(S^*)$<br>Single diastereoisomer<br>Pure enantiomer |
| 98 | B3 | $X_1 = X_2 = X_3 = X_4 = CH$ | pyrimidin-5-yl | $C_5(RS); C_6(RS)$<br>Single diastereoisomer<br>(trans) |
| 99 | B3 | $X_1 = X_2 = X_3 = X_4 = CH$ | pyrimidin-5-yl | $C_5(RS); C_6(RS)$<br>Single diastereoisomer<br>(cis) |
| 100 | B3 | $X_1 = X_2 = X_3 = X_4 = CH$ | 5-methoxypyridin-3-yl | $C_5(RS); C_6(RS)$ |
| 122 | B15 | $X_1 = X_2 = X_3 = X_4 = CH$ | N-(5-chloropyridine-2-carboxamido) | $C_5(S^*); C_6(R^*)$<br>Single diastereoisomer<br>(cis)<br>Pure enantiomer |
| 123 | B15 | $X_1 = CF$<br>$X_2 = X_3 = X_4 = CH$ | N-(6-methoxypyrimidine-3-carboxamido) | $C_5(R); C_6(R)$<br>Single diastereoisomer<br>(trans)<br>Pure enantiomer |
| 124 | B15 | $X_1 = CF$<br>$X_2 = X_3 = X_4 = CH$ | N-(5-cyanopyridine-2-carboxamido) | $C_5(R^*); C_6(R^*)$<br>Single diastereoisomer<br>(trans)<br>Pure enantiomer |

TABLE 4-continued

| Co. No. | Ex. No. | $X_1, X_2, X_3, X_4$ | ----L—Ar | stereochemistry |
|---|---|---|---|---|
| 125 | B15 | $X_1$ = CF<br>$X_2$ = $X_3$ = $X_4$ = CH | pyridine-2-carboxamide with 5-CN | $C_5(S^*); C_6(S^*)$<br>Single diastereoisomer<br>(trans)<br>Pure enantiomer |
| 126 | B15 | $X_1$ = CF<br>$X_2$ = $X_3$ = $X_4$ = CH | 3,5-dichloropyridine-2-carboxamide | $C_5(R^*); C_6(R^*)$<br>Single diastereoisomer<br>(trans)<br>Pure enantiomer |
| 127 | B14 | $X_1$ = CF<br>$X_2$ = $X_3$ = $X_4$ = CH | pyrimidin-5-yl | $C_5(S^*); C_6(R^*)$<br>(cis)<br>Single diastereoisomer<br>Pure enantiomer |
| 128 | B15 | $X_1$ = CF<br>$X_2$ = $X_3$ = $X_4$ = CH | 3,5-dichloropyridine-2-carboxamide | $C_5(S^*); C_6(S^*)$<br>Single diastereoisomer<br>(trans)<br>Pure enantiomer |
| 129 | B15 | $X_1$ = CF<br>$X_2$ = $X_3$ = $X_4$ = CH | 5-methoxypyrazine-2-carboxamide | $C_5(S^*); C_6(S^*)$<br>Single diastereoisomer<br>(trans)<br>Pure enantiomer |
| 130 | B15 | $X_1$ = CF<br>$X_2$ = $X_3$ = $X_4$ = CH | 5-chloro-3-fluoropyridine-2-carboxamide | $C_5(S^*); C_6(S^*)$<br>Single diastereoisomer<br>(trans)<br>Pure enantiomer |
| 131 | B15 | $X_1$ = $X_2$ = $X_3$ = $X_4$ = CH | 5-methoxypyrazine-2-carboxamide | $C_5(R^*); C_6(R^*)$<br>Single diastereoisomer<br>(trans)<br>Pure enantiomer |
| 132 | B15 | $X_1$ = $X_2$ = $X_3$ = $X_4$ = CH | 5-methoxypyrazine-2-carboxamide | $C_5(S^*); C_6(S^*)$<br>Single diastereoisomer<br>(trans)<br>Pure enantiomer |

TABLE 4-continued

[Structure: 2H-1,4-oxazine core with $H_2N$, O, H, F, methyl substituents labeled at positions 5 and 6, connected to a phenyl ring with $X_1, X_2, X_3, X_4$ positions and an L-Ar substituent]

| Co. No. | Ex. No. | $X_1, X_2, X_3, X_4$ | ----L—Ar | stereochemistry |
|---|---|---|---|---|
| 133 | B15 | $X_1$ = CF<br>$X_2$ = $X_3$ = $X_4$ = CH | [N-H linked C(=O)-pyridine with F and Cl substituents] | $C_5(R^*)$; $C_6(R^*)$<br>Single diastereoisomer<br>(trans)<br>Pure enantiomer |
| 134 | B15 | $X_1$ = CF<br>$X_2$ = $X_3$ = $X_4$ = CH | [N-H linked C(=O)-pyridine with Cl substituent] | $C_5(R^*)$; $C_6(R^*)$<br>Single diastereoisomer<br>(trans)<br>Pure enantiomer |
| 135 | B15 | $X_1$ = CF<br>$X_2$ = $X_3$ = $X_4$ = CH | [N-H linked C(=O)-pyridine with Cl substituent] | $C_5(S^*)$; $C_6(S^*)$<br>Single diastereoisomer<br>(trans)<br>Pure enantiomer |
| 136 | B15 | $X_1$ = CF<br>$X_2$ = $X_3$ = $X_4$ = CH | [N-H linked C(=O)-pyridine with Cl substituent] | $C_5(R^*)$; $C_6(S^*)$<br>Single diastereoisomer<br>(cis)<br>Pure enantiomer |
| 137 | B15 | $X_1$ = CF<br>$X_2$ = $X_3$ = $X_4$ = CH | [N-H linked C(=O)-pyridine with Cl substituent] | $C_5(S^*)$; $C_6(R^*)$<br>Single diastereoisomer<br>(cis)<br>Pure enantiomer |
| 148 | B14 | $X_1$ = $X_3$ = CF<br>$X_2$ = $X_4$ = CH | [pyrimidine] | $C_5(S^*)$; $C_6(S^*)$<br>Single diastereoisomer<br>(trans)<br>Pure enantiomer |
| 163 | B15 | $X_1$ = $X_2$ = $X_3$ = $X_4$ = CH | [N-H linked C(=O)-pyridine with F and Cl substituents] | $C_5(R^*)$; $C_6(R^*)$<br>Single diastereoisomer<br>(trans)<br>Pure enantiomer |
| 164 | B15 | $X_1$ = $X_2$ = $X_3$ = $X_4$ = CH | [N-H linked C(=O)-pyridine with F and Cl substituents] | $C_5(S^*)$; $C_6(S^*)$<br>Single diastereoisomer<br>(trans)<br>Pure enantiomer |

TABLE 4-continued

| Co. No. | Ex. No. | $X_1, X_2, X_3, X_4$ | ----L—Ar | stereochemistry |
|---|---|---|---|---|
| 208 | B15 | $X_1$ = CF<br>$X_2 = X_3 = X_4$ = CH | pyridine-2-carboxamide with 5-OMe | $C_5(R); C_6(R)$<br>Single diastereoisomer<br>Pure enantiomer |
| 209 | B15 | $X_1$ = CF<br>$X_2 = X_3 = X_4$ = CH | pyridine-2-carboxamide with 3-Cl, 5-CN | $C_5(R); C_6(R)$<br>Single diastereoisomer<br>Pure enantiomer |
| 330 | B15 | $X_1$ = CF<br>$X_2 = X_3 = X_4$ = CH | pyridine-2-carboxamide with 3-F, 5-CN | $C_5(R); C_6(R)$<br>Single diastereoisomer<br>Pure enantiomer |
| 331 | B15 | $X_1$ = CF<br>$X_2 = X_3 = X_4$ = CH | pyrazine-2-carboxamide with 5-OCH$_2$CF$_3$ | $C_5(R); C_6(R)$<br>Single diastereoisomer<br>Pure enantiomer |
| 332 | B15 | $X_1$ = CF<br>$X_2 = X_3 = X_4$ = CH | pyrazine-2-carboxamide with 5-CHF$_2$ | $C_5(R); C_6(R)$<br>Single diastereoisomer<br>Pure enantiomer |
| 333 | B15 | $X_1$ = CF<br>$X_2 = X_3 = X_4$ = CH | pyridine-2-carboxamide with 3-Me, 5-Cl | $C_5(R); C_6(R)$<br>Single diastereoisomer<br>Pure enantiomer |
| 371 | B15 | $X_1$ = CF<br>$X_2 = X_3 = X_4$ = CH | pyrazine-2-carboxamide with 5-OEt | $C_5(R); C_6(R)$<br>Single diastereoisomer<br>Pure enantiomer |

TABLE 4-continued

[Structure: oxazine ring with H₂N-C(=N)-, C5 bearing methyl, C6 bearing H and F, connected to aryl ring with X₁, X₂, X₃, X₄ positions and L-Ar substituent]

| Co. No. | Ex. No. | X₁, X₂, X₃, X₄ | ----L—Ar | stereochemistry |
|---|---|---|---|---|
| 380 | B15 | X₁ = CF<br>X₂ = X₃ = X₄ = CH | [pyrazine-2-carboxamide with 5-(2-methoxyethoxy) substituent] | $C_5(R); C_6(R)$<br>Single diastereoisomer<br>Pure enantiomer |
| 397 | B15 | X₁ = X₂ = X₃ = X₄ = CH | [pyrazine-2-carboxamide with 5-ethoxy substituent] | $C_5(R); C_6(R)$<br>Single diastereoisomer<br>Pure enantiomer |
| 402 | B15 | X₁ = CF<br>X₂ = X₃ = X₄ = CH | [3,5-difluoropyridine-2-carboxamide] | $C_5(R); C_6(R)$<br>Single diastereoisomer<br>Pure enantiomer |
| 404 | B15 | X₁ = X₂ = X₃ = X₄ = CH | [3,5-difluoropyridine-2-carboxamide] | $C_5(R); C_6(R)$<br>Single diastereoisomer<br>Pure enantiomer |

TABLE 5

[Structure: oxazine ring with H₂N-C(=N)-, C5 bearing methyl, C6 bearing H and CF₃, connected to aryl ring with X₁, X₂, X₃, X₄ positions and L-Ar substituent]

| Co. No. | Ex. No. | X₁, X₂, X₃, X₄ | ----L—Ar | stereochemistry |
|---|---|---|---|---|
| 101 | B3 | X₁ = X₂ = X₃ = X₄ = CH | [3-methoxypyridin-5-yl] | $C_5(R^*); C_6(R^*)$<br>Single diastereoisomer<br>Pure enantiomer |
| 102 | B3 | X₁ = X₂ = X₃ = X₄ = CH | [3-methoxypyridin-5-yl] | $C_5(S^*); C_6(R^*)$<br>Single diastereoisomer<br>Pure enantiomer |

TABLE 5-continued

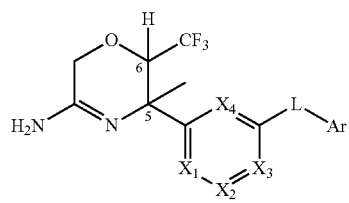

| Co. No. | Ex. No. | $X_1, X_2, X_3, X_4$ | ----L—Ar | stereochemistry |
|---|---|---|---|---|
| 103 | B3 | $X_1 = X_2 = X_3 = X_4 = CH$ | 5-methoxypyridin-3-yl | $C_5(R^*)$; $C_6(R^*)$ Single diastereoisomer Pure enantiomer |
| 104 | B3 | $X_1 = X_2 = X_3 = X_4 = CH$ | 5-methoxypyridin-3-yl | $C_5(S^*)$; $C_6(S^*)$ Single diastereoisomer Pure enantiomer |
| 105 | B14 | $X_1 = CF$ $X_2 = X_3 = X_4 = CH$ | 5-methoxypyridin-3-yl | $C_5(RS)$; $C_6(RS)$ Single diastereoisomer (cis) |
| 106 | B14 | $X_1 = CF$ $X_2 = X_3 = X_4 = CH$ | pyrimidin-5-yl | $C_5(RS)$; $C_6(RS)$ Single diastereoisomer (cis) |
| 107 | B16 | $X_1 = CF$ $X_2 = X_3 = X_4 = CH$ | 5-chloropyridine-2-carboxamide | $C_5(RS)$; $C_6(RS)$ Single diastereoisomer (cis) |
| 108 | B3 | $X_1 = X_2 = X_3 = X_4 = CH$ | 5-methoxypyridin-3-yl | $C_5(RS)$; $C_6(RS)$ Single diastereoisomer (cis) |
| 165 | B21 | $X_1 = CF$ $X_2 = X_3 = X_4 = CH$ | 5-chloropyridine-2-carboxamide | $C_5(R)$; $C_6(R)$ Single diastereoisomer Pure enantiomer |
| 166 | B21 | $X_1 = CF$ $X_2 = X_3 = X_4 = CH$ | 5-methoxypyrazine-2-carboxamide | $C_5(R)$; $C_6(R)$ Single diastereoisomer Pure enantiomer |
| 167 | B21 | $X_1 = CF$ $X_2 = X_3 = X_4 = CH$ | 3,5-dichloropyridine-2-carboxamide | $C_5(R)$; $C_6(R)$ Single diastereoisomer Pure enantiomer |

TABLE 5-continued

| Co. No. | Ex. No. | $X_1, X_2, X_3, X_4$ | ----L—Ar | stereochemistry |
|---|---|---|---|---|
| 168 | B21 | $X_1$ = CF<br>$X_2 = X_3 = X_4$ = CH | -NH-C(O)-pyrimidin-4-yl | $C_5(R); C_6(R)$<br>Single diastereoisomer<br>Pure enantiomer |
| 169 | B21 | $X_1$ = CF<br>$X_2 = X_3 = X_4$ = CH | -NH-C(O)-(5-cyanopyridin-2-yl) | $C_5(R); C_6(R)$<br>Single diastereoisomer<br>Pure enantiomer |
| 170 | B21 | $X_1$ = CF<br>$X_2 = X_3 = X_4$ = CH | -NH-C(O)-(5-chloropyridin-2-yl) | $C_5(R); C_6(S)$<br>Single diastereoisomer<br>Pure enantiomer |
| 171 | B14 | $X_1 = X_2 = X_3 = X_4$ = CH | 5-cyanopyridin-3-yl | $C_5(RS); C_6(RS)$<br>Single diastereoisomer<br>(cis) |
| 204 | B14 | $X_1 = X_2 = X_3 = X_4$ = CH | 5-cyanopyridin-3-yl | $C_5(R^*); C_6(R^*)$<br>Single diastereoisomer<br>(cis) |
| 205 | B14 | $X_1 = X_2 = X_3 = X_4$ = CH | 5-cyanopyridin-3-yl | $C_5(S^*); C_6(S^*)$<br>Single diastereoisomer<br>(cis) |
| 206 | B14 | $X_1 = X_2 = X_3 = X_4$ = CH | 5-cyanopyridin-3-yl | $C_5(S^*); C_6(R^*)$<br>Single diastereoisomer<br>(trans) |
| 207 | B14 | $X_1 = X_2 = X_3 = X_4$ = CH | 5-cyanopyridin-3-yl | $C_5(R^*); C_6(S^*)$<br>Single diastereoisomer<br>(trans) |
| 238 | B14 | $X_1$ = CF<br>$X_2 = X_3 = X_4$ = CH | pyrimidin-5-yl | $C_5(RS); C_6(RS)$<br>Single diastereoisomer<br>(cis) |

TABLE 5-continued

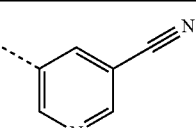

| Co. No. | Ex. No. | $X_1, X_2, X_3, X_4$ | ----L—Ar | stereochemistry |
|---|---|---|---|---|
| 239 | B14 | $X_1$ = CF<br>$X_2$ = $X_3$ = $X_4$ = CH | 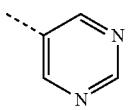 | $C_5$(RS); $C_6$(RS)<br>Single diastereoisomer<br>(cis) |
| 254 | B14 | $X_1$ = $X_3$ = CF<br>$X_2$ = $X_4$ = CH | 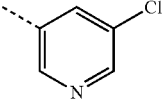 | $C_5$(R); $C_6$(R)<br>Single diastereoisomer<br>Pure enantiomer |
| 255 | B14 | $X_1$ = $X_3$ = CF<br>$X_2$ = $X_4$ = CH | 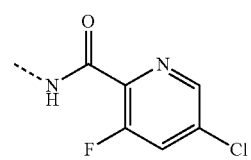 | $C_5$(R); $C_6$(R)<br>Single diastereoisomer<br>Pure enantiomer |
| 260 | B21 | $X_1$ = CF<br>$X_2$ = $X_3$ = $X_4$ = CH | 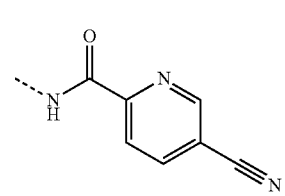 | $C_5$(R); $C_6$(R)<br>Single diastereoisomer<br>Pure enantiomer |
| 261 | B21 | $X_1$ = $X_2$ = $X_3$ = $X_4$ = CH | 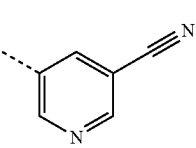 | $C_5$(R); $C_6$(R)<br>Single diastereoisomer<br>Pure enantiomer |
| 265 | B14 | $X_1$ = CF<br>$X_2$ = $X_3$ = $X_4$ = CH | 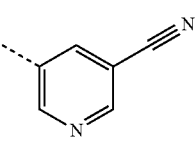 | $C_5$(R*); $C_6$(R*)<br>Single diastereoisomer<br>(cis) |
| 266 | B14 | $X_1$ = CF<br>$X_2$ = $X_3$ = $X_4$ = CH | 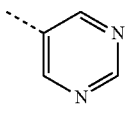 | $C_5$(S*); $C_6$(S*)<br>Single diastereoisomer<br>(cis) |
| 267 | B14 | $X_1$ = CF<br>$X_2$ = $X_3$ = $X_4$ = CH | 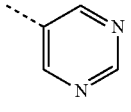 | $C_5$(S*); $C_6$(S*)<br>Single diastereoisomer<br>(cis) |
| 268 | B14 | $X_1$ = CF<br>$X_2$ = $X_3$ = $X_4$ = CH |  | $C_5$(R*); $C_6$(R*)<br>Single diastereoisomer<br>(cis) |

TABLE 5-continued

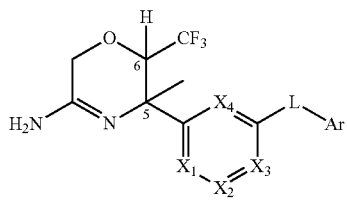

| Co. No. | Ex. No. | $X_1, X_2, X_3, X_4$ | ----L—Ar | stereochemistry |
|---|---|---|---|---|
| 308 | B21 | $X_1$ = CF<br>$X_2 = X_3 = X_4$ = CH | 3-chloro-5-cyanopyridine-2-carboxamide | $C_5(R); C_6(R)$<br>Single diastereoisomer<br>Pure enantiomer |
| 316 | B14 | $X_1 = X_3$ = CF<br>$X_2 = X_4$ = CH | 5-fluoropyridin-3-yl | $C_5(R); C_6(S)$<br>Single diastereoisomer<br>Pure enantiomer |
| 317 | B14 | $X_1 = X_3$ = CF<br>$X_2 = X_4$ = CH | 5-cyanopyridin-3-yl | $C_5(R); C_6(S)$<br>Single diastereoisomer<br>Pure enantiomer |
| 339 | B21 | $X_1 = X_2 = X_3 = X_4$ = CH | 5-chloro-3-fluoropyridine-2-carboxamide | $C_5(R); C_6(R)$<br>Single diastereoisomer<br>Pure enantiomer |
| 340 | B14 | $X_1 = X_2 = X_3 = X_4$ = CH | 5-chloropyridin-3-yl | $C_5(R); C_6(R)$<br>Single diastereoisomer<br>Pure enantiomer |
| 341 | B14 | $X_1 = X_2 = X_3 = X_4$ = CH | 5-fluoropyridin-3-yl | $C_5(R); C_6(R)$<br>Single diastereoisomer<br>Pure enantiomer |
| 342 | B14 | $X_1 = X_2 = X_3 = X_4$ = CH | 5-ethynylpyridin-3-yl | $C_5(R); C_6(R)$<br>Single diastereoisomer<br>Pure enantiomer |
| 343 | B14 | $X_1 = X_2 = X_3 = X_4$ = CH | pyrimidin-5-yl | $C_5(R); C_6(R)$<br>Single diastereoisomer<br>Pure enantiomer |
| 350 | B14 | $X_1 = X_3$ = CF<br>$X_2 = X_4$ = CH | 5-cyanopyridin-3-yl | $C_5(R); C_6(S)$<br>Single diastereoisomer<br>Pure enantiomer |

TABLE 5-continued

[Structure: core scaffold with H$_2$N-C(=N)- attached to a morpholine-like ring bearing CF$_3$ and methyl groups at position 6 and 5, connected via X$_1$-X$_4$ aromatic ring to L-Ar]

| Co. No. | Ex. No. | X$_1$, X$_2$, X$_3$, X$_4$ | ----L—Ar | stereochemistry |
|---|---|---|---|---|
| 351 | B14 | X$_1$ = X$_3$ = CF<br>X$_2$ = X$_4$ = CH | 5-cyanopyridin-3-yl | C$_5$(R); C$_6$(R)<br>Single diastereoisomer<br>Pure enantiomer |
| 357 | B21 | X$_1$ = CF<br>X$_2$ = X$_3$ = X$_4$ = CH | N-H amide of 5-cyano-3-fluoropyridine-2-carboxamide | C$_5$(R); C$_6$(R)<br>Single diastereoisomer<br>Pure enantiomer |
| 372 | B21 | X$_1$ = CF<br>X$_2$ = X$_3$ = X$_4$ = CH | N-H amide of 5-ethoxypyrazine-2-carboxamide | C$_5$(R); C$_6$(R)<br>Single diastereoisomer<br>Pure enantiomer |
| 373 | B21 | X$_1$ = CF<br>X$_2$ = X$_3$ = X$_4$ = CH | N-H amide of 5-(2-methoxyethoxy)pyrazine-2-carboxamide | C$_5$(R); C$_6$(R)<br>Single diastereoisomer<br>Pure enantiomer |
| 374 | B21 | X$_1$ = CF<br>X$_2$ = X$_3$ = X$_4$ = CH | N-H amide of 5-(difluoromethyl)pyrazine-2-carboxamide | C$_5$(R); C$_6$(R)<br>Single diastereoisomer<br>Pure enantiomer |
| 375 | B21 | X$_1$ = X$_2$ = X$_3$ = X$_4$ = CH | N-H amide of 5-ethoxypyrazine-2-carboxamide | C$_5$(R); C$_6$(R)<br>Single diastereoisomer<br>Pure enantiomer |
| 376 | B21 | X$_1$ = X$_2$ = X$_3$ = X$_4$ = CH | N-H amide of 5-(2-methoxyethoxy)pyrazine-2-carboxamide | C$_5$(R); C$_6$(R)<br>Single diastereoisomer<br>Pure enantiomer |

TABLE 5-continued

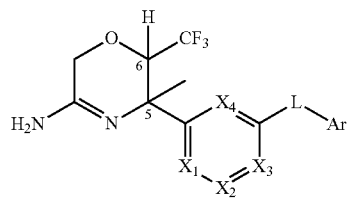

| Co. No. | Ex. No. | $X_1, X_2, X_3, X_4$ | ----L—Ar | stereochemistry |
|---|---|---|---|---|
| 377 | B21 | $X_1 = X_2 = X_3 = X_4 = CH$ | *pyrazine-2-carboxamide, 5-methoxy* | $C_5(R); C_6(R)$<br>Single diastereoisomer<br>Pure enantiomer |
| 378 | B21 | $X_1 = X_2 = X_3 = X_4 = CH$ | *3-fluoro-5-cyano-pyridine-2-carboxamide* | $C_5(R); C_6(R)$<br>Single diastereoisomer<br>Pure enantiomer |
| 379 | B14 | $X_1 = X_2 = X_3 = X_4 = CH$ | *5-methoxy-pyridin-3-yl* | $C_5(R); C_6(R)$<br>Single diastereoisomer<br>Pure enantiomer |
| 403 | B21 | $X_1 = CF$<br>$X_2 = X_3 = X_4 = CH$ | *3,5-difluoro-pyridine-2-carboxamide* | $C_5(R); C_6(R)$<br>Single diastereoisomer<br>Pure enantiomer |

TABLE 6

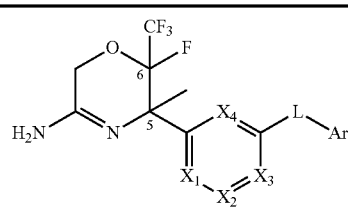

| Co. No. | Ex. No. | $X_1, X_2, X_3, X_4$ | ----L—Ar | stereochemistry |
|---|---|---|---|---|
| 109 | B17 | $X_1 = CF$<br>$X_2 = X_3 = X_4 = CH$ | *5-chloro-pyridine-2-carboxamide* | $C_5(S^*); C_6(R^*)$<br>Single diastereoisomer<br>Pure enantiomer<br>•2HCl salt |
| 110 | B17 | $X_1 = CF$<br>$X_2 = X_3 = X_4 = CH$ | *5-chloro-pyridine-2-carboxamide* | $C_5(R^*); C_6(S^*)$<br>Single diastereoisomer<br>Pure enantiomer |

TABLE 6-continued

| Co. No. | Ex. No. | $X_1, X_2, X_3, X_4$ | ----L—Ar | stereochemistry |
|---|---|---|---|---|
| 111 | B14 | $X_1$ = CF<br>$X_2 = X_3 = X_4$ = CH | pyrimidin-5-yl | $C_5(R^*);C_6(S^*)$<br>Single diastereoisomer<br>Pure enantiomer |
| 112 | B15 | $X_1 = X_2 = X_3 = X_4$ = CH | -NHC(O)-(5-chloropyridin-2-yl) | $C_5(S^*);C_6(S^*)$<br>Single diastereoisomer<br>Pure enantiomer |
| 113 | B15 | $X_1 = X_2 = X_3 = X_4$ = CH | -NHC(O)-(5-chloropyridin-2-yl) | $C_5(R^*);C_6(S^*)$<br>Single diastereoisomer<br>Pure enantiomer |
| 114 | B15 | $X_1 = X_2 = X_3 = X_4$ = CH | -NHC(O)-(5-chloropyridin-2-yl) | $C_5(S^*);C_6(R^*)$<br>Single diastereoisomer<br>Pure enantiomer |
| 115 | B15 | $X_1 = X_2 = X_3 = X_4$ = CH | -NHC(O)-(5-chloropyridin-2-yl) | $C_5(R^*);C_6(R^*)$<br>Single diastereoisomer<br>Pure enantiomer |
| 116 | B3 | $X_1 = X_2 = X_3 = X_4$ = CH | pyrimidin-5-yl | $C_5(R^*);C_6(R^*)$<br>Single diastereoisomer<br>Pure enantiomer |
| 117 | B3 | $X_1 = X_2 = X_3 = X_4$ = CH | pyrimidin-5-yl | $C_5(R^*);C_6(S^*)$<br>Single diastereoisomer<br>Pure enantiomer |
| 118 | B3 | $X_1 = X_2 = X_3 = X_4$ = CH | 5-methoxypyridin-3-yl | $C_5(R^*);C_6(S^*)$<br>Single diastereoisomer<br>Pure enantiomer |
| 119 | B3 | $X_1 = X_2 = X_3 = X_4$ = CH | 5-methoxypyridin-3-yl | $C_5(R^*);C_6(R^*)$<br>Single diastereoisomer<br>Pure enantiomer |
| 120 | B3 | $X_1 = X_2 = X_3 = X_4$ = CH | 5-methoxypyridin-3-yl | $C_5(RS);C_6(RS)$ |

TABLE 6-continued

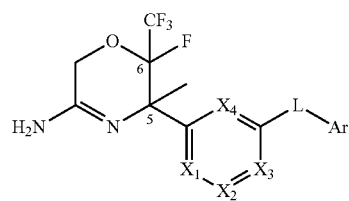

| Co. No. | Ex. No. | $X_1, X_2, X_3, X_4$ | ---L—Ar | stereochemistry |
|---|---|---|---|---|
| 138 | B14 | $X_1$ = CF<br>$X_2 = X_3 = X_4$ = CH | pyrimidin-5-yl | $C_5(R^*);C_6(S^*)$<br>Single diastereoisomer<br>(trans)<br>Pure enantiomer |
| 139 | B4 | $X_1 = X_2 = X_3 = X_4$ = CH | pyrimidin-5-yl | $C_5(S^*);C_6(R^*)$<br>Single diastereoisomer<br>(trans)<br>Pure enantiomer |
| 140 | B4 | $X_1 = X_2 = X_3 = X_4$ = CH | pyrimidin-5-yl | $C_5(S^*);C_6(S^*)$<br>Single diastereoisomer<br>(cis)<br>Pure enantiomer |
| 141 | B4 | $X_1 = X_2 = X_3 = X_4$ = CH | 5-methoxypyridin-3-yl | $C_5(S^*);C_6(R^*)$<br>Single diastereoisomer<br>(trans)<br>Pure enantiomer |
| 142 | B4 | $X_1 = X_2 = X_3 = X_4$ = CH | 5-methoxypyridin-3-yl | $C_5(S^*);C_6(S^*)$<br>Single diastereoisomer<br>(cis)<br>Pure enantiomer |
| 159 | B17 | $X_1$ = CF<br>$X_2 = X_3 = X_4$ = CH | 5-chloro-pyridine-2-carboxamide | $C_5(S^*);C_6(R^*)$<br>Single diastereoisomer<br>Pure enantiomer<br>•2HCl salt |
| 172 | B17 | $X_1 = X_2 = X_3 = X_4$ = CH | 5-chloro-3-fluoro-pyridine-2-carboxamide | $C_5(R^*);C_6(R^*)$<br>Single diastereoisomer<br>(cis)<br>Pure enantiomer |
| 173 | B17 | $X_1 = X_2 = X_3 = X_4$ = CH | 5-chloro-3-fluoro-pyridine-2-carboxamide | $C_5(R^*);C_6(S^*)$<br>Single diastereoisomer<br>(trans)<br>Pure enantiomer |
| 174 | B17 | $X_1 = X_2 = X_3 = X_4$ = CH | 5-chloro-3-fluoro-pyridine-2-carboxamide | $C_5(S^*);C_6(S^*)$<br>Single diastereoisomer<br>(cis)<br>Pure enantiomer |

TABLE 6-continued

[Structure shown: A bicyclic core with an oxazine ring containing O at position 6, CF₃ and F substituents at C6, a methyl group and connection at C5, H₂N-C=N group, connected via X₁=X₂-X₃=X₄ aromatic ring to L-Ar]

| Co. No. | Ex. No. | X₁, X₂, X₃, X₄ | ----L—Ar | stereochemistry |
|---|---|---|---|---|
| 175 | B17 | X₁ = X₂ = X₃ = X₄ = CH | 3-fluoro-5-chloropyridine-2-carboxamide | C₅(S*);C₆(R*) Single diastereoisomer (trans) Pure enantiomer |
| 176 | B17 | X₁ = X₂ = X₃ = X₄ = CH | 5-methoxypyrazine-2-carboxamide | C₅(R*);C₆(R*) Single diastereoisomer (cis) Pure enantiomer |
| 177 | B17 | X₁ = X₂ = X₃ = X₄ = CH | 5-methoxypyrazine-2-carboxamide | C₅(R*);C₆(S*) Single diastereoisomer (trans) Pure enantiomer |
| 178 | B17 | X₁ = X₂ = X₃ = X₄ = CH | 5-methoxypyrazine-2-carboxamide | C₅(S*);C₆(S*) Single diastereoisomer (cis) Pure enantiomer |
| 179 | B17 | X₁ = X₂ = X₃ = X₄ = CH | 5-methoxypyrazine-2-carboxamide | C₅(S*);C₆(R*) Single diastereoisomer (trans) Pure enantiomer |
| 180 | B17 | X₁ = CF, X₂ = X₃ = X₄ = CH | 5-methoxypyrazine-2-carboxamide | C₅(R);C₆(S) Single diastereoisomer (trans) Pure enantiomer |
| 181 | B17 | X₁ = CF, X₂ = X₃ = X₄ = CH | 3,5-dichloropyridine-2-carboxamide | C₅(R);C₆(S) Single diastereoisomer (trans) Pure enantiomer |
| 182 | B17 | X₁ = CF, X₂ = X₃ = X₄ = CH | pyrimidine-4-carboxamide | C₅(R);C₆(S) Single diastereoisomer (trans) Pure enantiomer |

TABLE 6-continued

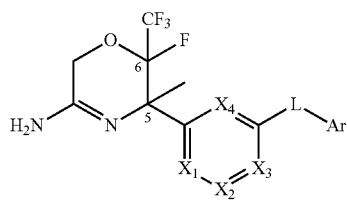

| Co. No. | Ex. No. | $X_1, X_2, X_3, X_4$ | ----L—Ar | stereochemistry |
|---|---|---|---|---|
| 183 | B17 | $X_1$ = CF<br>$X_2 = X_3 = X_4$ = CH | pyridine-2-carboxamide, 5-CN | $C_5(R);C_6(S)$<br>Single diastereoisomer<br>(trans)<br>Pure enantiomer |
| 184 | B17 | $X_1$ = CF<br>$X_2 = X_3 = X_4$ = CH | pyrazine-2-carboxamide, 5-OMe | $C_5(R);C_6(R)$<br>Single diastereoisomer<br>(cis)<br>Pure enantiomer |
| 185 | B17 | $X_1$ = CF<br>$X_2 = X_3 = X_4$ = CH | pyridine-2-carboxamide, 3,5-diCl | $C_5(R);C_6(R)$<br>Single diastereoisomer<br>(cis)<br>Pure enantiomer |
| 186 | B17 | $X_1$ = CF<br>$X_2 = X_3 = X_4$ = CH | pyridine-2-carboxamide, 5-Cl | $C_5(R);C_6(R)$<br>Single diastereoisomer<br>(cis)<br>Pure enantiomer |
| 187 | B17 | $X_1 = X_2 = X_3 = X_4$ = CH | pyrimidine-4-carboxamide | $C_5(R^*);C_6(R^*)$<br>Single diastereoisomer<br>(cis)<br>Pure enantiomer |
| 188 | B17 | $X_1 = X_2 = X_3 = X_4$ = CH | pyrimidine-4-carboxamide | $C_5(R^*);C_6(S^*)$<br>Single diastereoisomer<br>(trans)<br>Pure enantiomer |
| 189 | B17 | $X_1 = X_2 = X_3 = X_4$ = CH | pyrimidine-4-carboxamide | $C_5(S^*);C_6(S^*)$<br>Single diastereoisomer<br>(cis)<br>Pure enantiomer |
| 190 | B17 | $X_1 = X_2 = X_3 = X_4$ = CH | pyrimidine-4-carboxamide | $C_5(S^*);C_6(R^*)$<br>Single diastereoisomer<br>(trans)<br>Pure enantiomer |

TABLE 6-continued

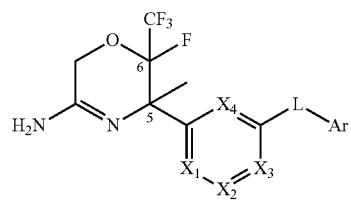

| Co. No. | Ex. No. | $X_1, X_2, X_3, X_4$ | ----L—Ar | stereochemistry |
|---|---|---|---|---|
| 191 | B17 | $X_1 = X_2 = X_3 = X_4 = CH$ | -NHC(O)-(5-methylpyridin-2-yl) | $C_5(S^*);C_6(S^*)$ Single diastereoisomer (cis) Pure enantiomer |
| 192 | B17 | $X_1 = X_2 = X_3 = X_4 = CH$ | -NHC(O)-(5-methylpyridin-2-yl) | $C_5(S^*);C_6(R^*)$ Single diastereoisomer (trans) Pure enantiomer |
| 193 | B17 | $X_1 = X_2 = X_3 = X_4 = CH$ | -NHC(O)-(5-methylpyridin-2-yl) | $C_5(R^*);C_6(S^*)$ Single diastereoisomer (trans) Pure enantiomer |
| 194 | B17 | $X_1 = X_2 = X_3 = X_4 = CH$ | -NHC(O)-(5-methylpyridin-2-yl) | $C_5(R^*);C_6(R^*)$ Single diastereoisomer (cis) Pure enantiomer |
| 210 | B14 | $X_1 = X_3 = CF$ $X_2 = X_4 = CH$ | pyrimidin-5-yl | $C_5(R);C_6(R)$ Single diastereoisomer Pure enantiomer |
| 211 | B14 | $X_1 = X_3 = CF$ $X_2 = X_4 = CH$ | pyrimidin-5-yl | $C_5(R);C_6(S)$ Single diastereoisomer Pure enantiomer |
| 212 | B14 | $X_1 = X_3 = CF$ $X_2 = X_4 = CH$ | 5-chloropyridin-3-yl | $C_5(R);C_6(R)$ Single diastereoisomer Pure enantiomer |
| 213 | B14 | $X_1 = X_3 = CF$ $X_2 = X_4 = CH$ | 5-chloropyridin-3-yl | $C_5(R);C_6(S)$ Single diastereoisomer Pure enantiomer |
| 240 | B15 | $X_1 = X_2 = X_3 = X_4 = CH$ | -NHC(O)-(5-cyanopyridin-2-yl) | $C_5(R);C_6(R)$ Single diastereoisomer Pure enantiomer |

TABLE 6-continued

[Structure: H₂N-C(=N)-... 6-membered ring with O, C6 bearing CF₃ and F, C5 bearing methyl and connected to aryl ring (X₁-X₄) with L-Ar substituent]

| Co. No. | Ex. No. | X₁, X₂, X₃, X₄ | ----L—Ar | stereochemistry |
|---|---|---|---|---|
| 241 | B15 | X₁ = X₂ = X₃ = X₄ = CH | –NHC(O)-(2-pyridyl-5-CN) | C₅(R);C₆(S) Single diastereoisomer Pure enantiomer |
| 242 | B15 | X₁ = X₂ = X₃ = X₄ = CH | –NHC(O)-(3,5-dichloro-2-pyridyl) | C₅(R);C₆(R) Single diastereoisomer Pure enantiomer |
| 243 | B15 | X₁ = X₂ = X₃ = X₄ = CH | –NHC(O)-(3,5-dichloro-2-pyridyl) | C₅(R);C₆(S) Single diastereoisomer Pure enantiomer |
| 245 | B15 | X₁ = X₂ = X₃ = X₄ = CH | –NHC(O)-(3-chloro-5-cyano-2-pyridyl) | C₅(R);C₆(R) Single diastereoisomer Pure enantiomer |
| 246 | B15 | X₁ = X₂ = X₃ = X₄ = CH | –NHC(O)-(3-chloro-5-cyano-2-pyridyl) | C₅(R);C₆(S) Single diastereoisomer Pure enantiomer |
| 247 | B15 | X₁ = X₂ = X₃ = X₄ = CH | –NHC(O)-(5-methoxy-2-pyridyl) | C₅(R);C₆(R) Single diastereoisomer Pure enantiomer |
| 248 | B15 | X₁ = X₂ = X₃ = X₄ = CH | –NHC(O)-(5-methoxy-2-pyridyl) | C₅(R);C₆(S) Single diastereoisomer Pure enantiomer |
| 263 | B17 | X₁ = CF; X₂ = X₃ = X₄ = CH | –NHC(O)-(5-(2,2,2-trifluoroethoxy)pyrazin-2-yl) | C₅(R);C₆(RS) Two diastereoisomers |

TABLE 6-continued

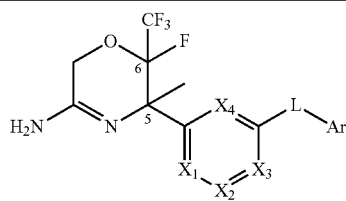

| Co. No. | Ex. No. | $X_1, X_2, X_3, X_4$ | ----L—Ar | stereochemistry |
|---|---|---|---|---|
| 304 | B17 | $X_1$ = CF<br>$X_2 = X_3 = X_4$ = CH | pyridine-2-carboxamide, 5-OMe | $C_5(R);C_6(R)$<br>Single diastereoisomer<br>Pure enantiomer |
| 305 | B17 | $X_1$ = CF<br>$X_2 = X_3 = X_4$ = CH | pyridine-2-carboxamide, 5-OMe | $C_5(R);C_6(S)$<br>Single diastereoisomer<br>Pure enantiomer |
| 306 | B17 | $X_1$ = CF<br>$X_2 = X_3 = X_4$ = CH | pyridine-2-carboxamide, 3-Cl, 5-CN | $C_5(R);C_6(R)$<br>Single diastereoisomer<br>Pure enantiomer |
| 307 | B17 | $X_1$ = CF<br>$X_2 = X_3 = X_4$ = CH | pyridine-2-carboxamide, 3-Cl, 5-CN | $C_5(R);C_6(S)$<br>Single diastereoisomer<br>Pure enantiomer |
| 318 | B21 | $X_1$ = CF<br>$X_2 = X_3 = X_4$ = CH | pyrazine-2-carboxamide, 5-OCH$_2$CF$_3$ | $C_5(R);C_6(R)$<br>Single diastereoisomer<br>Pure enantiomer |
| 319 | B21 | $X_1$ = CF<br>$X_2 = X_3 = X_4$ = CH | pyrazine-2-carboxamide, 5-OCH$_2$CF$_3$ | $C_5(R);C_6(S)$<br>Single diastereoisomer<br>Pure enantiomer |
| 355 | B21 | $X_1$ = CF<br>$X_2 = X_3 = X_4$ = CH | pyridine-2-carboxamide, 3-F, 5-Cl | $C_5(R);C_6(S)$<br>Single diastereoisomer<br>Pure enantiomer |
| 356 | B21 | $X_1$ = CF<br>$X_2 = X_3 = X_4$ = CH | pyridine-2-carboxamide, 3-F, 5-Cl | $C_5(R);C_6(R)$<br>Single diastereoisomer<br>Pure enantiomer |

TABLE 7

[Structure: morpholine-fused aminoimine with R5 at C5, phenyl with X1 and L-Ar substituents]

| Co. No. | Ex. No. | R5 | X1 | ----L—Ar | C5-stereochemistry |
|---|---|---|---|---|---|
| 152 | B18 | ----CF3 | X1 = H | 3-methoxypyridin-5-yl | RS |
| 153 | B19 | cyclopropyl | X1 = H | N-H-C(O)-(5-chloropyridin-2-yl) | RS |
| 195 | B19 | cyclopropyl | X1 = H | N-H-C(O)-(5-chloropyridin-2-yl) | R* Pure enantiomer |
| 196 | B19 | cyclopropyl | X1 = H | N-H-C(O)-(5-chloropyridin-2-yl) | S* Pure enantiomer |
| 299 | B23 | cyclopropyl | X1 = F | N-H-C(O)-(5-methoxypyrazin-2-yl) | R Pure enantiomer |

TABLE 8

[Structure: morpholine-fused aminoimine with methyl at C5, phenyl with X2 and L-Ar substituents]

| Co. No. | Ex. No. | X2 | ----L—Ar | C5-stereochemistry |
|---|---|---|---|---|
| 197 | B15 | C—CF3 | N-H-C(O)-(5-chloropyridin-2-yl) | RS |

TABLE 9

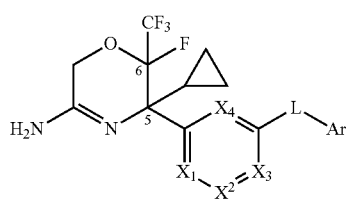

| Co. No. | Ex. No. | $X_1, X_2, X_3, X_4$ | ----L—Ar | stereochemistry |
|---|---|---|---|---|
| 198 | B23 | $X_1 = X_2 = X_3 = X_4 = CH$ | -NH-C(O)-pyridyl-CN | $C_5(R);C_6(R)$<br>Single diastereoisomer<br>Pure enantiomer |
| 199 | B23 | $X_1 = X_2 = X_3 = X_4 = CH$ | -NH-C(O)-pyridyl-CN | $C_5(R);C_6(S)$<br>Single diastereoisomer<br>Pure enantiomer |
| 202 | B23 | $X_1 = X_2 = X_3 = X_4 = CH$ | -NH-C(O)-pyrazinyl-OMe | $C_5(R);C_6(R)$<br>Single diastereoisomer<br>Pure enantiomer<br>•HCl salt |
| 203 | B23 | $X_1 = X_2 = X_3 = X_4 = CH$ | -NH-C(O)-pyrazinyl-OMe | $C_5(R);C_6(S)$<br>Single diastereoisomer<br>Pure enantiomer<br>•HCl salt |
| 262 | B23 | $X_1 = CF$<br>$X_2 = X_3 = X_4 = CH$ | -NH-C(O)-pyridyl-CN | $C_5(R);C_6(S)$<br>Single diastereoisomer<br>Pure enantiomer |
| 271 | B25 | $X_1 = CF$<br>$X_2 = X_3 = X_4 = CH$ | -pyridyl-CN | $C_5(R);C_6(S)$<br>Single diastereoisomer<br>Pure enantiomer |
| 312 | B25 | $X_1 = CF$<br>$X_2 = X_3 = X_4 = CH$ | -pyrimidinyl | $C_5(R);C_6(S)$<br>Single diastereoisomer<br>Pure enantiomer |

TABLE 10

| Co. No. | Ex. No. | $X_1, X_2, X_3, X_4$ | ----L—Ar | stereochemistry |
|---|---|---|---|---|
| 214 | B24 | $X_1 = CF$<br>$X_2 = X_3 = X_4 = CH$ | 5-cyanopyridine-2-carboxamide | $C_5(R); C_6(R)$<br>Single diastereoisomer<br>Pure enantiomer |
| 215 | B24 | $X_1 = CF$<br>$X_2 = X_3 = X_4 = CH$ | 5-cyanopyridine-2-carboxamide | $C_5(R); C_6(S)$<br>Single diastereoisomer<br>Pure enantiomer |
| 216 | B24 | $X_1 = CF$<br>$X_2 = X_3 = X_4 = CH$ | 5-methoxypyrazine-2-carboxamide | $C_5(R); C_6(R)$<br>Single diastereoisomer<br>Pure enantiomer |
| 217 | B24 | $X_1 = CF$<br>$X_2 = X_3 = X_4 = CH$ | 5-methoxypyrazine-2-carboxamide | $C_5(R); C_6(S)$<br>Single diastereoisomer<br>Pure enantiomer |
| 218 | B24 | $X_1 = CF$<br>$X_2 = X_3 = X_4 = CH$ | 3-chloro-5-cyanopyridine-2-carboxamide | $C_5(R); C_6(R)$<br>Single diastereoisomer<br>Pure enantiomer |
| 219 | B24 | $X_1 = CF$<br>$X_2 = X_3 = X_4 = CH$ | 5-chloro-3-fluoropyridine-2-carboxamide | $C_5(R); C_6(R)$<br>Single diastereoisomer<br>Pure enantiomer |
| 220 | B24 | $X_1 = CF$<br>$X_2 = X_3 = X_4 = CH$ | 5-chloro-3-fluoropyridine-2-carboxamide | $C_5(R); C_6(S)$<br>Single diastereoisomer<br>Pure enantiomer |
| 221 | B24 | $X_1 = CF$<br>$X_2 = X_3 = X_4 = CH$ | 5-methoxypyridine-2-carboxamide | $C_5(R); C_6(R)$<br>Single diastereoisomer<br>Pure enantiomer |

TABLE 10-continued

| Co. No. | Ex. No. | $X_1, X_2, X_3, X_4$ | ----L—Ar | stereochemistry |
|---|---|---|---|---|
| 222 | B25 | $X_1 = CF$<br>$X_2 = X_3 = X_4 = CH$ | 5-cyanopyridin-3-yl | $C_5(R);C_6(R)$<br>Single diastereoisomer<br>Pure enantiome |
| 223 | B25 | $X_1 = CF$<br>$X_2 = X_3 = X_4 = CH$ | 5-cyanopyridin-3-yl | $C_5(R);C_6(S)$<br>Single diastereoisomer<br>Pure enantiomer |
| 224 | B25 | $X_1 = CF$<br>$X_2 = X_3 = X_4 = CH$ | pyrimidin-5-yl | $C_5(R);C_6(S)$<br>Single diastereoisomer<br>Pure enantiomer |
| 244 | B28 | $X_1 = CF$<br>$X_2 = X_3 = X_4 = CH$ | 5-methoxypyrazine-2-carboxamide | $C_5(R);C_6(R)$<br>Single diastereoisomer<br>Pure enantiomer<br>•HCl salt |
| 249 | B28 | $X_1 = X_2 = X_3 = X_4 = CH$ | 5-chloro-3-fluoropyridine-2-carboxamide | $C_5(R);C_6(S)$<br>Single diastereoisomer<br>Pure enantiomer |
| 250 | B28 | $X_1 = X_2 = X_3 = X_4 = CH$ | 5-chloro-3-fluoropyridine-2-carboxamide | $C_5(R);C_6(R)$<br>Single diastereoisomer<br>Pure enantiomer |
| 251 | B28 | $X_1 = X_2 = X_3 = X_4 = CH$ | 5-cyanopyridine-2-carboxamide | $C_5(R);C_6(R)$<br>Single diastereoisomer<br>Pure enantiomer |
| 256 | B28 | $X_1 = X_2 = X_3 = X_4 = CH$ | 3,5-dichloropyridine-2-carboxamide | $C_5(R);C_6(R)$<br>Single diastereoisomer<br>Pure enantiomer |
| 257 | B25 | $X_1 = X_2 = X_3 = X_4 = CH$ | pyrimidin-5-yl | $C_5(R);C_6(R)$<br>Single diastereoisomer<br>Pure enantiomer |

TABLE 10-continued

[Structure: 2-amino-3-cyclopropyl-3-fluoro-morpholine-like ring with C5 bearing substituent connected through X1-X2-X3-X4 aryl ring to L-Ar group. H2N-C=N-C5(cyclopropyl, with O-CH2 and CHF at C6)-aryl(X1-X4)-L-Ar]

| Co. No. | Ex. No. | $X_1, X_2, X_3, X_4$ | ----L—Ar | stereochemistry |
|---|---|---|---|---|
| 258 | B25 | $X_1 = X_2 = X_3 = X_4 = CH$ | pyrimidin-5-yl | $C_5(R);C_6(S)$ Single diastereoisomer Pure enantiomer |
| 259 | B24 | $X_1 = CF$ $X_2 = X_3 = X_4 = CH$ | N-H-C(=O)-(3,5-dichloropyridin-2-yl) | $C_5(R);C_6(R)$ Single diastereoisomer Pure enantiomer |
| 264 | B24 | $X_1 = CF$ $X_2 = X_3 = X_4 = CH$ | N-H-C(=O)-(5-(2,2,2-trifluoroethoxy)pyrazin-2-yl) | $C_5(R);C_6(R)$ Single diastereoisomer Pure enantiomer |
| 272 | B28 | $X_1 = X_2 = X_3 = X_4 = CH$ | N-H-C(=O)-(5-bromo-3-methylpyridin-2-yl) | $C_5(R);C_6(S)$ Single diastereoisomer Pure enantiomer |
| 273 | B25 | $X_1 = CF$ $X_2 = X_3 = X_4 = CH$ | 5-chloropyridin-3-yl | $C_5(R);C_6(S)$ Single diastereoisomer Pure enantiomer |
| 274 | B28 | $X_1 = X_2 = X_3 = X_4 = CH$ | N-H-C(=O)-(5-(2,2,2-trifluoroethoxy)pyrazin-2-yl) | $C_5(R);C_6(S)$ Single diastereoisomer Pure enantiomer |
| 275 | B28 | $X_1 = X_2 = X_3 = X_4 = CH$ | N-H-C(=O)-(5-(2,2,2-trifluoroethoxy)pyrazin-2-yl) | $C_5(R);C_6(R)$ Single diastereoisomer Pure enantiomer |
| 276 | B28 | $X_1 = X_2 = X_3 = X_4 = CH$ | N-H-C(=O)-(3,5-dichloropyridin-2-yl) | $C_5(R);C_6(S)$ Single diastereoisomer Pure enantiomer |
| 280 | B28 | $X_1 = X_2 = X_3 = X_4 = CH$ | N-H-C(=O)-(5-cyanopyridin-2-yl) | $C_5(R);C_6(S)$ Single diastereoisomer Pure enantiomer |

TABLE 10-continued

| Co. No. | Ex. No. | $X_1, X_2, X_3, X_4$ | ----L—Ar | stereochemistry |
|---|---|---|---|---|
| 292 | B25 | $X_1$ = CF<br>$X_2 = X_3 = X_4$ = CH | 3-ethynylpyridin-5-yl | $C_5(R);C_6(R)$<br>Single diastereoisomer<br>Pure enantiomer |
| 293 | B25 | $X_1$ = CF<br>$X_2 = X_3 = X_4$ = CH | 3-ethynylpyridin-5-yl | $C_5(R);C_6(S)$<br>Single diastereoisomer<br>Pure enantiomer |
| 294 | B25 | $X_1$ = CF<br>$X_2 = X_3 = X_4$ = CH | 3-chloropyridin-5-yl | $C_5(R);C_6(R)$<br>Single diastereoisomer<br>Pure enantiomer |
| 295 | B25 | $X_1$ = CF<br>$X_2 = X_3 = X_4$ = CH | 3-chloropyridin-5-yl | $C_5(R);C_6(S)$<br>Single diastereoisomer<br>Pure enantiomer |
| 296 | B25 | $X_1$ = CF<br>$X_2 = X_3 = X_4$ = CH | pyrimidin-5-yl | $C_5(R);C_6(R)$<br>Single diastereoisomer<br>Pure enantiomer |
| 297 | B28 | $X_1 = X_2 = X_3 = X_4$ = CH | N-H amide to 5-chloro-3-methylpyridin-2-yl | $C_5(R);C_6(R)$<br>Single diastereoisomer<br>Pure enantiomer |
| 298 | B28 | $X_1 = X_2 = X_3 = X_4$ = CH | N-H amide to 5-chloro-3-methylpyridin-2-yl | $C_5(R);C_6(S)$<br>Single diastereoisomer<br>Pure enantiomer |
| 309 | B28 | $X_1 = X_2 = X_3 = X_4$ = CH | N-H amide to 3-chloro-5-cyanopyridin-2-yl | $C_5(R);C_6(S)$<br>Single diastereoisomer<br>Pure enantiomer |
| 311 | B25 | $X_1 = X_2 = X_3 = X_4$ = CH | 5-cyanopyridin-3-yl | $C_5(R);C_6(R)$<br>Single diastereoisomer<br>Pure enantiomer |

TABLE 10-continued

[Structure: core scaffold with H₂N group, N, O, F, cyclopropyl, positions labeled 5 and 6, linked to a ring X₁=X₂, X₂=X₃, X₃=X₄ with L—Ar substituent]

| Co. No. | Ex. No. | X₁, X₂, X₃, X₄ | ----L—Ar | stereochemistry |
|---|---|---|---|---|
| 313 | B28 | X₁ = X₂ = X₃ = X₄ = CH | [3-methyl-5-bromopyridine-2-carboxamide] | C₅(R);C₆(R) Single diastereoisomer Pure enantiomer |
| 314 | B24 | X₁ = CF, X₂ = X₃ = X₄ = CH | [3-methyl-5-bromopyridine-2-carboxamide] | C₅(R);C₆(R) Single diastereoisomer Pure enantiomer |
| 315 | B24 | X₁ = CF, X₂ = X₃ = X₄ = CH | [3-methyl-5-chloropyridine-2-carboxamide] | C₅(R);C₆(R) Single diastereoisomer Pure enantiomer |
| 321 | B25 | X₁ = CF, X₂ = X₃ = X₄ = CH | [3-(2,2,2-trifluoroethoxy)pyridin-5-yl] | C₅(R);C₆(R) Single diastereoisomer Pure enantiomer |
| 322 | B25 | X₁ = CF, X₂ = X₃ = X₄ = CH | [3-(2,2,2-trifluoroethoxy)pyridin-5-yl] | C₅(R);C₆(S) Single diastereoisomer Pure enantiomer |
| 325 | B26 | X₁ = X₂ = X₃ = X₄ = CH | [3,5-difluoropyridine-2-carboxamide] | C₅(R);C₆(R) Single diastereoisomer Pure enantiomer |
| 326 | B26 | X₁ = X₂ = X₃ = X₄ = CH | [3,5-difluoropyridine-2-carboxamide] | C₅(R);C₆(S) Single diastereoisomer Pure enantiomer |
| 327 | B26 | X₁ = X₂ = X₃ = X₄ = CH | [3-fluoro-5-cyanopyridine-2-carboxamide] | C₅(R);C₆(R) Single diastereoisomer Pure enantiomer |
| 337 | B26 | X₁ = X₂ = X₃ = X₄ = CH | [5-(difluoromethyl)pyrazine-2-carboxamide] | C₅(R);C₆(R) Single diastereoisomer Pure enantiomer |

TABLE 10-continued

| Co. No. | Ex. No. | $X_1, X_2, X_3, X_4$ | ----L—Ar | stereochemistry |
|---|---|---|---|---|
| 344 | B24 | $X_1 = CF$<br>$X_2 = X_3 = X_4 = CH$ | pyrazine-2-carboxamide, 5-(2-methoxyethoxy) | $C_5(R);C_6(R)$<br>Single diastereoisomer<br>Pure enantiomer |
| 345 | B24 | $X_1 = CF$<br>$X_2 = X_3 = X_4 = CH$ | 3-fluoro-5-cyanopyridine-2-carboxamide | $C_5(R);C_6(R)$<br>Single diastereoisomer<br>Pure enantiomer |
| 347 | B26 | $X_1 = X_2 = X_3 = X_4 = CH$ | pyrazine-2-carboxamide, 5-(2-methoxyethoxy) | $C_5(R);C_6(R)$<br>Single diastereoisomer<br>Pure enantiomer |
| 348 | B26 | $X_1 = X_2 = X_3 = X_4 = CH$ | 3-chloro-5-cyanopyridine-2-carboxamide | $C_5(R);C_6(R)$<br>Single diastereoisomer<br>Pure enantiomer |
| 349 | B26 | $X_1 = X_2 = X_3 = X_4 = CH$ | 5-ethoxypyrazine-2-carboxamide | $C_5(R);C_6(R)$<br>Single diastereoisomer<br>Pure enantiomer |
| 370 | B24 | $X_1 = CF$<br>$X_2 = X_3 = X_4 = CH$ | 5-ethoxypyrazine-2-carboxamide | $C_5(R);C_6(R)$<br>Single diastereoisomer<br>Pure enantiomer |
| 406 | B25 | $X_1 = X_2 = X_3 = X_4 = CH$ | 3-(2,2,2-trifluoroethoxy)pyridin-5-yl | $C_5(R);C_6(R)$<br>Single diastereoisomer<br>Pure enantiomer |

TABLE 10-continued

[Structure: morpholine with O, F, cyclopropyl at position 6; H2N-C=N at position 5, with X1-X4 ring and L-Ar substituent]

| Co. No. | Ex. No. | X1, X2, X3, X4 | ----L—Ar | stereochemistry |
|---|---|---|---|---|
| 407 | B25 | X1 = X2 = X3 = X4 = CH | [pyridine with OCH2CF3] | C5(R);C6(S) Single diastereoisomer Pure enantiomer |

TABLE 11

[Structure: morpholine with O, CF3, cyclopropyl at position 6; H2N-C=N at position 5, with X1-X4 ring and L-Ar substituent]

| Co. No. | Ex. No. | X1, X2, X3, X4 | ----L—Ar | stereochemistry |
|---|---|---|---|---|
| 225 | B26 | X1 = X2 = X3 = X4 = CH | [C(=O)NH-pyridine-CN] | C5(R);C6(R) Single diastereoisomer Pure enantiomer •HCl salt |
| 226 | B26 | X1 = X2 = X3 = X4 = CH | [C(=O)NH-pyridine-CN] | C5(R);C6(S) Single diastereoisomer Pure enantiomer |
| 227 | B26 | X1 = X2 = X3 = X4 = CH | [C(=O)NH-pyrazine-OMe] | C5(R);C6(R) Single diastereoisomer Pure enantiomer |
| 228 | B26 | X1 = X2 = X3 = X4 = CH | [C(=O)NH-pyrazine-OMe] | C5(R);C6(S) Single diastereoisomer Pure enantiomer |
| 229 | B27 | X1 = CF X2 = X3 = X4 = CH | [C(=O)NH-pyridine-CN] | C5(R);C6(R) Single diastereoisomer Pure enantiomer |

TABLE 11-continued

| Co. No. | Ex. No. | $X_1, X_2, X_3, X_4$ | ----L—Ar | stereochemistry |
|---|---|---|---|---|
| 230 | B27 | $X_1 = CF$<br>$X_2 = X_3 = X_4 = CH$ | N-H–C(=O)–pyrazine–OMe | $C_5(R);C_6(R)$<br>Single diastereoisomer<br>Pure enantiomer |
| 231 | B27 | $X_1 = CF$<br>$X_2 = X_3 = X_4 = CH$ | N-H–C(=O)–pyridine–OMe | $C_5(R);C_6(R)$<br>Single diastereoisomer<br>Pure enantiomer |
| 232 | B27 | $X_1 = CF$<br>$X_2 = X_3 = X_4 = CH$ | N-H–C(=O)–pyridine (F, Cl) | $C_5(R);C_6(R)$<br>Single diastereoisomer<br>Pure enantiomer |
| 233 | B27 | $X_1 = CF$<br>$X_2 = X_3 = X_4 = CH$ | N-H–C(=O)–pyridine–Cl | $C_5(R);C_6(R)$<br>Single diastereoisomer<br>Pure enantiomer |
| 234 | B27 | $X_1 = CF$<br>$X_2 = X_3 = X_4 = CH$ | N-H–C(=O)–pyridine (Cl, Cl) | $C_5(R);C_6(R)$<br>Single diastereoisomer<br>Pure enantiomer |
| 235 | B27 | $X_1 = CF$<br>$X_2 = X_3 = X_4 = CH$ | N-H–C(=O)–pyridine (Cl, CN) | $C_5(R);C_6(R)$<br>Single diastereoisomer<br>Pure enantiomer |
| 253 | B29 | $X_1 = X_2 = X_3 = X_4 = CH$ | pyridine–CN | $C_5(R);C_6(R)$<br>Single diastereoisomer<br>Pure enantiomer |
| 269 | B29 | $X_1 = X_2 = X_3 = X_4 = CH$ | pyrimidine | $C_5(R);C_6(R)$<br>Single diastereoisomer<br>Pure enantiomer |
| 270 | B29 | $X_1 = X_2 = X_3 = X_4 = CH$ | pyridine–F | $C_5(R);C_6(R)$<br>Single diastereoisomer<br>Pure enantiomer |

TABLE 11-continued

| Co. No. | Ex. No. | $X_1, X_2, X_3, X_4$ | ----L—Ar | stereochemistry |
|---|---|---|---|---|
| 286 | B29 | $X_1 = X_2 = X_3 = X_4 = CH$ | pyrimidin-5-yl | $C_5(R); C_6(S)$<br>Single diastereoisomer<br>Pure enantiomer |
| 287 | B27 | $X_1 = X_2 = X_3 = X_4 = CH$ | 3-F, 5-Cl-pyridine-2-carboxamide | $C_5(R); C_6(S)$<br>Single diastereoisomer<br>Pure enantiomer |
| 288 | B26 | $X_1 = X_2 = X_3 = X_4 = CH$ | 3-F, 5-Cl-pyridine-2-carboxamide | $C_5(R); C_6(R)$<br>Single diastereoisomer<br>Pure enantiomer |
| 289 | B26 | $X_1 = X_2 = X_3 = X_4 = CH$ | 5-(2,2,2-trifluoroethoxy)pyrazine-2-carboxamide | $C_5(R); C_6(R)$<br>Single diastereoisomer<br>Pure enantiomer |
| 290 | B26 | $X_1 = X_2 = X_3 = X_4 = CH$ | 3-Cl, 5-CN-pyridine-2-carboxamide | $C_5(R); C_6(S)$<br>Single diastereoisomer<br>Pure enantiomer |
| 291 | B26 | $X_1 = X_2 = X_3 = X_4 = CH$ | 3-Cl, 5-CN-pyridine-2-carboxamide | $C_5(R); C_6(R)$<br>Single diastereoisomer<br>Pure enantiomer |
| 323 | B27 | $X_1 = CF$<br>$X_2 = X_3 = X_4 = CH$ | 5-(CHF$_2$)-pyrazine-2-carboxamide | $C_5(R); C_6(R)$<br>Single diastereoisomer<br>Pure enantiomer |
| 324 | B27 | $X_1 = CF$<br>$X_2 = X_3 = X_4 = CH$ | 3-methyl, 5-Cl-pyridine-2-carboxamide | $C_5(R); C_6(R)$<br>Single diastereoisomer<br>Pure enantiomer |

TABLE 11-continued

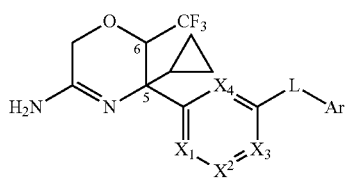

| Co. No. | Ex. No. | $X_1, X_2, X_3, X_4$ | ----L—Ar | stereochemistry |
|---|---|---|---|---|
| 328 | B27 | $X_1$ = CF<br>$X_2 = X_3 = X_4$ = CH | 3-fluoro-5-cyano-pyridine-2-carboxamide | $C_5(R);C_6(R)$<br>Single diastereoisomer<br>Pure enantiomer |
| 329 | B29 | $X_1 = X_2 = X_3 = X_4$ = CH | 5-chloropyridin-3-yl | $C_5(R);C_6(R)$<br>Single diastereoisomer<br>Pure enantiomer |
| 338 | B26 | $X_1 = X_2 = X_3 = X_4$ = CH | 5-(2-methoxyethoxy)pyrazine-2-carboxamide | $C_5(R);C_6(R)$<br>Single diastereoisomer<br>Pure enantiomer |
| 346 | B27 | $X_1$ = CF<br>$X_2 = X_3 = X_4$ = CH | 5-(2-methoxyethoxy)pyrazine-2-carboxamide | $C_5(R);C_6(R)$<br>Single diastereoisomer<br>Pure enantiomer |
| 405 | B26 | $X_1 = X_2 = X_3 = X_4$ = CH | 3-fluoro-5-cyano-pyridine-2-carboxamide | $C_5(R);C_6(R)$<br>Single diastereoisomer<br>Pure enantiomer |

TABLE 12

| Co. No. | Ex. No. | $X_1, X_2, X_3, X_4$ | $R^3, R^4$ | ----L—Ar | stereochemistry |
|---|---|---|---|---|---|
| 252 | B23 | $X_1$ = CF<br>$X_2 = X_3 = X_4$ = CH | $R^3 = CF_3$<br>$R^4$ = F | pyrazine-2-carboxamide, 5-methoxy | $C_5(RS);C_6(RS)$ |
| 281 | B24 | $X_1$ = CF<br>$X_2 = X_3 = X_4$ = CH | $R^3$ = H<br>$R^4$ = F | pyrazine-2-carboxamide, 5-methoxy | $C_5(RS);C_6(RS)$<br>Single diastereoisomer<br>(trans) |
| 282 | B24 | $X_1$ = CF<br>$X_2 = X_3 = X_4$ = CH | $R^3$ = H<br>$R^4$ = F | pyrazine-2-carboxamide, 5-methoxy | $C_5(RS);C_6(RS)$<br>Single diastereoisomer<br>(cis) |
| 283 | B24 | $X_1$ = CF<br>$X_2 = X_3 = X_4$ = CH | $R^3$ = H<br>$R^4$ = F | pyridine-2-carboxamide, 3-F, 5-Cl | $C_5(RS);C_6(RS)$<br>Single diastereoisomer<br>(trans) |
| 284 | B27 | $X_1$ = CF<br>$X_2 = X_3 = X_4$ = CH | $R^3$ = H<br>$R^4 = CF_3$ | pyridine-2-carboxamide, 3-Cl, 5-CN | $C_5(RS);C_6(RS)$<br>Single diastereoisomer<br>(cis) |
| 285 | B27 | $X_1$ = CF<br>$X_2 = X_3 = X_4$ = CH | $R^3$ = H<br>$R^4 = CF_3$ | pyrazine-2-carboxamide, 5-methoxy | $C_5(RS);C_6(RS)$<br>Single diastereoisomer<br>(cis) |
| 300 | B23 | $X_1$ = CF<br>$X_2 = X_3 = X_4$ = CH | $R^3 = CF_3$<br>$R^4$ = F | pyrazine-2-carboxamide, 5-methoxy | $C_5(RS);C_6(RS)$<br>Single diastereoisomer<br>(cis) |
| 301 | B23 | $X_1$ = CF<br>$X_2 = X_3 = X_4$ = CH | $R^3 = CF_3$<br>$R^4$ = F | pyrazine-2-carboxamide, 5-methoxy | $C_5(RS);C_6(RS)$<br>Single diastereoisomer<br>(trans) |

TABLE 12-continued

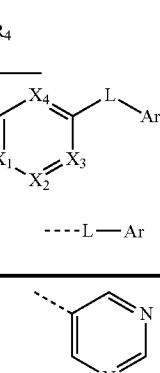

| Co. No. | Ex. No. | $X_1, X_2, X_3, X_4$ | $R^3, R^4$ | ----L—Ar | stereochemistry |
|---|---|---|---|---|---|
| 302 | B25 | $X_1 = CF$<br>$X_2 = X_3 = X_4 = CH$ | $R^3 = CF_3$<br>$R^4 = F$ | 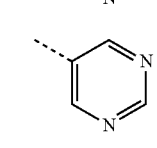 | $C_5(RS);C_6(RS)$<br>Single diastereoisomer<br>(cis) |
| 303 | B25 | $X_1 = CF$<br>$X_2 = X_3 = X_4 = CH$ | $R^3 = CF_3$<br>$R^4 = F$ | 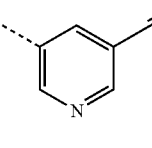 | $C_5(RS);C_6(RS)$<br>Single diastereoisomer<br>(trans) |
| 310 | B29 | $X_1 = CF$<br>$X_2 = X_3 = X_4 = CH$ | $R^3 = H$<br>$R^4 = CF_3$ | 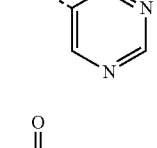 | $C_5(RS);C_6(RS)$<br>Single diastereoisomer<br>(cis) |
| 320 | B25 | $X_1 = X_2 = X_3 = X_4 = CH$ | $R^3 = H$<br>$R^4 = F$ | 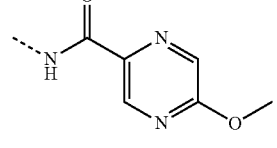 | $C_5(R);C_6(R)$<br>Single diastereoisomer<br>Pure enantiomer |
| 334 | B23 | $X_1 = X_2 = X_3 = X_4 = CH$ | $R^3 = H$<br>$R^4 = CF_3$ | 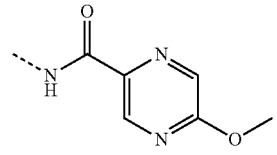 | $C_5(RS);C_6(RS)$<br>Single diastereoisomer<br>(trans) |
| 359 | B25 | $X_1 = X_2 = X_3 = X_4 = CH$ | $R^3 = H$<br>$R^4 = CF_3$ | 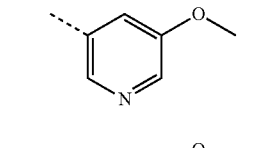 | $C_5(R);C_6(R)$<br>Single diastereoisomer<br>Pure enantiomer |
| 360 | B14 | $X_1 = X_2 = X_3 = X_4 = CH$ | $R^3 = H$<br>$R^4 = CF_3$ | 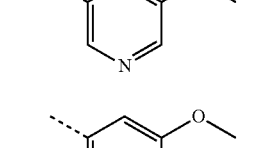 | $C_5(R);C_6(R)$<br>Single diastereoisomer<br>(cis) |
| 361 | B24 | $X_1 = X_2 = X_3 = X_4 = CH$ | $R^3 = H$<br>$R^4 = CF_3$ | 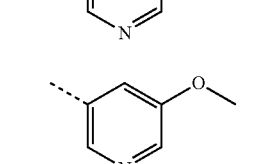 | $C_5(R);C_6(S)$<br>Single diastereoisomer<br>(trans) |
| 362 | B14 | $X_1 = X_2 = X_3 = X_4 = CH$ | $R^3 = H$<br>$R^4 = CF_3$ | 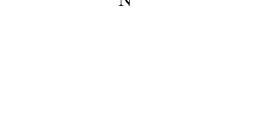 | $C_5(R);C_6(R)$<br>Single diastereoisomer<br>(cis) |
| 363 | B14 | $X_1 = X_2 = X_3 = X_4 = CH$ | $R^3 = H$<br>$R^4 = CF_3$ | | $C_5(R);C_6(S)$<br>Single diastereoisomer<br>(trans) |

TABLE 12-continued

| Co. No. | Ex. No. | $X_1, X_2, X_3, X_4$ | $R^3, R^4$ | ----L—Ar | stereochemistry |
|---|---|---|---|---|---|
| 364 | B25 | $X_1 = X_2 = X_3 = X_4 = CH$ | $R^3 = H$<br>$R^4 = CF_3$ | pyrazine-2-carboxamide with $CF_2$ at 5-position | $C_5(R);C_6(R)$<br>Single diastereoisomer<br>Pure enantiomer |
| 365 | B25 | $X_1 = X_2 = X_3 = X_4 = CH$ | $R^3 = H$<br>$R^4 = CF_3$ | pyrazine-2-carboxamide with OMe at 5-position | $C_5(R);C_6(S)$<br>Single diastereoisomer<br>Pure enantiomer |
| 366 | B25 | $X_1 = X_2 = X_3 = X_4 = CH$ | $R^3 = H$<br>$R^4 = CF_3$ | pyridine-2-carboxamide, 3-Cl, 5-CN | $C_5(R);C_6(R)$<br>Single diastereoisomer<br>Pure enantiomer |
| 368 | B25 | $X_1 = X_2 = X_3 = X_4 = CH$ | $R^3 = H$<br>$R^4 = CF_3$ | pyrazine-2-carboxamide, 5-O-CH$_2$CH$_2$-OMe | $C_5(R);C_6(R)$<br>Single diastereoisomer<br>Pure enantiomer |
| 369 | B25 | $X_1 = X_2 = X_3 = X_4 = CH$ | $R^3 = H$<br>$R^4 = CF_3$ | pyridine-2-carboxamide, 3-F, 5-CN | $C_5(R);C_6(R)$<br>Single diastereoisomer<br>Pure enantiomer |
| 395 | B23 | $X_1 = CF$<br>$X_2 = X_3 = X_4 = CH$ | $R^3 = H$<br>$R^4 = CF_3$ | pyrazine-2-carboxamide, 5-O-CH$_2$CH$_2$-OMe | $C_5(RS);C_6(RS)$<br>Single diastereoisomer<br>(cis) |

TABLE 12-continued

[Structure: oxazine ring with H₂N-C=N, position 5 bearing ethyl and aryl (X₁-X₄), position 6 with R₃, R₄; aryl connected via L to Ar]

| Co. No. | Ex. No. | X₁, X₂, X₃, X₄ | R³, R⁴ | ----L—Ar | stereochemistry |
|---|---|---|---|---|---|
| 396 | B23 | X₁ = CF<br>X₂ = X₃ = X₄ = CH | R³ = H<br>R⁴ = CF₃ | [3-fluoro-5-cyano-pyridine-2-carboxamide, N-linked] | C₅(RS);C₆(RS)<br>Single diastereoisomer<br>(cis) |

TABLE 13

[Structure: oxazine ring with H₂N-C=N, position 5 with methyl and aryl (X₁, X₃), position 6 with R₃, R₄; aryl connected via L to Ar]

| Co. No. | Ex. No. | X₁, X₃ | R³, R⁴ | ----L—Ar | stereochemistry |
|---|---|---|---|---|---|
| 121 | B4<br>(method B) | X₁ = N<br>X₃ = CH | R³ = R⁴ = H | [3,5-dichlorophenyl] | RS |
| 277 | B30 | X₁ = CH<br>X₃ = N | R³ = H<br>R⁴ = F | [3,5-dichlorophenyl] | C₅(R*);C₆(R*)<br>Single diastereoisomer<br>Pure enantiomer |
| 278 | B30 | X₁ = CH<br>X₃ = N | R³ = H<br>R⁴ = F | [3,5-dichlorophenyl] | C₅(S*);C₆(S*)<br>Single diastereoisomer<br>Pure enantiomer |
| 279 | B30 | X₁ = CH<br>X₃ = N | R³ = H<br>R⁴ = F | [3,5-dichlorophenyl] | C₅(RS);C₆(RS)<br>Single diastereoisomer<br>(cis) |
| 335 | B30 | X₁ = CH<br>X₃ = N | R³ = H<br>R⁴ = F | [pyrimidin-5-yl] | C₅(RS);C₆(RS)<br>Single diastereoisomer<br>(trans) |

TABLE 13-continued

| Co. No. | Ex. No. | $X_1, X_3$ | $R^3, R^4$ | ----L—Ar | stereochemistry |
|---|---|---|---|---|---|
| 336 | B31 | $X_1$ = CH<br>$X_3$ = N | $R^3$ = H<br>$R^4$ = F | pyrazine-2-carboxamide with 5-methoxy (amide linker) | $C_5(RS);C_6(RS)$<br>Single diastereoisomer<br>(trans) |
| 352 | B30 | $X_1$ = CH<br>$X_3$ = N | $R^3$ = CF$_3$<br>$R^4$ = F | 5-methoxypyridin-3-yl | $C_5(RS);C_6(RS)$<br>Single diastereoisomer<br>(trans) |
| 353 | B30 | $X_1$ = CH<br>$X_3$ = N | $R^3$ = CF$_3$<br>$R^4$ = F | pyrimidin-5-yl | $C_5(RS);C_6(RS)$<br>Single diastereoisomer<br>(trans) |
| 354 | B30 | $X_1$ = CH<br>$X_3$ = N | $R^3$ = CF$_3$<br>$R^4$ = F | 5-cyanopyridin-3-yl | $C_5(RS);C_6(RS)$<br>Single diastereoisomer<br>(trans) |
| 358 | B30 | $X_1$ = CH<br>$X_3$ = N | $R^3$ = H<br>$R^4$ = F | 5-methoxypyridin-3-yl | $C_5(RS);C_6(RS)$<br>Single diastereoisomer<br>(cis) |
| 367 | B30 | $X_1$ = CH<br>$X_3$ = N | $R^3$ = H<br>$R^4$ = CF$_3$ | 5-chloropyridin-3-yl | $C_5(RS);C_6(RS)$<br>Single diastereoisomer<br>(trans) |
| 381 | B31 | $X_1$ = CH<br>$X_3$ = N | $R^3$ = H<br>$R^4$ = F | 3,5-dichloropyridine-2-carboxamide | $C_5(RS);C_6(RS)$<br>Single diastereoisomer<br>(trans) |
| 382 | B31 | $X_1$ = CH<br>$X_3$ = N | $R^3$ = H<br>$R^4$ = F | 3,5-dichloropyridine-2-carboxamide | $C_5(RS);C_6(RS)$<br>Single diastereoisomer<br>(cis) |
| 383 | B30 | $X_1$ = N<br>$X_3$ = CH | $R^3$ = H<br>$R^4$ = F | pyrimidin-5-yl | $C_5(RS);C_6(RS)$<br>Single diastereoisomer<br>(trans) |
| 384 | B30 | $X_1$ = N<br>$X_3$ = CH | $R^3$ = H<br>$R^4$ = F | 5-methoxypyridin-3-yl | $C_5(RS);C_6(RS)$<br>Single diastereoisomer<br>(trans) |

TABLE 13-continued

| Co. No. | Ex. No. | $X_1, X_3$ | $R^3, R^4$ | ----L—Ar | stereochemistry |
|---|---|---|---|---|---|
| 385 | B30 | $X_1$ = N<br>$X_3$ = CH | $R^3$ = H<br>$R^4$ = F | 5-cyanopyridin-3-yl | $C_5(RS);C_6(RS)$<br>Single diastereoisomer<br>(trans) |
| 386 | B30 | $X_1$ = CH<br>$X_3$ = N | $R^3$ = H<br>$R^4$ = F | pyrimidin-5-yl | $C_5(RS);C_6(RS)$<br>Single diastereoisomer<br>(cis) |
| 387 | B31 | $X_1$ = CH<br>$X_3$ = N | $R^3$ = H<br>$R^4$ = F | NH-C(O)-(5-chloro-3-fluoropyridin-2-yl) | $C_5(RS);C_6(RS)$<br>Single diastereoisomer<br>(trans) |
| 388 | B31 | $X_1$ = CH<br>$X_3$ = N | $R^3$ = H<br>$R^4$ = F | NH-C(O)-(5-cyanopyridin-2-yl) | $C_5(RS);C_6(RS)$<br>Single diastereoisomer<br>(trans) |
| 389 | B31 | $X_1$ = CH<br>$X_3$ = N | $R^3$ = H<br>$R^4$ = F | NH-C(O)-(5-ethoxypyrazin-2-yl) | $C_5(RS);C_6(RS)$<br>Single diastereoisomer<br>(trans) |
| 390 | B31 | $X_1$ = N<br>$X_3$ = CH | $R^3$ = H<br>$R^4$ = F | NH-C(O)-(5-chloro-3-fluoropyridin-2-yl) | $C_5(RS);C_6(RS)$<br>Single diastereoisomer<br>(trans) |
| 391 | B31 | $X_1$ = N<br>$X_3$ = CH | $R^3$ = H<br>$R^4$ = F | NH-C(O)-(5-cyanopyridin-2-yl) | $C_5(RS);C_6(RS)$<br>Single diastereoisomer<br>(trans) |
| 392 | B31 | $X_1$ = N<br>$X_3$ = CH | $R^3$ = H<br>$R^4$ = F | NH-C(O)-(5-methoxypyrazin-2-yl) | $C_5(RS);C_6(RS)$<br>Single diastereoisomer<br>(trans) |

TABLE 13-continued

| Co. No. | Ex. No. | $X_1, X_3$ | $R^3, R^4$ | ----L—Ar | stereochemistry |
|---|---|---|---|---|---|
| 393 | B31 | $X_1 = N$<br>$X_3 = CH$ | $R^3 = H$<br>$R^4 = F$ | N-(pyrazin-2-yl)carboxamide with 5-ethoxy | $C_5(RS);C_6(RS)$<br>Single diastereoisomer<br>(trans) |
| 394 | B31 | $X_1 = N$<br>$X_3 = CH$ | $R^3 = H$<br>$R^4 = F$ | 3,5-dichloropyridine-2-carboxamide | $C_5(RS);C_6(RS)$<br>Single diastereoisomer<br>(trans) |
| 398 | B31 | $X_1 = CH$<br>$X_3 = N$ | $R^3 = H$<br>$R^4 = CF_3$ | 5-methoxypyrazine-2-carboxamide | $C_5(RS);C_6(RS)$<br>Single diastereoisomer<br>(cis) |
| 399 | B31 | $X_1 = N$<br>$X_3 = CH$ | $R^3 = H$<br>$R^4 = CF_3$ | 5-methoxypyrazine-2-carboxamide | $C_5(RS);C_6(RS)$<br>Single diastereoisomer<br>(cis) |
| 400 | B30 | $X_1 = N$<br>$X_3 = CH$ | $R^3 = H$<br>$R^4 = CF_3$ | pyrimidin-5-yl | $C_5(RS);C_6(RS)$<br>Single diastereoisomer<br>(trans) |
| 401 | B30 | $X_1 = N$<br>$X_3 = CH$ | $R^3 = H$<br>$R^4 = CF_3$ | pyrimidin-5-yl | $C_5(RS);C_6(RS)$<br>Single diastereoisomer<br>(cis) |

C. Analytical Part

LCMS

For (LC)MS-characterization of the compounds of the present invention, the following methods were used.

General Procedure A

The HPLC measurement was performed using an HP 1100 (Agilent Technologies) system comprising a pump (quaternary or binary) with degasser, an autosampler, a column oven, a diode-array detector (DAD) and a column as specified in the respective methods. The MS detector was configured with either an electrospray ionization source or an ESCI dual ionization source (electrospray combined with atmospheric pressure chemical ionization). Nitrogen was used as the nebulizer gas. The source temperature was maintained either at 140° C. or 100° C. Data acquisition was performed either with MassLynx-Openlynx software or Chemsation-Agilent Data Browser software.

General Procedure B

The UPLC (Ultra Performance Liquid Chromatography) measurement was performed using an Acquity UPLC (Waters) system comprising a sampler organizer, a binary pump with degasser, a four column's oven, a diode-array detector (DAD) and a column as specified in the respective methods. The MS detector was configured with an ESCI dual ionization source (electrospray combined with atmospheric pressure chemical ionization). Nitrogen was used as the nebulizer gas. The source temperature was maintained at 140° C. Data acquisition was performed with MassLynx-Openlynx software.

General Procedure C

The LC measurement was performed using an Acquity UPLC (Waters) system comprising a binary pump, a sample organizer, a column heater (set at 55° C.), a diode-array detector (DAD) and a column as specified in the respective methods below. Flow from the column was split to a MS spectrometer. The MS detector was configured with an electrospray ionization source. Mass spectra were acquired by scanning from 100 to 1000 in 0.18 seconds using a dwell time of 0.02 seconds. The capillary needle voltage was 3.5 kV and the source temperature was maintained at 140° C. Nitrogen was used as 15 the nebulizer gas. Data acquisition was performed with a Waters-Micromass MassLynx-Openlynx data system.

General Procedure D

The LC measurement was performed using a UPLC (Ultra Performance Liquid Chromatography) Acquity (Waters) system comprising a binary pump with degasser, an autosampler, a diode-array detector (DAD) and a column as specified in the respective methods below, the column is hold at a temperature of 40° C. Flow from the column was brought to a MS detector. The MS detector was configured with an electrospray ionization source. The capillary needle voltage was 3 kV and the source temperature was maintained at 130° C. on the Quattro (triple quadrupole mass spectrometer from Waters). Nitrogen was used as the nebulizer gas. Data acquisition was performed with a Waters-Micromass MassLynx-Openlynx data system.

General Procedure E

The HPLC measurement was performed using an Alliance HT 2790 (Waters) system comprising a quaternary pump with degasser, an autosampler, a column oven (set at 40° C., unless otherwise indicated), a diode-array detector (DAD) and a column as specified in the respective methods below. Flow from the column was split to a MS spectrometer. The MS detector was configured with an electrospray ionization source. Mass spectra were acquired by scanning from 100 to 1000 in 1 second using a dwell time of 0.1 second. The capillary needle voltage was 3 kV and the source temperature was maintained at 140° C. Nitrogen was used as the nebulizer gas. Data acquisition was performed with a Waters-Micromass MassLynx-Openlynx data system.

General Procedure F

The LC measurement was performed using a UPLC (Ultra Performance Liquid Chromatography) Acquity (Waters) system comprising a binary pump with degasser, an autosampler, a diode-array detector (DAD) and a column as specified in the respective methods below, the column is hold at a temperature of 40° C. Flow from the column was brought to a MS detector. The MS detector was configured with an electrospray ionization source. The capillary needle voltage was 3 kV and the source temperature was maintained at 130° C. on the Quattro (triple quadrupole mass spectrometer from Waters). Nitrogen was used as the nebulizer gas. Data acquisition was performed with a Waters-Micromass MassLynx-Openlynx data system.

Method 1:

In addition to the general procedure A: Reversed phase HPLC was carried out on a Gemini-NX-C18 column (3.0 µm, 2.0×30 mm) from Phenomenex, with a flow rate of 1.0 ml/min, at 60° C. The gradient conditions used are: 95% A (1 g/l ammonium bicarbonate solution+5% of acetonitrile), 5% B (acetonitrile/methanol 1/1), to 100% B and equilibrated to initial conditions up to 9 minutes run, 2 µl injection volume. High-resolution mass spectra (Time of Flight, TOF detector) were acquired by scanning from 100 to 750 in 0.5 seconds using a dwell time of 0.3 seconds. The capillary needle voltage was 2.5 kV for positive ionization mode and 2.9 kV for negative ionization mode. The cone voltage was 20 V for both positive and negative ionization modes. Leucine-Enkephaline was the standard substance used for the lock mass calibration.

Method 2:

In addition to the general procedure A: Reversed phase HPLC was carried out on an ACE-C18 column (3.0 µm, 4.6×30 mm) from Advanced Chromatography Technologies, with a flow rate of 1.5 ml/min, at 60° C. The gradient conditions used are: 80% A (1 g/l ammonium bicarbonate solution), 10% B (acetonitrile), 10% C (methanol) to 50% B and 50% C in 6.5 minutes, to 100% B at 7 minutes and equilibrated to initial conditions at 7.5 minutes until 9.0 minutes. A pre-run offset of 1.03 min. and a post-run of 1 min. to equilibrate the system at initial conditions Injection volume 5 µl. High-resolution mass spectra (Time of Flight, TOF detector) were acquired only in positive ionization mode by scanning from 100 to 750 in 0.5 seconds using a dwell time of 0.1 seconds. The capillary needle voltage was 2.5 kV for positive ionization mode and the cone voltage was 20 V. Leucine-Enkephaline was the standard substance used for the lock mass calibration.

Method 3:

In addition to the general procedure A: Reversed phase HPLC was carried out on an Eclipse Plus-C18 column (3.5 µm, 2.1×30 mm) from Agilent, with a flow rate of 1.0 ml/min, at 60° C. without split to the MS detector. The gradient conditions used are: 95% A (0.5 g/l ammonium acetate solution+5% acetonitrile), 5% B (mixture of acetonitrile/methanol, 1/1), to 100% B in 5.0 minutes, kept till 5.15 minutes and equilibrated to initial conditions at 5.30 minutes until 7.0 minutes. Injection volume 2 µl. Low-resolution mass spectra (single quadrupole, SQD detector) were acquired by scanning from 100 to 1000 in 0.1 second using an inter-channel delay of 0.08 second. The capillary needle voltage was 3 kV. The cone voltage was 20 V for positive ionization mode and 30 V for negative ionization mode.

Method 4:

In addition to the general procedure A: Reversed phase HPLC was carried out on an Xbridge-C18 column (5.0 µm, 4.6×100 mm) from Waters, with a flow rate of 1.2 ml/min, at room temperature. The gradient conditions used are: 80% A (ammonium bicarbonate, 1 g/l), 20% B (methanol), to 100% B at 6.0 minutes, kept till 6.5 minutes and equilibrated to initial conditions at 7.0 minutes until 9.0 minutes, 5 µl injection volume. Low-resolution mass spectra (single quadrupole MSD detector) were acquired in electrospray mode by scanning from 100 to 1000 in 0.99 seconds, step size of 0.30 and peak width of 0.10 minutes. The capillary needle voltage was 1.0 kV and the fragmentor voltage was 70V for both positive and negative ionization modes.

Method 5:

In addition to the general procedure B: Reversed phase UPLC was carried out on a BEH-C18 column (1.7 µm, 2.1×50 mm) from Waters, with a flow rate of 1.0 ml/min, at 50° C. without split to the MS detector. The gradient conditions used are: 95% A (0.5 g/l ammonium acetate solution+5% acetonitrile), 5% B (acetonitrile), to 40% A, 60% B in 3.8 minutes, to 5% A, 95% B in 4.6 minutes, kept till 5.0 minutes. Injection volume 2 µl. Low-resolution mass spectra (single quadrupole, SQD detector) were acquired by scanning from 100 to 1000 in 0.1 seconds using an inter-channel delay of 0.08 second. The capillary needle voltage was 3 kV. The cone voltage was 25 V for positive ionization mode and 30 V for negative ionization mode.

Method 6:

In addition to the general procedure C: Reversed phase UPLC (Ultra Performance Liquid Chromatography) was carried out on a bridged ethylsiloxane/silica hybrid (BEH) C18 column (1.7 m, 2.1×50 mm; Waters Acquity) with a flow rate of 0.8 ml/min. Two mobile phases (mobile phase A: 0.1% formic acid in H$_2$O/methanol 95/5; mobile phase B: methanol) were used to run a gradient condition from 95% A and 5% B to 5% A and 95% B in 1.3 minutes and hold for 0.2 minutes. An injection volume of 0.5 μl was used. Cone voltage was 10 V for positive ionization mode and 20 V for negative ionization mode.

Method 7:

In addition to the general procedure C: Reversed phase UPLC (Ultra Performance Liquid Chromatography) was carried out on a bridged ethylsiloxane/silica hybrid (BEH) C18 column (1.7 m, 2.1×50 mm; Waters Acquity) with a flow rate of 0.8 ml/min. Two mobile phases (25 mM ammonium acetate in H$_2$O/acetonitrile 95/5; mobile phase B: acetonitrile) were used to run a gradient condition from 95% A and 5% B to 5% A and 95% B in 1.3 minutes and hold for 0.7 minutes. An injection volume of 0.75 μl was used. Cone voltage was 10 V for positive ionization mode and 20 V for negative ionization mode.

Method 8:

In addition to the general procedure C: Reversed phase UPLC (Ultra Performance Liquid Chromatography) was carried out on a bridged ethylsiloxane/silica hybrid (BEH) C18 column (1.7 μm, 2.1×50 mm; Waters Acquity) with a flow rate of 0.8 ml/min. Two mobile phases (25 mM ammonium acetate in H$_2$O/acetonitrile 95/5; mobile phase B: acetonitrile) were used to run a gradient condition from 95% A and 5% B to 5% A and 95% B in 1.3 minutes and hold for 0.3 minutes. An injection volume of 0.5 μl was used. Cone voltage was 30 V for positive ionization mode and 30 V for negative ionization mode.

Method 9:

Same gradient as, method 5; column used: RRHD Eclipse Plus-C18 (1.8 μm, 2.1×50 mm) from Agilent.

Method 10:

In addition to the general procedure D: Reversed phase UPLC was carried out on a Waters Acquity BEH (bridged ethylsiloxane/silica hybrid) Phenyl-Hexyl column (1.7 μm, 2.1×100 mm) with a flow rate of 0.343 ml/min. Two mobile phases (mobile phase A: 95% 7 mM ammonium acetate/5% acetonitrile; mobile phase B: 100% acetonitrile) were employed to run a gradient condition from 84.2% A and 15.8% B (hold for 0.49 minutes) to 10.5% A and 89.5% B in 2.18 minutes, hold for 1.94 min and back to the initial conditions in 0.73 min, hold for 0.73 minutes. An injection volume of 2 ml was used. Cone voltage was 20V for positive and negative ionization mode. Mass spectra were acquired by scanning from 100 to 1000 in 0.2 seconds using an interscan delay of 0.1 seconds.

Method 11:

In addition to the general procedure B: Reversed phase UPLC was carried out on a BEH-C18 column (1.7 μm, 2.1×50 mm) from Waters, with a flow rate of 1.0 ml/min, at 50° C. without split to the MS detector. The gradient conditions used are: 95% A (0.50 g/l ammonium hydrogencarbonate solution+5% acetonitrile), 5% B (acetonitrile), to 40% A, 60% B in 3.8 minutes, to 5% A, 95% B in 4.6 minutes, kept till 5.0 minutes. Injection volume 2.0 μl. Low-resolution mass spectra (single quadrupole, SQD detector) were acquired by scanning from 100 to 1000 in 0.1 seconds using an inter-channel delay of 0.08 second. The capillary needle voltage was 3 kV. The cone voltage was 25 V for positive ionization mode and 30 V for negative ionization mode.

Method 12:

In addition to the general procedure: Reversed phase HPLC was carried out on an Xterra MS C18 column (3.5 m, 4.6×100 mm) with a flow rate of 1.6 ml/min. Three mobile phases (mobile phase A: 95% 25 mM ammoniumacetate+5% acetonitrile; mobile phase B: acetonitrile; mobile phase C: methanol) were employed to run a gradient condition from 100% A to 50% B and 50% C in 6.5 minutes, to 100% B in 0.5 minute, 100% B for 1 minute and reequilibrate with 100% A for 1.5 minutes. An injection volume of 10 μl was used.

Cone voltage was 10 V for positive ionization mode and 20 V for negative ionization mode.

Method 13:

In addition to the general procedure C. Reversed phase UPLC (Ultra Performance Liquid Chromatography) was carried out on a bridged ethylsiloxane/silica hybrid (BEH) C18 column (1.7 μm, 2.1×50 mm; Waters Acquity) with a flow rate of 0.8 ml/min. Two mobile phases (10 mM ammonium acetate in H$_2$O/acetonitrile 95/5; mobile phase B: acetonitrile) were used to run a gradient condition from 95% A and 5% B to 5% A and 95% B in 1.3 minutes and hold for 0.3 minutes. An injection volume of 0.5 μl was used. Cone voltage was 10 V for positive ionization mode and 20 V for negative ionization mode.

Method 14:

In addition to the general procedure C. Reversed phase UPLC (Ultra Performance Liquid Chromatography) was carried out on a bridged ethylsiloxane/silica hybrid (BEH) C18 column (1.7 m, 2.1×50 mm; Waters Acquity) with a flow rate of 0.8 ml/min. Two mobile phases (10 mM ammonium acetate in H$_2$O/acetonitrile 95/5; mobile phase B: acetonitrile) were used to run a gradient condition from 95% A and 5% B to 5% A and 95% B in 1.3 minutes and hold for 0.3 minutes. An injection volume of 0.5 μl was used. Cone voltage was 30 V for positive ionization mode and 30 V for negative ionization mode.

Method 15:

In addition to the general procedure B: Reversed phase UPLC was carried out on a RRHD Eclipse Plus-C18 (1.8 μm, 2.1×50 mm) from Agilent, with a flow rate of 1.0 ml/min, at 50° C. without split to the MS detector. The gradient conditions used are: 95% A (0.5 g/l ammonium acetate solution+5% acetonitrile), 5% B (acetonitrile), to 40% A, 60% B in 1.2 minutes, to 5% A, 95% B in 1.8 minutes, kept till 2.0 minutes. Injection volume 2.0 μl. Low-resolution mass spectra (single quadrupole, SQD detector) were acquired by scanning from 100 to 1000 in 0.1 seconds using an inter-channel delay of 0.08 second. The capillary needle voltage was 3 kV. The cone voltage was 25 V for positive ionization mode and 30 V for negative ionization mode.

Method 16:

In addition to the general procedure B: Reversed phase UPLC was carried out on a RRHD Eclipse Plus-C18 (1.8 μm, 2.1×50 mm) from Agilent, with a flow rate of 1.0 ml/min, at 50° C. without split to the MS detector. The gradient conditions used are: 95% A (0.5 g/l ammonium acetate solution+5% acetonitrile), 5% B (acetonitrile), to 40% A, 60% B in 3.8 minutes, to 5% A, 95% B in 4.6 minutes, kept till 5.0 minutes. Injection volume 2.0 μl. Low-resolution mass spectra (single quadrupole, SQD detector) were acquired by scanning from 100 to 1000 in 0.1 seconds using an inter-channel delay of 0.08 second. The capillary needle voltage was 3 kV. The cone voltage was 25 V for positive ionization mode and 30 V for negative ionization mode.

Method 17:

In addition to the general procedure VDR2: Reversed phase UPLC was carried out on a Waters Acquity BEH (bridged ethylsiloxane/silica hybrid) C18 column (1.7 m, 2.1×100 mm) with a flow rate of 0.343 ml/min. Two mobile phases (mobile phase A: 95% 7 mM ammonium acetate/5% acetonitrile; mobile phase B: 100% acetonitrile) were employed to run a gradient condition from 84.2% A and 15.8% B (hold for 0.49 minutes) to 10.5% A and 89.5% B in 2.18 minutes, hold for 1.94 min and back to the initial conditions in 0.73 min, hold for 0.73 minutes. An injection volume of 2 μl was used. Cone voltage was 20V for positive and negative ionization mode. Mass spectra were acquired by scanning from 100 to 1000 in 0.2 seconds using an interscan delay of 0.1 seconds.

Method 18:

In addition to the general procedure C: Reversed phase UPLC (Ultra Performance Liquid Chromatography) was carried out on a bridged ethylsiloxane/silica hybrid (BEH) C18 column (1.7 m, 2.1×50 mm; Waters Acquity) with a flow rate of 0.8 ml/min. Two mobile phases (10 mM ammonium acetate in H$_2$O/acetonitrile 95/5; mobile phase B: acetonitrile) were used to run a gradient condition from 95% A and 5% B to 5% A and 95% B in 1.3 minutes and hold for 0.3 minutes. An injection volume of 0.5 μl was used. Cone voltage was 10 V for positive ionization mode and 20 V for negative ionization mode.

Melting Points

Values are either peak values or melt ranges, and are obtained with experimental uncertainties that are commonly associated with this analytical method.

Mettler FP62 Apparatus (Indicated by FP62 in Table 11)

For a number of compounds, melting points were determined in open capillary tubes on a Mettler FP62 apparatus. Melting points were measured with a temperature gradient of 1, 3, 5 or 10° C./minute. Maximum temperature was 300° C. The melting point was read from a digital display.

Mettler FP 81HT/FP90 Apparatus (Indicated by FP90 in Table 11)

For a number of compounds, melting points were determined in open capillary tubes on a Mettler FP81HT/FP90 apparatus. Melting points were measured with a temperature gradient of 1, 3, 5 or 10° C./minute. Maximum temperature was 300° C. The melting point was read from a digital display.

DSC823e (Indicated by DSC in Table 11)

For a number of compounds, melting points were determined with a DSC823e (Mettler-Toledo). Melting points were measured with a temperature gradient of 30 C/minute. Maximum temperature was 400° C.

TABLE 14

Analytical data - R$_t$ means retention time (in minutes), [M + H]$^+$ means the protonated mass of the compound, method refers to the method used for (LC)MS.

| Co. Nr. | R$_t$ | [M + H]$^+$ | Method | Melting Point |
|---|---|---|---|---|
| 1 | 1.66 | 267 | 5 | 217.2° C. (FP90) |
| 2 | 6.79 | 335 | 4 | 197° C. (FP90) |
| 3 | 0.49 | 269 | 5 | n.d. |
| 4 | 1.03 | 298 | 5 | 150° C. (FP90) |
| 5 | 1.43 | 345 | 5 | n.d. |
| 6 | 0.81 | 329 | 5 | 155.6° C. (FP90) |
| 7 | 1.87 | 326 | 1 | 171.8° C. (FP90) |
| 8 | 0.62 | 298 | 6 | 79.5° C. (DSC) |
| 9 | 1.02 | 431 | 6 | 193.3° C. (DSC) |
| 10 | 1.38 | 292 | 5 | n.d. |
| 11 | 1.05 | 282 | 5 | 64.9° C. (FP90) |
| 12 | 2.74 | 345 | 3 | n.d. |
| 13 | 2.95 | 415 | 2 | n.d. |
| 14 | 2.41 | 379 | 3 | 138.1° C. (FP90) |
| 15 | 1.06 | 431 | 8 | n.d. |
| 16 | 0.67 | 324 | 8 | n.d. |
| 17 | 1.5 | 363 | 5 | 185.8° C. (FP90) |
| 18 | 2.03 | 312 | 3 | n.d. |
| 19 | 2 | 312 | 3 | n.d. |
| 20 | 1.57 | 359 | 5 | 173.2° C. (FP90) |
| 21 | 1.50 | 397 | 5 | 154.4° C. (FP90) |
| 22 | 0.74 | 398 | 8 | 139.8° C. (DSC) |
| 23 | 0.74 | 338 | 8 | 221.4° C. (DSC) |
| 24 | 1.42 | 343 | 5 | 97.7° C. (FP90) |
| 25 | 1.26 | 347 | 5 | 171.4° C. (FP90) |
| 26 | 0.76 | 398 | 7 | 156.8° C. (DSC) |
| 27 | 0.75 | 380 | 8 | 152.7° C. (FP90) |
| 28 | 3.27 | 330 | 12 | n.d. |
| 29 | 0.75 | 368 | 8 | n.d. |
| 30 | 1.25 | 343 | 5 | 96:4° C. (FP90) |
| 31 | 2.41 | 371 | 5 | 98° C. (FP90) |
| 32 | 1.70 | 328 | 5 | 70.1° C. (FP90) |
| 33 | 1.89 | 333 | 5 | n.d. |
| 34 | 2.22 | 337 | 5 | n.d. |
| 35 | 1.29 | 381 | 5 | 152.7° C. (FP90) |
| 36 | 2.4 | 387 | 5 | n.d. |
| 37 | 2.04 | 339 | 5 | n.d. |
| 38 | 1.73 | 397 | 5 | 160.9° C. (FP90) |
| 39 | 1.18 | 360 | 5 | 178.8° C. (FP90) |
| 40 | 0.94 | 344 | 5 | 159.2° C. (FP90) |
| 41 | 1.55 | 362 | 5 | 108.0° C. (FP90) |
| 42 | 0.70 | 335 | 7 | n.d. |
| 43 | 1.12 | 354 | 5 | 163.5° C. (FP90) |
| 44 | 1.51 | 363 | 5 | 149.5° C. (FP90) |
| 45 | 1.81 | 392 | 5 | 107.5° C. (FP90) |
| 46 | 1.14 | 431 | 8 | 140.4° C. (FP90) |
| 47 | 1.88 | 333 | 5 | 100.8° C. (FP90) |
| 48 | 2.82 | 371 | 11 | 130.3° C. (FP90) |
| 49 | 0.61 | 336 | 8 | n.d. |
| 50 | 3.56 | 336 | 12 | 116.3° C. (DSC) |
| 51 | 1.4 | 292 | 5 | n.d. |
| 52 | 2.35 | 335 | 5 | n.d. |
| 53 | 1.39 | 287 | 10 | n.d. |
| 54 | 1.41 | 287 | 10 | n.d. |
| 55 | 1.62 | 305 | 10 | 104.3 |
| 56 | 1.95 | 316 | 10 | n.d. |
| 57 | 1.15 | 360 | 5 | 190.8° C. (FP90) |
| 58 | 0.64 | 287 | 5 | 178.3° C. (FP90) |
| 59 | 1.82 | 305 | 1 | 164° C. (FP90) |
| 60 | 1.80 | 381 | 5 | n.d. |
| 61 | 2.21 | 363 | 10 | 142.3° C. (FP90) |
| 62 | 0.72 | 363 | 8 | n.d. |
| 63 | 1.21 | 316 | 5 | 167.0° C. (FP90) |
| 64 | 1.01 | 336 | 5 | n.d. |
| 65 | 1.50 | 363 | 5 | 185.8° C. (FP90) |
| 66 | 2.13 | 334 | 3 | 169.6° C. (FP90) |
| 67 | 0.48 | 191 | 8 | 131.8° C. (DSC) |
| 68 | 0.75 | 380 | 8 | n.d. |
| 69 | 0.99 | 428 | 8 | n.d. |
| 70 | 1.07 | 431 | 8 | 170° C. (DSC) |
| 71 | 1.14 | 431 | 8 | n.d. |
| 72 | 0.63 | 331 | 7 | 213.1° C. (DSC) |
| 73 | 4.61 | 371 | 12 | n.d. |
| 74 | 0.55 | 295 | 8 | 193.3° C. (DSC) |
| 75 | 0.7 | 305 | 8 | 227.7° C. (DSC) |
| 76 | 1.65 | 372 | 9 | n.d. |
| 77 | 1.83 | 399 | 9 | n.d. |
| 78 | 2.01 | 415 | 9 | n.d. |
| 79 | 1.68 | 378 | 9 | n.d. |
| 80 | 1.31 | 360 | 5 | n.d. |
| 81 | 0.76 | 323 | 8 | n.d. |
| 82 | 0.7 | 323 | 7 | n.d. |
| 83 | 0.72 | 323 | 7 | n.d. |
| 84 | 0.78 | 323 | 7 | 195.3° C. (DSC) |
| 85 | 1.0 | 363 | 6 | 160.8° C. (DSC) |
| 86 | 0.79 | 363 | 7 | 157.7° C. (DSC) |
| 87 | 0.67 | 316 | 8 | 139.23 |
| 88 | 3.97 | 316 | 12 | n.d. |
| 89 | 3.96 | 316 | 12 | n.d. |

TABLE 14-continued

Analytical data - $R_t$ means retention time (in minutes), $[M + H]^+$ means the protonated mass of the compound, method refers to the method used for (LC)MS.

| Co. Nr. | $R_t$ | $[M + H]^+$ | Method | Melting Point |
|---|---|---|---|---|
| 90 | 4.48 | 363 | 12 | 178.6° C. (DSC) |
| 91 | 0.8 | 363 | 7 | n.d. |
| 92 | 0.67 | 316 | 8 | n.d. |
| 93 | 0.67 | 316 | 8 | n.d. |
| 94 | 0.53 | 287 | 8 | 115.4° C. (DSC) |
| 95 | 0.53 | 287 | 8 | 115.4° C. (DSC) |
| 96 | 0.56 | 287 | 8 | n.d. |
| 97 | 0.56 | 287 | 8 | n.d. |
| 98 | 0.54 | 287 | 8 | 189.3° C. (DSC) |
| 99 | 0.55 | 287 | 8 | 204.3° C. (DSC) |
| 100 | 0.68 | 316 | 8 | 139.2° C. (DSC) |
| 101 | 0.77 | 366 | 8 | n.d. |
| 102 | 0.78 | 366 | 8 | n.d. |
| 103 | 0.8 | 366 | 8 | n.d. |
| 104 | 0.77 | 366 | 8 | n.d. |
| 105 | 0.89 | 384 | 8 | 196.9° C. (DSC) |
| 106 | 0.76 | 355 | 8 | 173.8° C. (DSC) |
| 107 | 0.99 | 431 | 7 | 277.6° C. (DSC) |
| 108 | 0.78 | 366 | 8 | n.d. |
| 109 | 1.05 | 449 | 8 | n.d. |
| 110 | 1.06 | 449 | 7 | n.d. |
| 111 | 0.82 | 373 | 8 | n.d. |
| 112 | 1.03 | 431 | 8 | 207.3° C. (DSC) |
| 113 | 1.02 | 431 | 8 | n.d. |
| 114 | 1.03 | 431 | 8 | n.d. |
| 115 | 1.04 | 431 | 8 | n.d. |
| 116 | 0.81 | 355 | 8 | n.d. |
| 117 | 0.80 | 355 | 8 | n.d. |
| 118 | 0.92 | 384 | 8 | n.d. |
| 119 | 0.93 | 384 | 8 | n.d. |
| 120 | 0.82 | 355 | 8 | 228.5° C. (DSC) |
| 121 | 2.0 | 336 | 9 | 158.1° C. (FP90) |
| 122 | 4.49 | 363 | 12 | 178.2° C. (DSC) |
| 123 | 1.72 | 378 | 9 | n.d. |
| 124 | 1.63 | 372 | 9 | 223.4° C. (FP90) |
| 125 | 1.63 | 372 | 9 | 227.7° C. (FP90) |
| 126 | 2.01 | 415 | 9 | 94.6° C. (FP90) |
| 128 | 2.03 | 415 | 9 | 93.3° C. (FP90) |
| 129 | 1.69 | 378 | 9 | 210.6° C. (FP90) |
| 130 | 1.84 | 399 | 9 | 116.4° C. (FP90) |
| 131 | 1.36 | 360 | 9 | n.d. |
| 132 | 1.36 | 360 | 9 | n.d. |
| 133 | 1.86 | 399 | 9 | n.d. |
| 134 | 0.84 | 381 | 8 | 227.7° C. (DSC) |
| 135 | 0.84 | 381 | 8 | 227.2° C. (DSC) |
| 136 | 0.75 | 381 | 8 | n.d. |
| 137 | 0.75 | 381 | 8 | n.d. |
| 138 | 0.82 | 373 | 8 | n.d. |
| 139 | 0.81 | 355 | 8 | n.d. |
| 140 | 0.81 | 355 | 8 | n.d. |
| 141 | 0.92 | 384 | 8 | n.d. |
| 142 | 0.93 | 384 | 8 | n.d. |
| 143 | 0.77 | 377 | 8 | 149.7° C. (DSC) |
| 144 | 0.6 | 364 | 7 | 215.1° C. (DSC) |
| 145 | 0.79 | 334 | 8 | n.d. |
| 146 | 0.72 | 380 | 8 | 118.5° C. (DSC) |
| 147 | 0.74 | 398 | 8 | 139.8° C. (DSC) |
| 148 | 0.69 | 323 | 8 | 186.2° C. (DSC) |
| 149 | 0.62 | 331 | 7 | 187.4° C. (DSC) |
| 150 | 0.6 | 331 | 8 | n.d. |
| 151 | 1.63 | 359 | 9 | 180° C. (FP90) |
| 152 | 1.86 | 352 | 5 | 202.5° C. (FP90) |
| 153 | 1.78 | 371 | 5 | 161.5° C. (FP90) |
| 154 | 1.1 | 431 | 8 | n.d. |
| 155 | 1.60 | 305 | 10 | n.d. |
| 156 | 1.9 | 316 | 10 | n.d. |
| 157 | 1.10 | 431 | 8 | 168.1° C. (FP90) |
| 158 | 1.05 | 449 | 8 | n.d. |
| 159 | 1.05 | 449 | 8 | n.d. |
| 161 | 0.78 | 351 | 14 | 150.57° C. (DSC) |
| 162 | 0.8 | 351 | 14 | 174.75° C. (DSC) |
| 163 | 0.69 | 381 | 13 | n.d. |
| 164 | 0.73 | 381 | 14 | n.d. |
| 165 | 0.97 | 431 | 14 | 218.30° C. (DSC) |
| 166 | 0.88 | 428 | 14 | 252.48° C. (DSC) |
| 167 | 0.97 | 465 | 14 | 214.23° C. (DSC) |
| 168 | 0.76 | 398 | 14 | n.d. |
| 169 | 0.86 | 422 | 14 | 239.91° C. (DSC) |
| 170 | 0.95 | 431 | 14 | n.d. |
| 171 | 0.8 | 361 | 13 | n.d. |
| 172 | 0.98 | 449 | 14 | 180.17° C. (DSC) |
| 173 | 0.98 | 449 | 14 | n.d. |
| 174 | 0.98 | 449 | 14 | 179.18° C. (DSC) |
| 175 | 0.98 | 449 | 14 | n.d. |
| 176 | 0.95 | 428 | 13 | n.d. |
| 177 | 0.95 | 428 | 13 | n.d. |
| 178 | 0.95 | 428 | 13 | n.d. |
| 179 | 0.95 | 428 | 13 | n.d. |
| 180 | 0.95 | 446 | 14 | n.d. |
| 181 | 1.03 | 484 | 14 | 200.16° C. (DSC) |
| 182 | 0.83 | 416 | 14 | n.d. |
| 183 | 0.93 | 440 | 14 | 196.01° C. (DSC) |
| 184 | 0.97 | 446 | 14 | 198.43° C. (DSC) |
| 185 | 1.04 | 484 | 14 | 165.14° C. (DSC) |
| 186 | 1.05 | 449 | 14 | n.d. |
| 187 | 0.81 | 398 | 14 | 189.64° C. (DSC) |
| 188 | 0.81 | 398 | 14 | n.d. |
| 189 | 0.81 | 398 | 14 | 189.29° C. (DSC) |
| 190 | 0.81 | 398 | 14 | n.d. |
| 191 | 0.98 | 411 | 14 | n.d. |
| 192 | 0.98 | 411 | 14 | n.d. |
| 193 | 0.98 | 411 | 14 | n.d. |
| 194 | 0.98 | 411 | 14 | n.d. |
| 195 | 1.74 | 371 | 9 | n.d. |
| 196 | 1.77 | 371 | 9 | n.d. |
| 197 | 0.89 | 413 | 13 | 175.32° C. (DSC) |
| 198 | 0.99 | 448 | 13 | 151.98° C. |
| 199 | 1.04 | 448 | 13 | 196.12° C. |
| 202 | 1.01 | 454 | 13 | n.d. |
| 203 | 1.07 | 454 | 13 | n.d. |
| 204 | 0.76 | 361 | 14 | n.d. |
| 205 | 0.76 | 361 | 14 | n.d. |
| 206 | 0.83 | 361 | 13 | n.d. |
| 207 | 0.82 | 361 | 13 | n.d. |
| 208 | 1.75 | 377 | 16 | 185.6° C. (FP90) |
| 209 | 1.66 | 406 | 16 | 125.5° C. (FP90) |
| 210 | 2.29 | 391 | 16 | >300° C. (FP90) |
| 211 | 2.14 | 391 | 16 | 62° C. (FP90) |
| 212 | 3.13 | 424 | 16 | 145.3° C. (FP90) |
| 213 | 3.00 | 424 | 16 | 70.1° C. (FP90) |
| 214 | 0.90 | 398 | 13 | n.d. |
| 215 | 0.94 | 398 | 13 | n.d. |
| 216 | 0.96 | 404 | 13 | n.d. |
| 217 | 0.95 | 404 | 13 | n.d. |
| 218 | 0.92 | 432 | 13 | n.d. |
| 219 | 0.95 | 425 | 13 | n.d. |
| 220 | 0.99 | 425 | 13 | n.d. |
| 221 | 0.93 | 398 | 13 | n.d. |
| 222 | 0.90 | 331 | 18 | n.d. |
| 223 | 0.93 | 355 | 18 | n.d. |
| 224 | 0.80 | 331 | 18 | n.d. |
| 225 | 0.91 | 430 | 18 | n.d. |
| 226 | 0.90 | 430 | 13 | 231.49° C. (DSC) |
| 227 | 0.95 | 430 | 13 | n.d. |
| 228 | 0.92 | 435 | 13 | n.d. |
| 229 | 0.99 | 448 | 18 | 181.79° C. (DSC) |
| 230 | 1.01 | 454 | 18 | n.d. |
| 231 | 1.02 | 453 | 18 | n.d. |
| 232 | 1.12 | 381 | 18 | n.d. |
| 233 | 1.10 | 457 | 18 | n.d. |
| 234 | 1.09 | 491 | 18 | n.d. |
| 235 | n.d. | | | n.d. |
| 238 | 0.74 | 355 | 13 | n.d. |
| 239 | 0.83 | 379 | 13 | n.d. |
| 240 | 2.70 | 422 | 17 | n.d. |
| 241 | 2.70 | 422 | 17 | n.d. |
| 242 | 2.92 | 465 | 17 | n.d. |
| 243 | 2.93 | 465 | 17 | n.d. |

TABLE 14-continued

Analytical data - $R_t$ means retention time (in minutes), [M + H]$^+$ means the protonated mass of the compound, method refers to the method used for (LC)MS.

| Co. Nr. | $R_t$ | [M + H]$^+$ | Method | Melting Point |
|---|---|---|---|---|
| 244 | 0.79 | 386 | 18 | n.d. |
| 245 | 2.70 | 456 | 17 | n.d. |
| 246 | 2.70 | 456 | 17 | n.d. |
| 247 | 2.76 | 427 | 17 | n.d. |
| 248 | 2.77 | 427 | 17 | n.d. |
| 249 | 0.85 | 407 | 18 | n.d. |
| 250 | 0.83 | 407 | 18 | n.d. |
| 251 | 0.77 | 380 | 18 | n.d. |
| 252 | 1.30 | 460 | 16 | n.d. |
| 253 | 5.2 | 387 | 12 | b.r. |
| 254 | 1.85 | 373 | 16 | 101.3° C. (FP90) |
| 255 | 2.79 | 406 | 16 | 141.4° C. (FP90) |
| 256 | 0.86 | 423 | 13 | n.d. |
| 257 | 0.61 | 313 | 13 | n.d. |
| 258 | 0.61 | 313 | 13 | n.d. |
| 259 | 0.98 | 441 | 18 | n.d. |
| 260 | 0.93 | 449 | 18 | n.d. |
| 261 | 0.79 | 404 | 18 | n.d. |
| 262 | 1.03 | 466 | 18 | n.d. |
| 263 | 3.12 3.18 | 514 | 9 | n.d. |
| 264 | 1.04 | 472 | 18 | n.d. |
| 265 | 0.84 | 379 | 13 | n.d. |
| 266 | 0.84 | 379 | 13 | n.d. |
| 267 | 0.74 | 355 | 13 | n.d. |
| 268 | 0.72 | 355 | 13 | n.d. |
| 269 | 0.78 | 363 | 13 | n.d. |
| 270 | 0.95 | 380 | 13 | n.d. |
| 271 | 1.04 | 423 | 13 | n.d. |
| 272 | 0.99 | 447 | 18 | n.d. |
| 273 | 1.05 | 364 | 13 | n.d. |
| 274 | 0.96 | 454 | 18 | n.d. |
| 275 | 0.94 | 454 | 13 | n.d. |
| 276 | 0.89 | 423 | 18 | n.d. |
| 277 | 1.01 | 354 | 18 | n.d. |
| 278 | 1.01 | 354 | 18 | n.d. |
| 279 | 1.05 | 354 | 18 | b.r. |
| 280 | 0.76 | 380 | 18 | b.r. |
| 281 | 2 | 392 | 16 | n.d. |
| 282 | 2.21 | 392 | 16 | n.d. |
| 283 | 2.16 | 413 | 16 | n.d. |
| 284 | 2.61 | 470 | 16 | n.d. |
| 285 | 2.61 | 442 | 16 | n.d. |
| 286 | 0.78 | 363 | 13 | b.r. |
| 287 | 0.97 | 457 | 18 | b.r. |
| 288 | 0.98 | 457 | 18 | b.r. |
| 289 | 1.07 | 504 | 18 | b.r. |
| 290 | 5.92 | 464 | 8 | b.r. |
| 291 | 5.58 | 464 | 8 | b.r. |
| 292 | 0.81 | 367 | 18 | n.d. |
| 293 | 0.81 | 367 | 18 | n.d. |
| 294 | 1 | 364 | 13 | n.d. |
| 295 | 1.05 | 364 | 13 | b.r. |
| 296 | 0.78 | 331 | 13 | 129.74° C. |
| 297 | 0.98 | 403 | 18 | n.d. |
| 298 | 0.99 | 403 | 18 | n.d. |
| 299 | 2.92 | 386 | 3 | 196.4° C. |
| 300 | 1.03 | 460 | 13 | n.d. |
| 301 | 1.05 | 460 | 13 | 196.44° C. |
| 302 | 0.91 | 387 | 13 | n.d. |
| 303 | 0.93 | 387 | 13 | 204.89° C. |
| 304 | 0.97 | 445 | 18 | b.r. |
| 305 | 0.96 | 445 | 18 | 123.80° C. |
| 306 | 0.94 | 474 | 18 | b.r. |
| 307 | 0.96 | 474 | 18 | b.r. |
| 308 | 0.89 | 456 | 18 | n.d. |
| 309 | 0.79 | 4.14 | 13 | n.d. |
| 310 | 1.18 | 393 | 15 | n.d. |
| 311 | 0.77 | 337 | 18 | n.d. |
| 312 | 0.98 | 399 | 13 | n.d. |
| 313 | 1 | 447 | 18 | n.d. |
| 314 | 1.07 | 465 | 18 | 132.03° C. |
| 315 | 1.06 | 421 | 18 | n.d. |
| 316 | 0.97 | 390 | 13 | n.d. |
| 317 | 0.94 | 397 | 13 | 177.94° C. |
| 318 | 1.1 | 514 | 13 | b.r. |
| 319 | 1.09 | 514 | 13 | b.r. |
| 320 | 0.58 | 301 | 18 | b.r. |
| 321 | 1.04 | 428 | 13 | n.d. |
| 322 | 1.07 | 428 | 13 | n.d. |
| 323 | 1.02 | 474 | 13 | n.d. |
| 324 | 1.18 | 471 | 13 | n.d. |
| 325 | 0.74 | 391 | 18 | n.d. |
| 326 | 0.75 | 391 | 18 | n.d. |
| 327 | 0.74 | 398 | 13 | n.d. |
| 328 | 0.98 | 466 | 13 | n.d. |
| 329 | 1.03 | 396 | 13 | n.d. |
| 330 | 4.31 | 390 | 12 | b.r. |
| 331 | 5.29 | 446 | 12 | b.r. |
| 332 | 4.59 | 398 | 12 | n.d. |
| 333 | 5.26 | 395 | 12 | b.r. |
| 334 | 2.39 | 442 | 9 | n.d. |
| 335 | 0.45 | 288 | 13 | 193.74° C. |
| 336 | 0.67 | 361 | 18 | b.r. |
| 337 | 0.78 | 406 | 18 | n.d. |
| 338 | 0.91 | 480 | 18 | b.r. |
| 339 | 0.84 | 431 | 18 | n.d. |
| 340 | 0.85 | 370 | 18 | n.d. |
| 341 | 0.78 | 354 | 18 | n.d. |
| 342 | 0.86 | 374 | 18 | n.d. |
| 343 | 0.63 | 337 | 18 | n.d. |
| 344 | 0.89 | 448 | 18 | n.d. |
| 345 | 0.86 | 416 | 18 | n.d. |
| 346 | 1.00 | 498 | 13 | n.d. |
| 347 | 0.78 | 430 | 13 | n.d. |
| 348 | 0.78 | 414 | 13 | n.d. |
| 349 | 0.86 | 400 | 18 | n.d. |
| 350 | 0.89 | 397 | 13 | n.d. |
| 351 | 0.94 | 397 | 13 | n.d. |
| 352 | 0.81 | 385 | 13 | 160.28° C. |
| 353 | 0.70 | 356 | 18 | b.r. |
| 354 | 0.84 | 380 | 13 | 160.26° C. |
| 355 | 0.98 | 467 | 18 | 186.08° C. |
| 356 | 1.00 | 467 | 18 | 207.57° C. |
| 357 | 0.84 | 440 | 18 | b.r. |
| 358 | 0.57 | 617 | 18 | b.r. |
| 359 | 0.83 | 424 | 18 | 224.24° C. |
| 360 | 0.81 | 380 | 18 | n.d. |
| 361 | 0.82 | 380 | 18 | n.d. |
| 362 | 0.69 | 351 | 18 | n.d. |
| 363 | 0.71 | 351 | 18 | n.d. |
| 364 | 0.84 | 444 | 18 | n.d. |
| 365 | 0.85 | 424 | 18 | b.r. |
| 366 | 0.83 | 452 | 18 | n.d. |
| 367 | 0.91 | 389 | 18 | b.r. |
| 368 | 0.83 | 468 | 18 | b.r. |
| 369 | 0.79 | 436 | 18 | b.r. |
| 370 | 0.97 | 418 | 18 | n.d. |
| 371 | 0.84 | 392 | 18 | n.d. |
| 372 | 0.96 | 442 | 18 | n.d. |
| 373 | 0.87 | 472 | 18 | n.d. |
| 374 | 0.89 | 448 | 18 | n.d. |
| 375 | 0.87 | 424 | 18 | n.d. |
| 376 | 0.78 | 454 | 18 | n.d. |
| 377 | 0.78 | 410 | 18 | n.d. |
| 378 | 0.74 | 422 | 18 | n.d. |
| 379 | 4.54 | 366 | 12 | n.d. |
| 380 | 0.76 | 422 | 18 | n.d. |
| 381 | 0.78 | 398 | 13 | n.d. |
| 382 | 0.81 | 398 | 13 | n.d. |
| 383 | 0.46 | 288 | 18 | n.d. |
| 384 | 0.60 | 317 | 18 | b.r. |
| 385 | 0.58 | 312 | 18 | b.r. |
| 386 | 0.48 | 288 | 13 | b.r. |
| 387 | 0.72 | 382 | 18 | b.r. |
| 388 | 0.64 | 355 | 18 | b.r. |
| 389 | 0.77 | 375 | 18 | b.r. |
| 390 | 0.68 | 382 | 18 | b.r. |

TABLE 14-continued

Analytical data - $R_t$ means retention time (in minutes), $[M + H]^+$ means the protonated mass of the compound, method refers to the method used for (LC)MS.

| Co. Nr. | $R_t$ | $[M + H]^+$ | Method | Melting Point |
|---|---|---|---|---|
| 391 | 0.62 | 355 | 18 | b.r. |
| 392 | 0.64 | 361 | 18 | b.r. |
| 393 | 0.73 | 375 | 18 | b.r. |
| 394 | 0.74 | 398 | 18 | b.r. |
| 395 | 2.61 | 486 | 9 | n.d. |
| 396 | 2.44 | 454 | 9 | n.d. |
| 397 | 0.77 | 374 | 18 | n.d. |
| 398 | 0.79 | 411 | 18 | n.d. |
| 399 | 0.78 | 411 | 18 | n.d. |
| 400 | 0.60 | 338 | 18 | n.d. |
| 401 | 0.56 | 338 | 18 | n.d. |
| 402 | 0.76 | 383 | 18 | n.d. |
| 403 | 0.87 | 433 | 18 | n.d. |
| 404 | 0.68 | 365 | 18 | n.d. |
| 405 | 0.88 | 448 | 18 | b.r. |
| 406 | 0.93 | 410 | 18 | n.d. |
| 407 | 0.93 | 410 | 18 | n.d. | n.d. means not determined,
b.r. means broad range

SFC-MS Methods:
General Procedure a for SFC-MS Methods

The SFC measurement was performed using an Analytical SFC system from Berger Instruments (Newark, Del., USA) comprising a dual pump control module (FCM-1200) for delivery of carbon dioxide ($CO_2$) and modifier, a thermal control module for column heating (TCM2100) with temperature control in the range 1-150° C. and column selection valves (Valco, VICI, Houston, Tex., USA) for six different columns. The photodiode array detector (Agilent 1100, Waldbronn, Germany) is equipped with a high-pressure flow cell (up to 400 bar) and configured with a CTC LC Mini PAL auto sampler (Leap Technologies, Carrboro, N.C., USA). A ZQ mass spectrometer (Waters, Milford, Mass., USA) with an orthogonal Z-electrospray interface is coupled with the SFC-system. Instrument control, data collection and processing were performed with an integrated platform consisting of the SFC ProNTo software and Masslynx software.

General Procedure B

The SFC measurement was performed using an Analytical SFC system from Berger instruments (Newark, Del., USA) comprising a FCM-1200 dual pump fluid control module for delivering carbon dioxide (CO2) and modifier, a CTC Analytics automatic liquid sampler, a TCM-20000 thermal control module for column heating from room temperature to 80° C. An Agilent 1100 UV photodiode array detector equipped with a high-pressure flow cell standing up to 400 bars was used. Flow from the column was split to a MS spectrometer. The MS detector was configured with an atmospheric pressure ionization source. The following ionization parameters for the Waters ZQ mass spectrophotometer are: corona: 9 µa, source temp: 140° C., cone: 30 V, probe temp 450° C., extractor 3 V, desolvatation gas 400 L/hr, cone gas 70 L/hr. Nitrogen was used as the nebulizer gas. Data acquisition was performed with a Waters-Micromass MassLynx-Openlynx data system.

Method 1

In addition to the general procedure A: The chiral separation in SFC was carried out on a CHIRALCEL OD-H column (4.6×500 mm) at 50° C. with a flow rate of 3.0 ml/min. The mobile phase is CO2, 20% iPrOH (containing 0.2% $iPrNH_2$) hold 17.50 min, 20-50% MeOH (containing 0.2% $iPrNH_2$) hold 4.10 min.

Method 2

In addition to the general procedure A: The chiral separation in SFC was carried out on a CHIRALCEL OD-H column (4.6×500 mm) at 50° C. with a flow rate of 3.0 ml/min. The mobile phase is C02, 45% MeOH (containing 0.2% $iPrNH_2$) hold 22 min.

Method 3

In addition to the general procedure A: The chiral separation in SFC was carried out on a CHIRALPAK AD-H column (4.6×500 mm) at 50° C. with a flow rate of 3.0 ml/min. The mobile phase is CO2, 25% iPrOH (containing 0.2% $iPrNH_2$) hold 19.60 min from 20-40% iPrOH (containing 0.2% $iPrNH_2$), at 10% rate and hold 3.00 min at 50%.

Method 4

In addition to the general procedure A: The chiral separation in SFC was carried out on a CHIRALPAK AD-H column (4.6×500 mm) at 50° C. with a flow rate of 3.0 ml/min. The mobile phase is C02, 10-40% iPrOH (containing 0.2% $iPrNH_2$) at 1.6% rate, then from 40-50% iPrOH (containing 0.2% $iPrNH_2$), at 5% rate and hold 3.60 min.

Method 5

In addition to the general procedure A: The chiral separation in SFC was carried out on a CHIRALPAK AD-H column (4.6×500 mm) at 50° C. with a flow rate of 3.0 ml/min. The mobile phase is CO2, 20% iPrOH (containing 0.6% $iPrNH_2$) hold 15.00 min.

Method 6

In addition to the general procedure A: The chiral separation in SFC was carried out on a CHIRALPAK AD-H column (4.6×500 mm) at 50° C. with a flow rate of 3.0 ml/min. The mobile phase is CO2, 10% MeOH (containing 0.2% $iPrNH_2$) hold 15.00 min.

Method 7

In addition to the general procedure A: The chiral separation in SFC was carried out on a CHIRALPAK AD-H column (4.6×500 mm) at 50° C. with a flow rate of 3.0 ml/min. The mobile phase is CO2, 30% MeOH (containing 0.2% $iPrNH_2$) hold 15.00 min.

Method 8

In addition to the general procedure: The chiral separation in SFC was carried out on a AD-H column (4.6×500 mm) at 50° C. with a flow rate of 3.0 ml/min. The mobile phase is C02, 15% MeOH (containing 0.2% $iPrNH_2$) hold 15.00 min.

Method 9

In addition to the general procedure B: The chiral separation in SFC was carried out on a CHIRALPAK AD DAICEL column (10 µm, 4.6×250 mm) at 35° C. with a 10 flow rate of 3.0 ml/min. The mobile phase is CO2, 60% iPrOH, 40% iPrOH (containing 0.3% $iPrNH_2$) hold 7 min.

Method 10

In addition to the general procedure B: The chiral separation in SFC was carried out on a CHIRALPAK AD DAICEL column (10 µm, 4.6×250 mm) at 35° C. with a 15 flow rate of 3.0 ml/min. The mobile phase is CO2 60% EtOH, 20% EtOH 20% iPrOH (containing 0.3% $iPrNH_2$) hold 7 min.

Method 11

In addition to the general procedure B: The chiral separation in SFC was carried out on a CHIRALCEL OD-H DAICEL column (10 µm, 4.6×250 mm) at 35° C. with a flow rate of 3.0 ml/min. The mobile phase is CO2, 70% Methanol, 30% EtOH (containing 0.3% $iPrNH_2$) hold 7 min.

Method 12

In addition to the general procedure A: The chiral separation in SFC was carried out on a CHIRALCEL OD-H column (4.6×500 mm) at 50° C. with a flow rate of 3.0 ml/min. The mobile phase is $CO_2$, 45% iPrOH (containing 0.2% $iPrNH_2$) hold 20 min from 45-50% iPrOH (containing 0.2% $iPrNH_2$) at 10% rate and hold 3 min at 50%.

Method 13
In addition to the general procedure A: The chiral separation in SFC was carried out on a CHIRALPAK AD-H column (4.6×500 mm) at 50° C. with a flow rate of 3.0 ml/min. The mobile phase is $CO_2$, 15% MEOH (containing 0.2% $iPrNH_2$) hold 15 minutes.

Method 14
In addition to the general procedure A: The chiral separation in SFC was carried out on a CHIRALCEL OD-H column (4.6×500 mm) at 50° C. with a flow rate of 3.0 ml/min. The mobile phase is $CO_2$, 25% MeOH (containing 0.2% $iPrNH_2$) hold 15 minutes.

Method 15
In addition to the general procedure A: The chiral separation in SFC was carried out on a CHIRALPAK AS-H column (4.6×500 mm) at 50° C. with a flow rate of 3.0 ml/min. The mobile phase is $CO_2$, 15% iPrOH (containing 0.2% $iPrNH_2$) hold 18 min from 15-50% iPrOH (containing 0.2% $iPrNH_2$) at 10% rate and hold 3 min at 50%.

Method 16
In addition to the general procedure B: The chiral separation in SFC was carried out on a CHIRALCEL OD DAICEL column (10 μm, 4.6×250 mm) with a flow rate of 3.0 ml/min. The mobile phase is CO2, 40% MeOH, 60% EtOH (containing 0.3% iPrNH2) hold 7 min. in isocratic mode.

Method 17
In addition to the general procedure A: The chiral separation in SFC was carried out on a CHIRALPAK AD-H column (4.6×500 mm) at 50° C. with a flow rate of 3.0 ml/min. The mobile phase is $CO_2$, 35% iPrOH (containing 0.2% $iPrNH_2$) hold 19 min from 35-50% iPrOH (containing 0.2% $iPrNH_2$) at 10% rate and hold 4.10.

Method 18
In addition to the general procedure A: The chiral separation in SFC was carried out on a CHIRALPAK AD-H column (4.6×500 mm) at 50° C. with a flow rate of 3.0 ml/min. The mobile phase is $CO_2$, 25% iPrOH (containing 0.2% $iPrNH_2$) hold 18 min from 25-50% iPrOH (containing 0.2% $iPrNH_2$) at 10% rate and hold 4.10.

Method 19
In addition to the general procedure A: The chiral separation in SFC was carried out on a CHIRALCEL OD-H column (4.6×500 mm) at 50° C. with a flow rate of 3.0 ml/min. The mobile phase is $CO_2$, 15% MeOH (containing 0.2% $iPrNH_2$) hold 15 minutes. Enantiopure samples were contaminated with an unknown impurity and hence no UV area % is reported. After SFC purification and analysis, the samples were purified further via trituration with DIPE.

Method 20
In addition to the general procedure A: The chiral separation in SFC was carried out on a CHIRALPAK AS-H column (4.6×500 mm) at 50° C. with a flow rate of 3.0 ml/min. The mobile phase is $CO_2$, 15% EtOH (containing 0.2% $iPrNH_2$) hold 18 min, 15-50% EtOH (containing 0.2% $iPrNH_2$) at 10% rate and hold 3.10.

Method 21
In addition to the general procedure A: The chiral separation in SFC was carried out on a CHIRALCEL OJ-H column (4.6×250 mm) at 35° C. with a flow rate of 3.0 ml/min. The mobile phase is $CO_2$, 30% iPrOH hold 7 minutes.

Method 22
In addition to the general procedure A: The chiral separation in SFC was carried out on a CHIRALCEL OJ-H column (4.6×250 mm) at 35° C. with a flow rate of 3.0 ml/min. The mobile phase is $CO_2$, 25% iPrOH hold 7 minutes.

Method 23
In addition to the general procedure A: The chiral separation in SFC was carried out on a CHIRALCEL OJ-H column (4.6×250 mm) at 35° C. with a flow rate of 3.0 ml/min. The mobile phase is $CO_2$, 20% iPrOH hold 7 minutes.

Method 24
In addition to the general procedure A: The chiral separation in SFC was carried out on a CHIRALPAK AS-H column (4.6×500 mm) at 50° C. with a flow rate of 3.0 ml/min. The mobile phase is $CO_2$, 10% MeOH (containing 0.2% $iPrNH_2$) hold 17 min, from 10-50% MeOH (containing 0.2% $iPrNH_2$) at 10% rate and hold 3.60.

Method 25
In addition to the general procedure A: The chiral separation in SFC was carried out on a CHIRALPAK AD-H column (4.6×500 mm) at 50° C. with a flow rate of 3.0 ml/min. The mobile phase is $CO_2$, 15% EtOH (containing 0.2% $iPrNH_2$) hold 15 min.

Method 26
In addition to the general procedure A: The chiral separation in SFC was carried out on a CHIRALCEL OD-H column (4.6×500 mm) at 50° C. with a flow rate of 3.0 ml/min. The mobile phase is $CO_2$, 120% MeOH (containing 0.2% $iPrNH_2$) hold 15 min.

Method 27
In addition to the general procedure A: The chiral separation in SFC was carried out on a CHIRALPAK AD-H column (4.6×500 mm) at 50° C. with a flow rate of 3.0 ml/min. The mobile phase is $CO_2$, 20% iPrOH (containing 0.2% $iPrNH_2$) hold 16.30 min from 30-50% iPrOH (containing 0.2% $iPrNH_2$) at 10% rate and hold 3 min.

Method 28
In addition to the general procedure A: The chiral separation in SFC was carried out on a CHIRALCEL OJ-H column (4.6×500 mm) at 50° C. with a flow rate of 3.0 ml/min. The mobile phase is $CO_2$, 20% iPrOH (containing 0.2% $iPrNH_2$) hold 15 min.

Method 29
In addition to the general procedure A: The chiral separation in SFC was carried out on a CHIRALPAK AS-H column (4.6×500 mm) at 50° C. with a flow rate of 3.0 ml/min. The mobile phase is $CO_2$, 8% iPrOH (containing 0.2% $iPrNH_2$) hold 15 min.

Method 30
In addition to the general procedure A: The chiral separation in SFC was carried out on a CHIRALCEL OD-H column (4.6×500 mm) at 50° C. with a flow rate of 3.0 ml/min. The mobile phase is $CO_2$, 20% iPrOH (containing 0.2% $iPrNH_2$) hold 15 min.

Method 30
In addition to the general procedure A: The chiral separation in SFC was carried out on a CHIRALPAK AS-H column (4.6×500 mm) at 50° C. with a flow rate of 3.0 ml/min. The mobile phase is $CO_2$, 15% MeOH (containing 0.2% $iPrNH_2$) hold 15 min.

Method 31
In addition to the general procedure A: The chiral separation in SFC was carried out on a CHIRALPAK OJ-H column (4.6×500 mm) at 50° C. with a flow rate of 3.0 ml/min. The mobile phase is $CO_2$, 25% iPrOH (containing 0.2% $iPrNH_2$) hold 20.10 min from 25-40% iPrOH (containing 0.2% $iPrNH_2$) at 10% rate and hold 3 min.

TABLE 15

Analytical SFC data - $R_t$ means retention time (in minutes), $[M + H]^+$ means the protonated mass of the compound, method refers to the method used for (SFC)MS analysis of enantiomerically pure compounds.

| Co. Nr. | $R_t$ | $[M + H]^+$ | UV Area % | Method | Isomer Elution Order |
|---|---|---|---|---|---|
| 154 | 7.18 | 431 | 100 | 1 | A |
| 15 | 8.74 | 431 | 100 | 1 | B |
| 49 | 8.02 | 336 | 96.2 | 2 | B |
| 50 | 5.08 | 336 | 89.91 | 2 | A |
| 53 | 4.65 | 287 | 100 | 11 | B |
| 54 | 3.02 | 287 | 100 | 11 | A |
| 55 | 2.32 | 305 | 100 | 11 | A |
| 155 | 4.00 | 305 | 100 | 11 | B |
| 56 | 5.56 | 316 | 100 | 11 | A |
| 156 | 6.68 | 316 | 100 | 11 | B |
| 157 | 10.00 | 431 | 100 | 3 | A |
| 70 | 12.79 | 431 | 100 | 3 | B |
| 158 | 8.80 | 428 | 99.1 | 5 | A |
| 69 | 10.79 | 428 | 99.7 | 5 | B |
| 82 | 4.77 | 323 | 100 | 6 | A |
| 148 | 8.89 | 323 | 100 | 6 | B |
| 86 | 5.91 | 363 | 98.5 | 7 | A |
| 85 | 10.67 | 363 | 98.7 | 7 | B |
| 110 | 12.08 | 449 | 100 | 4 | A |
| 159 | 13.69 | 449 | 100 | 4 | B |
| 129 | 2.07 | 378 | 100 | 9 | A |
| 123 | 2.64 | 378 | 100 | 9 | B |
| 124 | 2.24 | 372 | 100 | 10 | A |
| 125 | 3.08 | 372 | 98.8 | 10 | B |
| 126 | 2.61 | 415 | 97.0 | 9 | B |
| 128 | 2.23 | 415 | 100 | 9 | A |
| 149 | 7.35 | 331 | 96.0 | 8 | B |
| 150 | 6.65 | 331 | 100 | 8 | A |
| 172 | 5.58 | 449 | 100 | 19 | A |
| 173 | 6.8 | 449 | 99 | 19 | B |
| 174 | 8.17 | 449 | 100 | 19 | C |
| 175 | 11.39 | 449 | 99 | 19 | D |
| 176 | 6.04 | 428 | 100 | 14 | A |
| 177 | 6.95 | 428 | 100 | 14 | B |
| 178 | 7.7 | 428 | 100 | 14 | C |
| 179 | 11.75 | 428 | 100 | 14 | D |
| 170 | 7.8 | 531 | 100 | 15 | A |
| 187 | 6.01 | 397 | 100 | 14 | A |
| 188 | 6.63 | 397 | 100 | 14 | B |
| 189 | 8.32 | 397 | 100 | 14 | C |
| 190 | 10.44 | 397 | 100 | 14 | D |
| 191 | 9.93 | 411 | 100 | 13 | C |
| 192 | 11.83 | 411 | 100 | 13 | D |
| 193 | 7.53 | 411 | 100 | 13 | B |
| 194 | 7.12 | 411 | 100 | 13 | A |
| 163 | 6.49 | 381 | 100 | 12 | A |
| 164 | 9.2 | 381 | 100 | 12 | B |
| 195 | 1.97 | 371 | 100 | 16 | A |
| 196 | 5.48 | 371 | 100 | 16 | B |
| 204 | 4.59 | 361 | 100 | 18 | A |
| 205 | 5.44 | 361 | 96.3 | 18 | B |
| 240 | 1.90 | 421 | 100 | 21 | A |
| 241 | 2.33 | 421 | 99 | 21 | B |
| 242 | 1.83 | 465 | 100 | 21 | A |
| 243 | 2.73 | 465 | 100 | 21 | B |
| 245 | 2.85 | 456 | 100 | 22 | A |
| 246 | 5.17 | 456 | 100 | 22 | B |
| 247 | 3.07 | 427 | 100 | 23 | A |
| 248 | 3.51 | 427 | 98 | 23 | B |
| 257 | 16.08 | 311 | 100 | 24 | B |
| 258 | 14.42 | 311 | 100 | 24 | A |
| 265 | 6.16 | 379 | 100 | 25 | A |
| 266 | 8.24 | 379 | 100 | 25 | B |
| 267 | 5.44 | 355 | 100 | 26 | A |
| 268 | 6.45 | 355 | 100 | 26 | B |
| 273 | 6.08 | 364 | 100 | 1 | B |
| 277 | 10.77 | 354 | 100 | 27 | C |
| 278 | 11.85 | 354 | 100 | 27 | D |
| 293 | 11.02 | 368 | 96 | 28 | B |
| 295 | 6.08 | 364 | 100 | 1 | B |
| 316 | 5.65 | 396 | 99 | 29 | B |
| 321 | 6.13 | 428 | 100 | 30 | A |
| 322 | 6.87 | 428 | 100 | 30 | B |
| 329 | 5.53 | 396 | 100 | 30 | A |
| 348 | 7.31 | 414 | 100 | 17 | A |
| 350 | 3.90 | 397 | 100 | 28 | B |
| 351 | 3.04 | 397 | 100 | 28 | A |
| 355 | 5.24 | 467 | 100 | 31 | A |
| 356 | 6.69 | 467 | 99 | 31 | B |

Isomer Elution Order: A means first eluting isomer; B means second eluting isomer, C means third eluting isomer; D means fourth eluting isomer.

Optical Rotations:

Optical rotations were measured on a Perkin-Elmer 341 polarimeter with a sodium lamp and reported as follows: $[\alpha]_\lambda^{t^\circ C.}$ (c g/100 ml, solvent).

TABLE 16

Analytical data - Optical rotation values for enantiomerically pure compounds

| Co. Nr. | $\alpha_D$ (°) | Wavelength (nm) | Concentration w/v % | Solvent | Temp. (° C.) |
|---|---|---|---|---|---|
| 1 | −103.61 | 589 | 0.1052 | MeOH | 20 |
| 2 | −88.8 | 589 | 0.68 | DMF | 20 |
| 21 | +15.1 | 589 | 0.58 | DMF | 20 |
| 23 | −14.9 | 589 | 0.55 | DMF | 20 |
| 24 | +23.1 | 589 | 0.57 | DMF | 20 |
| 25 | +18.9 | 589 | 0.55 | DMF | 20 |
| 28 | −31.51 | 589 | 0.53 | MeOH | 20 |
| 30 | +13 | 589 | 0.55 | DMF | 20 |
| 31 | −19.2 | 589 | 0.53 | DMF | 20 |
| 32 | −24.9 | 589 | 0.5 | DMF | 20 |
| 35 | +28.2 | 589 | 0.51 | DMF | 20 |
| 36 | −45.1 | 589 | 0.51 | DMF | 20 |
| 37 | −27.6 | 589 | 0.52 | DMF | 20 |
| 38 | +20.8 | 589 | 0.54 | DMF | 20 |
| 39 | +32.2 | 589 | 0.61 | DMF | 20 |
| 40 | +26.6 | 589 | 0.55 | DMF | 20 |
| 41 | +23.0 | 589 | 0.54 | DMF | 20 |
| 43 | +40.7 | 589 | 0.58 | DMF | 20 |
| 44 | +31.9 | 589 | 0.69 | DMF | 20 |
| 45 | +19.6 | 589 | 0.64 | DMF | 20 |
| 46 | −17.2 | 589 | 0.56 | DMF | 20 |
| 47 | −17.4 | 589 | 0.53 | DMF | 20 |
| 48 | −4.9 | 589 | 0.49 | DMF | 20 |
| 49 | +135.6 | 589 | 0.34 | MeOH | 20 |
| 50 | −111.25 | 589 | 0.33 | MeOH | 20 |
| 51 | −101.1 | 589 | 0.54 | DMF | 20 |
| 52 | −105.6 | 589 | 0.57 | DMF | 20 |
| 53 | +23.1 | 589 | 0.53 | DMF | 20 |
| 54 | −30.9 | 589 | 0.62 | DMF | 20 |
| 55 | −35.4 | 589 | 0.61 | DMF | 20 |
| 56 | −9.3 | 589 | 0.53 | DMF | 20 |
| 61 | −24.6 | 589 | 0.56 | DMF | 20 |
| 62 | 33.7 | 589 | 0.53 | DMF | 20 |
| 68 | −20.53 | 589 | 0.531 | MeOH | 20 |
| 85 | +11.46 | 589 | 0.4176 | MeOH | 20 |
| 86 | −12.21 | 589 | 0.49 | DMF | 20 |
| 123 | +56.34 | 589 | 0.465 | MeOH | 20 |
| 124 | +125 | 589 | 0.51 | DMF | 20 |
| 125 | −126.9 | 589 | 0.52 | DMF | 20 |
| 126 | +72.9 | 589 | 0.53 | DMF | 20 |
| 128 | −7.7 | 589 | 0.67 | MeOH | 20 |
| 129 | −57.9 | 589 | 0.51 | MeOH | 20 |
| 130 | −24.4 | 589 | 0.54 | MeOH | 20 |
| 131 | 7.5 | 589 | 0.53 | DMF | 20 |
| 132 | +93.3 | 589 | 0.51 | DMF | 20 |
| 133 | −6.5 | 589 | 0.52 | DMF | 20 |
| 155 | +39.1 | 589 | 0.46 | MeOH | 20 |

TABLE 16-continued

Analytical data - Optical rotation values for enantiomerically pure compounds

| Co. Nr. | $\alpha_D$ (°) | Wavelength (nm) | Concentration w/v % | Solvent | Temp. (° C.) |
|---|---|---|---|---|---|
| 156 | −9.3 | 589 | 0.534 | DMF | 20 |
| 163 | −11.38 | 589 | 0.545 | MeOH | 20 |
| 164 | +10.93 | 589 | 0.485 | MeOH | 20 |
| 165 | −36.83 | 589 | 0.23 | MeOH | 20 |
| 166 | −42.4 | 589 | 0.18 | MeOH | 20 |
| 167 | −37.69 | 589 | 0.159 | MeOH | 20 |
| 168 | −52.27 | 589 | 0.13 | MeOH | 20 |
| 169 | −31.6 | 589 | 0.1424 | MeOH | 20 |
| 180 | +75.6 | 589 | 0.17 | MeOH | 20 |
| 181 | +16.97 | 589 | 1.22 | MeOH | 20 |
| 182 | +89.21 | 589 | 0.14 | MeOH | 20 |
| 183 | +83.59 | 589 | 0.13 | MeOH | 20 |
| 184 | −128.56 | 589 | 0.22 | MeOH | 20 |
| 185 | −111.68 | 589 | 0.31 | MeOH | 20 |
| 186 | −123.1 | 589 | 0.14 | MeOH | 20 |
| 195 | −29.7 | 589 | 0.51 | DMF | 20 |
| 196 | +28.1 | 589 | 0.50 | DMF | 20 |
| 197 | −29.7 | 589 | 0.51 | DMF | 20 |
| 198 | −61.24 | 589 | 0.48 | MeOH | 20 |
| 199 | +102.24 | 589 | 0.49 | MeOH | 20 |
| 202 | −48.82 | 589 | 0.551 | MeOH | 20 |
| 203 | +63.22 | 589 | 0.522 | MeOH | 20 |
| 208 | +116.8 | 589 | 0.57 | DMF | 20 |
| 209 | +60.9 | 589 | 0.52 | DMF | 20 |
| 210 | −115.8 | 589 | 0.49 | DMF | 20 |
| 211 | +84.1 | 589 | 0.48 | DMF | 20 |
| 212 | −106.1 | 589 | 0.5 | DMF | 20 |
| 213 | +89.1 | 589 | 0.52 | DMF | 20 |
| 214 | +68.93 | 589 | 0.28 | MeOH | 20 |
| 218 | +32.48 | 589 | 0.4095 | DMF | 20 |
| 219 | +86.13 | 589 | 0.3425 | MeOH | 20 |
| 220 | −16.64 | 589 | 0.3485 | DMF | 20 |
| 221 | +98.19 | 589 | 0.2485 | DMF | 20 |
| 222 | +77.78 | 589 | 0.144 | MeOH | 20 |
| 223 | −58.64 | 589 | 0.191 | MeOH | 20 |
| 224 | −71.17 | 589 | 0.4145 | MeOH | 20 |
| 225 | +52 | 589 | 0.225 | MeOH | 20 |
| 227 | +80 | 589 | 0.38 | MeOH | 20 |
| 228 | −22.22 | 589 | 0.4635 | MeOH | 20 |
| 229 | +14.33 | 589 | 0.307 | MeOH | 20 |
| 230 | +9.26 | 589 | 0.3995 | DMF | 20 |
| 231 | +93.26 | 365 | 0.3485 | DMF | 20 |
| 233 | +6.38 | 589 | 0.423 | DMF | 20 |
| 234 | +11.01 | 589 | 0.227 | MeOH | 20 |
| 235 | +9.75 | 589 | 0.4925 | MeOH | 20 |
| 240 | +80.69 | 589 | 0.29 | DMF | 20 |
| 241 | −98.56 | 589 | 0.278 | DMF | 20 |
| 242 | +81.94 | 589 | 0.288 | DMF | 20 |
| 243 | −97.23 | 589 | 0.289 | DMF | 20 |
| 244 | −43.67 | 589 | 0.529 | DMF | 20 |
| 245 | +80.81 | 589 | 0.2945 | DMF | 20 |
| 246 | −91.96 | 589 | 0.286 | DMF | 20 |
| 247 | +86.99 | 589 | 0.346 | DMF | 20 |
| 248 | −107.16 | 589 | 0.2865 | DMF | 20 |
| 249 | −76.1 | 589 | 0.3825 | DMF | 20 |
| 250 | +38.73 | 589 | 0.4415 | DMF | 20 |
| 251 | +45.89 | 589 | 0.3835 | DMF | 20 |
| 253 | +52.07 | 589 | 0.4225 | DMF | 20 |
| 254 | −42 | 589 | 1.5 | DMF | 20 |
| 255 | −41.2 | 589 | 0.49 | DMF | 20 |
| 256 | +44.76 | 589 | 0.458 | DMF | 20 |
| 257 | +28.85 | 589 | 0.4125 | DMF | 20 |
| 259 | +54.47 | 589 | 0.514 | MeOH | 20 |
| 260 | −22.13 | 589 | 0.5875 | DMF | 20 |
| 262 | +157.72 | 589 | 0.3855 | DMF | 20 |
| 264 | +98.25 | 589 | 0.456 | DMF | 20 |
| 269 | +75.99 | 589 | 0.2145 | DMF | 20 |
| 271 | +170.76 | 589 | 0.407 | DMF | 20 |
| 272 | −46.77 | 589 | 0.2865 | DMF | 20 |
| 275 | +34.69 | 589 | 0.3805 | DMF | 20 |
| 276 | −49.84 | 589 | 0.4755 | DMF | 20 |
| 280 | −71.77 | 589 | 0.333 | DMF | 20 |
| 286 | −35.58 | 589 | 0.4075 | DMF | 20 |
| 288 | +74.75 | 589 | 0.4 | DMF | 20 |
| 289 | +76.5 | 589 | 0.4 | DMF | 20 |
| 290 | +12.22 | 589 | 0.27 | DMF | 20 |
| 291 | +74.64 | 589 | 0.28 | DMF | 20 |
| 292 | +110.67 | 589 | 0.4825 | DMF | 20 |
| 294 | +101.64 | 589 | 0.609 | DMF | 20 |
| 296 | +83.73 | 589 | 0.295 | DMF | 20 |
| 297 | +47.87 | 589 | 0.399 | DMF | 20 |
| 298 | −49.24 | 589 | 0.4265 | DMF | 20 |
| 299 | 63.6 | 589 | 0.61 | DMF | 20 |
| 304 | −97.01 | 589 | 0.535 | DMF | 20 |
| 305 | +122.96 | 589 | 0.575 | DMF | 20 |
| 306 | +101.54 | 589 | 0.39 | DMF | 20 |
| 307 | −100.24 | 589 | 0.41 | DMF | 20 |
| 308 | −33.79 | 589 | 0.586 | DMF | 20 |
| 309 | −61.61 | 589 | 0.336 | DMF | 20 |
| 311 | +13.39 | 589 | 0.3285 | DMF | 20 |
| 312 | +167.57 | 589 | 0.37 | DMF | 20 |
| 313 | +41.49 | 589 | 0.3495 | DMF | 20 |
| 314 | +117.36 | 589 | 0.4925 | DMF | 20 |
| 315 | +121.66 | 589 | 0.471 | DMF | 20 |
| 316 | −46.02 | 589 | 0.389 | DMF | 20 |
| 317 | −42.96 | 589 | 0.405 | DMF | 20 |
| 318 | −78.75 | 589 | 0.32 | DMF | 20 |
| 319 | +87.23 | 589 | 0.47 | DMF | 20 |
| 320 | −30.15 | 589 | 0.262 | DMF | 20 |
| 325 | +46.45 | 589 | 0.465 | DMF | 20 |
| 326 | −63.64 | 589 | 0.308 | DMF | 20 |
| 327 | +45.58 | 589 | 0.4015 | DMF | 20 |
| 337 | +41.65 | 589 | 0.425 | DMF | 20 |
| 338 | +73.84 | 589 | 0.409 | DMF | 20 |
| 340 | −10.56 | 589 | 0.36 | DMF | 20 |
| 341 | −10.94 | 589 | 0.393 | DMF | 20 |
| 342 | −13.75 | 589 | 0.4655 | DMF | 20 |
| 343 | −11.09 | 589 | 0.676 | DMF | 20 |
| 344 | +99.74 | 589 | 0.391 | DMF | 20 |
| 346 | +8.75 | 589 | 0.32 | DMF | 20 |
| 347 | +39.32 | 589 | 0.295 | DMF | 20 |
| 370 | +106.71 | 589 | 0.417 | DMF | 20 |
| 371 | +116.48 | 589 | 0.3915 | DMF | 20 |
| 374 | −20.86 | 589 | 0.532 | DMF | 20 |
| 380 | +93.87 | 589 | 0.506 | DMF | 20 |

NMR

For a number of compounds, $^1$H NMR spectra were recorded on a Bruker DPX-360, on a Bruker DPX-400 or on a Bruker Avance 600 spectrometer with standard pulse sequences, operating at 360 MHz, 400 MHz and 600 MHz respectively, using CHLOROFORM-d (deuterated chloroform, CDCl$_3$) or DMSO-d$_6$ (deuterated DMSO, dimethyl-d6 sulfoxide) as solvents. Chemical shifts (δ) are reported in parts per million (ppm) relative to tetramethylsilane (TMS), which was used as internal standard.

TABLE 17

| Co. Nr. | NMR result |
|---|---|
| 86 | $^1$H NMR (360 MHz, DMSO-d$_6$) δ ppm 1.29-1.55 (m, 3 H) 3.96 (d, J = 15.8 Hz, 1 H) 4.04 (d, J = 15.7 Hz, 1 H) 5.72 (d, J = 53.4 Hz, 1 H) 5.94 (br. s., 2 H) 7.13 (d, J = 8.1 Hz, 1 H) 7.31 (t, J = 7.9 Hz, |

TABLE 17-continued

| Co. Nr. | NMR result |
|---|---|
|  | 1 H) 7.76-7.79 (m, 1 H) 7.81 (d, J = 8.1 Hz, 1 H) 8.16 (d, J = 8.4 Hz, 1 H) 8.21 (dd, J = 8.4, 2.6 Hz, 1 H) 8.79 (d, J = 2.4 Hz, 1 H) 10.60 (s, 1 H) |
| 117 | $^1$H NMR (360 MHz, CHLOROFORM-d) δ ppm 1.86 (d, J = 2.6 Hz, 3 H) 4.38 (br. s., 1 H) 4.49 (d, J = 15.5 Hz, 1 H) 4.56 (d, J = 15.5 Hz, 1 H) 7.43-7.56 (m, 3 H) 8.93 (s, 2 H) 9.22 (s, 1 H) |
| 163 | $^1$H NMR (400 MHz, DMSO-d$_6$) δ ppm 1.43 (s, 3 H) 3.96 (d, J = 15.8 Hz, 1 H) 4.06 (d, J = 15.8 Hz, 1 H) 5.71 (d, J = 53.5 Hz, 1 H) 5.96 (br. s, 2 H) 7.14 (d, J = 8.0 Hz, 1 H) 7.32 (t, J = 7.9 Hz, 1 H) 7.67 (br. s, 1 H) 7.73 (dd, J = 8.0, 2.0 Hz, 1 H) 8.32 (dd, J = 10.3, 1.8 Hz, 1 H) 8.65 (d, J = 2.0 Hz, 1 H) 10.58 (br. s, 1 H) |
| 165 | $^1$H NMR (360 MHz, CHLOROFORM-d) δ ppm 1.69 (s, 3 H) 4.19-4.31 (m, 2 H) 4.28-4.54 (m, 2 H) 4.66 (q, J = 8.1 Hz, 1 H) 7.06 (dd, J = 11.7, 8.8 Hz, 1 H) 7.88 (dd, J = 8.4, 2.6 Hz, 1 H) 7.91 (dd, J = 6.8, 2.7 Hz, 1 H) 7.99-8.08 (m, 1 H) 8.25 (d, J = 8.4 Hz, 1 H) 8.56 (d, J = 2.2 Hz, 1 H) 9.88 (br. s, 1 H) |
| 166 | $^1$H NMR (360 MHz, CHLOROFORM-d) δ ppm 1.68 (s, 3 H) 4.07 (s, 3 H) 4.23 (s, 2 H) 4.27-4.41 (m, 2 H) 4.65 (q, J = 8.2 Hz, 1 H) 7.05 (dd, J = 11.7, 8.8 Hz, 1 H) 7.89 (dd, J = 6.8, 2.7 Hz, 1 H) 8.02 (ddd, J = 8.8, 4.4, 2.9 Hz, 1 H) 8.15 (d, J = 1.5 Hz, 1 H) 9.02 (d, J = 1.5 Hz, 1 H) 9.55 (s, 1 H) |
| 167 | $^1$H NMR (360 MHz, CHLOROFORM-d) δ ppm 1.67 (s, 3 H) 4.23 (s, 2 H) 4.33 (br. s, 2 H) 4.67 (q, J = 8.4 Hz, 1 H) 7.05 (dd, J = 11.5, 9.0 Hz, 1 H) 7.82 (dd, J = 7.0, 2.9 Hz, 1 H) 7.91 (d, J = 2.2 Hz, 1 H) 8.09 (ddd, J = 8.9, 4.3, 2.9 Hz, 1 H) 8.47 (d, J = 2.2 Hz, 1 H) 9.79 (s, 1 H) |
| 169 | $^1$H NMR (360 MHz, CHLOROFORM-d) δ ppm 1.68 (s, 3 H) 4.24 (s, 2 H) 4.35 (br. s, 2 H) 4.66 (q, J = 8.3 Hz, 1 H) 7.08 (dd, J = 11.5, 9.0 Hz, 1 H) 7.94 (dd, J = 6.6, 2.9 Hz, 1 H) 8.06 (ddd, J = 8.8, 4.4, 2.9 Hz, 1 H) 8.20 (dd, J = 8.2, 2.0 Hz, 1 H) 8.43 (d, J = 8.1 Hz, 1 H) 8.88 (s, 1 H) 9.91 (s, 1 H) |
| 170 | $^1$H NMR (360 MHz, CHLOROFORM-d) δ ppm 1.74 (s, 3 H) 4.27 (d, J = 15.7 Hz, 1 H) 4.34 (d, J = 15.7 Hz, 1 H) 4.37 (br. s, 2 H) 4.51 (q, J = 7.7 Hz, 1 H) 7.08 (dd, J = 11.9, 9.0 Hz, 1 H) 7.69 (dd, J = 7.0, 2.6 Hz, 1 H) 7.81 (dt, J = 9.1, 3.3 Hz, 1 H) 7.89 (dd, J = 8.4, 2.2 Hz, 1 H) 8.25 (d, J = 8.4 Hz, 1 H) 8.57 (d, J = 2.2 Hz, 1 H) 9.82 (s, 1 H) |
| 180 | $^1$H NMR (360 MHz, CHLOROFORM-d) δ ppm 1.87 (br. s., 3 H) 4.07 (s, 3 H) 4.33 (br. s, 2 H) 4.47 (d, J = 15.0 Hz, 1 H) 4.53 (d, J = 15.0 Hz, 1 H) 7.03 (dd, J = 12.4, 8.8 Hz, 1 H) 7.64 (dt, J = 8.9, 3.4 Hz, 1 H) 7.85 (dd, J = 7.3, 2.9 Hz, 1 H) 8.16 (d, J = 1.5 Hz, 1 H) 9.02 (d, J = 1.5 Hz, 1 H) 9.49 (s, 1 H) |
| 183 | $^1$H NMR (360 MHz, CHLOROFORM-d) δ ppm 1.87 (br. s., 3 H) 4.34 (br. s, 2 H) 4.47 (d, J = 15.4 Hz, 1 H) 4.52 (d, J = 15.3 Hz, 1 H) 7.05 (dd, J = 12.4, 8.8 Hz, 1 H) 7.69 (dt, J = 8.5, 3.1 Hz, 1 H) 7.86 (dd, J = 7.3, 2.6 Hz, 1 H) 8.21 (dd, J = 8.1, 1.8 Hz, 1 H) 8.43 (d, J = 8.1 Hz, 1 H) 8.91 (d, J = 1.8 Hz, 1 H) 9.85 (s, 1 H) |
| 199 | $^1$H NMR (360 MHz, DMSO-d$_6$) δ ppm 0.31-0.43 (m, 2 H) 0.43-0.58 (m, 2 H) 1.76-1.85 (m, 1 H) 4.32 (d, J = 15.4 Hz, 1 H) 4.68 (d, J = 15.7 Hz, 1 H) 6.03 (br. s, 2 H) 7.25 (d, J = 7.3 Hz, 1 H) 7.32 (t, J = 7.7 Hz, 1 H) 7.93 (d, J = 7.7 Hz, 1 H) 8.01 (s, 1 H) 8.29 (d, J = 8.1 Hz, 1 H) 8.59 (dd, J = 8.2, 2.0 Hz, 1 H) 9.21 (d, J = 2.0 Hz, 1 H) 10.86 (s, 1 H) |
| 204 | $^1$H NMR (360 MHz, CHLOROFORM-d) δ ppm 1.77 (s, 3 H) 4.02 (q, J = 7.2 Hz, 1 H) 4.37 (br. s, 2 H) 4.32 (d, J = 15.9 Hz, 1 H) 4.42 (d, J = 16.0 Hz, 1 H) 7.44-7.53 (m, 3 H) 7.58 (br. s, 1 H) 8.12 (t, J = 2.0 Hz, 1 H) 8.85 (d, J = 1.8 Hz, 1 H) 9.02 (d, J = 2.2 Hz, 1 H) |
| 214 | $^1$H NMR (360 MHz, CHLOROFORM-d) δ ppm 0.11-0.30 (m, 1 H) 0.32-0.41 (m, 1 H) 0.47 (td, J = 8.8, 3.7 Hz, 1 H) 0.55 (m, J = 9.5, 4.8, 4.8 Hz, 1 H) 1.65 (tt, J = 8.4, 4.2 Hz, 1 H) 3.99 (d, J = 15.4 Hz, 1 H) 4.23 (d, J = 15.4 Hz, 1 H) 4.44 (br. s., 2 H) 6.22 (d, J = 52.3 Hz, 1 H) 7.10 (dd, J = 11.3, 8.8 Hz, 1 H) 7.44 (dd, J = 6.8, 2.7 Hz, 1 H) 7.83 (ddd, J = 8.8, 4.0, 2.9 Hz, 1 H) 8.19 (dd, J = 8.2, 2.0 Hz, 1 H) 8.39 (d, J = 8.1 Hz, 1 H) 8.84-8.90 (m, 1 H) 9.80 (br. s., 1 H) |
| 215 | $^1$H NMR (360 MHz, CHLOROFORM-d) δ ppm 0.15-0.26 (m, 2 H) 0.30 (m, J = 5.5 Hz, 1 H) 0.47 (m, J = 5.5 Hz, 1 H) 1.48-1.59 (m, 1 H) 4.12 (d, J = 15.4 Hz, 1 H) 4.26 (d, J = 15.4 Hz, 1 H) 4.44 (br. s, 2 H) 6.24 (dd, J = 51.2, 2.0 Hz, 1 H) 7.11 (dd, J = 11.3, 8.8 Hz, 1 H) 7.87 (dd, J = 6.6, 2.9 Hz, 1 H) 8.02 (ddd, J = 8.9, 4.3, 2.9 Hz, 1 H) 8.20 (dd, J = 8.2, 2.0 Hz, 1 H) 8.42 (dd, J = 8.1, 0.7 Hz, 1 H) 8.87 (d, J = 2.2, 0.7 Hz, 1 H) 9.87 (s, 1 H) |
| 216 | $^1$H NMR (360 MHz, CHLOROFORM-d) δ ppm 0.15-0.26 (m, 1 H) 0.33-0.42 (m, 1 H) 0.42-0.50 (m, 1 H) 0.50-0.60 (m, 1 H) 1.58-1.74 (m, 1 H) 3.99 (d, J = 15.4 Hz, 1 H) 4.06 (s, 3 H) 4.22 (d, J = 15.7 Hz, 1 H) 4.34-4.60 (m, 2 H) 6.22 (d, J = 52.3 Hz, 1 H) 7.08 (dd, J = 11.7, 8.8 Hz, 1 H) 7.39 (dd, J = 6.8, 2.7 Hz, |

TABLE 17-continued

| Co. Nr. | NMR result |
|---|---|
| | 1 H) 7.82 (ddd, J = 8.8, 4.0, 2.9 Hz, 1 H) 8.13 (d, J = 1.5 Hz, 1 H) 8.99 (d, J = 1.5 Hz, 1 H) 9.46 (s, 1 H) |
| 217 | $^1$H NMR (360 MHz, CHLOROFORM-d) δ ppm 0.14-0.26 (m, 2 H) 0.26-0.36 (m, 1 H) 0.39-0.52 (m, 1 H) 1.41-1.63 (m, 1 H) 4.06 (s, 3 H) 4.11 (d, J = 15.5 Hz, 1 H) 4.25 (d, J = 15.5 Hz, 1 H) 4.43 (br. s., 2 H) 6.23 (dd, J = 51.6, 2.2 Hz, 1 H) 7.08 (dd, J = 11.5, 9.0 Hz, 1 H) 7.85 (dd, J = 6.6, 2.9 Hz, 1 H) 7.97 (ddd, J = 8.8, 4.0, 2.9 Hz, 1 H) 8.14 (d, J = 1.5 Hz, 1 H) 9.01 (d, J = 1.5 Hz, 1 H) 9.52 (s, 1 H) |
| 218 | $^1$H NMR (360 MHz, CHLOROFORM-d) δ ppm 0.14-0.27 (m, 1 H) 0.29-0.41 (m, 1 H) 0.43-0.50 (m, 1 H) 0.51-0.60 (m, 1 H) 1.56-1.72 (m, 1 H) 3.99 (d, J = 15.7 Hz, 1 H) 4.14 (br. s, 2 H) 4.23 (d, J = 15.7 Hz, 1 H) 6.22 (d, J = 52.0 Hz, 1 H) 7.09 (dd, J = 11.5, 9.0 Hz, 1 H) 7.31 (dd, J = 6.8, 2.7 Hz, 1 H) 7.85-7.92 (m, 1 H) 8.16 (d, J = 1.8 Hz, 1 H) 8.73 (d, J = 1.8 Hz, 1 H) 9.65 (br. s., 1 H) |
| 219 | $^1$H NMR (360 MHz, CHLOROFORM-d) δ ppm 0.12-0.27 (m, 1 H) 0.31-0.42 (m, 1 H) 0.42-0.50 (m, 1 H) 0.50-0.62 (m, 1 H) 1.65 (m, J = 8.3, 8.3, 4.9 Hz, 1 H) 3.99 (d, J = 15.4 Hz, 1 H) 4.22 (d, J = 15.4 Hz, 1 H) 4.52 (br. s, 2 H) 6.22 (d, J = 52.3 Hz, 1 H) 7.08 (dd, J = 11.5, 9.0 Hz, 1 H) 7.39 (dd, J = 6.8, 2.7 Hz, 1 H) 7.64 (dd, J = 9.9, 1.8 Hz, 1 H) 7.80 (dt, J = 8.6, 3.6 Hz, 1 H) 8.37 (d, J = 2.0 Hz, 1 H) 9.59 (s, 1 H) |
| 220 | $^1$H NMR (360 MHz, CHLOROFORM-d) δ ppm 0.13-0.36 (m, 3 H) 0.39-0.50 (m, 1 H) 1.51 (m, J = 8.1, 5.4, 2.6 Hz, 1 H) 4.12 (d, J = 15.4 Hz, 1 H) 4.26 (d, J = 15.4 Hz, 1 H) 4.48 (br. s., 2 H) 6.24 (dd, J = 51.2, 1.8 Hz, 1 H) 7.08 (d, J = 11.7, 8.8 Hz, 1 H) 7.65 (dd, J = 10.1, 2.0 Hz, 1 H) 7.83 (dd, J = 6.6, 2.9 Hz, 1 H) 7.99 (ddd, J = 8.8, 4.4, 2.9 Hz, 1 H) 8.37 (dd, J = 1.9, 0.7 Hz, 1 H) 9.66 (s, 1 H) |
| 227 | $^1$H NMR (400 MHz, DMSO-$d_6$) δ ppm 0.18-0.31 (m, 1 H) 0.31-0.36 (m, 1 H) 0.36-0.46 (m, 1 H) 0.48-0.64 (m, 1 H) 1.63-1.85 (m, 1 H) 4.02 (s, 3 H) 4.18 (d, J = 15.3 Hz, 1 H) 4.13-4.22 (m, 1 H) 4.31 (d, J = 15.4 Hz, 1 H) 5.75 (s, 2 H) 7.20 (dd, J = 8.1, 1.6 Hz, 1 H) 7.25 (t, J = 7.7 Hz, 1 H) 7.79 (dt, J = 8.0, 1.7 Hz, 1 H) 7.98 (t, J = 1.8 Hz, 1 H) 8.40 (d, J = 1.2 Hz, 1 H) 8.89 (d, J = 1.2 Hz, 1 H) 10.33 (s, 1 H) |
| 228 | $^1$H NMR (400 MHz, DMSO-$d_6$) δ ppm 0.24 (tdd, J = 8.7, 8.7, 5.7, 3.2 Hz, 1 H) 0.33-0.52 (m, 3 H) 1.33-1.48 (m, 1 H) 4.03 (s, 3 H) 4.06 (d, J = 15.7 Hz, 1 H) 4.12 (d, J = 15.7 Hz, 1 H) 4.41 (q, J = 8.5 Hz, 1 H) 5.59 (br. s., 2 H) 7.19-7.24 (m, 1 H) 7.28 (t, J = 7.7 Hz, 1 H) 7.76 (ddd, J = 7.9, 2.0, 1.0 Hz, 1 H) 7.85 (t, J = 1.8 Hz, 1 H) 8.34 (d, J = 1.6 Hz, 1 H) 8.87 (d, J = 1.2 Hz, 1 H) 10.08 (br. s, 1 H) |
| 254 | $^1$H NMR (500 MHz, CHLOROFORM-d) δ ppm 1.69 (s, 3 H) 4.21 (s, 2 H) 4.17-4.28 (m, 2 H) 4.61 (q, J = 8.4 Hz, 1 H) 6.96 (dd, J = 11.3, 9.8 Hz, 1 H) 8.02 (t, J = 8.8 Hz, 1 H) 8.93 (d, J = 1.4 Hz, 2 H) 9.21 (s, 1 H) |
| 257 | $^1$H NMR (400 MHz, DMSO-$d_6$) δ ppm 0.03-0.17 (m, 1 H) 0.20-0.32 (m, 1 H) 0.33-0.42 (m, 1 H) 0.43-0.52 (m, 1 H) 1.41-1.61 (m, 1 H) 3.90 (d, J = 15.8 Hz, 1 H) 4.03 (d, J = 15.6 Hz, 1 H) 5.93 (br. s., 2 H) 6.11 (d, J = 53.2 Hz, 1 H) 7.44 (dt, J = 8.0, 1.5 Hz, 1 H) 7.48 (t, J = 7.8 Hz, 1 H) 7.66 (dt, J = 7.3, 1.4 Hz, 1 H) 7.82 (s, 1 H) 9.13 (s, 2 H) 9.19 (s, 1 H) |
| 260 | $^1$H NMR (400 MHz, DMSO-$d_6$) δ ppm 1.55 (s, 3 H) 4.09 (d, J = 16.1 Hz, 0 H) 4.22 (d, J = 16.1 Hz, 1 H) 4.54 (q, J = 8.4 Hz, 1 H) 5.82 (s, 2 H) 7.12 (dd, J = 12.0, 8.8 Hz, 1 H) 7.69-7.84 (m, 1 H) 8.03 (dd, J = 7.0, 2.8 Hz, 1 H) 8.31 (dd, J = 10.3, 2.0 Hz, 1 H) 8.64 (dd, J = 1.9, 0.9 Hz, 1 H) 10.63 (s, 1 H) |
| 261 | $^1$H NMR (400 MHz, DMSO-$d_6$) δ ppm 1.89 (s, 3 H) 4.84 (d, J = 17.1 Hz, 1 H) 4.94 (q, J = 6.6 Hz, 1 H) 5.04 (d, J = 17.1 Hz, 1 H) 7.22 (dd, J = 7.8, 1.0 Hz, 1 H) 7.43 (t, J = 8.0 Hz, 1 H) 7.99 (t, J = 1.8 Hz, 1 H) 8.13 (dd, J = 8.0, 1.3 Hz, 1 H) 8.31 (dd, J = 8.0, 0.8 Hz, 1 H) 8.60 (dd, J = 8.2, 2.1 Hz, 1 H) 8.75 (br. s., 1 H) 9.21 (dd, J = 2.0, 0.8 Hz, 1 H) 9.45 (br. s., 1 H) 10.94 (s, 1 H) 11.00 (br. s., 1 H) |
| 268 | $^1$H NMR (360 MHz, CHLOROFORM-d) δ ppm 1.74 (s, 3 H) 3.97 (q, J = 7.0 Hz, 1 H) 4.28 (br. s., 2 H) 4.28 (d, J = 15.7 Hz, 1 H) 4.38 (d, J = 15.7 Hz, 1 H) 7.15-7.24 (m, 1 H) 7.41-7.51 (m, 2 H) 8.93 (d, J = 1.3 Hz, 2 H) 9.22 (s, 1 H) |
| 277 | $^1$H NMR (400 MHz, CHLOROFORM-d) δ ppm 1.72 (d, J = 2.1 Hz, 3 H) 4.52 (d, J = 17.0 Hz, 1 H) 4.63 (d, J = 17.0 Hz, 1 H) 5.58 (s, 2 H) 5.79 (d, J = 50.9 Hz, 1 H) 7.23 (dd, J = 5.2, 1.8 Hz, 1 H) 7.39 (t, J = 1.9 Hz, 1 H) 7.63-7.69 (m, 1 H) 7.90 (d, J = 1.9 Hz, 2 H) 8.70 (d, J = 5.2 Hz, 1 H) |
| 281 | $^1$H NMR (400 MHz, DMSO-$d_6$) δ ppm 0.67 (t, J = 7.3 Hz, 3 H) 1.52-1.68 (m, 1 H) 2.04-2.19 (m, 1 H) 3.92 (d, J = 15.7 Hz, 1 H) 4.04 (d, J = 15.7 Hz, 1 H) 4.01 (s, 3 H) 5.90 (d, J = 54.8 Hz, 1 H) 6.03 (br. s., 2 H) 7.15 (dd, J = 11.8, 8.8 Hz, 1 H) 7.68 (dd, |

TABLE 17-continued

| Co. Nr. | NMR result |
|---|---|
| | J = 7.2, 2.8 Hz, 1 H) 7.76 (ddd, J = 8.8, 4.2, 2.8 Hz, 1 H) 8.41 (d, J = 1.2 Hz, 1 H) 8.87 (d, J = 1.2 Hz, 1 H) 10.57 (s, 1 H) |
| 285 | ¹H NMR (500 MHz, DMSO-d₆) δ ppm 0.65 (t, J = 7.2 Hz, 3 H) 1.78-1.94 (m, 1 H) 2.05-2.19 (m, 1 H) 4.02 (s, 3 H) 4.06 (d, J = 16.2 Hz, 1 H) 4.20 (d, J = 16.0 Hz, 1 H) 4.54 (q, J = 8.5 Hz, 1 H) 5.87 (s, 2 H) 7.10 (dd, J = 11.8, 8.7 Hz, 1 H) 7.79 (dt, J = 7.5, 4.2 Hz, 1 H) 8.13 (dd, J = 7.1, 2.7 Hz, 1 H) 8.41 (d, J = 1.2 Hz, 1 H) 8.88 (d, J = 1.2 Hz, 1 H) 10.40 (s, 1 H) |
| 320 | ¹H NMR (360 MHz, CHLOROFORM-d) δ ppm 0.82 (t, J = 7.3 Hz, 3 H) 1.13 (d, J = 6.2 Hz, 2 H) 4.00 (d, J = 15.4 Hz, 1 H) 4.28 (d, J = 15.6 Hz, 1 H) 4.37 (br. s., 2 H) 5.76 (d, J = 52.3 Hz, 1 H) 7.39 (d, J = 7.3 Hz, 1 H) 7.44-7.55 (m, 3 H) 8.95 (s, 2 H) 9.21 (s, 1 H) |
| 327 | ¹H NMR (360 MHz, DMSO-d₆) δ ppm 0.03-0.18 (m, 1 H) 0.19-0.31 (m, 1 H) 0.31-0.39 (m, 1 H) 0.40-0.52 (m, 1 H) 1.30-1.44 (m, 1 H) 3.88 (d, J = 15.4 Hz, 1 H) 4.02 (d, J = 15.5 Hz, 1 H) 5.88 (d, J = 53.8 Hz, 1 H) 5.91 (br. s., 2 H) 7.22 (d, J = 7.7 Hz, 1 H) 7.32 (t, J = 8.1 Hz, 1 H) 7.63 (s, 1 H) 7.71 (d, J = 8.1 Hz, 1 H) 8.66 (dd, J = 10.1, 1.3 Hz, 1 H) 9.03 (s, 1 H) 10.76 (s, 1 H) |
| 330 | ¹H NMR (360 MHz, CHLOROFORM-d) δ ppm 1.65 (s, 3 H) 4.04 (d, J = 15.4 Hz, 1 H) 4.27 (d, J = 15.7 Hz, 1 H) 6.04 (d, J = 52.7 Hz, 1 H) 7.09 (dd, J = 11.3, 8.8 Hz, 1 H) 7.46 (dd, J = 6.8, 2.7 Hz, 1 H) 7.85-7.96 (m, 2 H) 8.70 (d, J = 1.8 Hz, 1 H) 9.53-9.71 (br. s., 1 H) |
| 332 | ¹H NMR (360 MHz, CHLOROFORM-d) δ ppm 1.66 (s, 3 H) 4.04 (d, J = 15.6 Hz, 1 H) 4.28 (d, J = 15.5 Hz, 1 H) 6.05 (d, J = 53.1 Hz, 1 H) 6.79 (t, J = 54.2 Hz, 1 H) 7.10 (dd, J = 11.3, 8.8 Hz, 1 H) 7.54 (dd, J = 7.0, 2.9 Hz, 1 H) 7.85 (ddd, J = 8.8, 4.0, 2.9 Hz, 1 H) 8.91 (s, 1 H) 9.51 (s, 1 H) 9.61 (br. s., 1 H) |
| 333 | ¹H NMR (360 MHz, DMSO-d₆) δ ppm 1.73 (s, 3 H) 2.58 (s, 3 H) 4.67 (d, J = 17.9 Hz, 1 H) 4.76 (d, J = 17.9 Hz, 1 H) 6.15 (d, J = 50.1 Hz, 1 H) 7.33 (dd, J = 11.9, 9.0 Hz, 1 H) 7.75 (dd, J = 7.3, 2.6 Hz, 1 H) 8.01 (ddd, J = 9.0, 4.2, 2.6 Hz, 1 H) 8.06 (dd, J = 2.2, 0.7 Hz, 1 H) 8.60 (d, J = 2.6 Hz, 1 H) 8.98 (br. s, 1 H) 9.68 (br. s, 1 H) 10.80 (s, 1 H) 11.18 (br. s, 1 H) |
| 335 | ¹H NMR (360 MHz, DMSO-d₆) δ ppm 1.49 (d, J = 1.5 Hz, 3 H) 4.00 (d, J = 16.1 Hz, 1 H) 4.08 (d, J = 16.1 Hz, 1 H) 6.01 (d, J = 52.3 Hz, 1 H) 6.01-6.32 (m, 2 H) 7.41 (dd, J = 5.1, 1.5 Hz, 1 H) 8.11 (s, 1 H) 8.70 (d, J = 5.1 Hz, 1 H) 9.26 (s, 1 H) 9.44 (s, 2 H) |
| 336 | ¹H NMR (360 MHz, DMSO-d₆) δ ppm 1.45 (s, 3 H) 4.01 (m, J = 15.7 Hz, 1 H) 4.03 (s, 3 H) 4.10 (d, J = 15.7 Hz, 1 H) 5.82 (d, J = 52.7 Hz, 1 H) 6.16 (br. s., 2 H) 7.24 (dd, J = 5.3, 1.6 Hz, 1 H) 8.23-8.37 (m, 2 H) 8.45 (d, J = 1.1 Hz, 1 H) 8.95 (d, J = 1.1 Hz, 1 H) 10.06 (s, 1 H) |
| 343 | ¹H NMR (360 MHz, CHLOROFORM-d) δ ppm 1.77 (s, 3 H) 4.00 (q, J = 7.0 Hz, 1 H) 4.31 (br. s, 2 H) 4.28 (s, 1 H) 4.41 (d, J = 15.7 Hz, 1 H) 7.46-7.52 (m, 3 H) 7.59 (br. s, 1 H) 8.95 (s, 2 H) 9.20 (s, 1 H) |
| 353 | ¹H NMR (360 MHz, DMSO-d₆) δ ppm 4.44 (d, J = 15.7 Hz, 1 H) 4.83 (d, J = 15.7 Hz, 1 H) 6.22 (s, 2 H) 7.45 (dd, J = 5.1, 1.8 Hz, 1 H) 8.00 (d, J = 1.5 Hz, 1 H) 8.73 (d, J = 5.1 Hz, 1 H) 9.28 (s, 1 H) 9.45 (s, 2 H) |
| 359 | ¹H NMR (360 MHz, DMSO-d₆) δ ppm 0.76 (t, J = 7.1 Hz, 3 H) 1.87-1.98 (m, 1 H) 2.03-2.14 (m, 1 H) 4.02 (s, 3 H) 4.19 (s, 2 H) 4.33 (q, J = 8.2 Hz, 1 H) 5.81 (s, 2 H) 7.15 (d, J = 7.7 Hz, 1 H) 7.27 (t, J = 8.1 Hz, 1 H) 7.78 (d, J = 8.1 Hz, 1 H) 7.89 (s, 1 H) 8.42 (s, 1 H) 8.90 (s, 1 H) 10.34 (s, 1 H) |
| 362 | ¹H NMR (360 MHz, CHLOROFORM-d) δ ppm 0.90 (t, J = 7.3 Hz, 3 H) 2.20 (q, J = 7.2 Hz, 2 H) 4.10 (q, J = 7.4 Hz, 1 H) 4.20-4.49 (m, 2 H) 7.46-7.53 (m, 3 H) 7.62 (s, 1 H) 8.96 (s, 2 H) 9.20 (s, 1 H) |
| 368 | ¹H NMR (360 MHz, DMSO-d₆) δ ppm 0.76 (t, J = 7.1 Hz, 3 H) 1.84-1.99 (m, 1 H) 2.02-2.16 (m, 1 H) 3.32 (s, 3 H) 3.72 (t, J = 4.0 Hz, 2 H) 4.19 (s, 2 H) 4.33 (m, J = 7.7 Hz, 1 H) 4.53 (t, J = 4.4 Hz, 2 H) 5.80 (s, 2 H) 7.15 (d, J = 7.7 Hz, 1 H) 7.27 (t, J = 8.1 Hz, 1 H) 7.79 (d, J = 8.1 Hz, 1 H) 7.89 (s, 1 H) 8.43 (s, 1 H) 8.87 (s, 1 H) 10.34 (s, 1 H) |
| 383 | ¹H NMR (360 MHz, CHLOROFORM-d) δ ppm 1.66 (d, J = 1.8 Hz, 3 H) 3.82 (br. s., 2 H) 4.08 (d, J = 15.7 Hz, 1 H) 4.38 (d, J = 15.7 Hz, 1 H) 6.22 (d, J = 53.1 Hz, 1 H) 7.39 (dd, J = 5.1, 1.5 Hz, 1 H) 7.66 (s, 1 H) 8.72 (d, J = 5.1 Hz, 1 H) 9.01 (s, 2 H) 9.28 (s, 1 H) |
| 387 | ¹H NMR (360 MHz, DMSO-d₆) δ ppm 1.44 (s, 3 H) 3.97 (d, J = 15.7 Hz, 1 H) 4.07 (d, J = 15.7 Hz, 1 H) 5.81 (d, J = 52.7 Hz, 1 H) 6.05 (br. s., 2 H) 7.23 (dd, J = 5.1, 1.5 Hz, 1 H) 8.21 (s, 1 H) 8.31 (d, J = 5.1 Hz, 1 H) 8.36 (dd, J = 10.6, 1.8 Hz, 1 H) 8.68 (d, J = 1.5 Hz, 1 H) 10.54 (s, 1 H) |
| 390 | ¹H NMR (360 MHz, DMSO-d₆) δ ppm 1.41 (d, J = 1.5 Hz, 3 H) 3.93 (d, J = 15.7 Hz, 1 H) 4.05 (d, J = 15.0 Hz, 1 H) 4.11 (q, J = 5.1 Hz, 1 H) 5.94 (d, J = 54.5 Hz, 1 H) 5.99 (br. s, 1 H) 7.72 (dd, J = 5.3, 2.0 Hz, 1 H) 7.79 (d, J = 2.0 Hz, 1 H) 8.36 (dd, J = 10.4, 2.0 |

TABLE 17-continued

| Co. Nr. | NMR result |
|---|---|
| | Hz, 1 H) 8.46 (d, J = 5.5 Hz, 1 H) 8.68 (br. d, J = 2.0 Hz, 1 H) 11.05 (br. s., 1 H) |
| 392 | $^1$H NMR (360 MHz, DMSO-$d_6$) δ ppm 1.42 (s, 3 H) 3.95 (d, J = 15.7 Hz, 1 H) 4.03 (s, 3 H) 4.06 (d, J = 15.7 Hz, 1 H) 5.92 (d, J = 54.5 Hz, 1 H) 6.02 (br. s., 2 H) 7.75 (dd, J = 5.5, 2.2 Hz, 1 H) 7.97 (d, J = 1.8 Hz, 1 H) 8.43 (d, J = 1.5 Hz, 1 H) 8.44 (d, J = 5.5 Hz, 1 H) 8.92 (d, J = 1.2 Hz, 1 H) 10.89 (s, 1 H) |
| 398 | $^1$H NMR (360 MHz, CHLOROFORM-d) δ ppm 1.75 (s, 3 H) 4.02 (q, J = 7.2 Hz, 1 H) 4.07 (s, 3 H) 4.32 (d, J = 15.5 Hz, 1 H) 4.37 (br. s., 2 H) 4.48 (d, J = 15.7 Hz, 1 H) 7.15 (dd, J = 5.3, 1.6 Hz, 1 H) 8.17 (d, J = 1.2 Hz, 1 H) 8.31 (d, J = 5.1 Hz, 1 H) 8.49 (d, J = 1.2 Hz, 1 H) 9.02 (d, J = 1.2 Hz, 1 H) 10.08 (s, 1 H) |
| 399 | $^1$H NMR (360 MHz, CHLOROFORM-d) δ ppm 1.72 (d, J = 1.1 Hz, 3 H) 4.08 (s, 3 H) 4.36 (br. s., 2 H) 4.35 (d, J = 16.1 Hz, 1 H) 4.42 (d, J = 16.1 Hz, 1 H) 5.00 (q, J = 8.1 Hz, 1 H) 7.71-7.76 (m, 2 H) 8.17 (d, J = 1.3 Hz, 1 H) 8.54 (br. d, J = 5.3 Hz, 1 H) 9.02 (d, J = 1.2 Hz, 1 H) 9.71 (br. s., 1 H |

D. Pharmacological Examples

The compounds provided in the present invention are inhibitors of the beta-site APP-cleaving enzyme 1 (BACE1). Inhibition of BACE1, an aspartic protease, is believed to be relevant for treatment of Alzheimer's Disease (AD). The production and accumulation of beta-amyloid peptides (Abeta) from the beta-amyloid precursor protein (APP) is believed to play a key role in the onset and progression of AD. Abeta is produced from the amyloid precursor protein (APP) by sequential cleavage at the N- and C-termini of the Abeta domain by beta-secretase and gamma-secretase, respectively.

Compounds of Formula (I) are expected to have their effect substantially at BACE1 by virtue of their ability to inhibit the enzymatic activity. The behaviour of such inhibitors tested using a biochemical Fluorescence Resonance Energy Transfer (FRET) based assay and a cellular αLisa assay in SKNBE2 cells described below and which are suitable for the identification of such compounds, and more particularly the compounds according to Formula (I), are shown in Table 17 and Table 18.

Biochemical FRET Based Assay

This assay is a Fluorescence Resonance Energy Transfer Assay (FRET) based assay. The substrate for this assay is an APP derived 13 amino acids peptide that contains the 'Swedish' Lys-Met/Asn-Leu mutation of the amyloid precursor protein (APP) beta-secretase cleavage site. This substrate also contains two fluorophores: (7-methoxycoumarin-4-yl) acetic acid (Mca) is a fluorescent donor with excitation wavelength at 320 nm and emission at 405 nm and 2,4-Dinitrophenyl (Dnp) is a proprietary quencher acceptor. The distance between those two groups has been selected so that upon light excitation, the donor fluorescence energy is significantly quenched by the acceptor, through resonance energy transfer. Upon cleavage by BACE1, the fluorophore Mca is separated from the quenching group Dnp, restoring the full fluorescence yield of the donor. The increase in fluorescence is linearly related to the rate of proteolysis.

Briefly in a 384-well format recombinant BACE1 protein in a final concentration of 1 µg/ml is incubated for 120 minutes at room temperature with 10 µm substrate in incubation buffer (40 mM Citrate buffer pH 5.0, 0.04% PEG, 4% DMSO) in the absence or presence of compound. Next the amount of proteolysis is directly measured by fluorescence measurement at T=0 and T=120 (excitation at 320 nm and emission at 405 nm). Results are expressed in RFU (Relative Fluorescence Units), as difference between T120 and T0.

A best-fit curve is fitted by a minimum sum of squares method to the plot of % Controlmin versus compound concentration. From this an $IC_{50}$ value (inhibitory concentration causing 50% inhibition of activity) can be obtained.

LC = Median of the low control values
 = Low control: Reaction without enzyme

HC = Median of the High control values
 = High Control: Reaction with enzyme

% Effect = $100 - [(sample - LC)/(HC - LC) * 100]$

% Control = $(sample/HC) * 100$

% Controlmin = $(sample - LC)/(HC - LC) * 100$

The following exemplified compounds were tested essentially as described above and exhibited the following the activity:

TABLE 18

| Co. Nr. | Biochemical FRET based assay $pIC_{50}$ |
|---|---|
| 1 | 4.62 |
| 2 | 5.72 |
| 3 | 5.10 |
| 4 | 5.439 |
| 5 | 6.54 |
| 6 | 5.29 |
| 7 | 5.39 |
| 8 | 5.69 |
| 9 | 5.46 |
| 10 | 5.12 |
| 11 | 4.84 |
| 12 | 6.89 |
| 13 | 5.37 |
| 14 | 6.28 |
| 15 | 5.56 |
| 16 | 5.66 |
| 17 | 6.78 |
| 18 | 5.54 |
| 19 | 5.38 |
| 20 | 6.78 |
| 21 | 7.29 |
| 22 | 6.7 |
| 23 | 5.86 |

TABLE 18-continued

| Co. Nr. | Biochemical FRET based assay pIC$_{50}$ |
|---|---|
| 24 | 6.77 |
| 25 | 6.93 |
| 26 | 5.67 |
| 27 | 6.35 |
| 28 | 6.18 |
| 29 | 6.11 |
| 30 | 6.05 |
| 31 | 4.76 |
| 32 | 4.87 |
| 33 | 4.91 |
| 34 | 5.05 |
| 35 | 7.11 |
| 36 | 5.13 |
| 37 | 5.45 |
| 38 | 6.91 |
| 39 | 6.9 |
| 40 | 6.04 |
| 41 | 6.33 |
| 42 | 5.74 |
| 43 | 7.14 |
| 44 | 7.21 |
| 45 | 5.53 |
| 46 | 5.6 |
| 47 | 5.95 |
| 48 | 5.73 |
| 49 | 4.6 |
| 50 | 6.93 |
| 51 | 5.41 |
| 52 | 6.06 |
| 53 | <4.52 |
| 54 | 5.41 |
| 55 | 5.55 |
| 56 | 5.69 |
| 57 | 6.53 |
| 58 | 5.11 |
| 59 | 5.36 |
| 60 | 5.65 |
| 61 | 5.45 |
| 62 | 7.21 |
| 63 | 5.46 |
| 64 | 6.41 |
| 65 | 6.78 |
| 66 | 5.69 |
| 67 | <4.52 |
| 68 | 6.35 |
| 69 | 5.29 |
| 70 | 5.77 |
| 71 | 6.25 |
| 72 | 5.58 |
| 73 | 6.99 |
| 74 | 5.38 |
| 75 | 5.01 |
| 76 | 7.32 |
| 77 | 7.28 |
| 78 | 7.26 |
| 79 | 7.22 |
| 80 | 7.01 |
| 81 | 5.05 |
| 82 | 6.2 |
| 83 | 6.01 |
| 84 | 4.64 |
| 85 | 5.19 |
| 86 | 7.41 |
| 87 | 5.81 |
| 88 | <4.52 |
| 89 | 5.26 |
| 90 | 6.37 |
| 91 | 7.03 |
| 92 | 4.82 |
| 93 | 6.33 |
| 94 | <4.52 |
| 95 | 5.85 |
| 96 | 4.95 |
| 97 | 5.21 |
| 98 | 5.55 |
| 99 | 4.68 |
| 100 | 5.81 |
| 101 | 6.75 |
| 102 | <4.52 |
| 103 | 5.68 |
| 104 | 5.03 |
| 105 | 5.81 |
| 106 | 5.36 |
| 107 | 6.88 |
| 108 | 5.89 |
| 109 | <4.52 |
| 110 | 7.59 |
| 111 | 5.83 |
| 112 | 5.31 |
| 113 | 7.57 |
| 114 | 5.17 |
| 115 | 6.21 |
| 116 | <4.52 |
| 117 | 6.36 |
| 118 | 6.72 |
| 119 | 4.95 |
| 120 | 5.55 |
| 121 | 5.73 |
| 122 | <4.52 |
| 123 | 7.53 |
| 124 | 7.69 |
| 125 | 5.86 |
| 126 | 7.44 |
| 127 | <4.52 |
| 128 | 5.24 |
| 129 | 4.83 |
| 130 | 5.72 |
| 131 | 7.45 |
| 132 | 5.96 |
| 133 | 7.59 |
| 134 | 7.68 |
| 135 | <4.52 |
| 136 | 5.09 |
| 137 | <4.52 |
| 138 | 5.83 |
| 139 | <4.52 |
| 140 | <4.52 |
| 141 | <4.52 |
| 142 | <4.52 |
| 143 | 7.48 |
| 144 | 7.11 |
| 145 | 4.67 |
| 146 | 6.26 |
| 147 | 6.7 |
| 148 | <4.52 |
| 149 | <4.52 |
| 150 | 5.96 |
| 151 | 6.4 |
| 152 | 5.41 |
| 153 | 7.05 |
| 154 | <4.52 |
| 155 | <4.52 |
| 156 | 5.69 |
| 157 | <4.52 |
| 158 | <4.52 |
| 159 | <4.52 |
| 161 | 4.53 |
| 162 | 5.21 |
| 163 | 7.39 |
| 164 | <4.52 |
| 165 | 7.46 |
| 166 | 7.3 |
| 167 | 7.46 |
| 168 | 6.08 |
| 169 | 7.25 |
| 170 | 7.21 |
| 171 | 5.95 |
| 172 | 6.29 |
| 173 | 7.66 |
| 174 | <4.52 |
| 175 | 6.53 |
| 176 | 5.89 |

TABLE 18-continued

| Co. Nr. | Biochemical FRET based assay pIC$_{50}$ |
|---|---|
| 177 | 7.6 |
| 178 | 4.7 |
| 179 | <4.52 |
| 180 | 7.35 |
| 181 | 7.58 |
| 182 | 6.26 |
| 183 | 7.39 |
| 184 | 6.39 |
| 185 | 6.78 |
| 186 | 6.75 |
| 187 | 4.99 |
| 188 | 6.36 |
| 189 | <4.52 |
| 190 | <4.52 |
| 191 | 4.73 |
| 192 | <4.52 |
| 193 | 7.13 |
| 194 | 5.7 |
| 195 | 7.27 |
| 196 | <4.52 |
| 197 | 6 |
| 198 | 6.52 |
| 199 | 7.83 |
| 202 | 6.32 |
| 203 | 7.69 |
| 204 | 6.44 |
| 205 | 4.8 |
| 206 | <4.52 |
| 207 | 5.46 |
| 208 | 7.57 |
| 209 | 7.4 |
| 210 | 4.92 |
| 211 | 5.85 |
| 212 | 5.19 |
| 213 | 6.36 |
| 214 | 6.96 |
| 215 | 6.3 |
| 216 | 7.05 |
| 217 | 6.22 |
| 218 | 6.9 |
| 219 | 7.03 |
| 220 | 6.33 |
| 221 | 6.9 |
| 222 | 5.13 |
| 223 | 4.61 |
| 224 | 4.83 |
| 225 | 7.45 |
| 226 | 6.86 |
| 227 | 7.45 |
| 228 | 6.67 |
| 229 | 7.35 |
| 230 | 7.34 |
| 231 | 7.47 |
| 232 | 7.51 |
| 233 | 7.5 |
| 234 | 7.6 |
| 235 | 7.48 |
| 238 | 6.08 |
| 239 | 5.98 |
| 240 | 7.59 |
| 241 | 6.49 |
| 242 | 7.69 |
| 243 | 6.58 |
| 244 | 7.11 |
| 245 | 7.66 |
| 246 | 6.5 |
| 247 | 7.55 |
| 248 | 6.31 |
| 249 | 6.66 |
| 250 | 7.22 |
| 251 | 7.31 |
| 252 | n.t. |
| 253 | 6.81 |
| 254 | 6.07 |
| 255 | 6.35 |
| 256 | 7.37 |
| 257 | 6.05 |
| 258 | n.t. |
| 259 | 7.07 |
| 260 | 7.32 |
| 261 | n.t. |
| 262 | 7.52 |
| 263 | n.t. |
| 264 | 7.04 |
| 265 | 6.28 |
| 266 | <4.52 |
| 267 | <4.52 |
| 268 | 6.44 |
| 269 | 6.8 |
| 270 | 6.88 |
| 271 | <4.52 |
| 272 | 7.04 |
| 273 | 5.16 |
| 274 | 6.58 |
| 275 | 7.21 |
| 276 | 6.76 |
| 277 | 6.66 |
| 278 | 5.06 |
| 279 | n.t. |
| 280 | 6.74 |
| 281 | 7.13 |
| 282 | 6.05 |
| 283 | 7.17 |
| 284 | 7.06 |
| 285 | 7 |
| 286 | 6.07 |
| 287 | 6.86 |
| 288 | 7.48 |
| 289 | 7.51 |
| 290 | 7.01 |
| 291 | 7.49 |
| 292 | 6.17 |
| 293 | 5.86 |
| 294 | 5.64 |
| 295 | 5.16 |
| 296 | 5.42 |
| 297 | 7.41 |
| 298 | 6.91 |
| 299 | 6.77 |
| 300 | 5.81 |
| 301 | 7.09 |
| 302 | <4.52 |
| 303 | 5.74 |
| 304 | 6.23 |
| 305 | 7.38 |
| 306 | 7.44 |
| 307 | 6.7 |
| 308 | 7.31 |
| 309 | 6.66 |
| 310 | 5.48 |
| 311 | 5.86 |
| 312 | 6.18 |
| 313 | 7.78 |
| 314 | 7.26 |
| 315 | 7.09 |
| 316 | 5.94 |
| 317 | 5.69 |
| 318 | 6.45 |
| 319 | 7.36 |
| 320 | n.t. |
| 321 | n.t. |
| 322 | n.t. |
| 323 | n.t. |
| 324 | n.t. |
| 325 | n.t. |
| 326 | n.t. |
| 327 | n.t. |
| 328 | n.t. |
| 329 | n.t. |
| 330 | n.t. |
| 331 | n.t. |
| 332 | n.t. |

TABLE 18-continued

| Co. Nr. | Biochemical FRET based assay $pIC_{50}$ |
|---|---|
| 333 | n.t. |
| 334 | n.t. |
| 335 | n.t. |
| 336 | n.t. |
| 337 | n.t. |
| 338 | n.t. |
| 339 | n.t. |
| 340 | n.t. |
| 341 | n.t. |
| 342 | n.t. |
| 343 | n.t. |
| 344 | n.t. |
| 345 | n.t. |
| 346 | n.t. |
| 347 | n.t. |
| 348 | n.t. |
| 349 | n.t. |
| 350 | n.t. |
| 351 | 5.69 |
| 352 | n.t. |
| 353 | n.t. |
| 354 | n.t. |
| 355 | n.t. |
| 356 | n.t. |
| 357 | n.t. |
| 358 | n.t. |
| 359 | n.t. |
| 360 | n.t. |
| 361 | n.t. |
| 362 | n.t. |
| 363 | n.t. |
| 364 | n.t. |
| 365 | n.t. |
| 366 | n.t. |
| 367 | n.t. |
| 368 | n.t. |
| 369 | n.t. |
| 370 | n.t. |
| 371 | n.t. |
| 372 | n.t. |
| 373 | n.t. |
| 374 | n.t. |
| 375 | n.t. |
| 376 | n.t. |
| 377 | n.t. |
| 378 | n.t. |
| 379 | n.t. |
| 380 | n.t. |
| 381 | n.t. |
| 382 | n.t. |
| 383 | n.t. |
| 384 | n.t. |
| 385 | n.t. |
| 386 | n.t. |
| 387 | n.t. |
| 388 | n.t. |
| 389 | n.t. |
| 390 | n.t. |
| 391 | n.t. |
| 392 | n.t. |
| 393 | n.t. |
| 394 | n.t. |
| 395 | n.t. |
| 396 | n.t. |
| 397 | n.t. |
| 398 | n.t. |
| 399 | n.t. |
| 400 | n.t. |
| 401 | n.t. |
| 402 | n.t. |
| 403 | n.t. |
| 404 | n.t. |
| 405 | n.t. |
| 406 | n.t. |
| 407 | n.t. |

Cellular αLisa Assay in SKNBE2 Cells

In two αLisa assays the levels of Abeta total and Abeta 1-42 produced and secreted into the medium of human neuroblastoma SKNBE2 cells are quantified. The assay is based on the human neuroblastoma SKNBE2 expressing the wild type Amyloid Precursor Protein (hAPP695). The compounds are diluted and added to these cells, incubated for 18 hours and then measurements of Abeta 1-42 and Abeta total are taken. Abeta total and Abeta 1-42 are measured by sandwich αLisa. αLisa is a sandwich assay using biotinylated antibody AbN/25 attached to streptavidin coated beads and antibody Ab4G8 or cAb42/26 conjugated acceptor beads for the detection of Abeta total and Abeta 1-42 respectively. In the presence of Abeta total or Abeta 1-42, the beads come into close proximity. The excitation of the donor beads provokes the release of singlet oxygen molecules that trigger a cascade of energy transfer in the acceptor beads, resulting in light emission. Light emission is measured after 1 hour incubation (excitation at 650 nm and emission at 615 nm).

A best-fit curve is fitted by a minimum sum of squares method to the plot of % Controlmin versus compound concentration. From this an $IC_{50}$ value (inhibitory concentration causing 50% inhibition of activity) can be obtained.

$LC$ = Median of the low control values
= Low control: cells preincubated without compound, without biotinylated Ab in the αLisa $HC$ = Median of the High control values
= High Control: cells preincubated without compound % Effect = $100 - [(sample - LC)/(HC - LC) * 100]$ % Control = $(sample/HC) * 100$ % Controlmin = $(sample - LC)/(HC - LC) * 100$ The following exemplified compounds were tested essentially as described above and exhibited the following the activity:

TABLE 19

| Co. Nr. | Cellular αLisa assay in SKNBE2 cells Abeta 42 $pIC_{50}$ | Cellular αLisa assay in SKNBE2 cells Abetatotal $pIC_{50}$ |
|---|---|---|
| 1 | 5.83 | 5.99 |
| 2 | 6.14 | 6.21 |
| 3 | 6.2 | 6.19 |
| 4 | 6.59 | 6.66 |
| 5 | 7.77 | 7.79 |
| 6 | 6.29 | 6.34 |
| 7 | 6.49 | 6.53 |
| 8 | 6.67 | 6.75 |
| 9 | <5 | 5.07 |
| 10 | 6. | 6.58 |
| 11 | 6.2 | 6.33 |
| 12 | 8.17 | 8.16 |
| 13 | 6.83 | 6.84 |
| 14 | 7.49 | 7.56 |
| 15 | 6.31 | 5.51 |
| 16 | 6.41 | 6.45 |
| 17 | 8.32 | 8.3 |
| 18 | 6.57 | 6.61 |
| 19 | 6.29 | 6.352 |
| 20 | 7.81 | 7.86 |
| 21 | 8.27 | 8.3 |
| 22 | 7.59 | 7.663 |

TABLE 19-continued

| Co. Nr. | Cellular αLisa assay in SKNBE2 cells Abeta 42 pIC$_{50}$ | Cellular αLisa assay in SKNBE2 cells Abetatotal pIC$_{50}$ |
|---|---|---|
| 23 | 6.89 | 6.85 |
| 24 | 7.77 | 7.73 |
| 25 | 7.93 | 7.9 |
| 26 | 6.72 | 6.74 |
| 27 | 7.06 | 7.04 |
| 28 | 7.07 | 7.04 |
| 29 | 6.67 | 6.67 |
| 30 | 7.57 | 7.66 |
| 31 | 5.76 | 5.86 |
| 32 | 6.2 | 6.25 |
| 33 | 5.72 | 5.75 |
| 34 | 5.54 | 5.58 |
| 35 | 8.37 | 8.4 |
| 36 | 5.98 | 6.09 |
| 37 | 6.77 | 6.79 |
| 38 | 8.39 | 8.35 |
| 39 | 8.27 | 8.38 |
| 40 | 7.31 | 7.32 |
| 41 | 7.31 | 7.33 |
| 42 | 5.85 | 5.9 |
| 43 | 8.34 | 8.45 |
| 44 | 8.39 | 8.3945 |
| 45 | 6.85 | 6.92 |
| 46 | 6.29 | 6.32 |
| 47 | 6.79 | 6.83 |
| 48 | 6.19 | 6.22 |
| 49 | 5.68 | 5.66 |
| 50 | 7.91 | 7.88 |
| 51 | 6.61 | 6.59 |
| 52 | 6.68 | 6.66 |
| 53 | 5.28 | <5 |
| 54 | 6.68 | 6.65 |
| 55 | 6.89 | 6.99 |
| 56 | 7.02 | 7.1 |
| 57 | 7.79 | 7.8 |
| 58 | 6.7 | 6.68 |
| 59 | 6.44 | 6.417 |
| 60 | 6.89 | 6.92 |
| 61 | 6.94 | 6.98 |
| 62 | 8.39 | 8.39 |
| 63 | 6.94 | 6.9 |
| 64 | 7.36 | 7.37 |
| 65 | 8.32 | 8.3 |
| 66 | 6.92 | 7.0 |
| 67 | 5.26 | 5.42 |
| 68 | 7.06 | 7.04 |
| 69 | 5.13 | <5 |
| 70 | 5.17 | 5.31 |
| 71 | <5 | <5 |
| 72 | 6.2 | 6.19 |
| 73 | 8.31 | 8.37 |
| 74 | 6.71 | 6.69 |
| 75 | 5.46 | 5.46 |
| 76 | 7.96 | 7.95 |
| 77 | 7.92 | 7.93 |
| 78 | 7.93 | 8.07 |
| 79 | 7.59 | 7.59 |
| 80 | 7.22 | 7.27 |
| 81 | 5.91 | 5.92 |
| 82 | 6.6 | 6.61 |
| 83 | 6.29 | 6.29 |
| 84 | 5.41 | 5.35 |
| 85 | 6.06 | 6.07 |
| 86 | 8.16 | 8.21 |
| 87 | 6.46 | 6.47 |
| 88 | 5.66 | 5.65 |
| 89 | 6.51 | 6.67 |
| 90 | 7.76 | 7.76 |
| 91 | 7.82 | 7.86 |
| 92 | 5.47 | 5.51 |
| 93 | 6.98 | 6.97 |
| 94 | 5.43 | 5.34 |
| 95 | 6.48 | 6.5 |
| 96 | 6.46 | 6.43 |
| 97 | 6.86 | 6.87 |
| 98 | 6.19 | 6.14 |
| 99 | 5.87 | 5.73 |
| 100 | 6.46 | 6.47 |
| 101 | 7.71 | 7.7 |
| 102 | <5 | <5 |
| 103 | 6.38 | 6.35 |
| 104 | 5.8 | 5.82 |
| 105 | 6.7 | 6.65 |
| 106 | 6.2 | 6.23 |
| 107 | 7.81 | 7.9 |
| 108 | 6.92 | 6.92 |
| 109 | 6.15 | 6.08 |
| 110 | 7.64 | 7.65 |
| 111 | 6.36 | 6.31 |
| 112 | 5.68 | 5.71 |
| 113 | 7.53 | 7.52 |
| 114 | 5.82 | 5.5 |
| 115 | 6.75 | 6.68 |
| 116 | 5.18 | 5.06 |
| 117 | 6.59 | 6.55 |
| 118 | 7.23 | 7.18 |
| 119 | 5.62 | 5.67 |
| 120 | 6.02 | 6.05 |
| 121 | 6.43 | 6.48 |
| 122 | 5.19 | 5.04 |
| 123 | 7.97 | 7.98 |
| 124 | 8.21 | 8.2 |
| 125 | 6.44 | 6.42 |
| 126 | 8.06 | 8.09 |
| 127 | <5 | <5 |
| 128 | 6.0 | 6.02 |
| 129 | 5.28 | 5.34 |
| 130 | 6.47 | 6.48 |
| 131 | 7.54 | 7.52 |
| 132 | 6.35 | 6.38 |
| 133 | 8.18 | 8.21 |
| 134 | 8.39 | 8.42 |
| 135 | 5.04 | 5.06 |
| 136 | 5.26 | 5.27 |
| 137 | <4.82 | <4.82 |
| 138 | 6.36 | 6.31 |
| 139 | <5 | <5 |
| 140 | <5 | <5 |
| 141 | <5 | <5 |
| 142 | <5 | <5 |
| 143 | 8.35 | 8.36 |
| 144 | 7.27 | 7.38 |
| 145 | 5.45 | 5.55 |
| 146 | 7.07 | 7.03 |
| 147 | 7.59 | 7.6 |
| 148 | <5 | <5 |
| 149 | 5.06 | 5.05 |
| 150 | 6.7 | 6.7 |
| 151 | 7.8 | 7.83 |
| 152 | 5.5 | 5.5 |
| 153 | 7.94 | 7.88 |
| 154 | <5 | <5 |
| 155 | <5 | <5 |
| 156 | 7.02 | 7.1 |
| 157 | <5 | <5 |
| 158 | <5 | <5 |
| 159 | 6.15 | 6.08 |
| 161 | <5 | <5 |
| 162 | 6.1 | 6.14 |
| 163 | 8.01 | 8.05 |
| 164 | <5 | <5 |
| 165 | 8.14 | 8.13 |
| 166 | 7.9 | 7.91 |
| 167 | 8.12 | 8.12 |
| 168 | 7.1 | 7.13 |
| 169 | 8.16 | 8.17 |
| 170 | 8 | 8 |
| 171 | 6.87 | 6.89 |
| 172 | 6.74 | 6.81 |
| 173 | 8.11 | 8.07 |

TABLE 19-continued

| Co. Nr. | Cellular αLisa assay in SKNBE2 cells Abeta 42 pIC$_{50}$ | Cellular αLisa assay in SKNBE2 cells Abetatotal pIC$_{50}$ |
|---|---|---|
| 174 | <5 | <5 |
| 175 | 5.18 | 5.24 |
| 176 | 6.34 | 6.38 |
| 177 | 7.83 | 7.84 |
| 178 | 5.33 | 5.35 |
| 179 | <5 | <5 |
| 180 | 7.47 | 7.55 |
| 181 | 7.87 | 7.87 |
| 182 | 6.68 | 6.69 |
| 183 | 7.84 | 7.86 |
| 184 | 6.44 | 6.44 |
| 185 | 6.7 | 6.71 |
| 186 | 6.75 | 6.78 |
| 187 | 5.92 | 5.95 |
| 188 | 6.91 | 6.93 |
| 189 | <5 | <5 |
| 190 | 5.2 | 5.25 |
| 191 | 5.04 | 5.46 |
| 192 | <5 | <5 |
| 193 | 7.19 | 7.23 |
| 194 | 6.08 | 6.13 |
| 195 | 8.01 | 8.02 |
| 196 | 6.92 | 6.95 |
| 197 | 6.77 | 6.78 |
| 198 | 6.7 | 6.69 |
| 199 | 7.78 | 7.77 |
| 202 | 6.27 | 6.27 |
| 203 | 7.43 | 7.43 |
| 204 | 7.05 | 7.06 |
| 205 | 5.55 | 5.47 |
| 206 | <5 | <5 |
| 207 | 6.33 | 6.24 |
| 208 | 7.96 | 8 |
| 209 | 7.81 | 7.86 |
| 210 | <5 | <5 |
| 211 | 5.66 | 5.76 |
| 212 | <5 | <5 |
| 213 | 5.39 | 5.43 |
| 214 | 6.1 | 6.15 |
| 215 | 6.51 | 6.52 |
| 216 | 6.22 | 6.2 |
| 217 | 6.28 | 6.31 |
| 218 | 6.07 | 6.08 |
| 219 | 6.51 | 6.55 |
| 220 | 6.45 | 6.46 |
| 221 | 6.24 | 6.31 |
| 222 | <5 | <5 |
| 223 | <5 | <5 |
| 224 | <5 | <5 |
| 225 | 8.2 | 8.18 |
| 226 | 7.41 | 7.47 |
| 227 | 8.09 | 8.1 |
| 228 | 7.31 | 7.35 |
| 229 | 7.85 | 7.84 |
| 230 | 7.86 | 7.87 |
| 231 | 7.91 | 7.93 |
| 232 | 8.02 | 8 |
| 233 | 7.92 | 7.89 |
| 234 | 7.94 | 7.99 |
| 235 | 7.84 | 7.85 |
| 238 | 6.65 | 6.66 |
| 239 | 6.65 | 6.65 |
| 240 | 7.98 | 7.99 |
| 241 | 6.9 | 6.92 |
| 242 | 7.91 | 7.91 |
| 243 | 6.62 | 6.58 |
| 244 | 7.04 | 7.11 |
| 245 | 8.18 | 8.23 |
| 246 | 6.92 | 6.99 |
| 247 | 7.79 | 7.84 |
| 248 | 6.64 | 6.68 |
| 249 | 7.05 | 7.09 |
| 250 | 7.36 | 7.4 |
| 251 | 7.38 | 7.42 |
| 252 | n.t. | n.t. |
| 253 | 7.31 | 7.3 |
| 254 | 6.46 | 6.5 |
| 255 | 6.4 | 6.46 |
| 256 | 7.54 | 7.58 |
| 257 | 5.99 | 6.01 |
| 258 | n.t. | n.t. |
| 259 | 6.87 | 6.9 |
| 260 | 8.18 | 8.19 |
| 261 | n.t. | n.t. |
| 262 | 7.16 | 7.13 |
| 263 | n.t. | n.t. |
| 264 | 6.46 | 6.5 |
| 265 | 7.16 | 7.16 |
| 266 | <5 | ~5 |
| 267 | 5.15 | <5 |
| 268 | 7 | 7.09 |
| 269 | 7.23 | 7.24 |
| 270 | 7.33 | 7.32 |
| 271 | <5 | <5 |
| 272 | 7.44 | 7.45 |
| 273 | 5.09 | 5.19 |
| 274 | 6.92 | 6.92 |
| 275 | 7.23 | 7.25 |
| 276 | 7.38 | 7.38 |
| 277 | 6.97 | 6.95 |
| 278 | 5.49 | 5.5 |
| 279 | n.t. | n.t. |
| 280 | 7.23 | 7.24 |
| 281 | 7.3 | 7.34 |
| 282 | 6.56 | 6.65 |
| 283 | 7.52 | 7.61 |
| 284 | 7.75 | 7.76 |
| 285 | 7.83 | 7.8 |
| 286 | 6.8 | 6.81 |
| 287 | 7.49 | 7.56 |
| 288 | 8.11 | 8.13 |
| 289 | 8 | 7.98 |
| 290 | 7.73 | 7.75 |
| 291 | 8.25 | 8.31 |
| 292 | 5.98 | 6.17 |
| 293 | 5.73 | 5.81 |
| 294 | 5.18 | 5.31 |
| 295 | 5.09 | 5.19 |
| 296 | <5 | <5 |
| 297 | 7.72 | 7.76 |
| 298 | 7.21 | 7.23 |
| 299 | 7.62 | 7.67 |
| 300 | 5.91 | 5.93 |
| 301 | 7.14 | 7.17 |
| 302 | <5 | <5 |
| 303 | 5.73 | 5.76 |
| 304 | 6.44 | 6.47 |
| 305 | 7.6 | 7.6 |
| 306 | 8.16 | 8.13 |
| 307 | 6.97 | 7.03 |
| 308 | 8.2 | 8.21 |
| 309 | 7.13 | 7.14 |
| 310 | 6.11 | 6.21 |
| 311 | 5.84 | 5.95 |
| 312 | 5.49 | 5.55 |
| 313 | 7.75 | 7.87 |
| 314 | 7.08 | 7.24 |
| 315 | 6.77 | 6.84 |
| 316 | 6.14 | 6.2 |
| 317 | 6.26 | 6.33 |
| 318 | 6.07 | 6.14 |
| 319 | 7.13 | 7.16 |
| 320 | n.t. | n.t. |
| 321 | n.t. | n.t. |
| 322 | n.t. | n.t. |
| 323 | n.t. | n.t. |
| 324 | n.t. | n.t. |
| 325 | n.t. | n.t. |
| 326 | n.t. | n.t. |
| 327 | n.t. | n.t. |

TABLE 19-continued

| Co. Nr. | Cellular αLisa assay in SKNBE2 cells Abeta 42 pIC$_{50}$ | Cellular αLisa assay in SKNBE2 cells Abetatotal pIC$_{50}$ |
|---|---|---|
| 328 | n.t. | n.t. |
| 329 | n.t. | n.t. |
| 330 | n.t. | n.t. |
| 331 | n.t. | n.t. |
| 332 | n.t. | n.t. |
| 333 | n.t. | n.t. |
| 334 | n.t. | n.t. |
| 335 | n.t. | n.t. |
| 336 | n.t. | n.t. |
| 337 | n.t. | n.t. |
| 338 | n.t. | n.t. |
| 339 | n.t. | n.t. |
| 340 | n.t. | n.t. |
| 341 | n.t. | n.t. |
| 342 | n.t. | n.t. |
| 343 | n.t. | n.t. |
| 344 | n.t. | n.t. |
| 345 | n.t. | n.t. |
| 346 | n.t. | n.t. |
| 347 | n.t. | n.t. |
| 348 | n.t. | n.t. |
| 349 | n.t. | n.t. |
| 350 | n.t. | n.t. |
| 351 | 6.26 | 6.33 |
| 352 | n.t. | n.t. |
| 353 | n.t. | n.t. |
| 354 | n.t. | n.t. |
| 355 | n.t. | n.t. |
| 356 | n.t. | n.t. |
| 357 | n.t. | n.t. |
| 358 | n.t. | n.t. |
| 359 | n.t. | n.t. |
| 360 | n.t. | n.t. |
| 361 | n.t. | n.t. |
| 362 | n.t. | n.t. |
| 363 | n.t. | n.t. |
| 364 | n.t. | n.t. |
| 365 | n.t. | n.t. |
| 366 | n.t. | n.t. |
| 367 | n.t. | n.t. |
| 368 | n.t. | n.t. |
| 369 | n.t. | n.t. |
| 370 | n.t. | n.t. |
| 371 | n.t. | n.t. |
| 372 | n.t. | n.t. |
| 373 | n.t. | n.t. |
| 374 | n.t. | n.t. |
| 375 | n.t. | n.t. |
| 376 | n.t. | n.t. |
| 377 | n.t. | n.t. |
| 378 | n.t. | n.t. |
| 379 | n.t. | n.t. |
| 380 | n.t. | n.t. |
| 381 | n.t. | n.t. |
| 382 | n.t. | n.t. |
| 383 | n.t. | n.t. |
| 384 | n.t. | n.t. |
| 385 | n.t. | n.t. |
| 386 | n.t. | n.t. |
| 387 | n.t. | n.t. |
| 388 | n.t. | n.t. |
| 389 | n.t. | n.t. |
| 390 | n.t. | n.t. |
| 391 | n.t. | n.t. |
| 392 | n.t. | n.t. |
| 393 | n.t. | n.t. |
| 394 | n.t. | n.t. |
| 395 | n.t. | n.t. |
| 396 | n.t. | n.t. |
| 397 | n.t. | n.t. |
| 398 | n.t. | n.t. |
| 399 | n.t. | n.t. |
| 400 | n.t. | n.t. |
| 401 | n.t. | n.t. |
| 402 | n.t. | n.t. |
| 403 | n.t. | n.t. |
| 404 | n.t. | n.t. |
| 405 | n.t. | n.t. |
| 406 | n.t. | n.t. |
| 407 | n.t. | n.t. | n.t. means not tested

Demonstration of In Vivo Efficacy

Aβ peptide lowering agents of the invention can be used to treat AD in mammals such as humans or alternatively demonstrating efficacy in animal models such as, but not limited to, the mouse, rat, or guinea pig. The mammal may not be diagnosed with AD, or may not have a genetic predisposition for AD, but may be transgenic such that it overproduces and eventually deposits Aβ in a manner similar to that seen in humans afflicted with AD.

Aβ peptide lowering agents can be administered in any standard form using any standard method. For example, but not limited to, Aβ peptide lowering agents can be in the form of liquid, tablets or capsules that are taken orally or by injection. Aβ peptide lowering agents can be administered at any dose that is sufficient to significantly reduce levels of Aβ peptides in the blood, blood plasma, serum, cerebrospinal fluid (CSF), or brain.

To determine whether acute administration of an Aβ42 peptide lowering agent would reduce Aβ peptide levels in vivo, non-transgenic rodents, e.g. mice or rats were used. Animals treated with the Aβ peptide lowering agent were examined and compared to those untreated or treated with vehicle and brain levels of soluble Aβ42 and total Aβ were quantitated by standard techniques, for example, using ELISA. Treatment periods varied from hours (h) to days and were adjusted based on the results of the Aβ42 lowering once a time course of onset of effect could be established.

A typical protocol for measuring Aβ42 lowering in vivo is shown but it is only one of many variations that could be used to optimize the levels of detectable Aβ. For example, Aβ peptide lowering compounds were formulated in 20% hydroxypropyl 3 cyclodextrin. The Aβ peptide lowering agents were administered as a single oral dose (p.o.) or a single subcutaneous dose (s.c.) to overnight fasted animals. After a certain time, usually 2 or 4 h (as indicated in Table 19), the animals were sacrificed and Aβ42 levels were analysed.

Blood was collected by decapitation and exsanguinations in EDTA-treated collection tubes. Blood was centrifuged at 1900 g for 10 minutes (min) at 4° C. and the plasma recovered and flash frozen for later analysis. The brain was removed from the cranium and hindbrain. The cerebellum was removed and the left and right hemisphere were separated. The left hemisphere was stored at −18° C. for quantitative analysis of test compound levels. The right hemisphere was rinsed with phosphate-buffered saline (PBS) buffer and immediately frozen on dry ice and stored at −80° C. until homogenization for biochemical assays.

Mouse brains from non-transgenic animals were resuspended in 8 volumes of 0.4% DEA (diethylamine)/50 mM NaCl containing protease inhibitors (Roche-11873580001 or 04693159001) per gram of tissue, e.g. for 0.158 g brain, add 1.264 ml of 0.4% DEA. All samples were homogenized in the FastPrep-24 system (MP Biomedicals) using lysing matrix D (MPBio #6913-100) at 6 m/s for 20 seconds. Homogenates were centrifuged at 221.300×g for 50 min. The resulting high speed supernatants were then transferred to fresh eppendorf tubes. Nine parts of supernatant were neutralized with 1 part 0.5 M Tris-HCl pH 6.8 and used to quantify Aβtotal and Aβ42.

To quantify the amount of Aβtotal and Aβ42 in the soluble fraction of the brain homogenates, Enzyme-Linked-Immunosorbent-Assays were used. Briefly, the standards (a dilution of synthetic Aβ1-40 and Aβ1-42, Bachem) were prepared in 1.5 ml Eppendorf tube in Ultraculture, with final concentrations ranging from 10000 to 0.3 pg/ml. The samples and standards were co-incubated with HRPO-labelled N-terminal antibody for Aβ42 detection and with the biotinylated mid-domain antibody 4G8 for Aβtotal detection. 50 μl of conjugate/sample or conjugate/standards mixtures were then added to the antibody-coated plate (the capture antibodies selectively recognize the C-terminal end of Aβ42, antibody JRF/cAβ42/26, for Aβ42 detection and the N-terminus of Aβ, antibody JRF/rAβ/2, for Aβtotal detection). The plate was allowed to incubate overnight at 4° C. in order to allow formation of the antibody-amyloid complex. Following this incubation and subsequent wash steps the ELISA for Aβ42 quantification was finished by addition of Quanta Blu fluorogenic peroxidase substrate according to the manufacturer's instructions (Pierce Corp., Rockford, Ill.). A reading was performed after 10 to 15 min (excitation 320 nm/emission 420 nm).

For Aβtotal detection, a Streptavidine-Peroxidase-Conjugate was added, followed 60 min later by an additional wash step and addition of Quanta Blu fluorogenic peroxidase substrate according to the manufacturer's instructions (Pierce Corp., Rockford, Ill.). A reading was performed after 10 to 15 min (excitation 320 nm/emission 420 nm).

In this model at least 20% Aβ42 lowering compared to untreated animals would be advantageous.

The following exemplified compounds were tested essentially as described above and exhibited the following activity:

TABLE 20

| Co. No. | Aβ42 (% Ctrl)_Mean | Aβtotal (% Ctrl)_Mean | Dose | Route of administration | Time after administration |
|---|---|---|---|---|---|
| 1 | 102 | 97 | 30 mpk | s.c. | 4 h |
| 8 | 92 | 98 | 30 mpk | s.c. | 4 h |
| 9 | 87 | 101 | 30 mpk | s.c. | 4 h |
| 12 | 95 | 98 | 30 mpk | s.c. | 4 h |
| 14 | 107 | 116 | 30 mpk | s.c. | 4 h |
| 44 | 56 | 67 | 30 mpk | s.c. | 4 h |
| 50 | 133 | 95 | 5 mpk | s.c. | 4 h |
| 52 | 68 | 114 | 30 mpk | s.c. | 2 h |
| 55 | 88 | 87 | 30 mpk | s.c. | 4 h |
| 59 | 114 | 95 | 30 mpk | s.c. | 2 h |
| 65 | 79 | 91 | 30 mpk | s.c. | 4 h |
| 82 | 57 | 44 | 30 mpk | s.c. | 2 h |
| 86 | 60 | 55 | 30 mpk | s.c. | 4 h |
| 96 | 116 | 104 | 30 mpk | s.c. | 4 h |
| 117 | 95 | 86 | 30 mpk | s.c. | 2 h |
| 123 | 38 | 38 | 10 mpk | p.o. | 4 h |
| 123 | 24 | 21 | 10 mpk | s.c. | 4 h |
| 124 | 23 | 25 | 30 mpk | p.o. | 4 h |
| 126 | 26 | 31 | 30 mpk | p.o. | 4 h |
| 126 | 27 | 32 | 30 mpk | s.c. | 4 h |
| 134 | 27 | 35 | 30 mpk | p.o. | 4 h |
| 166 | 50 | 43 | 30 mpk | p.o. | 4 h |
| 167 | 95 | 78 | 30 mpk | p.o. | 2 h |
| 169 | 38 | 39 | 30 mpk | p.o. | 4 h |
| 199 | 64 | 45 | 30 mpk | sc | 2 h |
| 204 | 113 | 103 | 30 mpk | sc | 4 h |
| 209 | 6 | 14 | 10 mpk | p.o. | 4 h |
| 216 | 45 | 39 | 30 mpk | p.o. | 4 h |
| 217 | 80 | 73 | 30 mpk | p.o. | 2 h |
| 218 | 99 | 90 | 30 mpk | sc | 2 h |
| 219 | 95 | 86 | 30 mpk | sc | 2 h |
| 227 | 77 | 66 | 30 mpk | p.o. | 2 h |
| 228 | 99 | 79 | 30 mpk | p.o. | 2 h | s.c. means subcutaneous;
p.o. means oral

Single Dose Pharmacology in the Beagle Dog

Compound 86 was tested to evaluate the effect on the beta-amyloid profile in cerebrospinal fluid (CSF) of dogs after a single dose, in combination with pharmacokinetic (PK) follow up and limited safety evaluation. 6 Beagle dogs (3 male, 3 female) were dosed with vehicle (4 ml/kg of an aqueous suspension of 20% cyclodextrin and Tween) and 6 Beagle dogs (3 male, 3 female) were dosed with compound 86 (20 mg/kg in 2 ml/kg of an aqueous 20% cyclodextrin solution) on an empty stomach. CSF was taken in conscious animals directly from the lateral ventricle via a cannula which was screwed in the skull and covered with subcutaneous tissue and skin, before and at 4, 8 and 24 hours after dosing. 8 Hours after dosing the animals got access to their regular meal for 30 minutes. Blood was taken for PK follow up (0.5, 1, 2, 4, 8 and 24 hours) and at the time of the CSF sampling, samples for serum analysis were taken. An additional sample for serum analysis was taken 10 days after dosing. The CSF samples were used for measurement of Abeta 1-37, Abeta 1-38, Abeta 1-40 and Abeta 1-42.

The decrease in Abeta 1-38, Abeta 1-40 and Abeta 1-42 at 24 hours post dosing, compared to own baseline, was almost maximal (>90%) while the decrease in Abeta 1-37 was somewhat less though still very pronounced (72% at 24 h). The effect on Abeta Compound 86 lowered Abeta 1-37, Abeta 1-38, Abeta 1-40 and Abeta 1-42 in CSF. is in line with a slow clearance of compound 86 resulting in high plasma levels (1439 ng/ml) up to at least 24 h post dosing. CSF levels at 24 h were 45 ng/ml. No acute or delayed changes in serum parameters (liver enzymes, bilirubin, . . . ) and no overt clinical abnormalities in behavior were seen.

Brief Assay Description for the Measurement of Transepithelial Transport of Test Compounds Through LLC-MDR1 Monolayers The purpose of this assay was to assess both the in vitro passive permeability of test compounds and their ability to be transported substrates of P-gp using LLC-PK1 cells stably transduced with MDR1 in a trans-well system. The positive control for transport was $^3$H-digoxin (30 nM) and the positive control inhibitor was GF120918 (5 μM). The marker compound for low permeability was $^{14}$C-Mannitol (1 μM). The test compound concentration was 1 μM.

The apical to basolateral (A to B) in the presence and absence of the P-gp inhibitor GF120918 and the basolateral to apical (B to A) permeation rates (Apparent Permeability) of the test compounds (Papp×10-6 cm/sec) were measured following an incubation period of 120 minutes. The integrity of the cellular monolayer was assessed in each incubation well through the inclusion of the fluorescent, low permeability marker compound, Fluorescein.

In detail, LLC-MDR1 cells were seeded on 24-well cell culture inserts (Millicell®-PCF, 0.4 μm, 13 mm diameter, 0.7 cm²) at 400,000 cells/cm². Cell culture medium consisted of Medium 199 supplemented with 10% Foetal Bovine Serum (FBS) and 100 U/ml Penicillin/streptomycin and was replaced the day after seeding and the day before the experiment. The transport experiment was performed 5 days after seeding. On the day of the experiment, solutions of the test compounds were applied to the apical or basolateral side of the monolayers to assess transport in the A to B and B to A directions, respectively. The medium used in the assay was (OPTI-MEM (1×) (GIBCO) with 1 w/v % Bovine Serum Albumin. Inserts were incubated at 37° C. in a humidified incubator containing 5% $CO_2$. Samples from the acceptor and donor compartments were collected after an incubation time of 120 min, to assess the permeability and to allow estimation of the test compound recovery during the experiment, respectively. Transport experiments were performed in triplicate. Absolute test compound concentrations were measured using LC-MS/MS and quantified via a calibration curve.

TABLE 21

| Co. No. | 6-position | A to B | A to B (+GF) | B to A | BA/AB |
|---|---|---|---|---|---|
| 44 | H | 5.3 | 24.6 | 38.8 | 7.3 |
| 134 | F | 8.9 | 15.4 | 17.7 | 2.0 |
| 12 | H | | | | 25.4 |
| 113 | F, CF3 | 9.0 | 11.0 | 9.8 | 1.1 |
| 86 | F | 13.2 | 18.3 | 20.9 | 1.6 |
| 39 | H | 3.7 | 15.4 | 34.2 | 9.3 |
| 123 | F | 17.6 | 20.0 | 19.7 | 1.1 |
| 166 | CF3 | 13.7 | 16.0 | 13.6 | 1.0 |
| 216 | F | 12.0 | 12.9 | 12.0 | 1.0 |
| 4 | H | | | | 25.9 |
| 43 | H | 1.4 | 10.3 | 26.6 | 18.5 |
| 93 | F | 7.4 | 23.5 | 34.3 | 4.6 |
| 100 | F | 7.6 | 23.4 | 27.4 | 3.6 |
| 169 | CF3 | 10.5 | 16.7 | 19.0 | 1.8 |
| 118 | F, CF3 | 12.0 | 16.5 | 15.0 | 1.3 |
| 54 | H | 2.0 | 10.3 | 34.5 | 14.1 |
| 106 | CF3 | 18.2 | 20.8 | 19.8 | 1.1 |
| 55 | H | 9.5 | 23.6 | 34.4 | 3.6 |
| 82 | F | 10.5 | 19.1 | 23.9 | 2.3 |

The invention claimed is:

1. A compound of Formula (I)

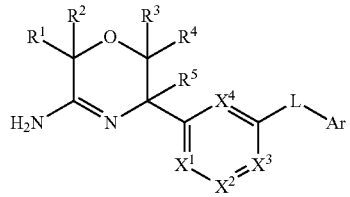

or a tautomer or a stereoisomeric form thereof, wherein
R1, $R^2$ and $R^3$ are independently selected from the group consisting of hydrogen and fluoro;
$R^4$ is trifluoromethyl;
$X^2$, $X^3$ and $X^4$ are CH, and $X^1$ is CF;
L is —N($R^7$)CO— wherein $R^7$ is hydrogen;
$R^5$ is methyl, ethyl or cyclopropyl; and
Ar is pyridyl, or pyrazyl, each optionally substituted with one or two substituents selected from halo, cyano, methoxy, trifluoroethoxy and difluoromethyl; or
an addition salt or a solvate thereof.

2. A compound according to claim 1 wherein the compound is selected from the group consisting of:
(5R,6S)—N-[3-[5-amino-2-fluoro-3,6-dihydro-3-methyl-2-(trifluoromethyl)-2H-1,4-oxazin-3-yl]-4-fluorophenyl]-5-cyano-2-pyridinecarboxamide;
(5R,6R)—N-[3-[5-amino-3,6-dihydro-3-methyl-2-(trifluoromethyl)-2H-1,4-oxazin-3-yl]-4-fluorophenyl]-3,5-dichloro-2-pyridinecarboxamide;
(5R,6R)—N-[3-[5-amino-3,6-dihydro-3-methyl-2-(trifluoromethyl)-2H-1,4-oxazin-3-yl]-4-fluorophenyl]-5-methoxy-2-pyrazinecarboxamide; and
(5R,6R)—N-[3-[5-amino-3,6-dihydro-3-methyl-2-(trifluoromethyl)-2H-1,4-oxazin-3-yl]-4-fluorophenyl]-5-cyano-2-pyridinecarboxamide.

3. A compound according to claim 2 wherein the compound is (5R,6R)—N-[3-[5-amino-3,6-dihydro-3-methyl-2-(trifluoromethyl)-2H-1,4-oxazin-3-yl]-4-fluorophenyl]-5-cyano-2-pyridinecarboxamide.

4. A pharmaceutical composition comprising a therapeutically effective amount of a compound of claim 1 and a pharmaceutically acceptable carrier.

* * * * *